US009701639B2

(12) United States Patent
Strohmeier et al.

(10) Patent No.: US 9,701,639 B2
(45) Date of Patent: Jul. 11, 2017

(54) CO-CRYSTALS OF MODULATORS OF CYSTIC FIBROSIS TRANSMEMBRANE CONDUCTANCE REGULATOR

(71) Applicant: Vertex Pharmaceuticals Incorporated, Boston, MA (US)

(72) Inventors: Mark Strohmeier, Arlington, MA (US); John Caesar, Jr., Lancaster, MA (US); Patrick Raymond Connelly, Harvard, MA (US); Majed Fawaz, Foxboro, MA (US); Eduard Luss-Lusis, Belmont, MA (US); Brian McClain, Harvard, MA (US); Ales Medek, Winchester, MA (US); Hai Miao, Winchester, MA (US); Kwame Wiredu Nti-Addae, Tewksbury, MA (US); Ping Yin, Arlington, MA (US); Yuegang Zhang, Wayland, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 14/877,914

(22) Filed: Oct. 7, 2015

(65) Prior Publication Data
US 2016/0096807 A1   Apr. 7, 2016

Related U.S. Application Data

(60) Provisional application No. 62/060,828, filed on Oct. 7, 2014.

(51) Int. Cl.
*C07D 215/56* (2006.01)
*A61K 31/225* (2006.01)
*A61K 31/47* (2006.01)
*A61K 45/06* (2006.01)
*C07C 69/34* (2006.01)

(52) U.S. Cl.
CPC .......... *C07D 215/56* (2013.01); *A61K 31/225* (2013.01); *A61K 31/47* (2013.01); *A61K 45/06* (2013.01); *C07C 69/34* (2013.01)

(58) Field of Classification Search
CPC .... C07D 215/56; A61K 31/225; A61K 31/47; A61K 45/06; C07C 39/34
See application file for complete search history.

(56) References Cited

U.S. PATENT DOCUMENTS

| 3,443,940 A | 5/1969 | Bloom et al. |
| 3,524,858 A | 8/1970 | Kaminsky et al. |
| 3,698,292 A | 10/1972 | Koester |
| 3,812,094 A | 5/1974 | MacLeay et al. |
| 3,931,145 A | 1/1976 | Stanley et al. |
| 3,992,540 A | 11/1976 | Clemence et al. |
| 4,107,310 A | 8/1978 | Allais et al. |
| 4,110,355 A | 8/1978 | Bloom et al. |
| 4,221,779 A | 9/1980 | Graham |
| 4,284,629 A | 8/1981 | Grohe et al. |
| 4,312,870 A | 1/1982 | Yokoyama |
| 4,450,166 A | 5/1984 | Clemence et al. |
| 4,450,167 A | 5/1984 | Le Martret et al. |
| 4,638,067 A | 1/1987 | Culbertson et al. |
| 4,777,252 A | 10/1988 | Slusarchyk et al. |
| 4,786,644 A | 11/1988 | Glamkowski et al. |
| 4,845,105 A | 7/1989 | Clemence et al. |
| 4,908,366 A | 3/1990 | Schriewer et al. |
| 4,956,465 A | 9/1990 | Schriewer et al. |
| 5,026,711 A | 6/1991 | Mendes et al. |
| 5,175,151 A | 12/1992 | Afonso et al. |
| 5,180,400 A | 1/1993 | Baudry et al. |
| 5,254,135 A | 10/1993 | Lang et al. |
| 5,281,612 A | 1/1994 | Domagala et al. |
| 5,322,847 A | 6/1994 | Marfat et al. |
| 5,352,690 A | 10/1994 | Sofia |
| 5,364,414 A | 11/1994 | Lang et al. |
| 5,378,694 A | 1/1995 | Afonso et al. |
| 5,380,713 A | 1/1995 | Balasubramanian et al. |
| 5,409,503 A | 4/1995 | Clausen et al. |
| 5,412,104 A | 5/1995 | Afonso et al. |
| 5,491,139 A | 2/1996 | Demuth, Jr. et al. |
| 5,527,763 A | 6/1996 | Miyazaki et al. |
| 5,536,727 A | 7/1996 | Witzel et al. |
| 5,573,868 A | 11/1996 | Umemoto et al. |
| 5,610,162 A | 3/1997 | Witzel et al. |

(Continued)

FOREIGN PATENT DOCUMENTS

| CA | 1025856 | 2/1978 |
| CA | 2065106 | 10/1992 |
| CA | 2769695 A1 | 2/2011 |
| CN | 1473827 | 2/2004 |
| CN | 101006076 A | 7/2007 |
| CN | 101287732 A | 10/2008 |
| CN | 101374849 A | 2/2009 |
| CN | 101384172 A | 3/2009 |
| CN | 101460489 A | 6/2009 |
| CN | 103044263 A | 4/2013 |

(Continued)

OTHER PUBLICATIONS

Bernstein, J. et al. (1995) "Patterns in Hydrogen Bonding: Functionality and Graph Set Analysis in Crystals" *Angew Chem Int Ed Engl*, 34:1555-1573.
Brown, R.K. et al., "6-Aminoindole," *J. Am. Chem. Soc.*, 1954, vol. 76, No. 20, pp. 5149-5150.

(Continued)

*Primary Examiner* — D M Seaman
(74) *Attorney, Agent, or Firm* — Finnegan, Henderson, Farabow, Garrett & Dunner, LLP

(57) ABSTRACT

The present disclosure relates to co-crystals comprising N-[2,4-bis(1,1-dimethylethyl)-5-hydroxyphenyl]-1,4-dihydro-4-oxoquinoline-3-carboxamide (Compound 1) and a co-former and methods for their preparation. The present disclosure further relates to pharmaceutical compositions comprising the co-crystal forms, as well as methods of treatment therewith and kits.

21 Claims, 37 Drawing Sheets

(56) References Cited

U.S. PATENT DOCUMENTS

| | | | |
|---|---|---|---|
| 5,663,179 | A | 9/1997 | Dumaitre et al. |
| 5,708,000 | A | 1/1998 | Charvet-Faury et al. |
| 5,728,691 | A | 3/1998 | Corpi Constantino |
| 5,744,471 | A | 4/1998 | Bare et al. |
| 5,750,754 | A | 5/1998 | Mills |
| 5,753,666 | A | 5/1998 | Beasley et al. |
| 5,804,588 | A | 9/1998 | Dyke et al. |
| 5,807,869 | A | 9/1998 | Furuya et al. |
| 5,811,553 | A | 9/1998 | Farina et al. |
| 5,834,485 | A | 11/1998 | Dyke et al. |
| 5,840,745 | A | 11/1998 | Buzzetti et al. |
| 5,874,424 | A | 2/1999 | Batchelor et al. |
| 5,891,878 | A | 4/1999 | Beasley et al. |
| 5,892,114 | A | 4/1999 | Goldmann et al. |
| 5,938,792 | A | 8/1999 | Lang et al. |
| 5,948,814 | A | 9/1999 | Hwang et al. |
| 6,039,974 | A | 3/2000 | MacLaren et al. |
| 6,069,151 | A | 5/2000 | Dyke et al. |
| 6,133,265 | A | 10/2000 | Blum et al. |
| 6,194,454 | B1 | 2/2001 | Dow |
| 6,215,016 | B1 | 4/2001 | Kawai et al. |
| 6,218,393 | B1 | 4/2001 | Ryder et al. |
| 6,258,822 | B1 | 7/2001 | Geyer et al. |
| 6,316,617 | B1 | 11/2001 | Blum et al. |
| 6,362,340 | B1 | 3/2002 | Dang |
| 6,395,750 | B1 | 5/2002 | Hedlund et al. |
| 6,413,956 | B1 | 7/2002 | Albaugh et al. |
| 6,429,207 | B1 | 8/2002 | Van Wagenen et al. |
| 6,444,617 | B1 | 9/2002 | Takaishi et al. |
| 6,448,254 | B1 | 9/2002 | Lubisch et al. |
| 6,515,001 | B2 | 2/2003 | Saxena et al. |
| 6,544,987 | B2 | 4/2003 | Guo et al. |
| 6,720,344 | B2 | 4/2004 | Kerwin et al. |
| 6,723,850 | B1 | 4/2004 | Guarna et al. |
| 6,790,858 | B2 | 9/2004 | Strehlke et al. |
| 6,849,648 | B2 | 2/2005 | Bunker et al. |
| 6,878,713 | B2 | 4/2005 | De Souza et al. |
| 6,930,131 | B2 | 8/2005 | Sabatucci et al. |
| 6,974,806 | B2 | 12/2005 | Terashita et al. |
| 6,977,001 | B2 | 12/2005 | Sauter et al. |
| 7,001,770 | B1 | 2/2006 | Atencio et al. |
| 7,037,913 | B2 | 5/2006 | Wang et al. |
| 7,084,156 | B2 | 8/2006 | DeVita et al. |
| 7,105,535 | B2 | 9/2006 | Berta et al. |
| 7,112,594 | B2 | 9/2006 | Ushio et al. |
| 7,179,839 | B2 | 2/2007 | Strobel et al. |
| 7,223,759 | B2 | 5/2007 | Zhou et al. |
| 7,407,976 | B2 | 8/2008 | Miller et al. |
| 7,495,103 | B2 | 2/2009 | Hadida-Ruah et al. |
| 7,553,855 | B2 | 6/2009 | Young et al. |
| 7,598,412 | B2 | 10/2009 | Hadida Ruah et al. |
| 7,645,789 | B2 | 1/2010 | Hadida Ruah et al. |
| 7,659,268 | B2 | 2/2010 | Hadida-Ruah et al. |
| 7,671,221 | B2 | 3/2010 | Hadida Ruah et al. |
| 7,691,902 | B2 | 4/2010 | Hadida Ruah et al. |
| 7,741,321 | B2 | 6/2010 | Hadida Ruah et al. |
| 7,754,739 | B2 | 7/2010 | Hadida Ruah et al. |
| 7,776,905 | B2 | 8/2010 | Hadida Ruah et al. |
| 7,846,951 | B2 | 12/2010 | Miller et al. |
| 7,939,558 | B2 | 5/2011 | Verkman et al. |
| 7,956,052 | B2 | 6/2011 | Hadida Ruah et al. |
| 7,973,038 | B2 | 7/2011 | Hadida Ruah et al. |
| 7,973,169 | B2 | 7/2011 | Hadida Ruah et al. |
| 7,977,322 | B2 | 7/2011 | Ruah et al. |
| 7,999,113 | B2 | 8/2011 | Hadida-Ruah et al. |
| 8,012,999 | B2 | 9/2011 | Hadida Ruah et al. |
| 8,039,491 | B2 | 10/2011 | Hadida Ruah et al. |
| 8,076,357 | B2 | 12/2011 | Young et al. |
| 8,101,767 | B2 | 1/2012 | Ruah et al. |
| 8,124,781 | B2 | 2/2012 | Siesel |
| 8,163,772 | B2 | 4/2012 | Demattei et al. |
| 8,188,283 | B2 | 5/2012 | Binch et al. |
| 8,227,615 | B2 | 7/2012 | Hadida-Ruah et al. |
| 8,232,302 | B2 | 7/2012 | Miller et al. |
| 8,242,149 | B2 | 8/2012 | Ruah et al. |
| 8,299,099 | B2 | 10/2012 | Ruah et al. |
| 8,314,239 | B2 | 11/2012 | Binch et al. |
| 8,314,256 | B2 | 11/2012 | Ruah et al. |
| 8,318,733 | B2 | 11/2012 | Hadida-Ruah et al. |
| 8,324,207 | B2 | 12/2012 | Hadida Ruah et al. |
| 8,324,242 | B2 | 12/2012 | Ruah et al. |
| 8,344,147 | B2 | 1/2013 | Ambhaikar et al. |
| 8,354,427 | B2 | 1/2013 | Van Goor |
| 8,362,253 | B2 | 1/2013 | Demattei et al. |
| 8,367,660 | B2 | 2/2013 | Binch et al. |
| 8,389,727 | B2 | 3/2013 | Zhang et al. |
| 8,399,479 | B2 | 3/2013 | Binch et al. |
| 8,404,849 | B2 | 3/2013 | Sun et al. |
| 8,404,865 | B2 | 3/2013 | Ambhaikar et al. |
| 8,410,132 | B2 | 4/2013 | Binch et al. |
| 8,410,274 | B2 | 4/2013 | Hurter et al. |
| 8,415,387 | B2 | 4/2013 | Ruah et al. |
| 8,431,605 | B2 | 4/2013 | Hadida Ruah et al. |
| 8,436,014 | B2 | 5/2013 | Zhang et al. |
| 8,461,156 | B2 | 6/2013 | Hadida Ruah et al. |
| 8,461,342 | B2 | 6/2013 | Siesel |
| 8,461,352 | B2 | 6/2013 | Ambhaikar et al. |
| 8,471,029 | B2 | 6/2013 | Arekar et al. |
| 8,476,442 | B2 | 7/2013 | Demattei et al. |
| 8,507,524 | B2 | 8/2013 | Ruah et al. |
| 8,507,534 | B2 | 8/2013 | Keshavarz-Shokri et al. |
| 8,507,687 | B2 | 8/2013 | Keshavarz-Shokri et al. |
| 8,513,282 | B2 | 8/2013 | Binch et al. |
| 8,518,441 | B2 | 8/2013 | Higuchi et al. |
| 8,524,767 | B2 | 9/2013 | Miller et al. |
| 8,524,910 | B2 | 9/2013 | Hadida Ruah et al. |
| 8,541,453 | B2 | 9/2013 | Hadida-Ruah et al. |
| 8,552,006 | B2 | 10/2013 | Binch et al. |
| 8,552,034 | B2 | 10/2013 | Verwijs et al. |
| 8,563,573 | B2 | 10/2013 | Ruah et al. |
| 8,563,593 | B2 | 10/2013 | Alargova et al. |
| 8,575,209 | B2 | 11/2013 | Ruah et al. |
| 8,586,615 | B2 | 11/2013 | Hadida-Ruah et al. |
| 8,592,602 | B2 | 11/2013 | Siesel |
| 8,598,181 | B2 | 12/2013 | Hadida Ruah et al. |
| 8,598,205 | B2 | 12/2013 | Binch et al. |
| 8,604,203 | B2 | 12/2013 | Binch et al. |
| 8,609,703 | B2 | 12/2013 | Ruah et al. |
| 8,614,325 | B2 | 12/2013 | Yang et al. |
| 8,614,327 | B2 | 12/2013 | Sheth et al. |
| 8,623,894 | B2 * | 1/2014 | DeMattei ............ C07D 215/233 514/312 |
| 8,623,905 | B2 | 1/2014 | Ruah et al. |
| 8,629,162 | B2 | 1/2014 | Hadida-Ruah et al. |
| 8,633,189 | B2 | 1/2014 | Binch et al. |
| 8,642,609 | B2 | 2/2014 | Makings et al. |
| 8,653,103 | B2 | 2/2014 | Keshavarz-Shokri et al. |
| 8,674,108 | B2 | 3/2014 | Luisi et al. |
| 8,710,075 | B2 | 4/2014 | Binch et al. |
| 8,716,338 | B2 | 5/2014 | Young |
| 8,722,704 | B2 | 5/2014 | Hadida Ruah et al. |
| 8,741,922 | B2 | 6/2014 | Zhang et al. |
| 8,741,925 | B2 | 6/2014 | Hadida-Ruah et al. |
| 8,741,933 | B2 | 6/2014 | Hadida Ruah et al. |
| 8,741,939 | B2 | 6/2014 | Hadida Ruah et al. |
| 8,742,122 | B2 | 6/2014 | Keshavarz-Shokri et al. |
| 8,748,612 | B2 | 6/2014 | Binch et al. |
| 8,754,222 | B2 | 6/2014 | Ambhaikar et al. |
| 8,754,224 | B2 | 6/2014 | Hurter et al. |
| 8,759,335 | B2 | 6/2014 | Hadida Ruah et al. |
| 8,765,957 | B2 | 7/2014 | Demattei et al. |
| 8,785,476 | B2 | 7/2014 | Arekar et al. |
| 8,785,640 | B2 | 7/2014 | Binch et al. |
| 8,796,308 | B2 | 8/2014 | Yang et al. |
| 8,796,312 | B2 | 8/2014 | Hadida Ruah et al. |
| 8,802,700 | B2 | 8/2014 | Sheth et al. |
| 8,802,844 | B2 | 8/2014 | Gallardo-Godoy |
| 8,802,868 | B2 | 8/2014 | Keshavarz-Shokri et al. |
| 8,816,093 | B2 | 8/2014 | Siesel |
| 8,822,451 | B2 | 9/2014 | Ruah et al. |
| 8,829,204 | B2 | 9/2014 | Hadida-Ruah et al. |
| 8,835,639 | B2 | 9/2014 | Demattei et al. |
| 8,846,718 | B2 | 9/2014 | Keshavarz-Shokri et al. |
| 8,846,753 | B2 | 9/2014 | Hadida Ruah et al. |

(56) References Cited

U.S. PATENT DOCUMENTS

| | | |
|---|---|---|
| 8,853,254 B2 | 10/2014 | Hadida Ruah et al. |
| 8,853,415 B2 | 10/2014 | Hadida Ruah et al. |
| 8,883,206 B2 | 11/2014 | Dokou et al. |
| 8,884,018 B2 | 11/2014 | Ambhaikar et al. |
| 8,889,875 B2 | 11/2014 | Ruah et al. |
| 8,912,199 B2 | 12/2014 | Hadida Ruah et al. |
| 8,952,049 B2 | 2/2015 | Ruah et al. |
| 8,952,050 B2 | 2/2015 | Ruah et al. |
| 8,962,856 B2 | 2/2015 | Hadida-Ruah et al. |
| 8,969,382 B2 | 3/2015 | Binch et al. |
| 8,969,386 B2 | 3/2015 | Hadida-Ruah et al. |
| 8,969,574 B2 | 3/2015 | Keshavarz-Shokri et al. |
| 8,993,600 B2 | 3/2015 | Hadida Ruah et al. |
| 8,999,976 B2 | 4/2015 | Binch et al. |
| 9,012,473 B2 | 4/2015 | Hadida Ruah et al. |
| 9,012,496 B2 | 4/2015 | Alargova et al. |
| 9,012,652 B2 | 4/2015 | Siesel |
| 9,035,072 B2 | 5/2015 | Belmont et al. |
| 9,045,425 B2 | 6/2015 | Luisi et al. |
| 9,051,303 B2 | 6/2015 | Keshavarz-Shokri et al. |
| 9,051,324 B2 | 6/2015 | Binch et al. |
| 9,079,916 B2 | 7/2015 | Hadida Ruah et al. |
| 9,090,619 B2 | 7/2015 | Hadida-Ruah et al. |
| 9,102,672 B2 | 8/2015 | Hadida-Ruah et al. |
| 9,139,530 B2 | 9/2015 | Hurter et al. |
| 9,150,552 B2 | 10/2015 | Keshavarz-Shokri et al. |
| 9,192,606 B2 | 11/2015 | Young |
| 9,216,969 B2 | 12/2015 | Ruah et al. |
| 9,241,934 B2 | 1/2016 | Verwijs et al. |
| 9,249,131 B2 | 2/2016 | Hadida Ruah et al. |
| 9,254,291 B2 | 2/2016 | Looker et al. |
| 9,314,455 B2 | 4/2016 | Keshavarz-Shokri et al. |
| 9,321,725 B2 | 4/2016 | Miller et al. |
| 9,351,962 B2 | 5/2016 | Hadida-Ruah et al. |
| 9,371,287 B2 | 6/2016 | Demattei et al. |
| 9,434,717 B2 | 9/2016 | Keshavarz-Shokri et al. |
| 9,504,683 B2 | 11/2016 | Hadida Ruah et al. |
| 9,522,145 B2 | 12/2016 | Hadida Ruah et al. |
| 2002/0173520 A1 | 11/2002 | Bjork et al. |
| 2003/0100501 A1 | 5/2003 | Davis et al. |
| 2003/0187026 A1 | 10/2003 | Li et al. |
| 2003/0195191 A1 | 10/2003 | Burton et al. |
| 2003/0195201 A1 | 10/2003 | Bo et al. |
| 2004/0033959 A1 | 2/2004 | Chen et al. |
| 2004/0043983 A1 | 3/2004 | Li |
| 2004/0082798 A1 | 4/2004 | Alonso-Alija et al. |
| 2004/0121005 A1 | 6/2004 | Altreuter et al. |
| 2005/0059035 A1 | 3/2005 | Huang et al. |
| 2005/0113423 A1 | 5/2005 | VanGoor et al. |
| 2005/0147669 A1 | 7/2005 | Lawrence et al. |
| 2005/0176741 A1 | 8/2005 | Okano et al. |
| 2005/0181041 A1 | 8/2005 | Goldman |
| 2005/0186261 A1 | 8/2005 | Avelar et al. |
| 2005/0187300 A1 | 8/2005 | Bajji et al. |
| 2005/0192315 A1 | 9/2005 | Jansson et al. |
| 2005/0208095 A1 | 9/2005 | Hunter et al. |
| 2005/0222199 A1 | 10/2005 | Hayman et al. |
| 2006/0003005 A1 | 1/2006 | Cao et al. |
| 2006/0148806 A1 | 7/2006 | Watanuki et al. |
| 2006/0178516 A1 | 8/2006 | Johnstone et al. |
| 2008/0071095 A1 | 3/2008 | Hadida-Ruah et al. |
| 2008/0317853 A1 | 12/2008 | Kashid et al. |
| 2009/0105272 A1 | 4/2009 | Grootenhuis et al. |
| 2009/0176839 A1 | 7/2009 | Keshavarz-Shokri et al. |
| 2009/0246820 A1 | 10/2009 | Singh et al. |
| 2009/0285887 A1 | 11/2009 | Abu-Baker et al. |
| 2010/0036130 A1 | 2/2010 | Siesel |
| 2010/0074949 A1 | 3/2010 | Rowe et al. |
| 2010/0087386 A1 | 4/2010 | Dudley et al. |
| 2010/0087416 A1 | 4/2010 | Griffith et al. |
| 2010/0125090 A1 | 5/2010 | Hadida Ruah et al. |
| 2010/0144798 A1 | 6/2010 | Vangoor et al. |
| 2010/0168094 A1 | 7/2010 | Binch et al. |
| 2010/0168158 A1 | 7/2010 | Binch et al. |
| 2010/0256184 A1 | 10/2010 | Rowe et al. |
| 2011/0008259 A1 | 1/2011 | Binch et al. |
| 2011/0064811 A1 | 3/2011 | Hurter et al. |
| 2011/0098311 A1 | 4/2011 | Van Goor et al. |
| 2011/0177999 A1 | 7/2011 | Singh et al. |
| 2011/0183948 A1 | 7/2011 | Levine et al. |
| 2011/0230519 A1 | 9/2011 | Arekar et al. |
| 2011/0251253 A1 | 10/2011 | Keshavarz-Shokri et al. |
| 2011/0257223 A1 | 10/2011 | Goor et al. |
| 2011/0288122 A1 | 11/2011 | Van Goor et al. |
| 2012/0035179 A1 | 2/2012 | Hadida-Ruah et al. |
| 2012/0046330 A1 | 2/2012 | Alargova et al. |
| 2012/0064157 A1 | 3/2012 | Dokou et al. |
| 2012/0071479 A1 | 3/2012 | Bhalay et al. |
| 2012/0122921 A1 | 5/2012 | Demattei et al. |
| 2012/0122922 A1 | 5/2012 | Young et al. |
| 2012/0184583 A1 | 7/2012 | Van Goor et al. |
| 2012/0214841 A1 | 8/2012 | Hurter et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2013/0012536 A1 | 1/2013 | Hadida Ruah et al. |
| 2013/0018071 A1 | 1/2013 | Arekar et al. |
| 2013/0029982 A1 | 1/2013 | Castro et al. |
| 2013/0029984 A1 | 1/2013 | Castro et al. |
| 2013/0053362 A1 | 2/2013 | Castro et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0109697 A1 | 5/2013 | Heckel et al. |
| 2013/0109717 A1 | 5/2013 | Demattei et al. |
| 2013/0131107 A1 | 5/2013 | Van Goor et al. |
| 2013/0143918 A1 | 6/2013 | Keshavarz-Shokri et al. |
| 2013/0143919 A1 | 6/2013 | Van Goor et al. |
| 2013/0158071 A1 | 6/2013 | Van Goor et al. |
| 2013/0186801 A1 | 7/2013 | Verwijs |
| 2013/0224293 A1 | 8/2013 | Dokou et al. |
| 2013/0231368 A1 | 9/2013 | Zhang et al. |
| 2013/0245010 A1 | 9/2013 | Hadida Ruah et al. |
| 2013/0245011 A1 | 9/2013 | Hadida Ruah et al. |
| 2013/0267521 A1 | 10/2013 | Castro et al. |
| 2013/0303484 A1 | 11/2013 | Grootenhuis et al. |
| 2013/0310329 A1 | 11/2013 | Maiuri et al. |
| 2013/0316981 A1 | 11/2013 | Hamprecht et al. |
| 2013/0331567 A1 | 12/2013 | Hadida-Ruah et al. |
| 2013/0344061 A1 | 12/2013 | Palombella et al. |
| 2014/0023706 A1 | 1/2014 | Verwijs et al. |
| 2014/0031391 A1 | 1/2014 | Hahn et al. |
| 2014/0080825 A1 | 3/2014 | Hadida-Ruah et al. |
| 2014/0088097 A1 | 3/2014 | Hamprecht et al. |
| 2014/0094499 A1 | 4/2014 | Alargova et al. |
| 2014/0100155 A1 | 4/2014 | Madden et al. |
| 2014/0112988 A1 | 4/2014 | Rowe et al. |
| 2014/0113914 A1 | 4/2014 | Bhalay et al. |
| 2014/0120060 A1 | 5/2014 | Palombella et al. |
| 2014/0142138 A1 | 5/2014 | Van Goor et al. |
| 2014/0142312 A1 | 5/2014 | Luisi et al. |
| 2014/0144429 A1 | 5/2014 | Wensley et al. |
| 2014/0155431 A1 | 6/2014 | Hadida-Ruah et al. |
| 2014/0155626 A1 | 6/2014 | Hadida Ruah et al. |
| 2014/0158127 A1 | 6/2014 | Boucher et al. |
| 2014/0163011 A1 | 6/2014 | Hadida-Ruah et al. |
| 2014/0163068 A1 | 6/2014 | Verwijs et al. |
| 2014/0170244 A1 | 6/2014 | Johnson |
| 2014/0221424 A1 | 8/2014 | Zha |
| 2014/0235631 A1 | 8/2014 | Bunt et al. |
| 2014/0235668 A1 | 8/2014 | Binch et al. |
| 2014/0243289 A1 | 8/2014 | Grootenhuis et al. |
| 2014/0255483 A1 | 9/2014 | Dokou et al. |
| 2014/0271599 A1 | 9/2014 | Heifetz |
| 2014/0274933 A1 | 9/2014 | Cole |
| 2014/0296164 A1 | 10/2014 | Mallon et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |
| 2014/0336393 A1 | 11/2014 | Ambhaikar et al. |
| 2014/0343098 A1 | 11/2014 | Sheth et al. |
| 2014/0350281 A1 | 11/2014 | Demattei et al. |

(56) References Cited

U.S. PATENT DOCUMENTS

| | | |
|---|---|---|
| 2015/0010628 A1 | 1/2015 | Dokou et al. |
| 2015/0024047 A1 | 1/2015 | Dokou et al. |
| 2015/0031722 A1 | 1/2015 | Hadida-Ruah et al. |
| 2015/0065487 A1 | 3/2015 | Hadida-Ruah et al. |
| 2015/0065497 A1 | 3/2015 | Hadida Ruah et al. |
| 2015/0065500 A1 | 3/2015 | Hadida-Ruah et al. |
| 2015/0080431 A1 | 3/2015 | Van Goor et al. |
| 2015/0094304 A1 | 4/2015 | Ruah et al. |
| 2015/0099270 A1 | 4/2015 | Dowling et al. |
| 2015/0119441 A1 | 4/2015 | Hadida Ruah et al. |
| 2015/0141459 A1 | 5/2015 | Van Goor et al. |
| 2015/0150879 A2 | 6/2015 | Van Goor et al. |
| 2015/0152348 A1 | 6/2015 | Tusa et al. |
| 2015/0164881 A1 | 6/2015 | Van Goor et al. |
| 2015/0164883 A1 | 6/2015 | Van Goor et al. |
| 2015/0166516 A1 | 6/2015 | Hadida-Ruah et al. |
| 2015/0174098 A1 | 6/2015 | Ruah et al. |
| 2015/0182517 A1 | 7/2015 | Alargova et al. |
| 2015/0203478 A1 | 7/2015 | Keshavarz-Shokri et al. |
| 2015/0216237 A1 | 8/2015 | Wensley et al. |
| 2015/0218122 A1 | 8/2015 | Tanoury et al. |
| 2015/0231142 A1 | 8/2015 | Van Goor et al. |
| 2015/0246031 A1 | 9/2015 | Dokou et al. |
| 2015/0293078 A1 | 10/2015 | Singh et al. |
| 2015/0320736 A1 | 11/2015 | Phenix et al. |
| 2015/0336898 A1 | 11/2015 | Grootenhuis et al. |
| 2015/0336956 A1 | 11/2015 | Hadida-Ruah et al. |
| 2016/0022664 A2 | 1/2016 | Van Goor et al. |
| 2016/0022665 A2 | 1/2016 | Van Goor et al. |
| 2016/0039800 A1 | 2/2016 | Young |
| 2016/0095858 A1 | 4/2016 | Miller et al. |
| 2016/0096807 A1 | 4/2016 | Strohmeier et al. |
| 2016/0143898 A1 | 5/2016 | Hadida Ruah et al. |
| 2016/0166540 A1 | 6/2016 | Looker et al. |
| 2016/0200712 A1 | 7/2016 | Siesel |
| 2016/0221952 A1 | 8/2016 | Yang et al. |
| 2016/0221995 A1 | 8/2016 | Keshavarz-Shokri et al. |
| 2016/0228414 A1 | 8/2016 | Hadida Ruah et al. |
| 2016/0229806 A1 | 8/2016 | Hurter et al. |
| 2016/0237079 A1 | 8/2016 | Hadida-Ruah et al. |
| 2016/0271105 A1 | 9/2016 | Hadida-Ruah et al. |
| 2016/0303096 A1 | 10/2016 | Verwijs et al. |
| 2016/0318931 A1 | 11/2016 | Hadida-Ruah et al. |
| 2016/0324788 A1 | 11/2016 | Hadida-Ruah et al. |
| 2016/0324846 A1 | 11/2016 | Verwijs et al. |
| 2016/0332997 A1 | 11/2016 | Hadida Ruah et al. |

FOREIGN PATENT DOCUMENTS

| | | |
|---|---|---|
| CN | 103224466 A | 7/2013 |
| CN | 103787968 A | 5/2014 |
| CN | 104530413 A | 4/2015 |
| CN | 104530415 A | 4/2015 |
| CN | 104530417 A | 4/2015 |
| CN | 104725314 A | 6/2015 |
| CN | 104725628 A | 6/2015 |
| DE | 2050966 | 4/1971 |
| DE | 2407744 | 8/1974 |
| DE | 2415763 | 10/1974 |
| DE | 3827253 A1 | 3/1989 |
| DE | 3903799 A1 | 8/1990 |
| DE | 4017516 A1 | 12/1991 |
| DE | 19601142 A1 | 1/1997 |
| DE | 19532235 A1 | 3/1997 |
| EA | 003945 B1 | 10/2003 |
| EA | 004043 B1 | 12/2003 |
| EP | 0004279 B1 | 12/1982 |
| EP | 0308702 A2 | 3/1989 |
| EP | 0332033 A2 | 9/1989 |
| EP | 0332930 A2 | 9/1989 |
| EP | 0343398 A2 | 11/1989 |
| EP | 0382034 A1 | 1/1990 |
| EP | 0363585 A1 | 4/1990 |
| EP | 0409025 A2 | 1/1991 |
| EP | 0425345 A1 | 5/1991 |
| EP | 0460996 A1 | 12/1991 |
| EP | 0472091 B1 | 11/1994 |
| EP | 0705835 A1 | 4/1996 |
| EP | 1224172 B1 | 7/2002 |
| EP | 1227084 B1 | 12/2005 |
| EP | 2815749 A1 | 12/2014 |
| FR | 960299 A | 4/1950 |
| FR | 2002888 A1 | 10/1969 |
| FR | 2324304 | 4/1977 |
| FR | 2340092 A2 | 9/1977 |
| FR | 2537140 A1 | 6/1984 |
| GB | 1433774 A | 4/1976 |
| GB | 2372986 A | 9/2002 |
| JP | 50-24296 A | 3/1975 |
| JP | 50-29574 A | 3/1975 |
| JP | 55-081878 A | 6/1980 |
| JP | 56-110612 A | 9/1981 |
| JP | 58-018361 A | 2/1983 |
| JP | 1988116431 | 11/1989 |
| JP | 2-138260 A | 5/1990 |
| JP | 3-34977 A | 2/1991 |
| JP | 3-193725 A | 8/1991 |
| JP | 6-72979 A | 3/1994 |
| JP | 6-509061 A | 10/1994 |
| JP | 7-33729 A | 2/1995 |
| JP | 7-82498 A | 3/1995 |
| JP | 7-179407 A | 7/1995 |
| JP | 8-208824 A | 8/1996 |
| JP | 8-301849 A | 11/1996 |
| JP | 9-71534 A | 3/1997 |
| JP | 11-116502 A | 4/1999 |
| JP | 11-513021 A | 9/1999 |
| JP | 2000-16982 A | 1/2000 |
| JP | 2000-505450 A | 5/2000 |
| JP | 2000-256358 A | 9/2000 |
| JP | 2001-502683 A | 2/2001 |
| JP | 2001-199965 A | 7/2001 |
| JP | 2001-233859 A | 8/2001 |
| JP | 2002-212179 A | 7/2002 |
| JP | 2002-296731 A | 10/2002 |
| JP | 2002-322054 A | 11/2002 |
| JP | 2002-322154 A | 11/2002 |
| JP | 2002-326935 A | 11/2002 |
| JP | 2003-12667 A | 1/2003 |
| JP | 2003-145933 A | 5/2003 |
| JP | 2003-238413 A | 8/2003 |
| JP | 2004-189738 A | 7/2004 |
| JP | 2004-532209 A | 10/2004 |
| JP | 2005-533770 A | 11/2005 |
| JP | 2006-206612 A | 8/2006 |
| JP | 2002-322154 A | 11/2007 |
| JP | 2008-504291 A | 2/2008 |
| JP | 2009-051827 A | 3/2009 |
| JP | 2009-051828 A | 3/2009 |
| JP | 2009-522278 A | 6/2009 |
| JP | 2012-107069 A | 6/2012 |
| JP | 4947658 B2 | 6/2012 |
| JP | 2013-173750 A | 9/2013 |
| JP | 2014-097964 A | 5/2014 |
| RU | 2155754 C2 | 9/2000 |
| RU | 2270186 C2 | 2/2006 |
| SU | 1360584 A3 | 12/1987 |
| SU | 1779243 A3 | 11/1992 |
| SU | 1796623 A1 | 2/1993 |
| WO | WO 1992/014714 A1 | 9/1992 |
| WO | WO 1992/018093 A1 | 10/1992 |
| WO | WO 1992/018483 A1 | 10/1992 |
| WO | WO 1994/014797 A1 | 7/1994 |
| WO | WO 1995/011244 A1 | 4/1995 |
| WO | WO 1995/32948 A1 | 12/1995 |
| WO | WO 1996/015099 A1 | 5/1996 |
| WO | WO 1996/019239 A1 | 6/1996 |
| WO | WO 1997/04779 A1 | 2/1997 |
| WO | WO 1997/23462 A1 | 7/1997 |
| WO | WO 1997/030999 A1 | 8/1997 |
| WO | WO 1998/17648 A1 | 4/1998 |
| WO | WO 1998/026127 A1 | 6/1998 |
| WO | WO 1998/031226 A1 | 7/1998 |
| WO | WO 1999/05096 A2 | 2/1999 |

(56) References Cited

FOREIGN PATENT DOCUMENTS

| | | |
|---|---|---|
| WO | WO 1999/32436 A1 | 7/1999 |
| WO | WO 1999/46237 A1 | 9/1999 |
| WO | WO 1999/46267 A1 | 9/1999 |
| WO | WO 2000/26197 A1 | 5/2000 |
| WO | WO 2000/68202 A1 | 11/2000 |
| WO | WO 2001/21159 A2 | 3/2001 |
| WO | WO 2001/30757 A1 | 5/2001 |
| WO | WO 2001/34570 A1 | 5/2001 |
| WO | WO 2001/40217 A1 | 6/2001 |
| WO | WO 2001/47924 A1 | 7/2001 |
| WO | WO 2001/87806 A2 | 11/2001 |
| WO | WO 2002/003938 A1 | 1/2002 |
| WO | WO 2002/006264 A1 | 1/2002 |
| WO | WO 2002/038126 A2 | 5/2002 |
| WO | WO 2002/078693 A2 | 10/2002 |
| WO | WO 2002/094809 A1 | 11/2002 |
| WO | WO 2003/043992 A1 | 5/2003 |
| WO | WO 2003/063821 A2 | 8/2003 |
| WO | WO 2003/101454 A1 | 12/2003 |
| WO | WO 2004/039783 A1 | 5/2004 |
| WO | WO 2004/048314 A1 | 6/2004 |
| WO | WO 2004/105779 A2 | 12/2004 |
| WO | WO 2005/035514 A2 | 4/2005 |
| WO | WO 2005/046696 A1 | 5/2005 |
| WO | WO 2005/049018 A1 | 6/2005 |
| WO | WO 2005/060956 A1 | 7/2005 |
| WO | WO 2005/075435 A1 | 8/2005 |
| WO | WO 2005/094805 A1 | 10/2005 |
| WO | WO 2005/120497 A2 | 12/2005 |
| WO | WO 2006/002421 A2 | 1/2006 |
| WO | WO 2006/020681 A2 | 2/2006 |
| WO | WO 2006/065479 A2 | 8/2006 |
| WO | WO 2006/101740 A2 | 9/2006 |
| WO | WO 2006/127588 A2 | 11/2006 |
| WO | WO 2007/021982 A2 | 2/2007 |
| WO | WO 2007/056341 A1 | 5/2007 |
| WO | WO 2007/067559 A2 | 6/2007 |
| WO | WO 2007/075901 A2 | 7/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/088999 A1 | 8/2007 |
| WO | WO 2007/106537 A2 | 9/2007 |
| WO | WO 2007/106960 A1 | 9/2007 |
| WO | WO 2007/117715 A2 | 10/2007 |
| WO | WO 2007/134279 A2 | 11/2007 |
| WO | WO 2008/083130 A2 | 7/2008 |
| WO | WO 2008/127399 A2 | 10/2008 |
| WO | WO 2008/147952 A1 | 12/2008 |
| WO | WO 2009/006315 A1 | 1/2009 |
| WO | WO 2009/023509 A2 | 2/2009 |
| WO | WO 2009/036412 A1 | 3/2009 |
| WO | WO 2009/038683 A2 | 3/2009 |
| WO | WO 2009/073757 A1 | 6/2009 |
| WO | WO 2009/076141 A2 | 6/2009 |
| WO | WO 2009/076593 A1 | 6/2009 |
| WO | WO 2010/019239 A2 | 2/2010 |
| WO | WO 2010/025126 A1 | 3/2010 |
| WO | WO 2010/037066 A2 | 4/2010 |
| WO | WO 2010/048526 A2 | 4/2010 |
| WO | WO 2010/048564 A1 | 4/2010 |
| WO | WO 2010/048573 A1 | 4/2010 |
| WO | WO 2010/053471 A1 | 5/2010 |
| WO | WO 2010/054138 A2 | 5/2010 |
| WO | WO 2010/107952 A2 | 9/2010 |
| WO | WO 2010/107955 A2 | 9/2010 |
| WO | WO 2010/107957 A2 | 9/2010 |
| WO | WO 2010/107958 A2 | 9/2010 |
| WO | WO 2010/108162 A1 | 9/2010 |
| WO | WO 2010/111464 A1 | 9/2010 |
| WO | WO 2010/111468 A2 | 9/2010 |
| WO | WO 2010/111471 A2 | 9/2010 |
| WO | WO 2010/111490 A2 | 9/2010 |
| WO | WO 2010/111497 A2 | 9/2010 |
| WO | WO 2010/111503 A2 | 9/2010 |
| WO | WO 2011/019413 A1 | 2/2011 |
| WO | WO 2011/056477 A2 | 5/2011 |
| WO | WO 2011/072275 A2 | 6/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/133951 A1 | 10/2011 |
| WO | WO 2011/133953 A1 | 10/2011 |
| WO | WO 2011/146901 A1 | 11/2011 |
| WO | WO 2012/027247 A2 | 3/2012 |
| WO | WO 2012/027731 A2 | 3/2012 |
| WO | WO 2012/030645 A1 | 3/2012 |
| WO | WO 2012/030647 A1 | 3/2012 |
| WO | WO 2012/030664 A1 | 3/2012 |
| WO | WO 2012/080729 A2 | 6/2012 |
| WO | WO 2012/106343 A2 | 8/2012 |
| WO | WO 2012/148953 A1 | 11/2012 |
| WO | WO 2012/154888 A1 | 11/2012 |
| WO | WO 2012/158885 A1 | 11/2012 |
| WO | WO 2012/168930 A2 | 12/2012 |
| WO | WO 2012/171954 A1 | 12/2012 |
| WO | WO 2013/002484 A1 | 1/2013 |
| WO | WO 2013/052844 A1 | 4/2013 |
| WO | WO 2013/067410 A1 | 5/2013 |
| WO | WO 2013/070659 A1 | 5/2013 |
| WO | WO 2013/090833 A1 | 6/2013 |
| WO | WO 2013/092674 A1 | 6/2013 |
| WO | WO 2013/093812 A2 | 6/2013 |
| WO | WO 2013/130767 A1 | 9/2013 |
| WO | WO 2013/140319 A1 | 9/2013 |
| WO | WO 2013/151758 A2 | 10/2013 |
| WO | WO 2013/157018 A1 | 10/2013 |
| WO | WO 2013/163517 A2 | 10/2013 |
| WO | WO 2013/164204 A1 | 11/2013 |
| WO | WO 2013/175116 A1 | 11/2013 |
| WO | WO 2013/181530 A1 | 12/2013 |
| WO | WO 2013/182383 A1 | 12/2013 |
| WO | WO 2013/182389 A2 | 12/2013 |
| WO | WO 2013/185112 A1 | 12/2013 |
| WO | WO 2014/011050 A1 | 1/2014 |
| WO | WO 2014/011053 A1 | 1/2014 |
| WO | WO 2014/012360 A1 | 1/2014 |
| WO | WO 2014/012935 A1 | 1/2014 |
| WO | WO 2014/014841 A1 | 1/2014 |
| WO | WO 2014/018932 A2 | 1/2014 |
| WO | WO 2014/026959 A1 | 2/2014 |
| WO | WO 2014/040077 A1 | 3/2014 |
| WO | WO 2014/045283 A1 | 3/2014 |
| WO | WO 2014/058974 A1 | 4/2014 |
| WO | WO 2014/061016 A1 | 4/2014 |
| WO | WO 2014/078842 A1 | 5/2014 |
| WO | WO 2014/081820 A1 | 5/2014 |
| WO | WO 2014/081821 A2 | 5/2014 |
| WO | WO 2014/086934 A1 | 6/2014 |
| WO | WO 2014/099673 A1 | 6/2014 |
| WO | WO 2014/100620 A2 | 6/2014 |
| WO | WO 2014/118805 A1 | 8/2014 |
| WO | WO 2014/124527 A1 | 8/2014 |
| WO | WO 2014/125506 A2 | 8/2014 |
| WO | WO 2014/135096 A1 | 9/2014 |
| WO | WO 2014/141135 A1 | 9/2014 |
| WO | WO 2014/151386 A1 | 9/2014 |
| WO | WO 2014/160478 A1 | 10/2014 |
| WO | WO 2014/186704 A2 | 11/2014 |
| WO | WO 2014/210159 A1 | 12/2014 |
| WO | WO 2015/007516 A1 | 1/2015 |
| WO | WO 2015/007517 A1 | 1/2015 |
| WO | WO 2015/007519 A1 | 1/2015 |
| WO | WO 2015/011086 A1 | 1/2015 |
| WO | WO 2015/018831 A1 | 2/2015 |
| WO | WO 2015/036552 A1 | 3/2015 |
| WO | WO 2015/051241 A1 | 4/2015 |
| WO | WO 2015/051244 A1 | 4/2015 |
| WO | WO 2015/052237 A1 | 4/2015 |
| WO | WO 2015/061204 A1 | 4/2015 |
| WO | WO 2015/070336 A1 | 5/2015 |
| WO | WO 2015/081891 A1 | 6/2015 |
| WO | WO 2015/090232 A1 | 6/2015 |
| WO | WO 2015/100025 A1 | 7/2015 |

(56) References Cited

FOREIGN PATENT DOCUMENTS

| WO | WO 2015/120110 A2 | 8/2015 |
| WO | 2015/128882 * | 9/2015 |
| WO | WO 2015/128882 A2 | 9/2015 |
| WO | WO 2015/138909 A1 | 9/2015 |
| WO | WO 2015/138934 A1 | 9/2015 |
| WO | WO 2015/143012 A1 | 9/2015 |

OTHER PUBLICATIONS

Brown, R.K., et al., "Derivatives of Indole, 6-Amino-3-indoleacetic Acid," *JACS*, 1955, vol. 77, No. 14, pp. 3839-3842.

Dhar, T.G. M. et al., "3-Cyanoindole-based Inhibitors of Inosine Monophosphate Dehydrogenase: Synthesis and Initial Structure-Activity Relationships," *Bioorg. Med. Chem. Lett.*, 2003, vol. 13, No. 20, pp. 3557-3560.

Grohe, K. et al., "Synthese von 1-amino-4-chinolon-3-carbonsauren," *Liebigs Annalen Der Chemie*, 1987, vol. 10, pp. 871-879.

Haynes, R.K., et al., "Amine Oxidation and the Chemistry of Quinone !mines. Part I. 3-Methoxy-4-t-butylaniline," *J. Chem. Soc, Perkins Trans.*, 1972, vol. 1, pp. 396-408.

Heilbron, Isidor M., et al., "The Intermolecular Condensation of Acetylmethylanthranilic Acid by Means of Phosphorus Pentachloride and the Formation of a Complex isoCyanine Dye," *J. Chem. Soc.*, 1928, pp. 934-941.

Hennequin, Laurent F., et al., "Design and Structure-Activity Relationship of a New Class of Potent Vegf Receptor Tyrosine Kinase Inhibitors," *J. Med. Chem.*, 1999, vol. 42, No. 26, pp. 5369-5389.

Hester, J.B., et al., "Enzyme Inhibitory Activity of 3-(2-Aminobutyl)indole Derivatives," *J. Med. Chem.*, 1964, vol. 7, No. 3, pp. 274-279.

Imanishi, T., et al., "Evidence that a Hybrid Molecule of Norfloxacin and Biphenylacetic Acid is a Potent Antagonist at the Gabaa Receptor," *Neuropharmacology*, 1996, vol. 35, No. 9/10, pp. 1271-1277.

International Search Report and Written Opinion issued Jan. 11, 2016, in International Patent Application No. PCT/US2015/054565.

International Search Report and Written Opinion issued Jan. 11, 2016, in International Patent Application No. PCT/US2015/054577.

Irie, Kazuhiro, et al., "Synthesis of 6-Substituted Indolactams by Microbial Conversion," *Tetrahedron*, 1995, vol. 51, No. 22, pp. 6255-6266.

Ito, Y., et al., "Inhibition of GABA, Receptor Chloride Channel by Quinolones and Norfloxacin-Biphenylacetic Acid Hybrid Compounds," *Neuropharmacology*, 1996, vol. 35, No. 9/10, pp. 1263-1269.

Johnson, Herbert E., et al., "Reactions of Indole. Iv. The Synthesis of Some Aminoindoles," *J. Org. Chem.*, 1963, vol. 28, No. 10, pp. 2794-2797.

Kaminsky, Daniel, et al., "Quinolone Antibacterial Agents. Oxolinic Acid and Related Compounds," *J. Med. Chem.*, 1968, vol. 11, No. 1, pp. 160-163.

Kapranov, N. I. et al., "Cystic fibrosis: Recent Progress and Problems" *Medical Genetics*, 2004, vol. 3, No. 9, pp. 398-412, with English translation.

Kurata, Hitoshi, et al., "A novel class of apical sodium-dependent bile acid transporter inhibitors: the amphiphilic 4-oxo-l-phenyl-1,4-dihydroquinoline derivatives," *Bioorg. Med. Chem. Lett.*, 2004, vol. 14, pp. 1183-1186.

Ma, Tonghui, et al., "High-affinity Activators of Cystic Fibrosis Transmembrane Conductance Regulator (CFTR) Chloride Conductance Identified by High-Throughput Screening," *J. Biol. Chem.*, 2002, vol. 277, No. 40, pp. 37235-37241.

Mashkovskiy, M.D., "Medicaments. Manual for Doctors" vol. 1, 14th Edition. Moscow: LLC "Novaya Volna", 2001; p. 11.

Motherwell, W.D.S. et al. (2000) "Automated assignment of graph-set descriptors for crystallographically symmetric molecules" *Acta Cryst*, B56:466-473.

Noone, P.G. et al., "'CFTR-opathies': disease phenotypes associated with cycstic fibrosis transmembrane regulator gene mutations" *Respiratory Research*, 2001, vol. 2, No. 6, pp. 1-5.

Nosova, E.V., et al., "Synthesis of new fluorinated derivatives of Quinolinecarboxylic acids," *Chem. Of Heter. Compounds*, 2002, vol. 38, No. 8, pp. 922-928.

Pérez-Guille, B., et al., "Pharmacokinetics of a cephalone (CQ-M-EPCA) in rats after oral, intraduodenal and intravenous administration," *International J. Pharm.*, 2004, vol. 282, No. 1-2, pp. 87-94.

Sen, A.B., et al., "Synthesis of Substituted Dinitrophenyl Ketones, and Phenylacetic Acids. Part I.," *J. Indian Chem. Soc.*, 1947, vol. 24, pp. 268-270.

Sen, A.B., et al., "Synthesis of Substituted Dinitro Phenylketones and Phenylacetic Acids. Part III.," *J. Indian Chem. Soc.*, 1948, vol. 25, pp. 282-284.

Sen, A.B., et al., "Synthesis of Substituted Dinitrophenyl Ketones and Phenylacetic Acids. Part IV.," *J. Indian Chem. Soc.*, 1948, vol. 25, No. 8, pp. 403-404.

Showalter, H.D. Hollis, et al., "Concise Syntheses of the Novel 1H-Pyrrolo[3,2-g]guinazoline Ring System and its [2,3-f] Angular Isomer," *J. Org. Chem.*, 1996, vol. 61, No. 3, pp. 1155-1158.

Srivastava, Sanjay K., et al., "Quinolones: Novel Probes in Antifilarial Chemotheraphy," *J. Med. Chem.*, 2000, vol. 43, No. 11, pp. 2275-2279.

Tzetis, M. et al., "CFTR gene mutations—including three novel nucleotide substitutions—and haplotype background in patients with asthma, disseminated bronchiectasis and chronic obstructive pulmonary disease" *Hum. Genet.*, 2001, vol. 108, pp. 216-221.

Van Es, T. et al., "N,1-Dialkyl-7-(alkylamino)-4-(alkylimino)-1,4-dihydroguinoline-3-carboxamides and their 4-oxo derivatives: Synthesis and properties," *S. Afr. J. Chem.*, 2001, vol. 54, pp. 102-117.

Van Es, T., et al., "1-alkyl-1,4-dihydro-4-iminoguinoline-3-carboxylic acids: Synthesis, Structure, and Properties," *S. Afr. J. Chem.*, 2002, vol. 55, pp. 13-33.

Accurso, F. J. et al. (2009) "Final results of a 14- and 28-day study of VX-770 in subjects with CF" *J. Cystic Fibrosis*, vol. 8, Supplement 2, Abstracts of the 32nd European Cystic Fibrosis Conference, Jun. 10-13, 2009, Abstract 97, p. S25.

American College of Chest Physicians (2004) Living Well With COPD: Chronic Bronchitis and Emphysema. Patient Education Guide. Northbrook, IL, USA; Product Code: 5032, 44 pages.

Archimica (Oct. 2006) Coupling Agent ®T3P—The Water Scavenger. High-Performance Amide/Peptide Bond Formations, Dehydrations and Condensations. [online] Retrieved Apr. 11, 2011, from the Internet: http://www.archimica.com/Pdf/ARCHIMICA_T3P_Brochure.pdf> (20 pages).

Ashizawa, K. (2002) *Polymorphism and Crystallization of the Pharmaceutical Drugs*, pp. 273, 278, 305-317 (Japanese).

Aulton, M.E. (Ed.) (2002) *Pharmaceutics: The Science of Dosage Design*. 2nd Ed. Churchill Livingston; pp. 304-321.

Berge, S.M. et al. (1977) "Pharmaceutical Salts" *J Pharmac Sci*, 66(1):1-19.

Bombeiri, C. et al. (1988) "Complete mutational screening of the CFTR gene in 120 patients with pulmonary disease" *Human Genet*, 103:718-722.

Brittain, H. (2001 Jul) "X-ray Diffraction III: Pharmaceutical Applications of X-ray Powder Diffraction" *Spectroscopy*, 16(7):14-18.

Brittain, H.G. (Apr. 1997) "Spectral Methods for the Characterization of Polymorphs and Solvates" *J Pharm Sci*, 86(4):405-412.

Brown, R.K. et al. (1956) "Some Indole Derivatives Tested for Antitubercular Activity" *J Org Chem*, 21:261-262.

Burvall, K.M. et al. (2002) "The tyrosine kinase inhibitor genistein increases basal cAMP and potentiates forskolin-induced cAMP accumulation in A549 human airway epithelial cells" *Mol Cell Biol*, 240:131-133.

Byrn, S. et al. (1995) "Pharmaceutical Solids: a Strategic Approach to Regulatory Considerations" *Pharmaceutical Research*, 12(7):945-954.

Chemical Abstracts Service, 'Registry' File, RN 174311-74-1. STN Database [online]. Entry Date: Mar. 19, 1996, retrieved on Apr. 25, 2013.

(56) References Cited

OTHER PUBLICATIONS

Chemical Abstracts Service, 'Registry' File, RN 325779-54-2. STN Database [online]. Entry Date: Mar. 6, 2001, retrieved on Jan. 28, 2016.
Chemical Abstracts Service, 'Registry' File, RN 329691-97-6. STN Database [online]. Entry Date: Apr. 2, 2001, retrieved on Jan. 28, 2016.
Chemical Abstracts Service, 'Registry' File, RN 329691-99-8. STN Database [online]. Entry Date: Apr. 2, 2001, retrieved on Jan. 28, 2016.
Chemical Abstracts Service, 'Registry' File, RN 329692-01-5. STN Database [online]. Entry Date: Apr. 2, 2001, retrieved on Jan. 28, 2016.
Chemical Abstracts Service, 'Registry' File, RN 329692-03-7. STN Database [online]. Entry Date: Apr. 2, 2001, retrieved on Jan. 28, 2016.
Chemical Abstracts Service, 'Registry' File, RN 329692-05-9. STN Database [online]. Entry Date: Apr. 2, 2001, retrieved on Jan. 28, 2016.
Chemical Abstracts Service, 'Registry' File, RN 329692-14-0. STN Database [online]. Entry Date: Apr. 2, 2001, retrieved on Jan. 28, 2016.
Chemical Abstracts Service, 'Registry' File, RN 625115-91-5. STN Database [online]. Entry Date: Dec. 9, 2003, retrieved on Apr. 25, 2013.
Chemical Abstracts Service, 'Registry' File, RN 629662-49-3. STN Database [online]. Entry Date: Dec. 22, 2003, retrieved on Jul. 24, 2015.
Chemical Abstracts Service, 'Registry' File, RN 849644-14-0; STN Database SciFinder0 [online]. Entry Date: Nov. 2, 2004, retrieved on Mar. 25, 2014.
Cai, Z-W. et al. "Targeting F508del-CFTR to develop rational new therapies for cystic fibrosis" *Acta Pharmacologica Sinica*, 32(6):693-701.
Caira, M.R. (Jan. 1, 1998) "Crystalline Polymorphism of Organic Compounds" *Topics in Chemistry*, 198:163-208.
Carta, A. et al. (2003) "Synthesis and Biological Evaluation of Triazolo[4,5-g]Quinolines, Imidazo[4,5-g]Quinolines and Pyriodo[2,3-g]Quinoxalines. Part II" *Heterocycles*, 60(4):833-842.
Clemence, F. et al. (Jul. 1998) "4-Hydroxy-3-quinolinecarboxamides with antiarthritic and analgesic activities" *6J Med Chem*, 31(7):1453-1462.
Clunes, M.T. et al. (2008) "Front-runners for pharmacotherapeutic correction of the airway ion transport defect in cystic fibrosis" *Current Opinion in Pharmacology*, 8(3):292-299.
Collawn, J.F. et al. (2010) "Targets for cystic fibrosis therapy: proteomic analysis and correction of mutant cystic fibrosis transmembrane conductance regulator" *Expert Review of Proteomics*, 7(4):495-506.
Cuthbert, a.W. (2010) "New horizons in the treatment of cystic fibrosis" *Br J Pharmacol*, 163:173-183.
De Meeus, A. et al. (1998) "Genetic Findings in Congenital Bilateral Aplasia of Vas Deferens Patients and Identification of Six Novel Mutations" *Human Mutation, Mutation in Brief*, #138 [online]. DOI: 10.1002/(SICI)1098-1004(1998)11:6<480::AID-HUMU10>3.0.00;2-2, 10 pages. Final publication in vol. 11(6), p. 480.
Dif, F. et al. (2004) "Severe osteopenia in CFTR-null mice" *Bone*, 35:595-603.
Dohmori, R. et al. (1976) "Synthetic Chemotherapeutic Agents. I. Synthesis of 2-Substituted Thiazolo[5,4-lquinoline Derivatives" *Chem Pharm Bull*, 24:130-135.
Eckford, P.D.W. et al. (2012) "Cystic Fibrosis Transmembrane Conductance Regulator (CTR) Potentiator VX-770 (Ivacaftor) Opens the Defective Channel Gate of Mutant CFTR in a Phosphorylation-dependent but ATP-independent Manner" *J Biol Chem*, 287(44):36639-36649.
Erlinger, S. (2011) "Molecular repair of a defective CFTR protein in cystic fibrosis" *Clinics and Research in Hepatology and Gastroenterology*, 35:254-256.

Ferec, C. et al. (2012) "Assessing the Disease-Liability of Mutations in CFTR" *Cold Spring Harbor Perspect Med*, 2:a009480 (13 pages).
Flume, P. A. et al. (2012) "Ivacaftor in Subjects With Cystic Fibrosis Who Are Homozygous for the *F508del-CFTR Mutation*" *Chest*, 142:718-724.
Galietta, L.J.V. et al. (2001) "Novel CFTR Chloride Channel Activators Identified by Screening of Combinatorial Libraries Based on Flavone and Benzoquinolizinium Lead Compounds" *J Biol Chem*, 276(23):19723-19728.
Grant, D.J.W. (1999) "Theory and Origin of Polymorphism" in *Polymorphism in Pharmaceutical Solids*, H.G. Brittain, Ed.; Ch.1, pp. 1-10.
Guillory, J.K. (1999) "Generation of Polymorphs, Hydrates, Solvates, and Amorphous Solids" in *Polymorphism in Pharmaceutical Solids*. H.G. Brittain, Ed.; Ch.5, pp. 183-226.
Guo, J-H. (Jun. 2004) "Lactose in Pharmaceutical Applications" *Drug Delivery*, vol. 4, No. 5 (7 pages).
Hama, T. et al. (2003) "Palladium-Catalyzed α-Arylation of Esters and Amides under More Neutral Conditions" *J Am Chem Soc*, 125(37):11176-11177.
Hancock, B.C. et al. (2000) "What is the True Solubility Advantage for Amorphous Pharmaceuticals?" *Pharmaceutical Research*, 17(4):397-404.
*Handbook for Preparing Crystal of Organic Compound—Principle and Know-how*, Maruzen Co., Ltd.: Jul. 25, 2008, pp. 57-84 (Japanese).
Hansen, K.T. et al. (Aug. 1991) "Carbamate ester prodrugs of dopaminergic compounds: synthesis, stability, and bioconversion" *J Pharm Sci*, 80(8):793-798.
Hoffman, H.E. et al. (2005) "Allele-Specific Inhibitors of Protein Tyrosine Phosphatases" *J Am Chem Soc*, 127(9):2824-2825.
International Patent Application No. PCTUS2005/022768, filed Jun. 24, 2005, by Vertex Pharmaceuticals Incorporated: International Search Report and Written Opinion, mailed Jul. 25, 2006.
International Patent Application No. PCT/US2006/048810, filed Dec. 21, 2006, by Vertex Pharmaceuticals Incorporated: International Search Report and Written Opinion, dated Jul. 26, 2007.
International Patent Application No. PCT/US2006/048900, filed Dec. 21, 2006, by Vertex Pharmaceuticals Incorporated: International Search Report and Written Opinion, dated May 25, 2007.
International Patent Application No. PCT/US2006/049421, filed Dec. 28, 2006, by Vertex Pharmaceuticals, Inc.: International Search Report and Written Opinion, mailed Sep. 25, 2007.
International Patent Application No. PCT/US2007/068857, filed May 14, 2007, by Vertex Pharmaceuticals Incorporated: International Search Report and Written Opinion, mailed Sep. 9, 2008.
International Patent Application No. PCT/US2008/010728, filed Sep. 15, 2008, by Vertex Pharmaceuticals Incorporated: International Search Report and Written Opinion, dated Jul. 14, 2010.
International Patent Application No. PCT/US2009/004629, filed Aug. 13, 2009, by Vertex Pharmaceuticals Incorporated: International Search Report and Written Opinion, dated Mar. 24, 2011.
International Patent Application No. PCT/US2010/024609, filed Feb. 18, 2010, by Vertex Pharmaceuticals Incorporated: International Search Report and Written Opinion, dated Jun. 1, 2010.
International Patent Application No. PCT/US2010/028062, filed Mar. 19, 2010, by Vertex Pharmaceuticals Incorporated: International Search Report and Written Opinion, dated May 27, 2010.
International Patent Application No. PCT/US2010/028069, filed Mar. 19, 2010, by Vertex Pharmaceuticals Incorporated: International Search Report and Written Opinion, dated Aug. 25, 2010.
International Patent Application No. PCT/US2010/059920, filed Dec. 10, 2010, by Vertex Pharmaceuticals Incorporated: International Search Report and Written Opinion, dated Feb. 3, 2011.
International Patent Application No. PCT/US2011/029276, filed Mar. 21, 2011, by Vertex Pharmaceuticals Incorporated: International Search Report and Written Opinion, dated May 11, 2011.
International Patent Application No. PCT/US2011/033687, filed Apr. 22, 2011, by Vertex Pharmaceuticals Incorporated: International Search Report and Written Opinion, dated Aug. 30, 2011.

(56) References Cited

OTHER PUBLICATIONS

International Patent Application No. PCT/US2011/033689, filed Apr. 22, 2011, by Vertex Pharmaceuticals Incorporated: International Search Report and Written Opinion, dated Aug. 30, 2011.
International Patent Application No. PCT/US2011/033693, filed Apr. 22, 2011, by Vertex Pharmaceuticals Incorporated: International Search Report and Written Opinion, dated Aug. 30, 2011.
International Patent Application No. PCT/US2011/037457, filed May 20, 2011, by Vertex Pharmaceuticals Incorporated: International Search Report and Written Opinion, dated Jul. 13, 2011.
International Patent Application No. PCT/US2011/049467, filed Aug. 26, 2011, by Vertex Pharmaceuticals Incorporated: International Search Report and Written Opinion, dated Apr. 2, 2012.
International Patent Application No. PCT/US2012/034578, filed Apr. 20, 2012, by Vertex Pharmaceuticals Incorporated: International Search Report and Written Opinion, dated Mar. 21, 2013.
International Patent Application No. PCT/US2012/063398, filed Nov. 2, 2012, by Vertex Pharmaceuticals Incorporated: International Search Report and Written Opinion, mailed Jan. 23, 2013.
International Patent Application No. PCT/US2013/028097, filed Feb. 27, 2013, by Vertex Pharmaceuticals Incorporated: International Search Report and Written Opinion, dated May 10, 2013.
International Patent Application No. PCT/US2013/044838, filed Jun. 7, 2013, by Vertex Pharmaceuticals Incorporated: International Search Report and Written Opinion, dated Aug. 5, 2013.
Iskandarani, B. et al. (1993) "Simultaneous Optimization of Capsule and Tablet Formulation Using Response Surface Methodology" *Drug Dev Industrial Pharmacy*, 19(16):2089-2101.
Jivraj, M. et al. (Feb. 2000) "An overview of the different excipients useful for the direct compression of tablets" PSTT, 3(2):58-63.
Johannesson, J. et al. (Aug. 2012) "CFTR Regulates Early Pathogenesis of Chronic Obstructive Lung Disease in βENaC-Overexpressing Mice" *PLoS One*, 7(8):e44059 (11 pages).
Jones, A.M. And J.M. Helm (2009) "Emerging Treatments in Cystic Fibrosis" *Drugs*, 69(14):1903-1910.
Levine, M.H. et al. (2005) "CFTR-Regulated Chloride Transport at the Ocular Surface in Living Mice Measured by Potential Differences" *Invest Ophthal Vis Sci*, 46(4):1428-1434.
Loo, T.W. et al. (2011) "Corrector-mediated rescue of misprocessed CFTR mutants can be reduced by the P-glycoprotein drug pump" *Biochem Pharmacol*, 83(3):345-354.
Mall, M. et al. (2000) "Effect of genistein on native epithelial tissue from normal individuals and CF patients and on ion channels expressed in Xenopus oocytes" *Br J Pharmacol*, 130:1884-1892.
Mandour, A.H. et al. (1999) "Aminolysis and Hydrolysis of Indolyl Oxazolones" *Egyptian J Chem*, 42(3):251-266.
Marivingt-Mounir, C. et al. (Feb. 2004) "Synthesis, SAR, crystal structure, and biological evaluation of benzoquinoliziniums as activators of wild-type and mutant cystic fibrosis transmembrane conductance regulator channels" *J Med Chem*, 47(4):962-972.
Miles, E.W. And R.S. Phillips (1985) "Photoinactivation and photoaffinity labeling of tryptophan synthase a2i32 complex by the product analogue 6-azido-L-tryptophan" *Biochem*, 24(17):4694-4703.
Nishikawa, Y. et al. (1989) "Synthesis and Antiallergic Activity of N-[4-(4-Diphenylmethy1-1-piperazinyObutyl]-1,4-dihydro-4-oxopyridine-3-carboxamides" *Chem Pharm Bull*, 37(5):1256-1259.
Notice of Allowance and Fee(s) Due for U.S. Appl. No. 13/290,491, mailed Oct. 25, 2012, Examiner Raymond J. Henley III.
Notice of Allowance and Fee(s) Due for U.S. Appl. No. 13/871,349, mailed Apr. 17, 2015, Examiner Celia C. Chang.
Notice of Allowance and Fee(s) Due for U.S. Appl. No. 13/871,349, mailed Aug. 12, 2014, Examiner Celia C. Chang.
Notice of Allowance and Fee(s) Due for U.S. Appl. No. 13/871,349, mailed Oct. 13, 2015, Examiner Celia C. Chang.
Notice of Allowance and Fee(s) Due for U.S. Appl. No. 13/887,839, mailed Feb. 2, 2015, Examiner Kristin Ann Vajda.
Notice of Allowance and Fee(s) Due for U.S. Appl. No. 13/887,839, mailed Jul. 7, 2014, Examiner Kristin Ann Vajda.
Notice of Allowance and Fee(s) Due for U.S. Appl. No. 13/887,839, mailed Oct. 16, 2014, Examiner Kristin Ann Vajda.
Notice of Allowance and Fee(s) Due for U.S. Appl. No. 13/887,839, mailed Sep. 30, 2015, Examiner Kristin Ann Vajda.
Notice of Allowance and Fee(s) Due for U.S. Appl. No. 13/972,151, mailed May 16, 2016, Examiner S.J. Yoo.
Notice of Allowance and Fee(s) Due for U.S. Appl. No. 13/972,151, mailed Sep. 8, 2016, Examiner S.J. Yoo.
Notice of Allowance and Fee(s) Due for U.S. Appl. No. 14/031,360, mailed Aug. 14, 2014, Examiner Randeep Singh.
Notice of Allowance and Fee(s) Due for U.S. Appl. No. 14/298,245, mailed Jul. 21, 2015, Examiner D. Margaret M. Seaman.
Notice of Allowance and Fee(s) Due for U.S. Appl. No. 4/298,245, mailed Nov. 12, 2015, Examiner D. Margaret M. Seaman.
Notice of Allowance and Fee(s) Due for U.S. Appl. No. 14/326,930, mailed Aug. 14, 2015, Examiner Timothy R. Rozof.
Notice of Allowance and Fee(s) Due for U.S. Appl. No. 14/326,930, mailed Dec. 8, 2015, Examiner Timothy R. Rozof.
Notice of Allowance and Fee(s) Due for U.S. Appl. No. 14/334,902, mailed Feb. 18, 2016, Examiner Timothy R. Rozof.
Notice of Allowance and Fee(s) Due for U.S. Appl. No. 14/334,902, mailed Oct. 19, 2015, Examiner Timothy R. Rozof.
Notice of Allowance and Fee(s) Due for U.S. Appl. No. 14/532,791, mailed Jul. 24, 2015, Examiner Samantha L. Shterengarts.
Notice of Allowance and Fee(s) Due for U.S. Appl. No. 14/532,791, mailed Mar. 01, 2016, Examiner Samantha L. Shterengarts.
Notice of Allowance and Fee(s) Due for U.S. Appl. No. 14/532,791, mailed Nov. 6, 2015, Examiner Samantha L. Shterengarts.
Notice of Allowance and Fee(s) Due for U.S. Appl. No. 14/567,475, mailed Jan. 5, 2016, Examiner Shawquia Jackson.
Notice of Allowance and Fee(s) Due for U.S. Appl. No. 14/567,475, mailed Sep. 21, 2015, Examiner Shawquia Jackson.
Notice of Allowance and Fee(s) Due for U.S. Appl. No. 14/579,098, mailed Feb. 1, 2016, Examiner Shawquia Jackson.
Notice of Allowability for U.S. Appl. No. 14/579,098, mailed Apr. 18, 2016, Examiner Shawquia Jackson.
Notice of Allowance and Fee(s) Due for U.S. Appl. No. 14/579,098, mailed May 12, 2016, Examiner Shawquia Jackson.
Notice of Allowance and Fee(s) Due for U.S. Appl. No. 14/656,043, mailed Aug. 4, 2016, Examiner Kevin E. Weddington.
Notice of Allowance and Fee(s) Due for U.S. Appl. No. 14/687,286, mailed Feb. 10, 2016, Examiner Nyeemah A. Grazier.
Notice of Allowance and Fee(s) Due for U.S. Appl. No. 14/687,286, mailed May 19, 2016, Examiner Nyeemah A. Grazier.
Notice of Allowance and Fee(s) Due for U.S. Appl. No. 14/687,286, mailed Sep. 28, 2016, Examiner Nyeemah A. Grazier.
Notice of Allowance and Fee(s) Due for U.S. Appl. No. 14/877,914, mailed Jul. 27, 2016, Examiner D. Margaret M. Seaman.
Notice of Allowance and Fee(s) Due for U.S. Appl. No. 14/877,914, mailed Nov. 14, 2016, Examiner D. Margaret M. Seaman.
Notice of Allowance and Fee(s) Due for U.S. Appl. No. 14/925,804, mailed May 17, 2016, Celia C. Chang.
Notice of Allowance and Fee(s) Due for U.S. Appl. No. 15/073,591, mailed Sep. 28, 2016, Celia C. Chang.
Paranjape, S.M. et al. (2008) "Atypical Cystic fibrosis and Cftr-Related Diseases" *Clinic Rev Allerg Immunol*, 35(3):116-123.
Paritala, H. et al. (2009) "Benzo(h)quinoline derivatives as G-quadruplex binding agents" *Bioorg Med Chem Lett*, 19(8):1584-1587.
Pedemonte, N. et al. (2005) "Phenylglycine and sulfonamide correctors of defective ΔF508 and G551D cystic fibrosis transmembrane conductance regulator chloride-channel gating" *Molecular Pharmacology*, 67(5):1797-1807.
Pedemonte, N. et al. (2005) "Small-molecule correctors of defective ΔF508-CFTR cellular processing identified by high-throughput screening" *J Clin Invest*, 115(9):2564-2571.
Pencharz, P.D. And P.R. Durie (2000) "Pathogenesis of malnutrition in cystic fibrosis, and its treatment" *Clin Nutr*, 19(6):387-394.
Porst, H. and L. Kny (1985) "Zur Struktur der Abbauprodukte von Neostigminbromid (on the Structure of Degradation Products of Neostigmine bromide" *Pharmazie*, 40(5):325-328. German with English translation.

(56) References Cited

OTHER PUBLICATIONS

Pubchem Compound No. CID 29877; Database Record No. 19962-04-0; Create Date Jul. 19, 2005 [online]. Retrieved from: http://pubchem.ncbi.nlm.nih.gov/summary/summary.cgi?cid=29877; on Jan. 16, 2014 (4 pages).
Roberts, R.M. (1949) "The reaction of diarylformamidines with ethyl malonate" *J Org Chem*, 14(2):277-284.
Sashida, H. et al. (1990) "Studies of Seven Membered Heterocycles. XXXII. Synthesis of N-Unsubstituted 1H-1, 4-Benzodiazepines Stabilized by Intramolecular Hydrogen Bonding" *Chem Pharm Bull*, 38(11):2919-2925.
Settimj, G. et al. (1988) "β-Carbolines as agonistic or antagonistic benzodiazepine receptor ligands. 1. Synthesis of some 5-, 6- and 7-amino derivatives of 3-methoxycarbonyl-13-carboline ((β-CCM) and of 3-ethoxycarbonyl-13-carboline ((β-CCE)" *J Heterocyclic Chem*, 25(5):1391-1397.
Shead et al. (2007) "Cystic fibrosis transmembrane conductance regulator (CFTR) is expressed in human bone" Thorax, 62:650-651.
Shioji, Y. (Jan. 27, 2003) Manufacture Technology of Solid Preparation. CMC Publishing Co., Ltd.; pp. 9, 12, and 13 (Japanese).
Silverman, R.B. (1992) *The Organic Chemistry of Drug Design and Drug Action*. San Diego, CA: Academic Press; pp. 5-51.
Sloane, P.A. et al. (2010) "Translational readthrough of remature stop codons combined with CFTR potentiation: potential for combination CFTR therapy" *Pediatric Pulmonology*, 45(33):313, Abstract 264.
Sloane, P.A. et al. (2012) "A Pharmacologic Approach to Acquired Cystic Fibrosis Transmembrane Conductance Regulator Dysfunction in Smoking Related Lung Disease" *PLoS ONE*, 7(6):e39809 (13 pages).
Thomson, S.A. et al. (2009) "Minitablets: New Modality to Deliver Medicines to Preschool-Aged Children" *Pediatrics*, 123:e235 (6 pages).
Thomson Scientific, Database WPI, Accession No. 2001-425173; Week 200145.
Tissen, C. et al. (2011) "Development of mini-tablets with 1 mm and 2 mm diameter" *Int J Pharmaceutics*, 416:164-170.
Tonghui, M.A. et al. (2002) "High-affinity Activators of Cystic Fibrosis Transmembrane Conductance Regulator (CFTR) Chloride Conductance Identified by High-throughput Screening" *J Biol Chem*, 277(40):37235-37241.
Tsui, L-C. (1992) "Mutations and Sequence Variations Detected in the Cystic Fibrosis Transmembrane Conductance Regulator (CFTR) Gene: A Report From the Cystic Fibrosis Genetic Analysis Consortium" *Human Mutation*, 1:197-203.
U.S. Department of Health and Human Services, Food and Drug Administration (Dec. 2002) *Guidance for Industry. Food-Effect Bioavailability and Fed Bioequivalence Studies*. (9 pages).
U.S. Appl. No. 13/091,411, filed Apr. 21, 2011, by Tanoury et al.
U.S. Appl. No. 14/077,885, filed Nov. 12, 2013, by Sheth et al.
U.S. Appl. No. 14/870,592, filed Sep. 30, 2015, by Zha.
U.S. Appl. No. 14/877,860, filed Oct. 7, 2015, by Strohmeier et al.
U.S. Appl. No. 14/920,836, filed Oct. 22, 2015, by Rowe et al.
U.S. Appl. No. 14/935,777, filed Nov. 9, 2015, by Alargova et al.
U.S. Appl. No. 14/951,142, filed Nov. 24, 2015, by Dokou et al.
U.S. Appl. No. 14/982,973, filed Dec. 29, 2015, by Hadida Ruah et al.
U.S. Appl. No. 14/994,487, filed Jan. 13, 2016, by Hadida Ruah et al.
U.S. Appl. No. 14/996,781, filed Jan. 15, 2016, Van Goor et al.
U.S. Appl. No. 15/035,969, filed May 11, 2016, by Swinney et al.
U.S. Appl. No. 15/043,049, filed Feb. 12, 2016, by Binch et al.
U.S. Appl. No. 15/056,436, filed Feb. 29, 2016, by Zhang et al.
U.S. Appl. No. 15/064,222, filed Mar. 8, 2016, by Bhalchandra Ambhaikar et al.
U.S. Appl. No. 15/160,100, filed May 20, 2016, by Demattei et al.
U.S. Appl. No. 15/170,263, filed Jun. 1, 2016, by Hadida-Ruah et al.
U.S. Appl. No. 15/173,325, filed Jun. 3, 2016, by Hadida-Ruah et al.
U.S. Appl. No. 15/181,114, filed Jun. 13, 2016, by Dokou et al.
U.S. Appl. No. 15/234,877, filed Aug. 11, 2016, by Hadida-Ruah et al.
U.S. Appl. No. 15/253,636, filed Aug. 31, 2016, by Rowe et al.
U.S. Appl. No. 15/297,983, filed Oct. 19, 2016, by Hadida Ruah et al.
U.S. Appl. No. 15/342,999, filed Nov. 3, 2016, by Alargova et al.
Van Goor, F. et al. (2006) "Rescue of ΔF580-Cftr trafficking and gating in human cystic fibrosis airway primary cultures by small molecules" *Am J Physiol Lung Cell Mol Physiol*, 290(6):L1117-L1130.
Van Goor, F. et al. (2009) "Rescue of CF airway epithelial cell function in vitro by a CFTR potentiator, VX-770" J. Cystic Fibrosis, vol. 8, Supplement 2, Abstracts of the 32nd European Cystic Fibrosis Conference Jun. 10-13, 2009, Abstract 67, p. S17.
Van Goor, F. et al. (2009) "Rescue of CF airway epithelial cell function in vitro by a CFTR potentiator, VX-770" *PNAS*, 106(44):18825-18830.
Vertex Pharmaceuticals, Inc. (May 17, 2006) "Vertex Pharmaceuticals Initiates Phase I Development for VX-770 in Cystic Fibrosis" [online]. Retrieved from: http://files.shareholder.com/downloads/Vrtx/641260063x0x84745/fc8ddd6d-3713-48bb-b689-0444fc7ad623/VRTX_News_2006_5_17_General.pdf (2 pages).
Vertex Pharmaceuticals, Inc. (Aug. 5, 2009) "Study of VX-770 in Cystic Fibrosis Subjects Age 12 and Older Homozygous for the F508del-CFTR Mutation" [online]. Clinical Trials. gov, Identifier: NCT00953706. Retrieved from the Internet: http://clinicaltrials.gov/archive/NCT00953706/2009_08_05, on Jul. 10, 2013 (2 pages).
Vertex Pharmaceuticals, Inc. (Jul. 12, 2010) "Study of the Effect of VX-770 on Hyperpolarized Helium-3 Magnetic Resonance Imaging in Subjects With Cystic Fibrosis and the G551D Mutation" [online]. ClinicalTrials.gov, Identifier: NCT01161537. Retrieved from the Internet: http://clinicaltrials.gov/archive/NCT01262352/2010_12_16, on Jul. 9, 2013 (2 page).
Vertex Pharmaceuticals, Inc. (Oct. 31, 2011) "Study of VX-809 Alone and in Combination With VX-770 in Cystic Fibrosis (CF) Patients Homozygous or Heterozygous for the F508del-CFTR Mutation" [online]. ClinicalTrials.gov, Identifier: NCT01225211. Retrieved from the Internet: http://clinicaltrials.gov/archive/NCT01225211/2011_10_31, on Jul. 10, 2013 (2 pages).
Vertex Pharmaceuticals, Inc. (Jan. 2012) *KALYDECO® (ivacaftor) Tablets. Patient Information*. Reference ID: 3079771 (13 pages).
Vestner, a. et al. (2008) "Neue Therapieansatze bei Cystischer Fibrose (New Therapy Approaches in Cystic Fibrosis" *Pharmazie in unserer Zeit*, 37(5): 354-355. doi:10.1002/pauz.200890069, with English translation.
Wentland, M.P. et al. (1993) "Mammalian Topoisomerase II Inhibitory Activity of 1-Cyclopropyl-6,8-difluoro-1,4-dihydro-7-(2,6-dimethyl-4-pyridinyl)-4-oxo-3-guinolinecarboxylic Acid and Related Derivatives" *J. Med. Chem.*, 36:2801-2809.
Yu, H. et al. (2010) "VX-770, an investigational CFTR potentiator, acts on multiple CFTR forms in vitro" *Pediatric Pulmonology*, 45(33):318-319, Abstract 280.
Yu, H. et al. (2012) "Ivacaftor potentiation of multiple CFTR channels with gating mutations" *J Cystic Fibrosis*, 11(3):237-245.
Zeitlin, P.L. (2000) "Pharmacologic restoration of ΔF508 CFTR-mediated chloride current" *Kidney International*, 57:832-837.
Zubrick, J.W. (1988) *The Organic Chem Lab Survival Manual. A Student's Guide to Techniques*. New York: John Wiley & Sons, Inc.; 346 pages.

\* cited by examiner

XRPD pattern of Compound 1:Glyceryltrioctanoate

TGA trace of Compound 1:Glyceryltrioctanoate

DSC thermogram of Compound 1:Glyceryltrioctanoate

1H NMR Spectrum of Compound 1:Glyceryltrioctanoate 13C ssNMR spectrum of Compound 1:Glyceryltrioleate TGA trace of Compound 1:Glyceryltrioleate DSC thermogram of Compound 1:Glyceryltrioleate 1H NMR Spectrum of Compound 1:Glyceryltrioleate XRPD pattern of Compound 1:Glyceryltrilinoleate 13C ssNMR spectrum of Compound 1:Glyceryltrilinoleate TGA trace of Compound 1:Glyceryltrilinoleate DSC thermogram of Compound 1:Glyceryltrilinoleate 1H NMR Spectrum of Compound 1:Glyceryltrilinoleate XRPD Diffraction Patterns of Cocrystals of Compound 1 with glyceryltriacetate (triacetin)

¹³C ssNMR spectrum of Compound 1:triacetin

XRPD Diffraction Patterns of Cocrystals of Compound 1 with glyceryltributyrate

XRPD Diffraction Patterns of Cocrystals of Compound 1 with glyceryltristearate 13C ssNMR spectrum of Compound 1:Glyceryltristearate DSC thermogram of
Cocrystals of Compound 1 with glyceryltristearate XRPD Diffraction Patterns of Cocrystals of Compound 1 with glyceryltripalmitate 13C ssNMR spectrum of Compound 1:Glyceryltripalmitate DSC thermogram of
Cocrystals of Compound 1 with glyceryltripalmitate XRPD Diffraction Patterns of Cocrystals of Compound 1 with glyceryltridodecanoate 13C ssNMR spectrum of Compound 1:Glyceryltridodecanoate XRPD Diffraction Patterns of Cocrystals of Compound 1 with glyceryltrimyristate 13C ssNMR spectrum of Compound 1:Glyceryltrimyristate DSC thermogram of
Cocrystals of Compound 1 with glyceryltrimyristate XRPD Diffraction Patterns of Cocrystals of Compound 1 with glyceryltrihexanoate XRPD Diffraction Patterns of Cocrystals of Compound 1 with glyceryltridecanoate Comparison of Dissolution Profiles

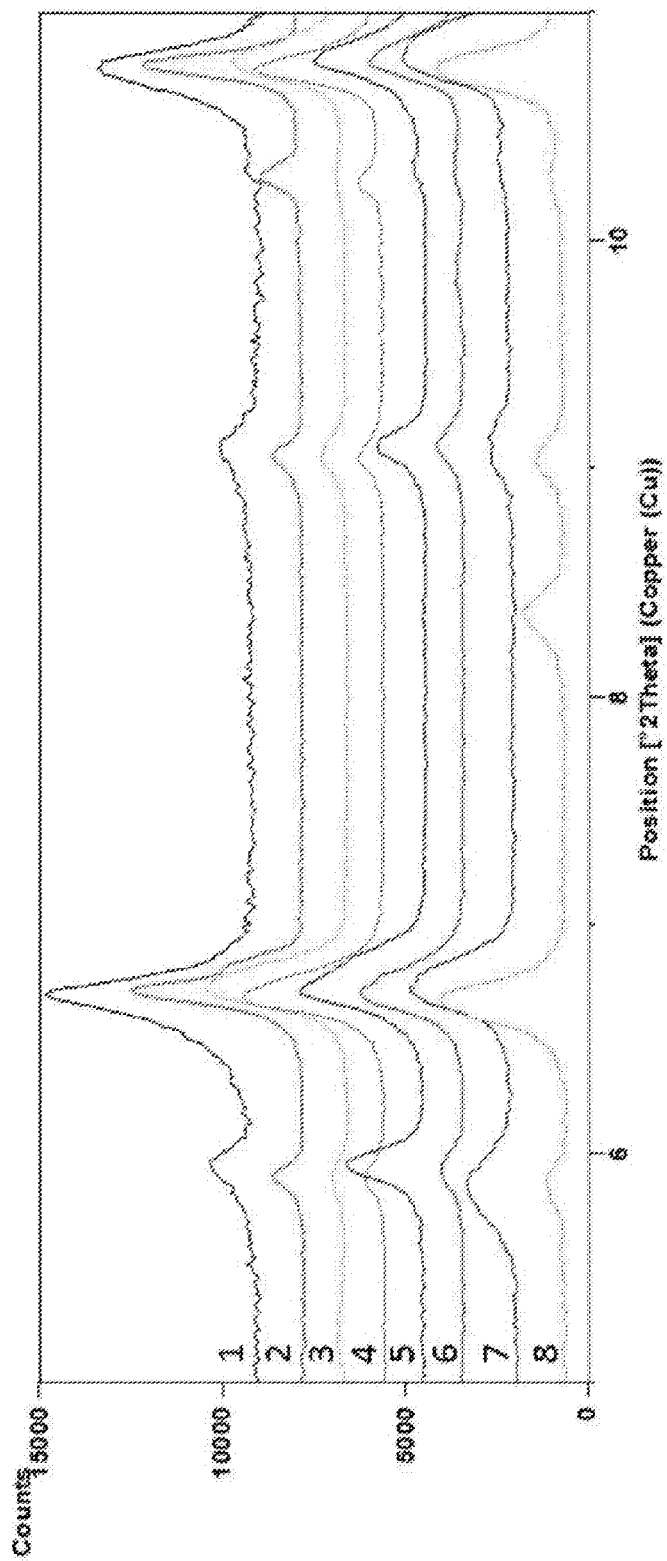

Figure 37

XRPD Diffraction Patterns of Cocrystals of Compound 1 with Different Triglycerides (1) Solid materials isolated the mixture of infant formula and Compound 1; (2) Compound 1:Glyceryltrilinoleate; (3) Compound 1:Glyceryltristearate; (4) Compound 1:Glyceryltrioleate; (5) Compound 1:Glyceryltrioctanoate; (6) Compound 1:Glyceryltridecanoate; (7) Compound 1:Glyceryltripalmitate; (8) Compound 1:Glyceryltridodecanoate

CO-CRYSTALS OF MODULATORS OF CYSTIC FIBROSIS TRANSMEMBRANE CONDUCTANCE REGULATOR

This application claims priority to U.S. provisional application No. 62/060,828, filed on Oct. 7, 2014, which is herein incorporated by reference in its entirety.

TECHNICAL FIELD

The present disclosure generally relates to co-crystals of N-[2,4-bis(1,1-dimethylethyl)-5-hydroxyphenyl]-1,4-dihydro-4-oxoquinoline-3-carboxamide (Compound 1), pharmaceutical compositions thereof, and methods therewith.

BACKGROUND

Cystic fibrosis (CF) is a recessive genetic disease that affects approximately 30,000 children and adults in the United States and approximately 30,000 children and adults in Europe. Despite progress in the treatment of CF, there is no cure.

CF is caused by mutations in the cystic fibrosis transmembrane conductance regulator (CFTR) gene that encodes an epithelial chloride ion channel responsible for aiding in the regulation of salt and water absorption and secretion in various tissues. Small molecule drugs known as potentiators that increase the probability of CFTR channel opening represent one potential therapeutic strategy to treat CF. Potentiators of this type are disclosed in WO 2006/002421, which is herein incorporated by reference in its entirety. Another potential therapeutic strategy involves small molecule drugs known as CF correctors that increase the number and function of CFTR channels. Correctors of this type are disclosed in WO 2005/075435, which is herein incorporated by reference in its entirety.

Specifically, CFTR is a cAMP/ATP-mediated anion channel that is expressed in a variety of cell types, including absorptive and secretory epithelial cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, greater than 1000 disease causing mutations in the CF gene have been identified (http://www.genet.sickkids.on.ca/cftr/app). The most prevalent mutation is a deletion of phenylalanine at position 508 of the CFTR amino acid sequence, and is commonly referred to as ΔF508-CFTR. This mutation occurs in approximately 70% of cystic fibrosis cases and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel (ENaC), $Na^+/2Cl^-/K^+$ co-transporter, $Na^+$—$K^+$-ATPase pump and the basolateral membrane $K^+$ channels that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and $Cl^-$ ion channels expressed on the basolateral surface of the cell. Secondary active transport of chloride from the luminal side leads to the accumulation of intracellular chloride, which can then passively leave the cell via channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease but for a wide range of other isolated and inherited diseases.

N-[2,4-bis(1,1-dimethylethyl)-5-hydroxyphenyl]-1,4-dihydro-4-oxoquinoline-3-carboxamide (Compound 1) is a potent and selective CF FR potentiator of wild-type and mutant (including, but not limited to, e.g., ΔF508 R117H CFTR, G551D CFTR, G178R CFTR, S549N CFTR, S549R CFTR, G551S CFTR, G970R CFTR, G1244E CFTR, S1251N CFTR, S1255P CFTR, and G1349D CFTR) forms of human CFTR. N-[2,4-bis(1,1-dimethylethyl)-5-hydroxyphenyl]-1,4-dihydro-4-oxoquinoline-3-carboxamide is useful for treatment of patients age 6 years and older with cystic fibrosis and one of the following mutations in the CFTR gene: G551D CFTR, G1244E CFTR, G1349D CFTR, G178R CFTR, G551S CFTR, S1251N CFTR, S1255P CFTR, S549N CFTR, S549R CFTR, or R117H CFTR Accordingly, stable bioavailable forms of Compound 1 that can be manufactured easily, including co-crystals comprising N-[2,4-bis(1,1-dimethylethyl)-5-hydroxyphenyl]-1, 4-dihydro-4-oxoquinoline-3-carboxamide, and pharmaceutical compositions thereof, may be useful for developing products and/or methods for treating patients suffering from CF thereof.

In one aspect, the disclosure provides a co-crystal comprising Compound 1 and a co-former, wherein Compound 1 is represented by the following formula:

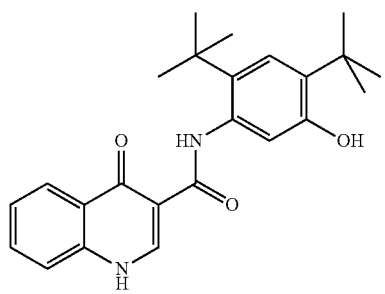 [SMILES: CC(C)(C)c1cc(C(C)(C)C)c(NC(=O)c2c[nH]c3ccccc3c2=O)cc1O]

and the co-former is chosen from the following structural formula:

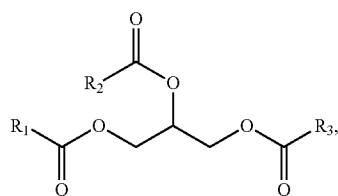

wherein $R_1$, $R_2$, and $R_3$ are independently $C_{1-29}$ aliphatic.

In some embodiments, the co-crystal is isolated.

In some embodiments, in the co-crystal, the stoichiometry of Compound 1 to the co-former ranges from 2 to 1 to 6 to 1.

In some embodiments, the stoichiometry of Compound 1 to the co-former in the co-crystal is 6 to 1.

In some embodiments, the stoichiometry of Compound 1 to the co-former in the co-crystal is about 6 to about 1.

In some embodiments, the stoichiometry of Compound 1 to the co-former in the co-crystal is 3 to 1.

In some embodiments, the stoichiometry of Compound 1 to the co-former in the co-crystal is about 3 to about 1.

In some embodiments, Compound 1 may form hexameric supermolecules (hexamers) in the co-crystal, wherein each of the hexamers contains six molecules of Compound 1 bound by hydrogen bonds as shown in FIG. 1.

In some embodiments, the co-crystals are capable of yielding a concentration of Compound 1 of greater than 0.4 mg/mL when dissolved in simulated intestinal fluid in fed state (FeSSIF).

In some embodiments, the co-crystals are capable of yielding a concentration of Compound 1 of greater than 0.4 mg/mL when dissolved in simulated intestinal fluid in fed state (FeSSIF) and the concentration is maintained for at least 10 hours.

In some embodiments, the co-crystals are characterized as having an X-ray powder diffraction pattern with characteristic peaks expressed in 2-theta±0.2 degrees at the following positions: 3.5, 6.9, and 10.9.

In yet some embodiments, the co-crystals are characterized as having a $^{13}C$ ssNMR spectrum with characteristic peaks expressed in ppm±0.1 at the following positions: 178.6, 155.0, and 119.4.

In yet some other embodiments, the co-crystals are characterized as having a $^{13}C$ ssNMR spectrum with characteristic peaks expressed in ppm±0.1 at the following positions: 178.6, 155.0, 130.5, and 119.4.

Another aspect of the present disclosure provides for pharmaceutical compositions comprising a therapeutic effective amount of Compound 1 and a pharmaceutically acceptable carrier or excipient, wherein at least 30% of Compound 1 is present in the form of co-crystals disclosed herein.

In some embodiments, the pharmaceutical composition further comprises an additional therapeutic agent.

For example, in one embodiment, the additional therapeutic agent is selected from a mucolytic agent, a bronchodilator, an antibiotic, an anti-infective agent, an anti-inflammatory agent, a CFTR modulator other than Compound 1, or a nutritional agent, or combinations thereof. In another embodiment, the additional therapeutic agent is a CFTR modulator other than Compound 1.

Further as an example, in one embodiment, the CFTR modulator is (3-(6-(1-(2,2-difluorobenzo[d][1,3]dioxol-5-yl)cyclopropanecarboxamido)-3-methylpyridin-2-yl)benzoic acid or (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide.

In another aspect, the present disclosure provides for a method treating or lessening the severity of a disease in a patient, wherein said disease is selected from cystic fibrosis, hereditary emphysema, COPD, or dry-eye disease, the method comprising the step of administering to the patient an effective amount of any of the co-crystals presented herein. For example, in one embodiment, the disease is cystic fibrosis.

In some embodiments, the method further comprises co-administering one or more additional therapeutic agents to the subject. For example, in one embodiment, the additional therapeutic agent is (3-(6-(1-(2,2-difluorobenzo[d][1,3]dioxol-5-yl)cyclopropanecarboxamido)-3-methylpyridin-2-yl)benzoic acid or (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In another embodiment, the additional therapeutic agent is administered concurrently with, prior to, or subsequent to the co-crystal.

Another aspect of the present disclosure provides for a method of preparing a co-crystal comprising Compound 1 and a co-former, wherein Compound 1 is represented by the following structural formula:

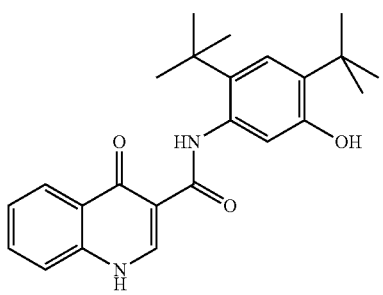 [SMILES: CC(C)(C)c1cc(C(C)(C)C)c(NC(=O)c2c[nH]c3ccccc3c2=O)cc1O]

the co-former is chosen from the following structural formula:

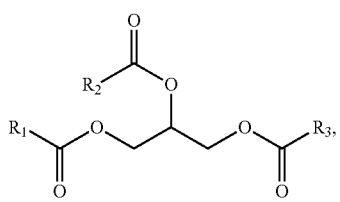

wherein $R_1$, $R_2$, and $R_3$ are independently $C_{1-29}$ aliphatic comprising the step of:
combining Compound 1 and the co-former to form the co-crystal.

One aspect of the present disclosure provides for a method of preparing a co-crystal comprising Compound 1 and a co-former, wherein Compound 1 is represented by the following structural formula:

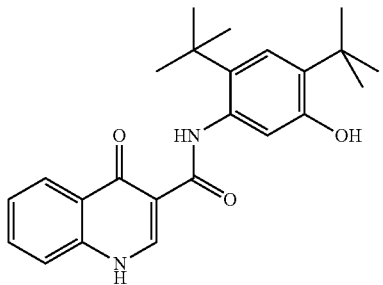 [SMILES: CC(C)(C)c1cc(C(C)(C)C)c(NC(=O)c2c[nH]c3ccccc3c2=O)cc1O]

the co-former is chosen from the following structural formula:

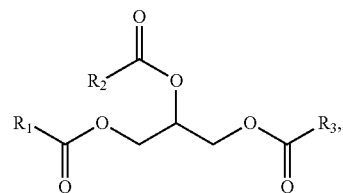

wherein $R_1$, $R_2$, and $R_3$ are independently $C_{1-29}$ aliphatic.

Another aspect of the present disclosure provides for a method of preparing co-crystals comprising Compound 1 and a co-former, wherein Compound 1 is represented by the following structural formula:

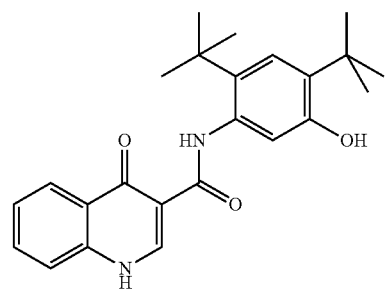 [SMILES: CC(C)(C)c1cc(C(C)(C)C)c(NC(=O)c2c[nH]c3ccccc3c2=O)cc1O]

the co-former is chosen from the following structural formula:

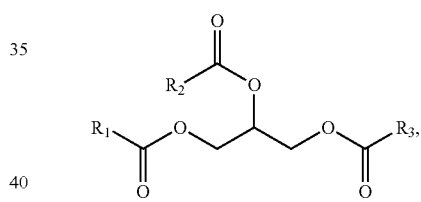

wherein $R_1$, $R_2$, and $R_3$ are independently $C_{1-29}$ aliphatic. comprising the steps of:
(a) preparing a mixture comprising Compound 1 and the co-former; and
(b) heating the mixture to 80° C.

Further another aspect of the present disclosure provides for a method of preparing co-crystals comprising Compound 1 and a co-former, wherein Compound 1 is represented by the following structural formula:

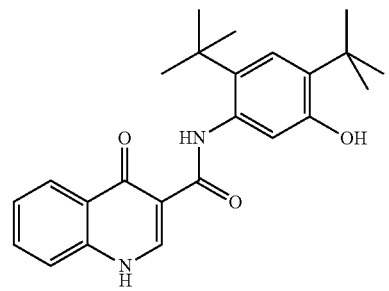

the co-former is chosen from the following structural formula:

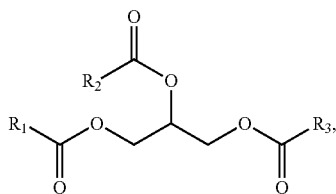

wherein $R_1$, $R_2$, and $R_3$ are independently $C_{1-29}$ aliphatic, comprising the steps of:

(a) preparing a mixture comprising Compound 1 and the co-former; and (b) heating the mixture to a temperature that is about 5 to 10° C. higher than the melting point of the co-former.

One aspect of the present disclosure provides for a method of preparing co-crystals comprising Compound 1 and a co-former, wherein Compound 1 is represented by the following structural formula:

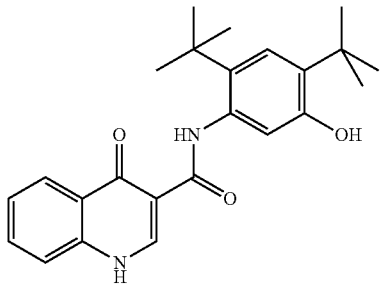

the co-former is chosen from the following structural formula:

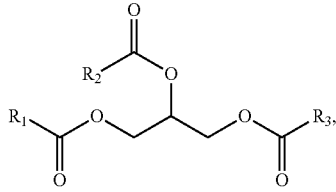

wherein $R_1$, $R_2$, and $R_3$ are independently $C_{1-29}$ aliphatic; comprising the steps of:

(a) preparing a mixture comprising Compound 1 and the co-former;

(b) heating the mixture;

(c) cooling down the mixture; and (d) repeating step (b) and (c).

Another aspect of the present disclosure provides for a method of preparing a co-crystal comprising Compound 1 and a co-former, wherein Compound 1 is represented by the following structural formula:

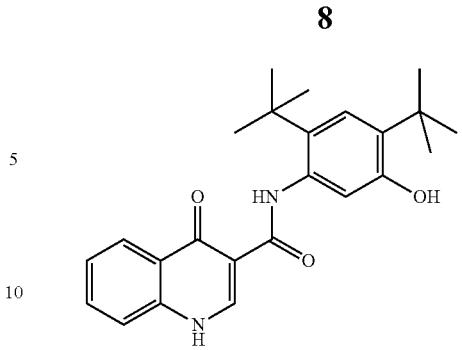

the co-former is chosen from the following structural formula:

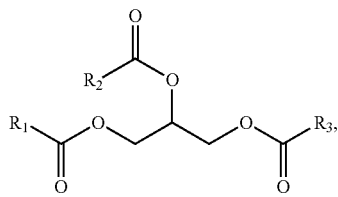

wherein $R_1$, $R_2$, and $R_3$ are independently $C_{1-29}$ aliphatic, comprising the steps of:

(a) preparing a mixture comprising Compound 1 and the co-former;

(b) heating the mixture to 80° C.;

(c) cooling the mixture down to 40° C.; and (d) repeating step (b) and (c).

In some embodiments, the mixture comprising Compound 1 and the co-former is heated for 12 hours. In other embodiments, the mixture comprising Compound 1 and the co-former is heated for at least 12 hours. In some embodiments, the mixture comprising Compound 1 and the co-former is heated for 24 hours. In other embodiments, the mixture comprising Compound 1 and the co-former is heated for at least 24 hours.

In some embodiments, co-crystals disclosed herein, such as Compound 1:triglyceride co-crystals, may exhibit several advantages. For example, Compound 1:triglyceride co-crystals may show a better maintenance of the supersaturation than both the neat amorphous and solid amorphous dispersed form of Compound 1 (Compound 1 SDD) over longer time periods. Further as an example, in-vivo the Compound 1:triglyceride co-crystals may be metabolized in the small intestine by lipid esterase (lipases), which would effectively remove the triglycerides and further boost the Compound 1 concentration according to Le-Chatelier's principle.

In some embodiments, co-crystals disclosed herein, such as Compound 1:triglyceride co-crystals, may have the following advantages over the solid amorphous dispersed form (Compound 1 SDD) of Compound 1: (1) the co-crystals may be formulated, stored, and used under conditions where they are thermodynamically stable; (2) a controlled crystallization may be developed that can reduces potential impurity levels (impurities include, but are not limited to, solvent); (3) a manufacturing process may be developed that is more efficient and cost effective (for example, less solvent can be used in manufacturing and a lower cost process than spray drying can be developed); and (4) a stabilizing polymer may not be required for formulating co-crystals.

BRIEF DESCRIPTION OF THE DRAWINGS

FIG. 1 (left) shows a hexamer (six molecules of Compound 1) which are present in a Compound 1:triglyceride co-crystal. FIG. 1 (right) shows a hexamer made of two trimers (A and B) each formed by three molecules of Compound 1 (trimer A: A1, A2, and A3; and trimer B: B1, B2, and B3).

FIG. 2 (left) shows a trimer A of compound 1 and the hydrogen bonds that may be present between the molecules of Compound 1 (A1, A2, and A3) within a trimer [R3,3(18)>b>b>b]. FIG. 2 (right) depicts hydrogen bonds that may be present within a molecule of compound 1 [S1,1(6)a], and hydrogen bonds that may be present in between two molecules of compound 1 from two trimers (A and B) [R2,2 (20)>c>c]. Trimers A and B form a hexamer.

FIG. 37 is an examplary XRPD diffraction patterns of cocrystals of Compound 1 with different pure triglycerides and cocrytals isolated from mixture of infant formula and Compound.

DETAILED DESCRIPTION OF THE EMBODIMENTS

Definitions

Figure 1:
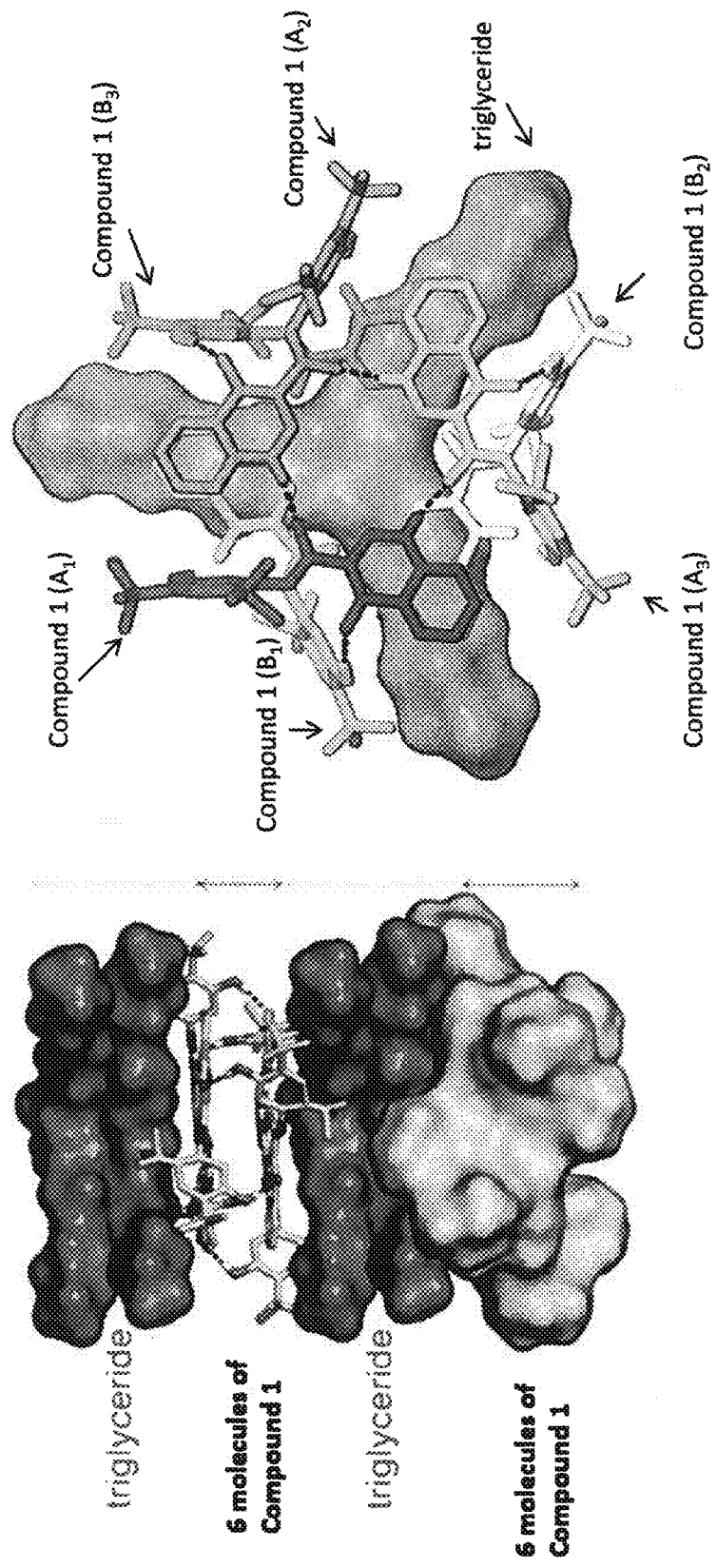
FIG. 1 shows structural features of the Compound 1:triglyceride co-crystal in some embodiments.

As used herein, the following definitions shall apply unless otherwise indicated.

As used herein, "a", "an", and "at least one" each means "one or more than one."

The term "ABC-transporter" as used herein means an ABC-transporter protein or a fragment thereof comprising a binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

As used herein, "CFTR" stands for cystic fibrosis transmembrane conductance regulator.

As used herein, "mutations" can refer to mutations in the CFTR gene or the CFTR protein. A "CFTR mutation" refers to a mutation in the CFTR gene, and a "CFTR mutation" refers to a mutation in the CFTR protein. A genetic defect or mutation, or a change in the nucleotides in a gene in general results in a mutation in the CHR protein translated from that gene. Genetic defects or mutations include, but are not limited to, ΔF508 CFTR, R117H CFTR, G551D CFTR, G178R CFTR, S549N CFTR, S549R CFTR, G551 S CFTR, G970R CFTR, G1244E CFTR, S1251N CFTR, S1255P CFTR, and G1349D R or ΔF508 CFTR, R117H CFTR, G551D CFTR, G178R CFTR, S549N CFTR, S549R CFTR, G551S CFTR, G970R CFTR, G1244E CFTR, S1251N CFTR, S1255P CFTR, and G1349D CFTR (see, e.g., http://www.genet.sickkids.on.ca/app for CFTR mutations).

As used herein, a "ΔF508 mutation" or "F508del mutation" is a specific mutation within the CFTR protein. The mutation is a deletion of the three nucleotides that comprise the codon for amino acid phenylalanine at position 508, resulting in CFTR protein that lacks this phenylalanine residue. The mutated CFTR protein is commonly referred to as "F508del."

The term "CFTR gating mutation" as used herein means a CFTR mutation that results in the production of a CFTR protein for which the predominant defect is a low channel open probability compared to normal CFTR (Van Goor, F., Hadida S. and Grootenhuis P., "Pharmacological Rescue of Mutant CFTR function for the Treatment of Cystic Fibrosis", Top. Med. Chem. 3: 91-120 (2008)). Gating mutations include, but are not limited to, G551D, G178R, S549N, S549R, G551S, G970R, G1244E, S1251N, S1255P, and G1349D.

As used herein, a patient who is "homozygous" for a particular mutation, e.g. F508del, has the same mutation on each allele.

As used herein, a patient who is "heterozygous" for a particular mutation, e.g. F508del, has this mutation on one allele and a different mutation on the other allele.

As used herein, the term "modulator" refers to a compound that increases the activity of a compound such as a protein. For example, a CFTR modulator is a compound that increases the activity of CFTR. The increase in activity resulting from a CFTR modulator may be through a corrector mechanism, a potentiator mechanism, or through a dual corrector and potentiator mechanism.

As used herein, the term "CFTR corrector" refers to a compound that increases the amount of functional CFTR protein to the cell surface, resulting in enhanced ion transport.

As used herein, the term "CFTR potentiator" refers to a compound that increases the channel activity of CFTR protein located at the cell surface, resulting in enhanced ion transport.

The term "crystalline" refers to solid materials comprising atoms, molecules, and/or ions arranged in ordered geometric patterns or lattices. Crystalline solids show definite melting points and have rigid long range order.

The term "co-crystal" as used herein means a crystalline entity containing at least two molecules in either stoichiometric or nonstoichiometric ratio. The co-crystal may optionally further contain ions.

The co-crystals typically comprise an active pharmaceutical ingredient (API) and a co-former. The co-former typically may be hydrogen-bonded directly to the API or may be hydrogen-bonded to an additional molecule that is bound to the API. Other modes of molecular recognition may also be present including, pi-stacking, guest-host complexation and van der Waals interactions.

As used herein, the term "co-former", or alternatively "co-crystal former," refers to a molecule such as a triglyceride in a co-crystal other than an API. The co-former may or may not undergo any changes after forming co-crystal with an API.

"Compound 1:triglyceride" refers to co-crystals comprising Compound 1 and a triglyceride. For example, "Compound 1:glyceryltrioctanoate" is used herein to refer to co-crystals comprising Compound 1 and glyceryltrioctanoate. "Compound 1:glyceryltrioleate" is used herein to refer to co-crystals comprising Compound 1 and glyceryltrioleate. "Compound 1:glyceryltrilinoleate" is used herein to refer to co-crystals comprising Compound 1 and glyceryltrilinoleate.

As used herein, the term "active pharmaceutical ingredient" or "API" refers to a biologically active compound.

The term "pure" as used herein means chemically pure or free from impurities detectable by routine chemical analysis, for example by HPLC.

"Substantially pure" as used herein means at least 70%, 75%, 80%, 85%, 90%, 95%, 97%, 98%, or 99% purity of the target material within a mixture.

As used herein, the term "isolated," as in an isolated co-crystal, refers to a co-crystal that is separated away from other materials, such as other crystalline materials that may be distinguished from the target co-crystal through routine analysis such as XRPD. In some embodiments, the co-crystals may be isolated or separated from other materials by filtration or centrifugation. In some embodiments, an isolated co-crystal may be at least 50% pure. In some embodiments, the isolated co-crystal may contain impurities such as, as non-limiting examples, residual co-former, solvent, or other materials presented in the medium in which the co-crystal was produced, which may be difficult to be removed from the co-crystal. In other embodiments, an isolated co-crystal may be substantially pure.

As used herein, the term "aliphatic" encompasses substituted or unsubstituted alkyl, alkenyl, and alkynyl groups. An "alkyl" group refers to a saturated aliphatic hydrocarbon group containing 1-29 carbon atoms. An alkyl group can be straight or branched. As used herein, an "alkenyl" group refers to an aliphatic carbon group that contains 2-29 carbon atoms and a double bond. Like an alkyl group, an alkenyl group can be straight or branched. As used herein, an "alkynyl" group refers to an aliphatic carbon group that contains 2-29 carbon atoms and has a triple bond. An alkynyl group can be straight or branched.

As used herein, the term "inducing," as in inducing CFTR activity, refers to increasing CFTR activity, whether by the corrector, potentiator, or other mechanism.

The term "modulating" as used herein means increasing or decreasing, e.g., activity, by a measurable amount.

The term "reduced CFTR" or "reduced CFTR function" as used herein means less than normal CFTR or less than normal CFTR function.

A "patient," "subject" or "individual" are used interchangeably and refer to either a human or non-human animal. The term includes mammals such as humans.

The terms "effective dose" or "effective amount" are used interchangeably herein and refer to that amount that produces the desired effect for which it is administered (e.g., improvement in CF or a symptom of CF or lessening the severity of CF or a symptom of CF). The exact amount will depend on the purpose of the treatment, and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement of CF or its symptoms or lessening the severity of CF or its symptoms in a subject. "Treatment," as used herein, includes, but is not limited to, the following: increased growth of the subject, increased weight gain, reduction of mucus in the lungs, improved pancreatic and/or liver function, reduced incidences of chest infections, and/or reduced instances of coughing or shortness of breath. Improvements in or lessening the severity of any of these conditions can be readily assessed according to standard methods and techniques known in the art.

As used herein, the term "in combination with" when referring to two or more compounds or agents means that the order of administration includes the compounds or agents being administered prior to, concurrent with, or subsequent to each other to the patient.

Co-Crystals

The present disclosure provides co-crystals comprising N-[2,4-bis(1,1-dimethylethyl)-5-hydroxyphenyl]-1,4-dihydro-4-oxoquinoline-3-carboxamide (Compound 1) having the structural formula:

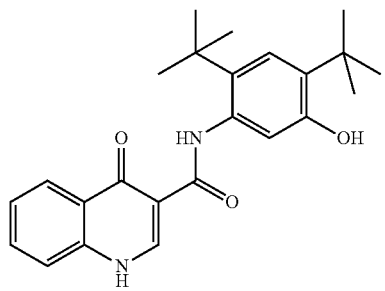 [SMILES: CC(C)(C)c1cc(C(C)(C)C)c(NC(=O)c2c[nH]c3ccccc3c2=O)cc1O]

Compound 1

Compound 1 is described in International PCT publication WO2006002421 and has the molecular formula of C24H28N2O3.

In one aspect, the present disclosure provides a co-crystal comprising Compound 1 and a co-former, wherein the co-former is chosen from the following structural formula:

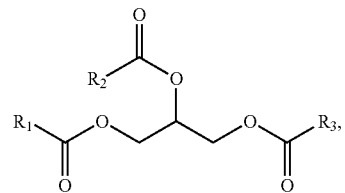

wherein $R_1$, $R_2$, and $R_3$ are independently $C_{1-29}$ aliphatic.

In some embodiments, the co-crystal is isolated.

In some embodiments, R1, R2, and R3 are independently C7-29 aliphatic.

In some embodiments, the co-former has an average molecular weight ranging from 470 to 1400 Da.

In some embodiments, the co-former is chosen from glyceryltrioleate, glyceryltristearate, glyceryltrihexanoate, glyceryltridecanoate, glyceryltrioctanoate, glyceryltrimyristate, glyceryltripalmitate, glyceryltributyrate, glyceryltrilinoleate, glyceryltridodecanoate, glyceryltripalmitoleate, glyceryltrierucate, glyceryltripropionate, palmitodiolein, triarachidonin, glyceryl trilinolenate, trierucin, glycerol triarachidate, glyceryl tri(cis-13-docosenoate), glyceryl tripetroselinate, glyceryl tribehenate, glyceryl trielaidate, glyceryltriacetate (triacetin), glyceryltributyrate.

In some embodiments, the co-former is chosen from:

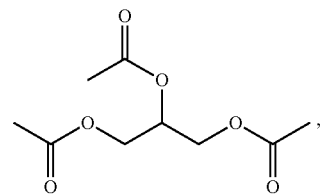

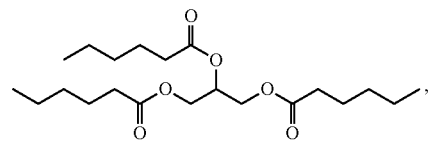

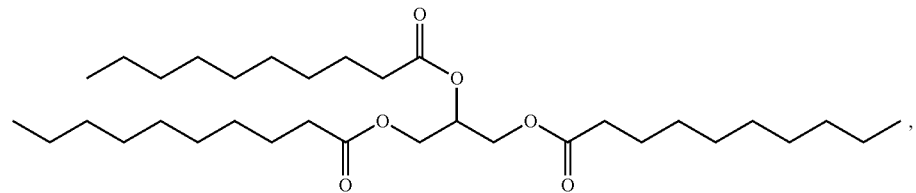

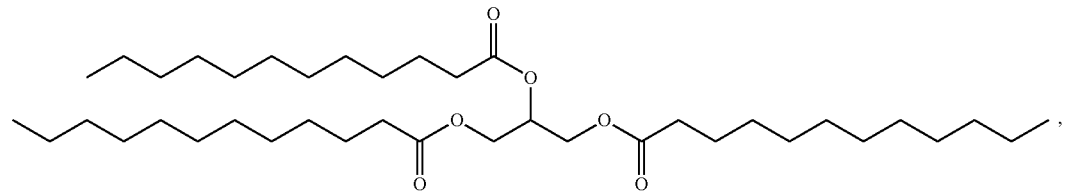

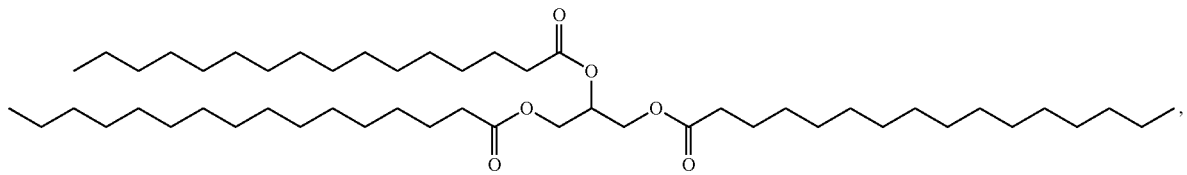

-continued

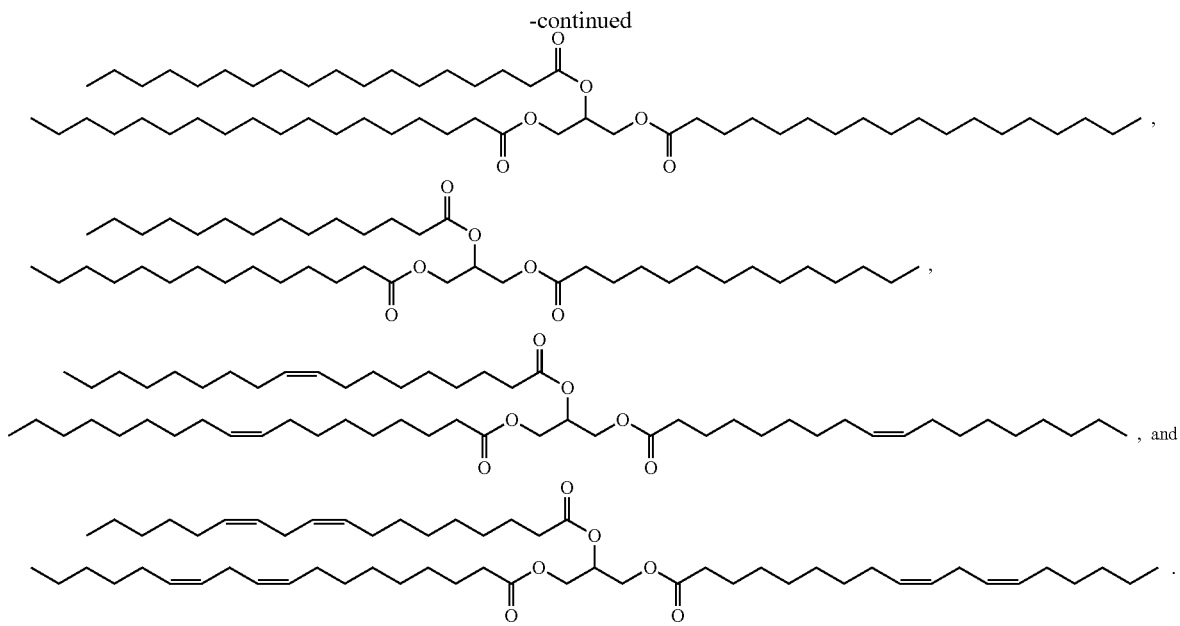

, and

In some embodiments, the co-former is chosen from: glyceryltrioleate, glyceryltristearate, glyceryltrihexanoate, glyceryltridecanoate, glyceroltrioctanoate, glyceryltrimyristate, glyceryltripalmitate, glyceryltrilinoleate, glyceryltridodecanoate, glyceryltripalmitoleate, glyceroltrierucate, palmitodiolein, triarachidonin, glyceryl trilinolenate, trierucin, glycerol triarachidate, glyceryl tri(cis-13-docosenoate), glyceryl tripetroselinate, glyceryl tribehenate, and glyceryl trielaidate.

In some embodiments, the co-former is chosen from glyceryltrioctanoate, glyceryltrioleate, glyceryltrilinoleate, glyceryltrihexanoate, glyeryltristearate, glyceryltridecanoate, glycerltripalmitate, glyceryltrimyristate, glyceryltripalmitate, glyceryltristearate, and glyceryltridodecanoate.

In some embodiments, the co-former is chosen from glyceryltriacetate and glyceryltributyrate.

In some embodiments, only one co-former is present in the co-crystal. As non-limiting examples, the co-crystal of Compound 1 comprises only glyceryltrioctanoate, only glyceryltrioleate, only glyceryltrilinoleate, only glyceryltrihexanoate, only glyeryltristearate, only glyceryltridecanoate, only glycerltripalmitate, only glyceryltridodecanoate, only glyceryltriacetate, or only glyceryltributyrate.

In some embodiments, more than one, such as two, three, four, five, or six triglycerides are present in the co-crystal. As non-limiting examples, the co-crystal of Compound 1 comprises two triglycerides, such as (i) glyceryltrioctanoate and glyceryltrioleate; (ii) glyceryltrioleate and glyceryltrilinoleate; or (iii) glyceryltrioctanoate and glyceryltrilinoleate.

In some embodiments, in the co-crystal, the stoichiometry of Compound 1 to the co-former ranges from 2 to 1 to 6 to 1. In one embodiments, in the co-crystal, the stoichiometry of Compound 1 to the co-former ranges from 3 to 1 to 6 to 1. In one embodiments, in the co-crystal, the stoichiometry of Compound 1 to the co-former ranges from 4 to 1 to 6 to 1. In one embodiments, in the co-crystal, the stoichiometry of Compound 1 to the co-former ranges from 5 to 1 to 6 to 1.

In one embodiment, in the co-crystal, the stoichiometry of Compound 1 to the co-former is about 6 to about 1. In one embodiment, in the co-crystal, the stoichiometry of Compound 1 to the co-former is 6 to 1.

As non-limiting examples, the co-crystal of Compound 1 comprises a co-former chosen from glyceryltrioleate, glyceryltrilinoleate, glyceryltristearate, and glyceryltripalmitate, and the stoichiometry of Compound 1 to the co-former in the co-crystal is about 6 to about 1. Further as non-limiting examples, in one embodiment, the co-crystal comprises Compound 1 and glyceryltrioleate, wherein the stoichiometry of Compound 1 to glyceryltrioleate is about 6 to about 1. In another embodiment, the co-crystal comprises Compound 1 and glyceryltrilinoleate, wherein the stoichiometry of Compound 1 to glyceryltrilinoleate is about 6 to about 1. In another embodiment, the co-crystal comprises Compound 1 and glyceryltristearate, wherein the stoichiometry of Compound 1 to glyceryltristearate is about 6 to about 1. In another embodiment, the co-crystal comprises Compound 1 and glyceryltripalmitate, wherein the stoichiometry of Compound 1 to glyceryltripalmitate is about 6 to about 1. In any of the above embodiments, the ratio or stoichiometry of Compound 1 to the co-former in Compound 1:triglyceride is 6 to 1.

In some embodiments, the stoichiometry of Compound 1 to the co-former in the co-crystal is about 3 to about 1. In one embodiment, the stoichiometry of Compound 1 to the co-former in the co-crystal is 3 to 1.

As non-limiting examples, the co-crystal of Compound 1 comprises a co-former chosen from glyceryltrioctanoate, glyceryltridodecanoate, and glyceryltridecanoate and the stoichiometry of Compound 1 to the triglyceride in the co-crystal is about 3 to about 1.

Further as non-limiting examples, in one embodiment, the present disclosure provides for a co-crystal comprising Compound 1 and glyceryltrioctanoate, wherein the stoichiometry of Compound 1 to glyceryltrioctanoate is about 3 to about 1. In another embodiment, the present disclosure provides a co-crystal comprising Compound 1 and glyceryltridodecanoate, wherein the stoichiometry of Compound 1 to glyceryltridodecanoate is about 3 to about 1. In another embodiment, the present disclosure provides a co-crystal comprising Compound 1 and glyceryltridecanoate, wherein the stoichiometry of Compound 1 to glyceryltridecanote is about 3 to about 1. In any of the above embodiments, the ratio or stoichiometry of Compound 1 to triglyceride co-former in Compound 1:triglyceride is 3 to 1.

In some embodiments, $R_1$, $R_2$, and $R_3$ are independently $C_{7-29}$ aliphatic and Compound 1 may be present in the form of a hexamer in the co-crystal.

In some embodiments, Compound 1 may be present in the form of a hexamer in the co-crystal, wherein each of the hexamers contains six molecules of Compound 1 bonded by hydrogen bonding as shown in FIG. 1.

In some embodiments, Compound 1 may be present in the form of a hexamer in the co-crystal, wherein each of the hexamers contains six molecules of Compound 1 bonded by hydrogen bonding as shown in FIG. 1, and further wherein $R_1$, $R_2$, and $R_3$ are independently $C_{7-29}$ aliphatic.

Figure 2:
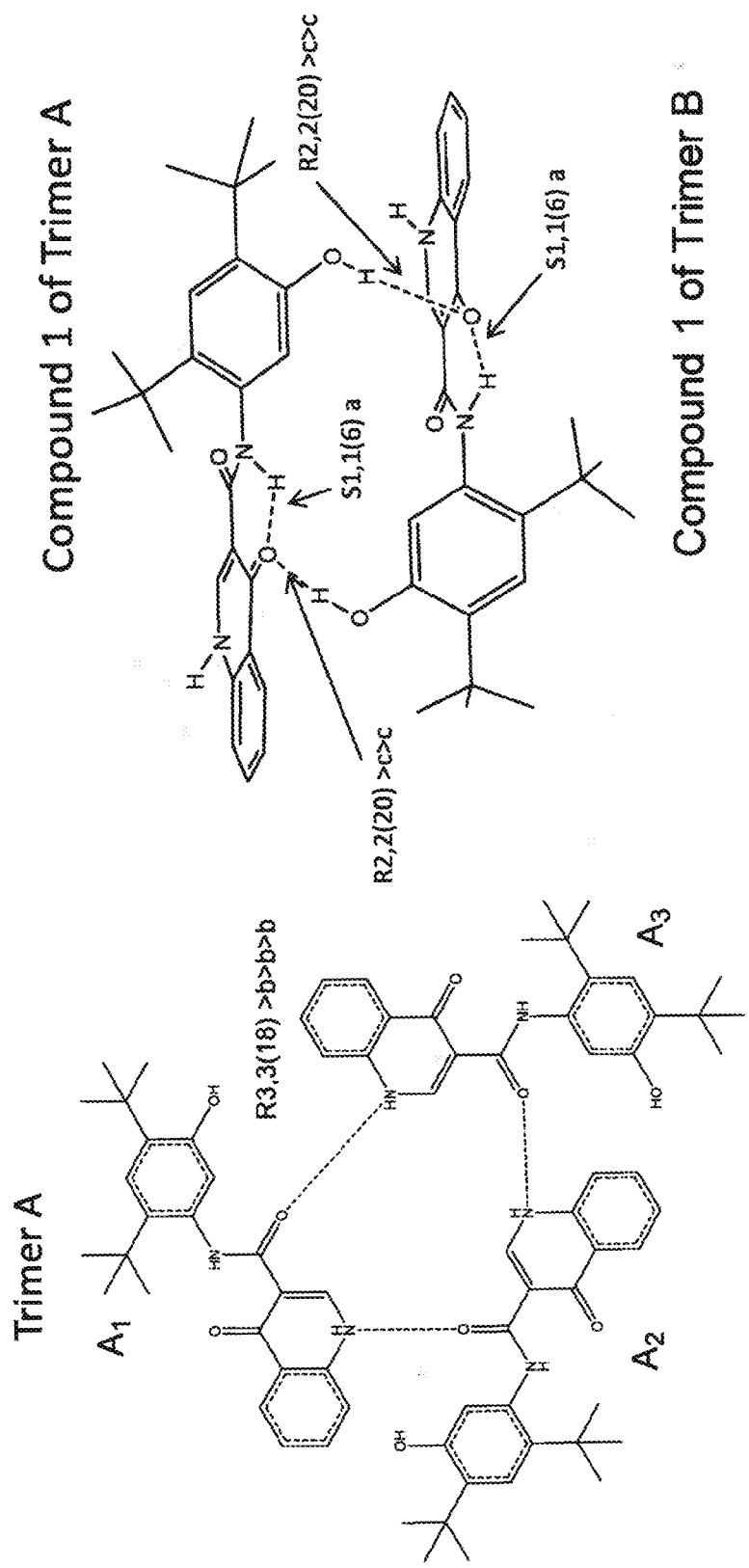
FIG. 2 shows examples of hydrogen bonding in a Compound 1:triglyceride co-crystal in some embodiments.

As a non-limiting example, as shown in FIG. 2 (left), in one embodiment, three molecules of Compound 1 (A1, A2, A3) may bound by three hydrogen bonds to form a Compound trimer, and two Compound 1 trimers may further bound by additional, such as six, hydrogen bonds to form a Compound 1 hexamer, wherein each of Compound 1 molecules in a given trimer is bound to the corresponding Compound 1 molecule in the second trimer by two hydrogen bonds as shown in FIG. 2 (right). In one embodiment, intramolecular hydrogen bonds are present in the hexamer of Compound 1 as shown in FIG. 2 (right).

In one embodiment, molecules of Compound 1 may be bound by the one or more of the following hydrogen bonds to form a hexamer:

S1,1(6) a;
R2,2(20)>c>c;
R3,3(18)>b>b>b;
R4,4(28)>b>c>b>c;
R4,4(30)>b>c>b<c;
R4,4(32)>b<c>b<c;
R5,5(36)>b>b<c<b<c;
R5,5(36)>b>b<c<b>c;
R5,5(36)>b>b>c<b<c;
R5,5(36)>b>b>c<b>c;
R6,6(40)>b>b>c>b>b>c;
R6,6(42)>b>b>c>b>b<c;
R6,6(44)>b>b<c>b>b<c.

A description of graph set notation may be found in Bernstein, J., Davis, R. E., Shimoni, L. & Chang, N.-L, "Patterns in Hydrogen Bonding: Functionality and Graph Set Analysis in Crystals," *Angew. Chem. Int. Ed. Engl.* 34, 1555-1573 (1995); W. D. S. Motherwell, G. P. Shields, and F. H. Allen, "Automated assignment of graph-set descriptors for crystallographically symmetric molecules," *Acta. Cryst.* B56, 466-473 (2000), and M. C. Etter, "Encoding and decoding hydrogen-bond patterns of organic compounds," *Acc. Chem. Res.,* 23, 120-126 (1990).

In yet another embodiment, a Compound 1 hexamer in a Compound 1:triglyceride co-crystal is stabilized by the presence of the triglyceride co-former.

In some embodiments, the co-crystals are capable of yielding a concentration of Compound 1 of greater than 0.4 mg/mL when dissolved in simulated intestinal fluid in fed state (FeSSIF).

In some embodiments, the co-crystals are capable of yielding a concentration of Compound 1 of greater than 0.4 mg/mL when dissolved in simulated intestinal fluid in fed state (FeSSIF) and the concentration is maintained for at least 10 hours.

In some embodiments, the co-crystals are characterized as having an X-ray powder diffraction pattern with characteristic peaks expressed in 2-theta±0.2 degrees at the following positions: 3.5, 6.9, and 10.9.

In some embodiments, the co-crystals are characterized as having an X-ray powder diffraction pattern with characteristic peaks expressed in 2-theta±0.2 degrees at the following positions: 3.5, 6.9, 9.2, 10.9, 16.9, and 18.0.

In some embodiments, the co-crystals are characterized as having an X-ray powder diffraction pattern with characteristic peaks expressed in 2-theta±0.2 degrees at the following positions: 3.5, 6.9, 9.2, 10.9, 16.9, 18.0, and 23.8.

In yet some embodiments, the co-crystals are characterized as having a 13C ssNMR spectrum with characteristic peaks expressed in ppm±0.1 at the following positions: 178.6, 155.0, and 119.4.

In also yet some embodiments, the co-crystals are characterized as having a 13C ssNMR spectrum with characteristic peaks expressed in ppm±0.1 at the following positions: 178.6, 155.0, 130.5, and 119.4.

The present disclosure also provides a co-crystal comprising Compound 1 and a co-crystal former selected from the group consisting of glyceryltrioctanoate, glyceryltrioleate, and glyceryltrilinoleate, wherein Compound 1 is represented by the following structural formula:

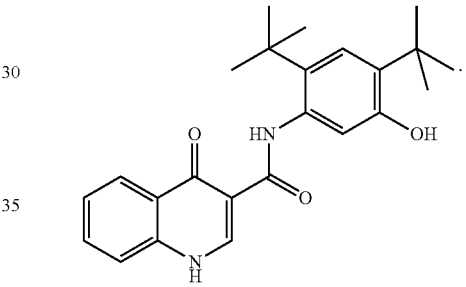

In some embodiments, the co-crystal described in the paragraph immediately above dissolves in simulated intestinal fluid in fed state (FeSSIF) to yield a concentration of Compound 1 of greater than 0.4 mg/mL and the concentration is maintained for at least 10 hours.

In one embodiment, the co-crystal former is glyceryltrioctanoate.

In one embodiment, the stoichiometry of Compound 1 to glyceryltrioctanoate is 3 to 1.

In one embodiment, the co-crystal is characterized as having an X-ray powder diffraction pattern with characteristic peaks expressed in 2-theta±0.2 degrees at the following positions: 3.5, 6.9, and 10.9.

In one embodiment, the co-crystal is characterized as having an X-ray powder diffraction pattern with characteristic peaks expressed in 2-theta±0.2 degrees at the following positions: 3.5, 6.0, 6.9, 9.1, 10.9, 16.9, 18.0, and 23.8.

In one embodiment, the co-crystal is characterized as having a 13C ssNMR spectrum with characteristic peaks expressed in ppm±0.1 at the following positions: 178.6, 155.0, and 119.4.

In one embodiment, the co-crystal is characterized as having an endothermic peak in differential scanning calorimetry (DSC) at 186.7±0.5° C.

In some embodiments, the co-crystal former is glyceryltrioleate.

In one embodiment, the stoichiometry of Compound 1 to glyceryltrioleate is 6 to 1.

In one embodiment, the co-crystal is characterized as having an X-ray powder diffraction pattern with characteristic peaks expressed in 2-theta±0.2 degrees at the following positions: 3.5, 6.9, and 10.9.

In one embodiment, the co-crystal is characterized as having an X-ray powder diffraction pattern with characteristic peaks expressed in 2-theta±0.2 degrees at the following positions: 3.5, 6.9, 9.2, 10.9, 16.9, 18.1 and 23.8.

In one embodiment, the co-crystal is characterized as having a 13C ssNMR spectrum with characteristic peaks expressed in ppm±0.1 at the following positions: 178.6, 155.0, 130.5, and 119.4.

In one embodiment, the co-crystal is characterized as having an endothermic peak in differential scanning calorimetry (DSC) at 197.5±0.5° C.

In some embodiments, the co-crystal former is glyceryltrilinoleate.

In one embodiment, the stoichiometry of Compound 1 to glyceryltrilinoleate is 6 to 1.

In one embodiment, the co-crystal is characterized as having an X-ray powder diffraction pattern with characteristic peaks expressed in 2-theta±0.2 degrees at the following positions: 3.5, 6.9, and 10.9.

In one embodiment, the co-crystal is characterized as having an X-ray powder diffraction pattern with characteristic peaks expressed in 2-theta±0.2 degrees at the following positions: 3.5, 6.0, 6.9, 9.2, 10.9, 17.0, 18.1, and 23.8.

In one embodiment, the co-crystal is characterized as having a 13C ssNMR spectrum with characteristic peaks expressed in ppm±0.1 at the following positions: 178.5, 155.0, 130.6, and 119.3.

In one embodiment, the co-crystal is characterized as having an endothermic peak in differential scanning calorimetry (DSC) at 182.3±0.5° C.

In alternative embodiments, deuterium (2H) may be incorporated into Compound 1 to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of kM/kD=2-7 are typical. If this rate difference is successfully applied to Compound 1, the profile of this compound in vivo can be drastically modified and result in improved pharmacokinetic properties. For a further discussion, see S. L. Harbeson and R. D. Tung, Deuterium In Drug Discovery and Development, Ann. Rep. Med. Chem. 2011, 46, 403-417, incorporated by reference herein in its entirety.

When discovering and developing therapeutic agents, a person skilled in the art attempts to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of Compound 1 with improved stability through resistance to such oxidative metabolism. Significant improvements in the pharmacokinetic profiles of Compound 1 are thereby obtained and can be expressed quantitatively in terms of increases in the in vivo half-life (t½), concentration at maximum therapeutic effect (Cmax), area under the dose response curve (AUC), and bioavailability; and in terms of reduced clearance, dose and materials costs.

For example, in one alternative embodiment, at least one hydrogen atoms in Compound 1 are replaced by deuterium atoms to provide a deuterated compound. In one alternative embodiment, one or both of the t-butyl groups in Compound 1 is replaced by d9-t-butyl. In another alternative embodiment, the t-butyl group adjacent to the OH group in Compound 1 is replaced d9-t-butyl (Compound 2). Co-crystals of Compound 2 may be formed using the methods described herein. A person skilled in the art would understand that the XRPD pattern of a co-crystal of Compound 2 and a triglyceride, or a co-crystal of any other of the deuterated compounds in these alternative embodiments and a triglyceride, would have the same characteristic peaks as a Compound 1:triglyceride co-crystal. Half-life determinations enable favorable and accurate determination of the extent to which resistance to oxidative metabolism has improved.

In some alternative embodiments, deuterium-hydrogen exchange in Compound 1 can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated compound will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv, Drug Res. 14, 1-40, 1985, Gillette et al, Biochemistry 33(10) 2927-2937, 1994, and Jarman et al. Carcinogenesis 16(4), 683-688, 1993.

Compound 1:Glyceryltrioctanoate

The co-crystal comprising Compound 1 and glyceryltrioctanoate is hereinafter referred to as "Compound 1:glyceryltrioctanoate".

Figure 3:
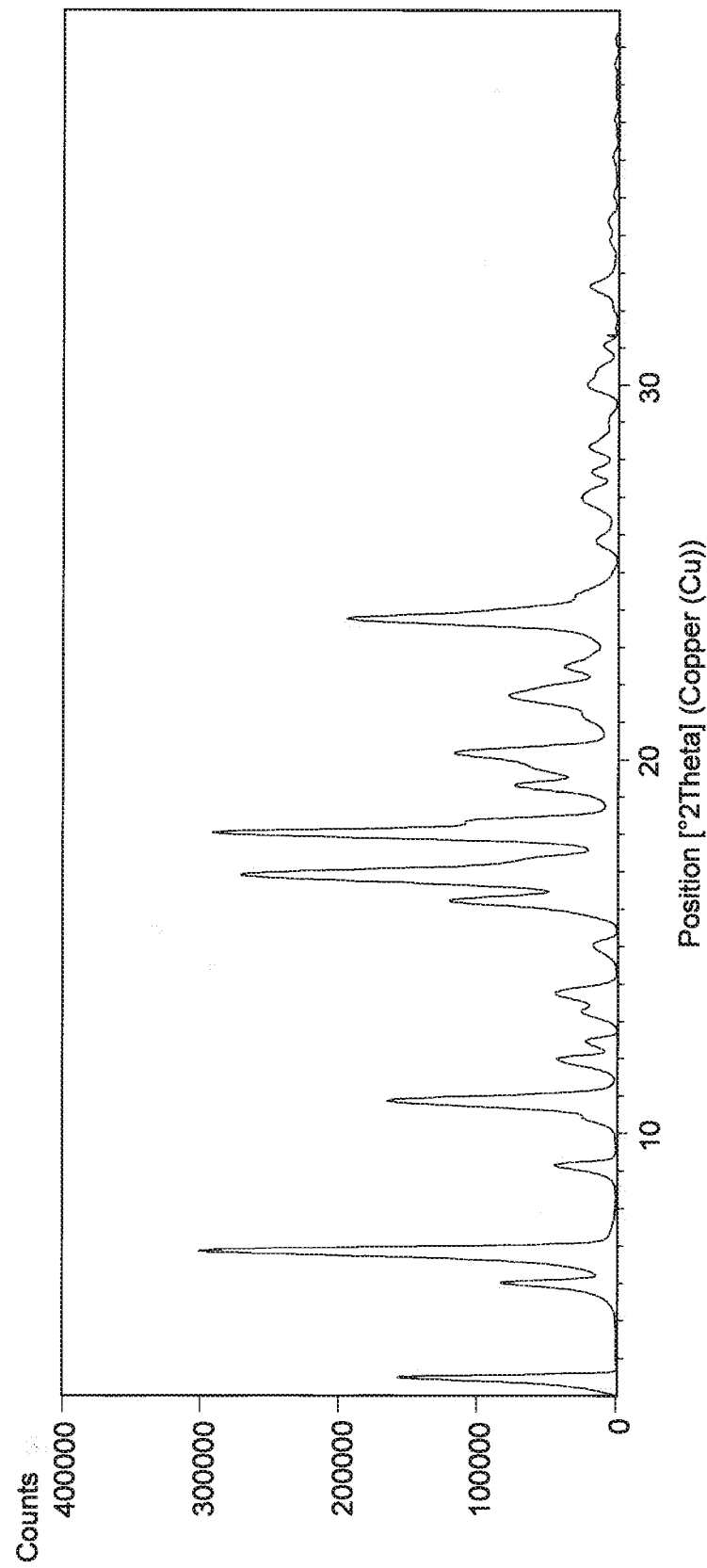
FIG. 3 is an examplary X-Ray Powder Diffraction (XRPD) pattern of Compound 1:glyceryltrioctanoate.
Figure 4:
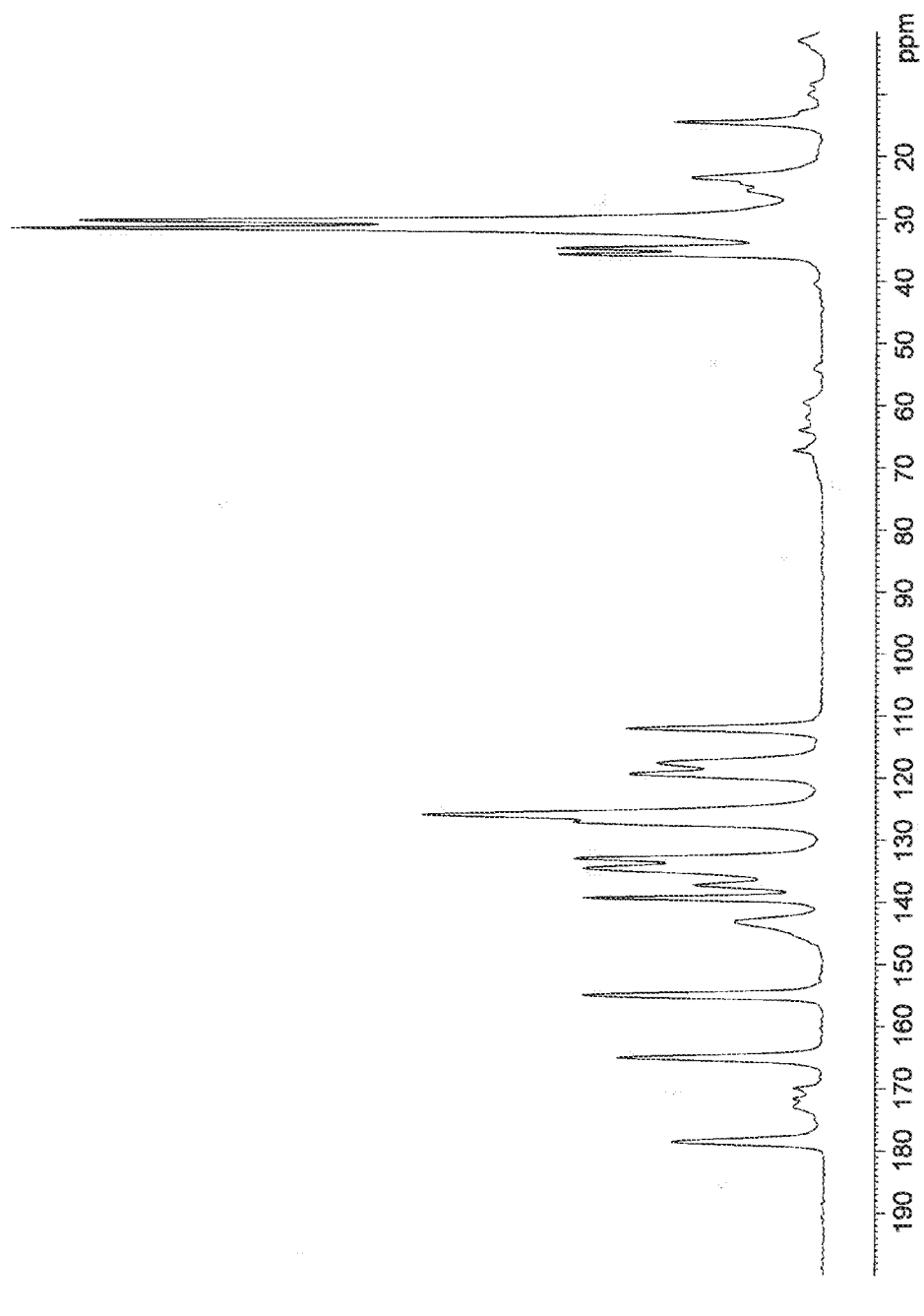
FIG. 4 is an examplary $^{13}C$ solid state nuclear magnetic resonance spectroscopy ($^{13}C$ ssNMR) spectrum of Compound 1:glyceryltrioctanoate.
Figure 5:
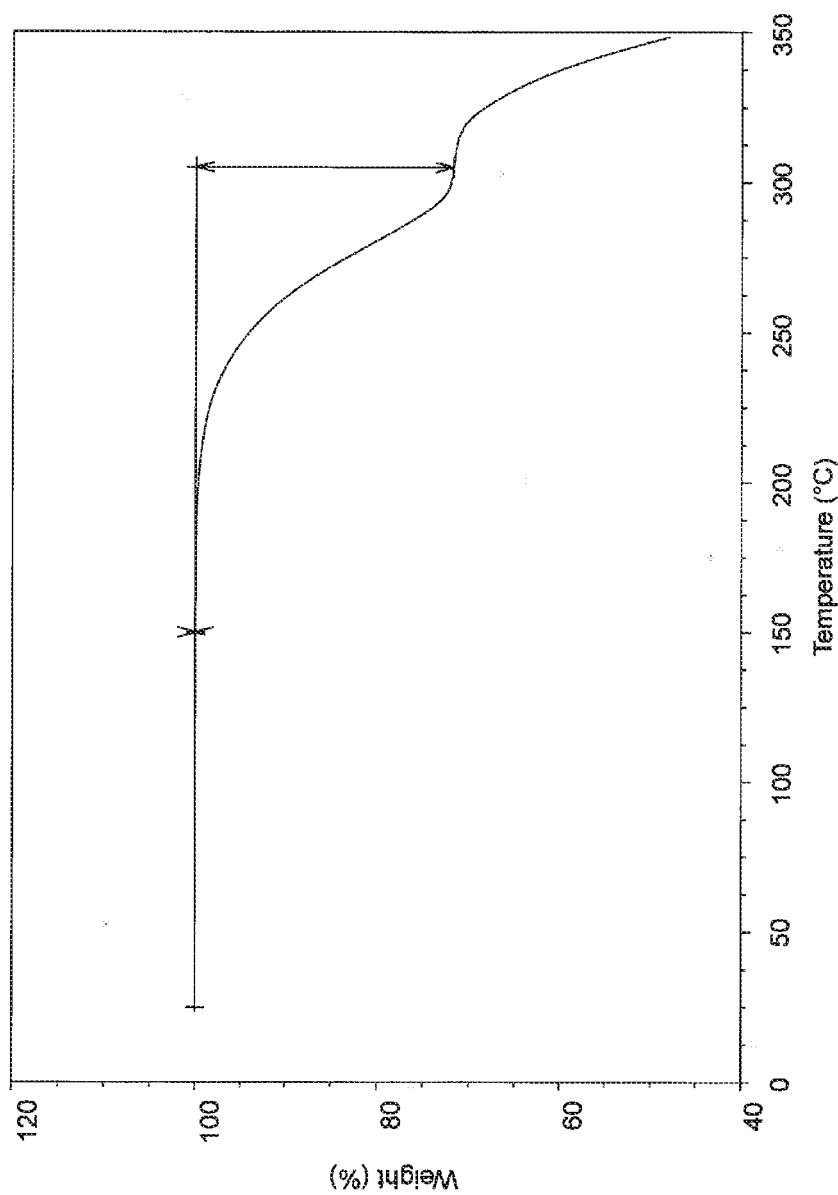
FIG. 5 is an examplary thermal gravimetric analysis (TGA) trace Compound 1:glyceryltrioctanoate.
Figure 6:
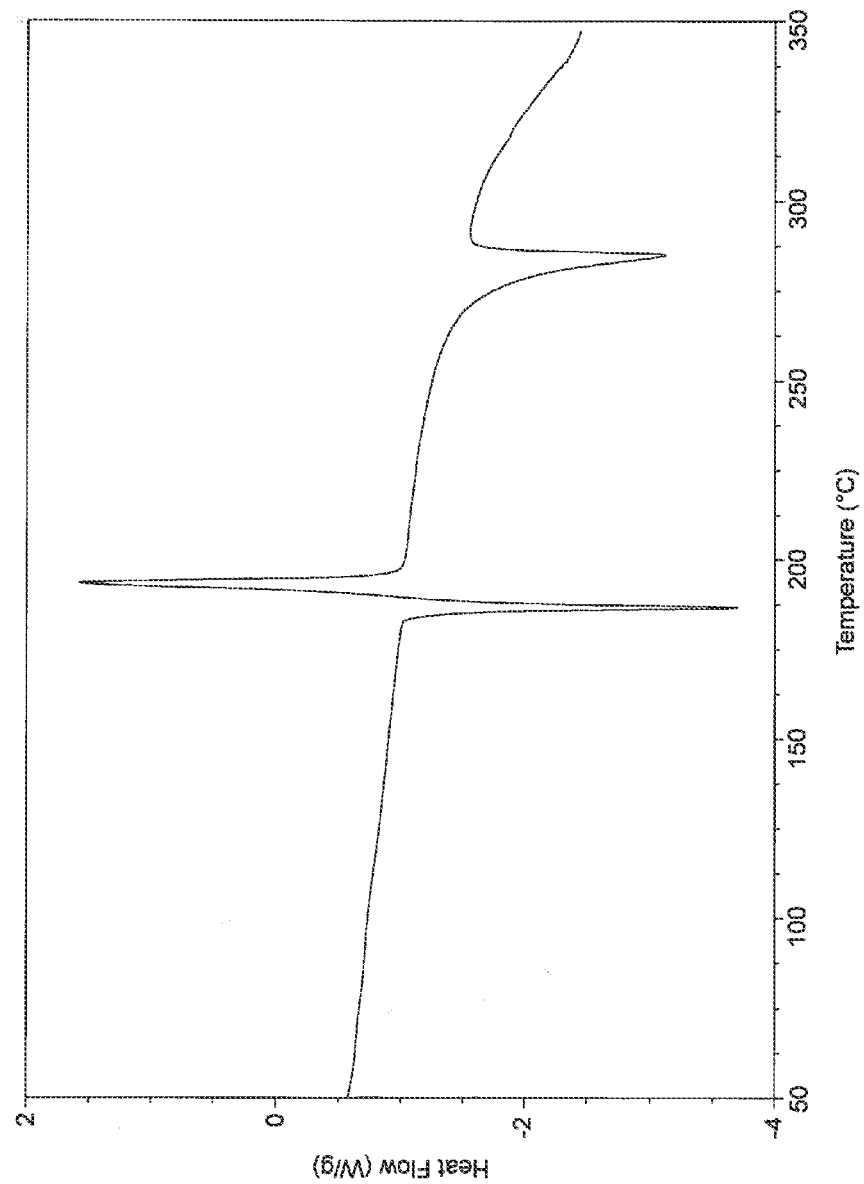
FIG. 6 is an examplary Differential Scanning calorimetry (DSC) thermogram of Compound 1:glyceryltrioctanoate.
Figure 7:
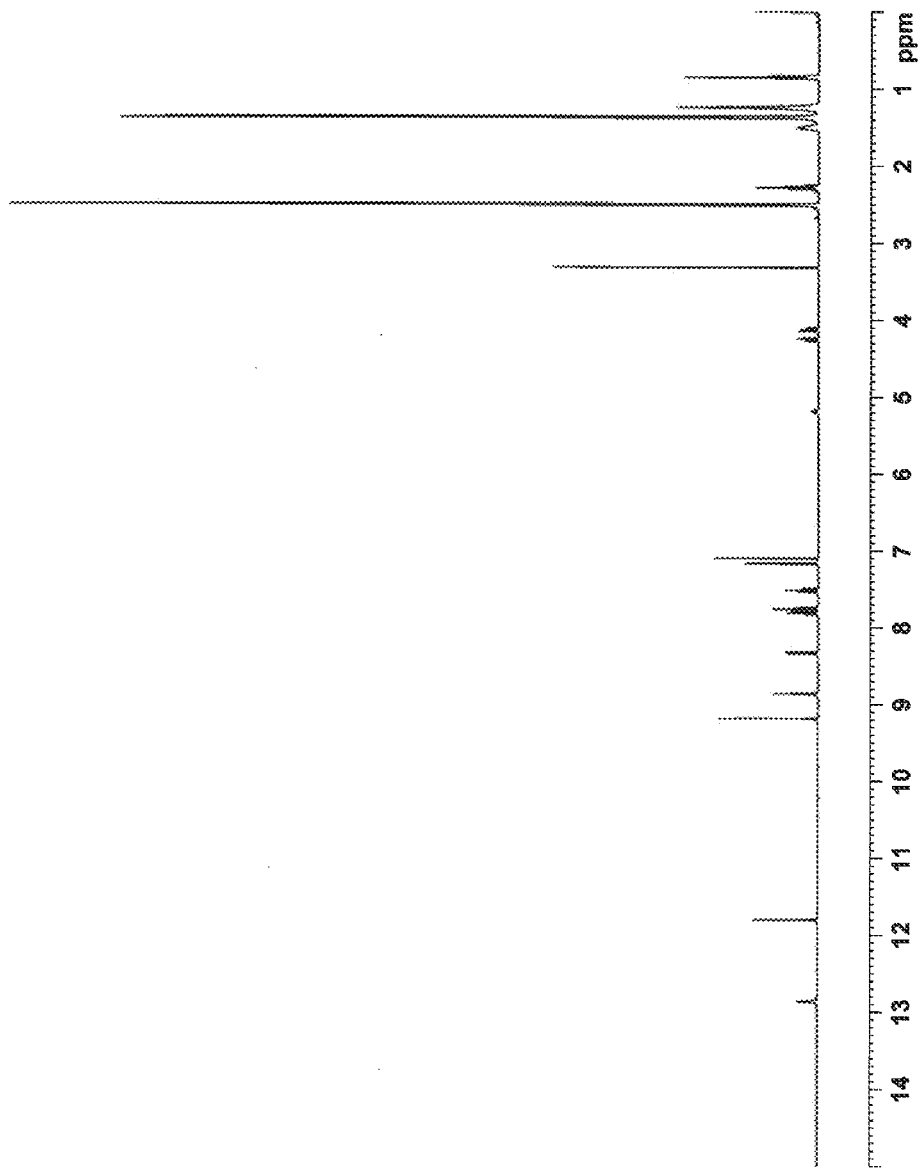
FIG. 7 is an examplary $^1H$ Nuclear Magnetic Resonance ($^1H$ NMR) spectrum of Compound 1:glyceryltrioctanoate in DMSO-$d_6$.

The characterization of Compound 1:glyceryltrioctanoate is detailed later in the Example section. FIG. 3 is an examplary X-Ray Powder Diffraction (XRPD) pattern of Compound 1:glyceryltrioctanoate. FIG. 4 is an examplary 13C solid state nuclear magnetic resonance spectroscopy (13C ssNMR) spectrum of Compound 1:glyceryltrioctanoate. FIG. 5 is an examplary thermal gravimetric analysis (TGA) trace Compound 1:glyceryltrioctanoate. FIG. 6 is an examplary Differential Scanning calorimetry (DSC) thermogram of Compound 1:glyceryltrioctanoate. FIG. 7 is an examplary 1H Nuclear Magnetic Resonance (1H NMR) spectrum of Compound 1:glyceryltrioctanoate in DMSO-d6.

In one embodiment, Compound 1:glyceryltrioctanoate is characterized as having an X-ray powder diffraction (XRPD) pattern with one or more characteristic peaks expressed in 2-theta±0.2 degrees at the following positions: 3.5, 6.0, 6.9, 9.1, 10.9, 12.0, 12.5, 13.2, 13.7, 15.0, 16.2, 16.9, 18.0, 19.3, 20.2, 21.7, 22.5, 23.8, 25.8, 27.0, 27.6, 28.3, 30.0, 31.0, and 32.6.

In one embodiment, Compound 1:glyceryltrioctanoate is characterized as having an X-ray powder diffraction pattern with characteristic peaks expressed in 2-theta±0.2 degrees at the following positions: 3.5, 6.9, and 10.9.

In another embodiment, Compound 1:glyceryltrioctanoate is characterized as having a X-ray powder diffraction pattern with characteristic peaks expressed in 2-theta±0.2 degrees at the following positions: 3.5, 6.0, 6.9, 9.1, 10.9, 16.9, 18.0, and 23.8.

In yet another embodiment, Compound 1:glyceryltrioctanoate is characterized as having an X-ray powder diffraction pattern with characteristic peaks expressed in 2-theta±0.2 degrees at the following positions: 3.5, 6.0, 6.9, 9.1, 10.9, 12.0, 12.5, 13.2, 13.7, 15.0, 16.2, 16.9, 18.0, 19.3, 20.2, 21.7, 22.5, 23.8, 25.8, 27.0, 27.6, 28.3, 30.0, 31.0, and 32.6.

In another embodiment, Compound 1:glyceryltrioctanoate is characterized as having an X-ray powder diffraction pattern substantially the same as shown in FIG. 3. The X-ray powder diffraction patterns are obtained at room temperature using Cu K alpha radiation.

In one embodiment, Compound 1:glyceryltrioctanoate is characterized as having a 13C solid state nuclear magnetic resonance (13C ssNMR) spectrum with one or more characteristic peaks expressed in ppm±0.1 selected from: 178.6, 172.9, 171.6, 169.9, 165.1, 155.0, 143.2, 139.4, 137.3, 134.6, 133.0, 126.0, 119.4, 117.7, 112.1, 67.3, 64.0, 62.0, 59.6, 54.2, 35.8, 34.8, 31.7, 30.5, 23.5, and 14.6.

In one embodiment, Compound 1:glyceryltrioctanoate is characterized as having a 13C ssNMR spectrum with characteristic peaks expressed in ppm±0.1 at the following positions: 178.6, 155.0, and 119.4.

In another embodiment, Compound 1:glyceryltrioctanoate is characterized by having a 13C ssNMR spectrum with characteristic peaks expressed in ppm±0.1 at the following positions 178.6, 155.0, 134.6, 126.0, 119.4, and 35.8.

In yet another embodiment, Compound 1:glyceryltrioctanoate is characterized as having a 13C ssNMR spectrum with characteristic peaks expressed in ppm±0.1 at the following positions: 178.6, 172.9, 171.6, 169.9, 165.1, 155.0, 143.2, 139.4, 137.3, 134.6, 133.0, 126.0, 119.4, 117.7, 112.1, 67.3, 64.0, 62.0, 59.6, 54.2, 35.8, 34.8, 31.7, 30.5, 23.5, and 14.6.

In one embodiment, Compound 1:glyceryltrioctanoate is characterized as having an endothermic peak in differential scanning calorimetry (DSC) at 186.7° C. In another embodiments, Compound 1:glyceryltrioctanoate is characterized as having an endothermic peak in differential scanning calorimetry (DSC) at 186.7±0.2° C. In another embodiments, Compound 1:glyceryltrioctanoate is characterized as having an endothermic peak in differential scanning calorimetry (DSC) at 186.7±0.5° C.

In some embodiments, the ratio or stoichiometry of Compound 1 to glyceryltrioctanoate in Compound 1:glyceryltrioctanoate is 3:1. In some embodiments, the ratio or stoichiometry of Compound 1 to glyceryltrioctanoate in Compound 1:glyceryltrioctanoate is about 3 to about 1.

Compound 1:Glyceryltrioleate

The co-crystal comprising Compound 1 and glyceryltrioleate is hereinafter referred to as "Compound 1:glyceryltrioleate".

Figure 8:
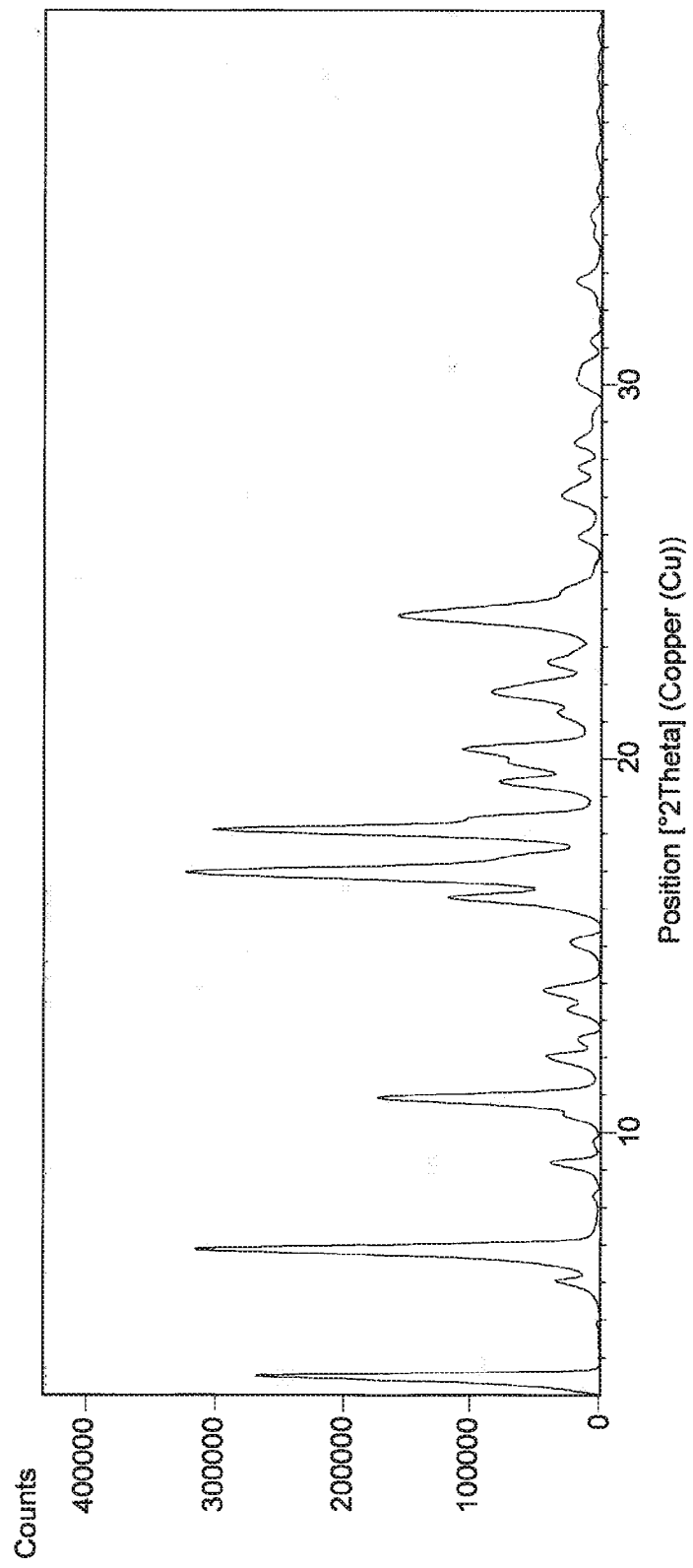
FIG. 8 is an examplary XRPD pattern of Compound 1:glyceryltrioleate.
Figure 9:
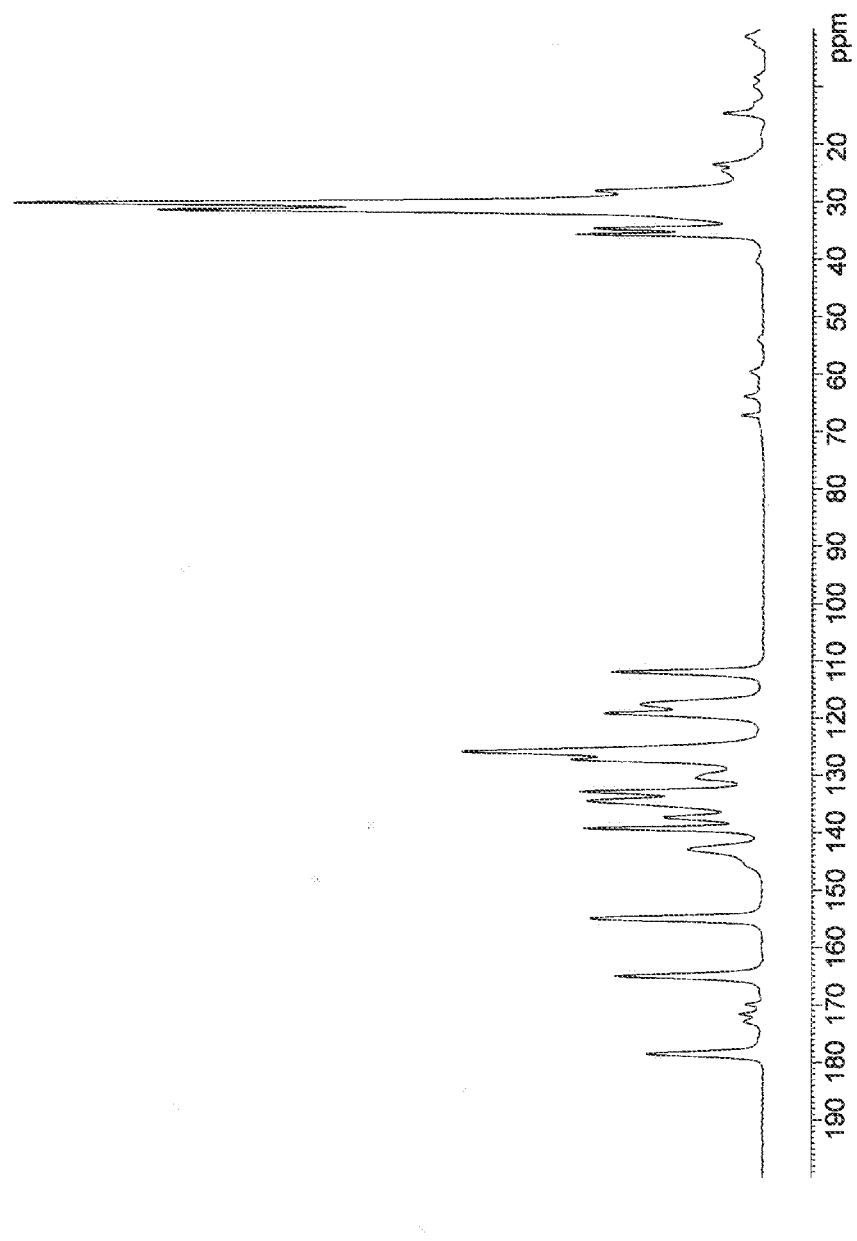
FIG. 9 is an examplary $^{13}C$ ssNMR spectrum of Compound 1:glyceryltrioleate.
Figure 10:
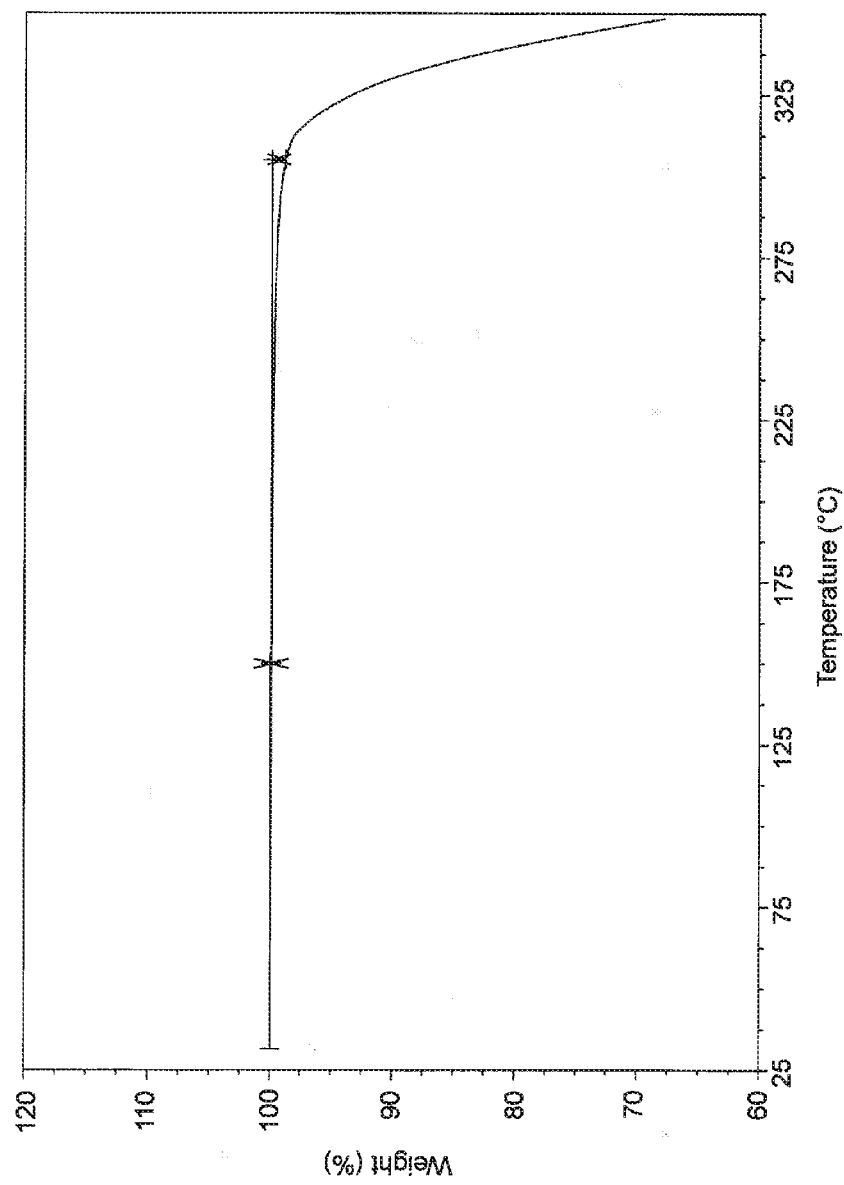
FIG. 10 is an examplary TGA trace Compound 1:glyceryltrioleate.
Figure 11:
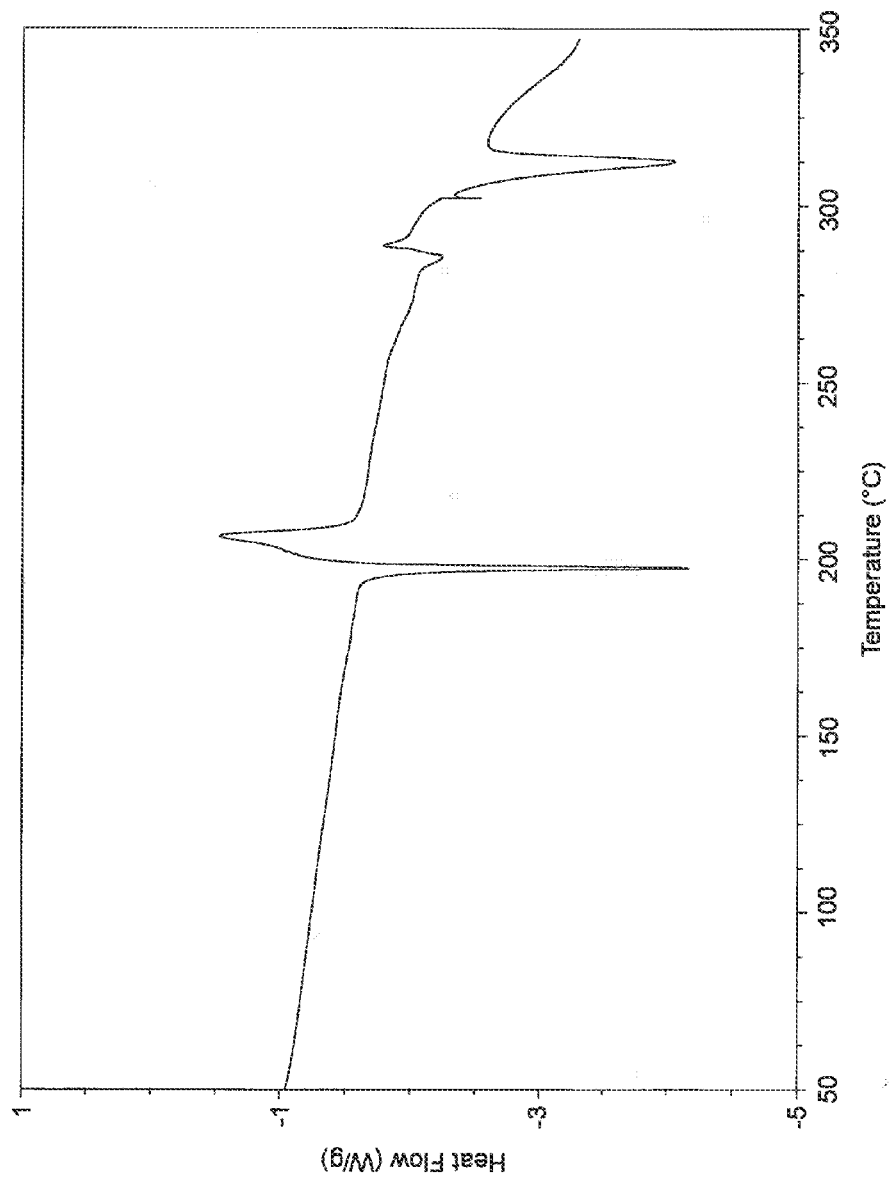
FIG. 11 is an examplary DSC thermogram of Compound 1:glyceryltrioleate.
Figure 12:
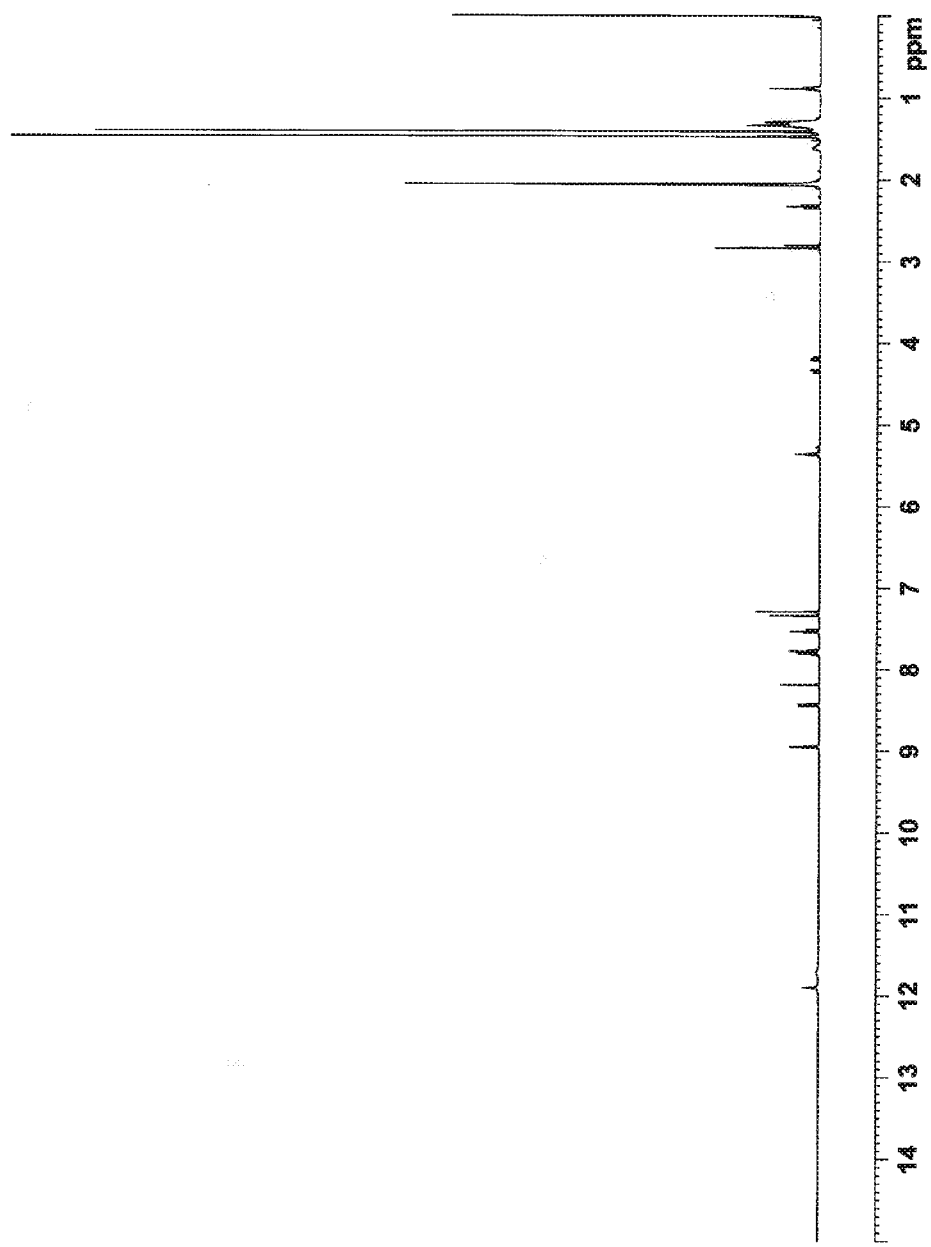
FIG. 12 is an examplary $^1H$ NMR spectrum of Compound 1:glyceryltrioleate in acetone-$d_6$.

The characterization of Compound 1:glyceryltrioleate is detailed later in the Example section. FIG. 8 is an examplary XRPD pattern of Compound 1:glyceryltrioleate. FIG. 9 is an examplary 13C ssNMR spectrum of Compound 1:glyceryltrioleate. FIG. 10 is an exemplary TGA trace Compound 1:glyceryltrioleate. FIG. 11 is an exemplary DSC thermogram of Compound 1:glyceryltrioleate. FIG. 12 is an examplary 1H NMR spectrum of Compound 1:glyceryltrioleate in acetone-d6.

In one embodiment, Compound 1:glyceryltrioleate is characterized as having an X-ray powder diffraction pattern with one or more characteristic peaks expressed in 2-theta±0.2 degrees at the following positions: 3.5, 6.9, 9.2, 9.8, 10.4, 10.9, 12.0, 12.7, 13.3, 13.8, 15.1, 16.3, 16.9, 18.1, 18.5, 19.4, 19.9, 20.2, 21.2, 21.8, 22.6, 23.8, 26.0, 27.0, 27.8, 28.5, 30.0, 30.7, and 32.7.

In one specific embodiment, Compound 1:glyceryltrioleate is characterized as having an X-ray powder diffraction pattern with characteristic peaks expressed in 2-theta±0.2 degrees at the following positions: 3.5, 6.9, and 10.9.

In another embodiment, Compound 1:glyceryltrioleate is characterized as having a X-ray powder diffraction pattern with characteristic peaks expressed in 2-theta±0.2 degrees at the following positions: 3.5, 6.9, 9.2, 10.9, 16.9, 18.1 and 23.8.

In yet another embodiment, Compound 1:glyceryltrioleate is characterized as having an X-ray powder diffraction pattern with characteristic peaks expressed in 2-theta±0.2 degrees at the following positions: 3.5, 6.9, 9.2, 9.8, 10.9, 12.0, 12.7, 13.3, 13.8, 15.1, 16.3, 16.9, 18.1, 18.5, 19.4, 19.9, 20.2, 21.2, 21.8, 22.6, 23.8, 26.0, 27.0, 27.8, 28.5, 30.0, 30.7, and 32.7. In one embodiment, Compound 1:glyceryltrioleate is characterized as having an X-ray powder diffraction pattern with characteristic peaks expressed in 2-theta±0.2 degrees at the following positions: 3.5, 6.9, 9.2, 9.8, 10.4, 10.9, 12.0, 12.7, 13.3, 13.8, 15.1, 16.3, 16.9, 18.1, 18.5, 19.4, 19.9, 20.2, 21.2, 21.8, 22.6, 23.8, 26.0, 27.0, 27.8, 28.5, 30.0, 30.7, and 32.7.

In another embodiment, Compound 1:glyceryltrioleate is characterized as having an XRPD powder diffraction pattern substantially the same as shown in FIG. 8. The X-ray powder diffraction patterns are obtained at room temperature using Cu K alpha radiation.

In one embodiment, Compound 1:glyceryltrioleate is characterized as having a 13C solid state nuclear magnetic resonance (13C ssNMR) spectrum with one or more characteristic peaks expressed in ppm±0.1 selected from: 178.6, 172.9, 171.6, 169.9, 165.0, 155.0, 142.9, 139.3, 137.4, 134.5, 133.0, 130.5, 127.3, 126.0, 119.4, 117.7, 112.1, 67.2, 63.9, 59.6, 35.8, 34.8, 31.7, 30.5, 28.2, 24.6, 23.6, and 14.7.

In one embodiment, Compound 1:glyceryltrioleate is characterized as having a 13C ssNMR spectrum with characteristic peaks expressed in ppm±0.1 at the following positions: 178.6, 155.0, 130.5, and 119.4.

In another embodiment, Compound 1:glyceryltrioleate is characterized by having a 13C ssNMR spectrum with characteristic peaks expressed in ppm±0.1 at the following positions: 178.6, 155.0, 134.5, 130.5, 126.0, 119.4, and 35.8.

In yet another embodiment, Compound 1:glyceryltrioleate is characterized as having a 13C ssNMR spectrum with characteristic peaks expressed in ppm±0.1 at the following positions: 178.6, 172.9, 171.6, 169.9, 165.0, 155.0, 142.9, 139.3, 137.4, 134.5, 133.0, 130.5, 127.3, 126.0, 119.4, 117.7, 112.1, 67.2, 63.9, 59.6, 35.8, 34.8, 31.7, 30.5, 28.2, 24.6, 23.6, and 14.7.

In one embodiment, Compound 1:glyceryltrioleate is characterized as having an endothermic peak in differential scanning calorimetry (DSC) at 197.5° C. In another embodiment, Compound 1:glyceryltrioleate is characterized as having an endothermic peak in differential scanning calorimetry (DSC) at 197.5±0.2° C. In another embodiment, Compound 1:glyceryltrioleate is characterized as having an endothermic peak in differential scanning calorimetry (DSC) at 197.5±0.5° C.

In some embodiments, the ratio or stoichiometry of Compound 1 to glyceryltrioleate in Compound 1:glyceryltrioleate is 6:1. In some embodiments, the ratio or stoichiometry of Compound 1 to glyceryltrioleate in Compound 1: glyceryltrioleate is about 6 to about 1.

Compound 1:Glyceryltrilinoleate

The co-crystal comprising Compound 1 and glyceryltrilinoleate is hereinafter referred to as "Compound 1:glyceryltrilinoleate".

Figure 13:
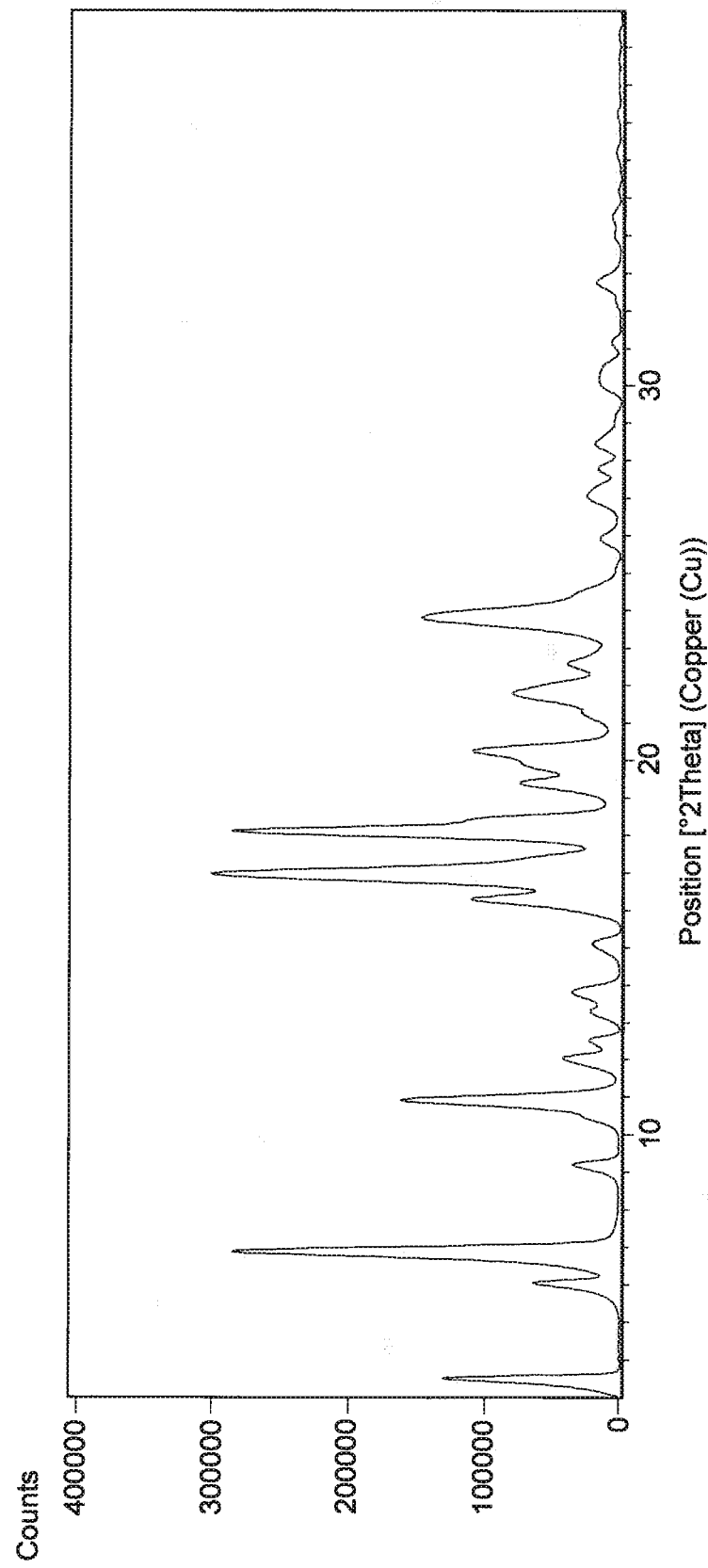
FIG. 13 is an examplary XRPD pattern of Compound 1:glyceryltrilinoleate.
Figure 14:
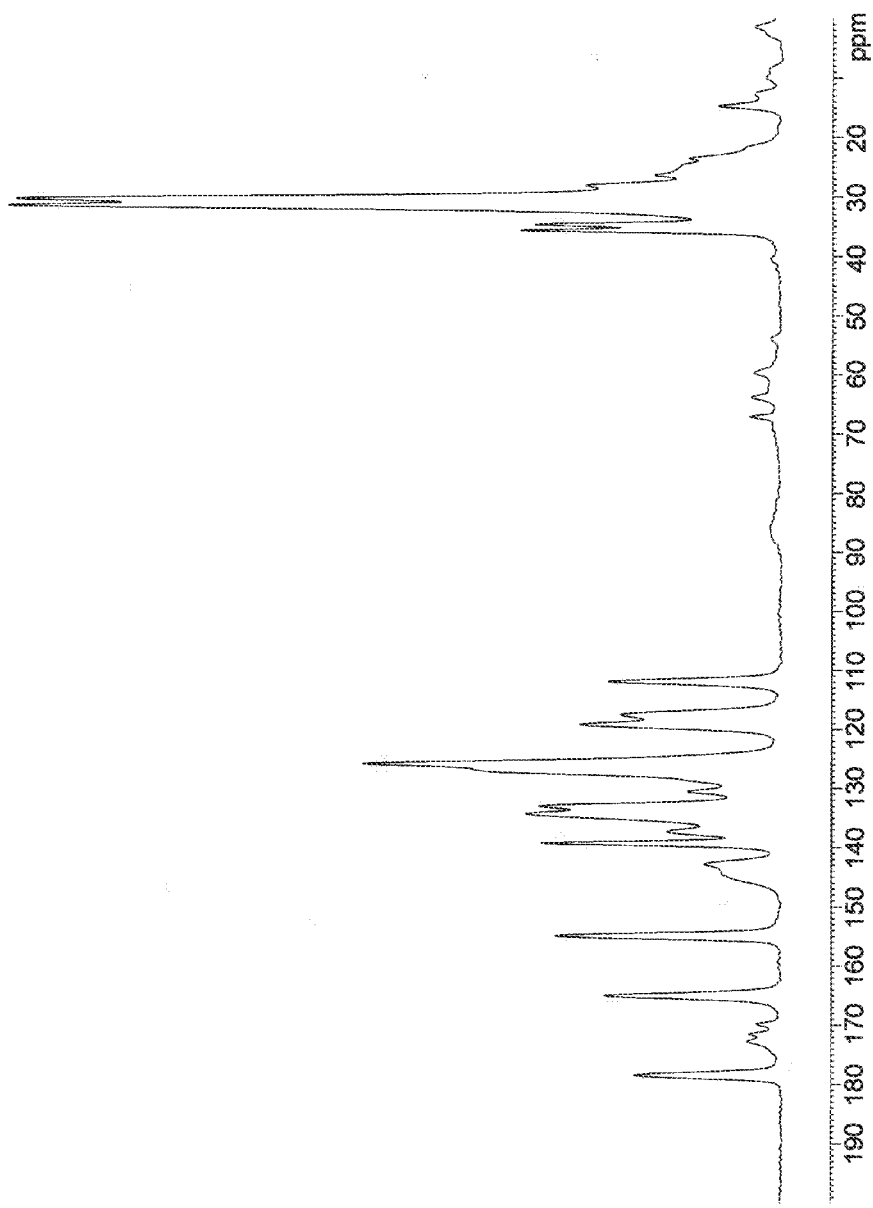
FIG. 14 is an examplary $^{13}C$ ssNMR spectrum of Compound 1:glyceryltrilinoleate.
Figure 15:
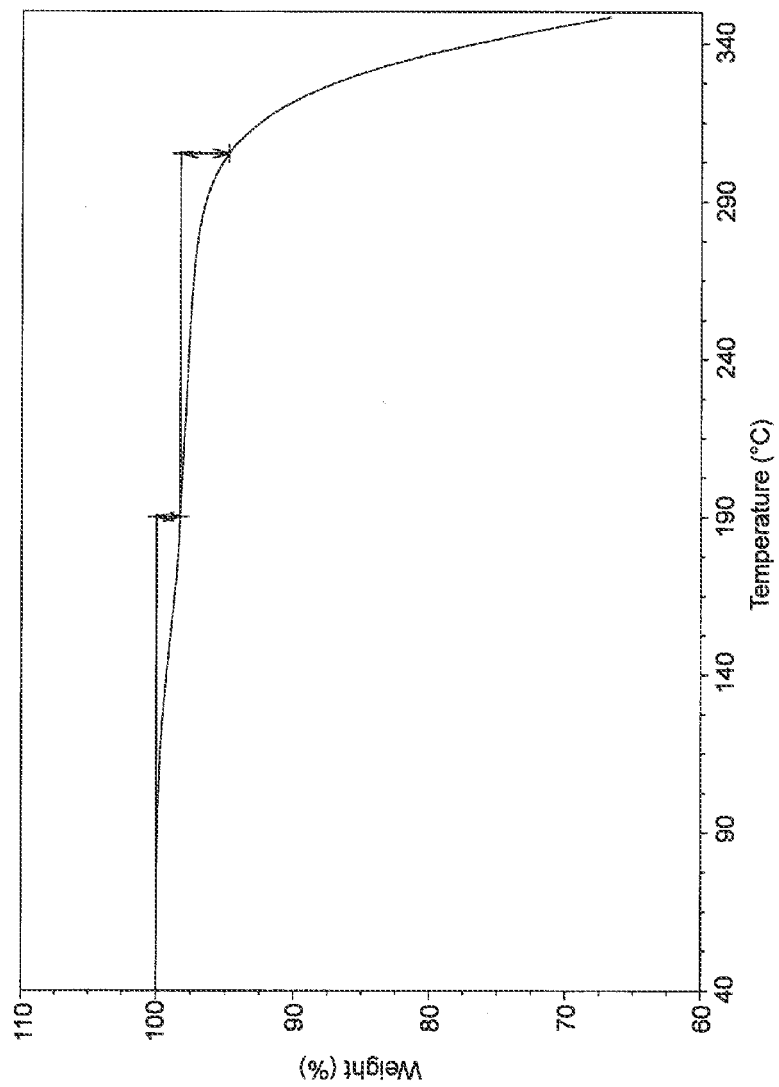
FIG. 15 is an examplary TGA trace Compound 1:glyceryltrilinoleate.
Figure 16:
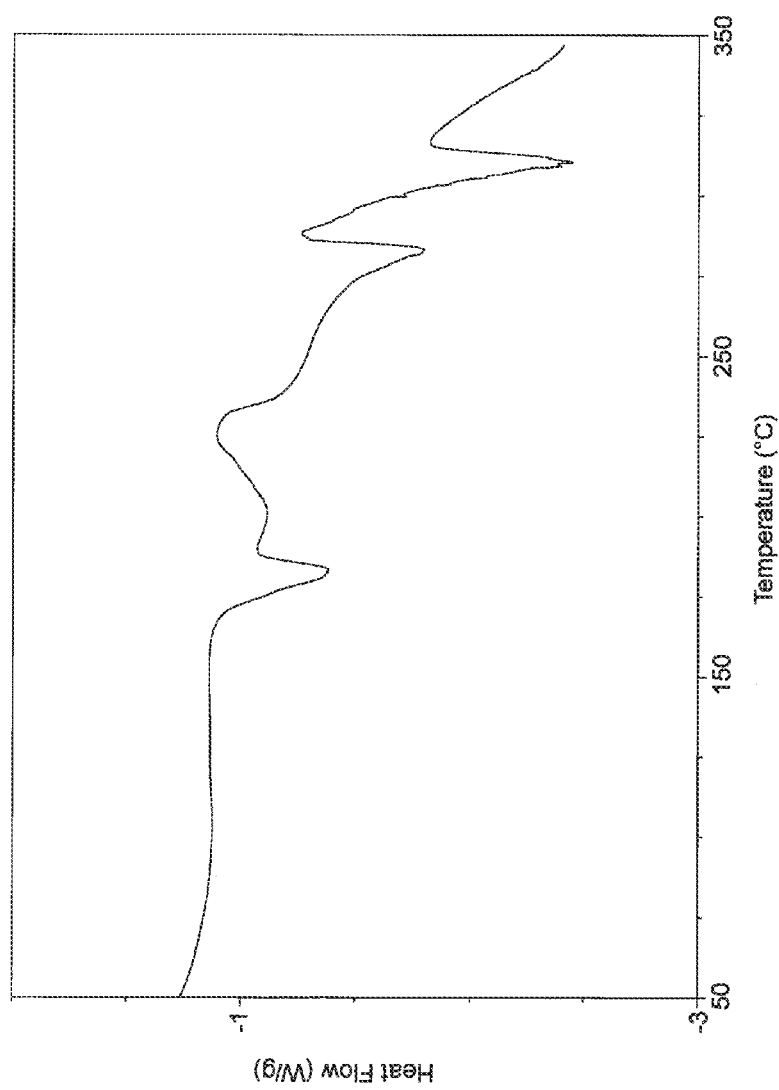
FIG. 16 is an examplary DSC thermogram of Compound 1:glyceryltrilinoleate.
Figure 17:
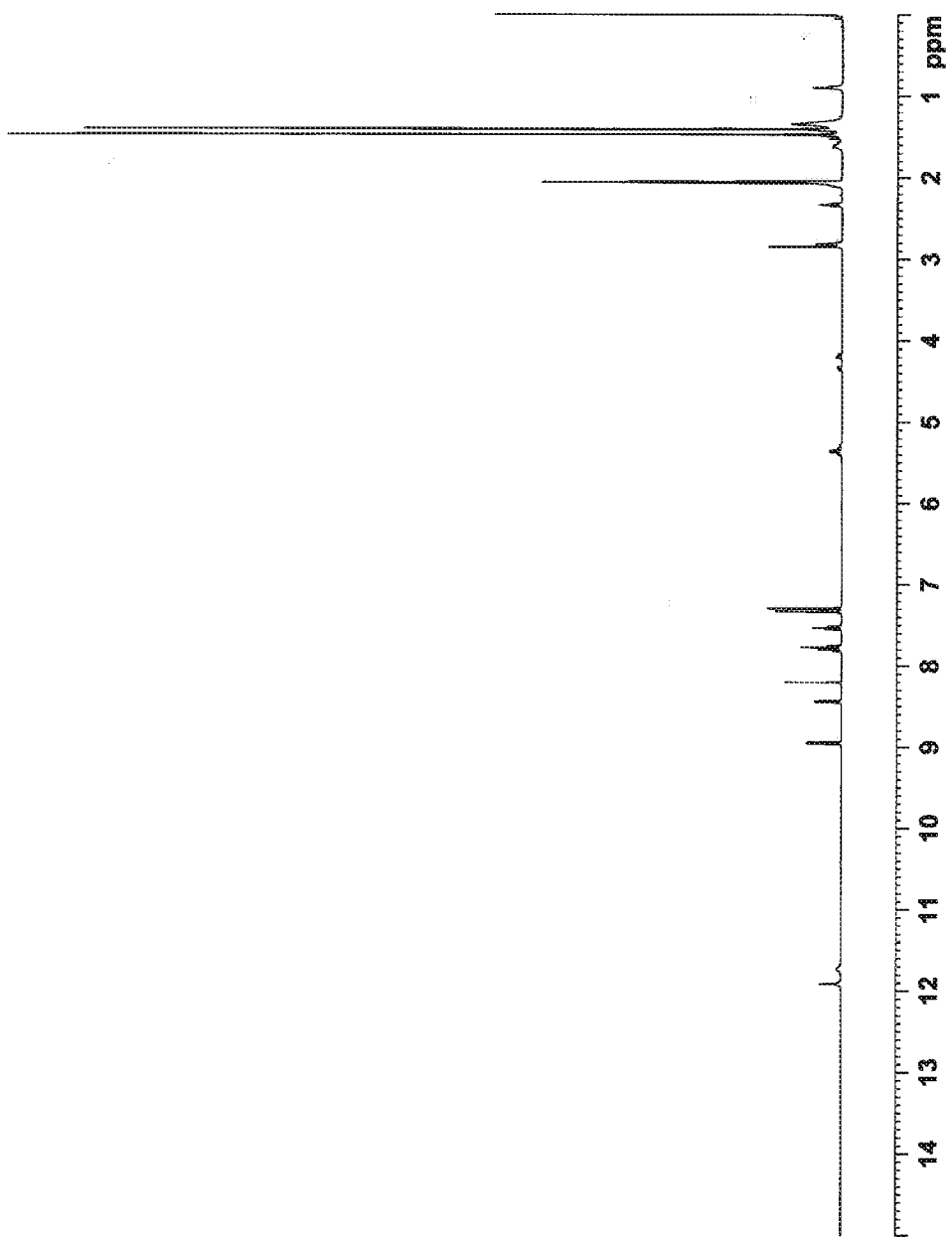
FIG. 17 is an examplary $^1H$ NMR spectrum of Compound 1:glyceryltrilinoleate in acetone-$d_6$.

The characterization of Compound 1:glyceryltrilinoleate is detailed later in the Example section. FIG. 13 is an examplary XRPD pattern of Compound 1:glyceryltrilinoleate. FIG. 14 is an examplary 13C ssNMR spectrum of Compound 1:glyceryltrilinoleate. FIG. 15 is an examplary TGA trace Compound 1:glyceryltrilinoleate. FIG. 16 is an examplary DSC thermogram of Compound 1:glyceryltrilinoleate. FIG. 17 is an examplary 1H NMR spectrum of Compound 1:glyceryltrilinoleate in acetone-d6.

In one embodiment, Compound 1:glyceryltrilinoleate is characterized as having an X-ray powder diffraction pattern with one or more characteristic peaks expressed in 2-theta±0.2 degrees at the following positions: 3.5, 6.0, 6.9, 9.2, 10.9, 12.0, 12.5, 13.8, 15.1, 16.3, 17.0, 18.1, 19.4, 20.2, 21.8, 22.6, 23.8, 25.9, 27.1, 27.8, 28.4, and 32.7.

In one specific embodiment, Compound 1:glyceryltrilinoleate is characterized as having an X-ray powder diffraction pattern with characteristic peaks expressed in 2-theta±0.2 degrees at the following positions: 3.5, 6.9, and 10.9.

In another embodiment, Compound 1:glyceryltrilinoleate is characterized as having a X-ray powder diffraction pattern with characteristic peaks expressed in 2-theta±0.2 degrees at the following positions: 3.5, 6.0, 6.9, 9.2, 10.9, 17.0, 18.1, and 23.8.

In yet another embodiment, Compound 1:glyceryltrilinoleate is characterized as having an X-ray powder diffraction pattern with characteristic peaks expressed in 2-theta±0.2 degrees at the following positions: 3.5, 6.0, 6.9, 9.2, 10.9, 12.0, 12.5, 13.8, 15.1, 16.3, 17.0, 18.1, 19.4, 20.2, 21.8, 22.6, 23.8, 25.9, 27.1, 27.8, 28.4, and 32.7.

In another embodiment, Compound 1:glyceryltrilinoleate is characterized as having an XRPD powder diffraction pattern substantially the same as shown in FIG. 13. The X-ray powder diffraction patterns are obtained at room temperature using Cu K alpha radiation.

In one embodiment, Compound 1:glyceryltrilinoleate is characterized as having a 13C solid state nuclear magnetic resonance (13C ssNMR) spectrum with one or more characteristic peaks expressed in ppm±0.1 selected from: 178.6, 172.8, 171.5, 169.8, 165.1, 155.0, 142.9, 139.3, 137.4, 134.4, 133.1, 130.6, 126.0, 119.4, 117.6, 112.0, 86.5, 67.2, 63.9, 59.7, 35.8, 34.8, 31.7, 30.6, 28.2, and 14.8.

In one embodiment, Compound 1:glyceryltrilinoleate is characterized as having a 13C ssNMR spectrum with characteristic peaks expressed in ppm±0.1 at the following positions: 178.6, 155.0, 130.6, and 119.4.

In another embodiment, Compound 1:glyceryltrioleate is characterized by having a 13C ssNMR spectrum with characteristic peaks expressed in ppm±0.1 at the following positions 178.6, 155.0, 134.4, 130.6, 126.0, 119.4, and 35.8.

In yet another embodiment, Compound 1:glyceryltrilinoleate is characterized as having a 13C ssNMR spectrum with characteristic peaks expressed in ppm±0.1 at the following positions: 178.6, 172.8, 171.5, 169.8, 165.1, 155.0, 142.9, 139.3, 137.4, 134.4, 133.1, 130.6, 126.0, 119.4, 117.6, 112.0, 86.5, 67.2, 63.9, 59.7, 35.8, 34.8, 31.7, 30.6, 28.2, and 14.8.

In one embodiment, Compound 1:glyceryltrilinoleate is characterized as having an endothermic peak in differential scanning calorimetry (DSC) at 182.3° C. In another embodiment, Compound 1:glyceryltrilinoleate is characterized as having an endothermic peak in differential scanning calorimetry (DSC) at 182.3±0.2° C. In another embodiment, Compound 1:glyceryltrilinoleate is characterized as having an endothermic peak in differential scanning calorimetry (DSC) at 182.3±0.5° C.

In some embodiments, the ratio or stoichiometry of Compound 1 to glyceryltrilinoleate in Compound 1:glyceryltrilinoleate is 6:1. In some embodiments, the ratio or stoichiometry of Compound 1 to glyceryltrilinoleate in Compound 1: glyceryltrilinoleate is about 6 to about 1.

Compound 1:Triacetin

The co-crystal comprising Compound 1 and glyceryltriacetate (triacetin) is hereinafter referred to as "Compound 1:glyceryltriacetate" or "Compound 1:triacetin".

Figure 18:
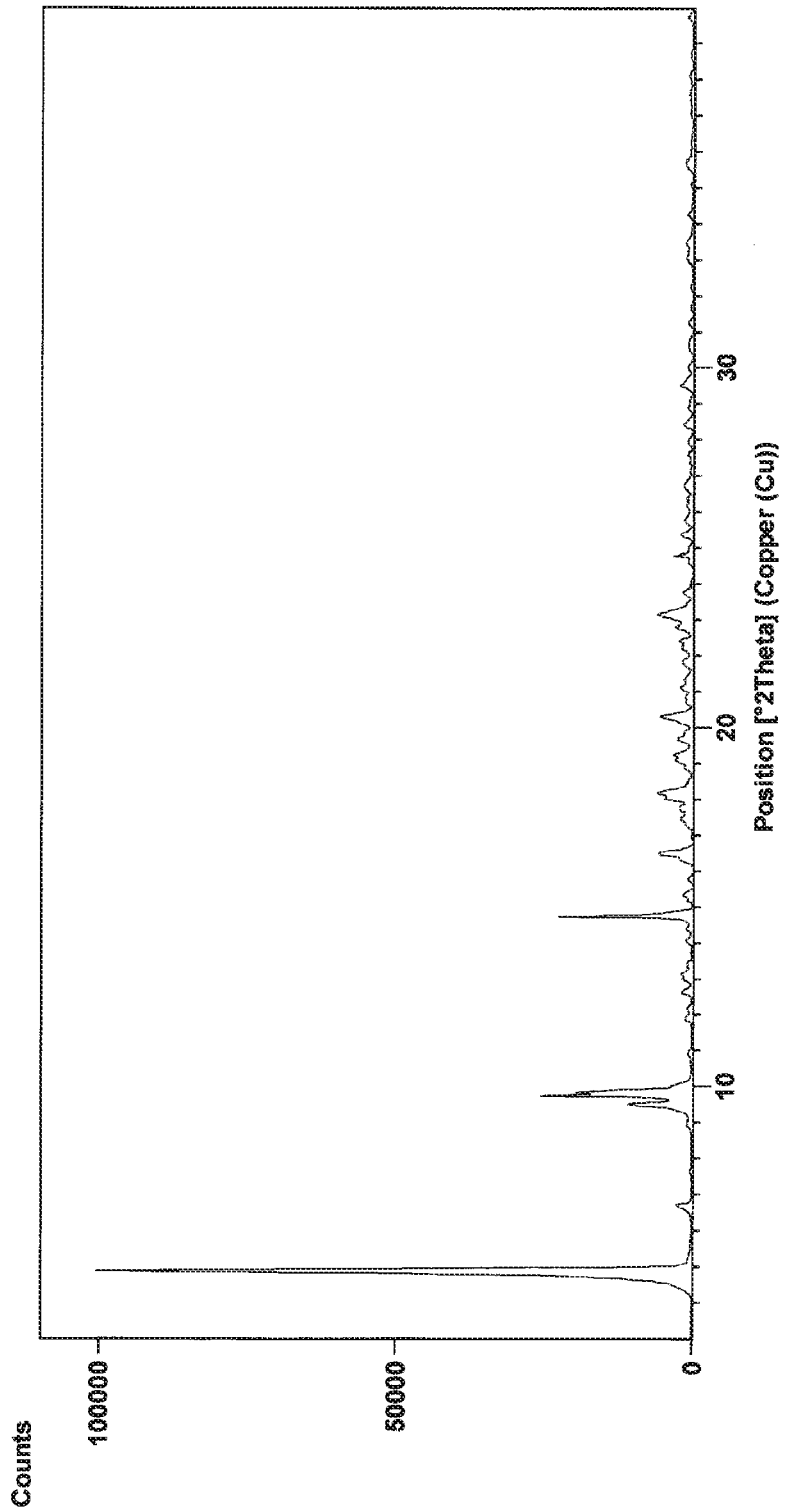
FIG. 18 is an examplary XPRD diffraction pattern of cocrystals of Compound 1 with glyceryltriacetate.
Figure 19:
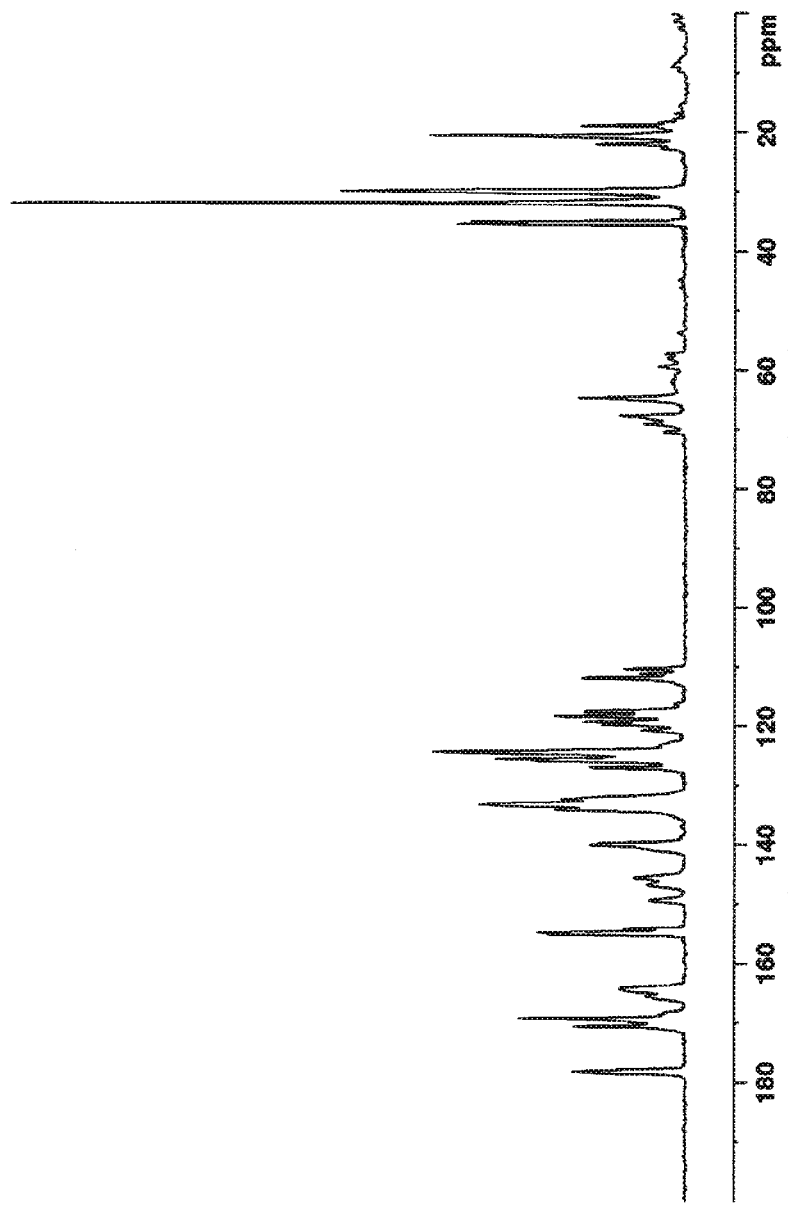
FIG. 19 is an examplary $^{13}C$ ssNMR spectrum of Compound 1:triacetin.
Figure 20:
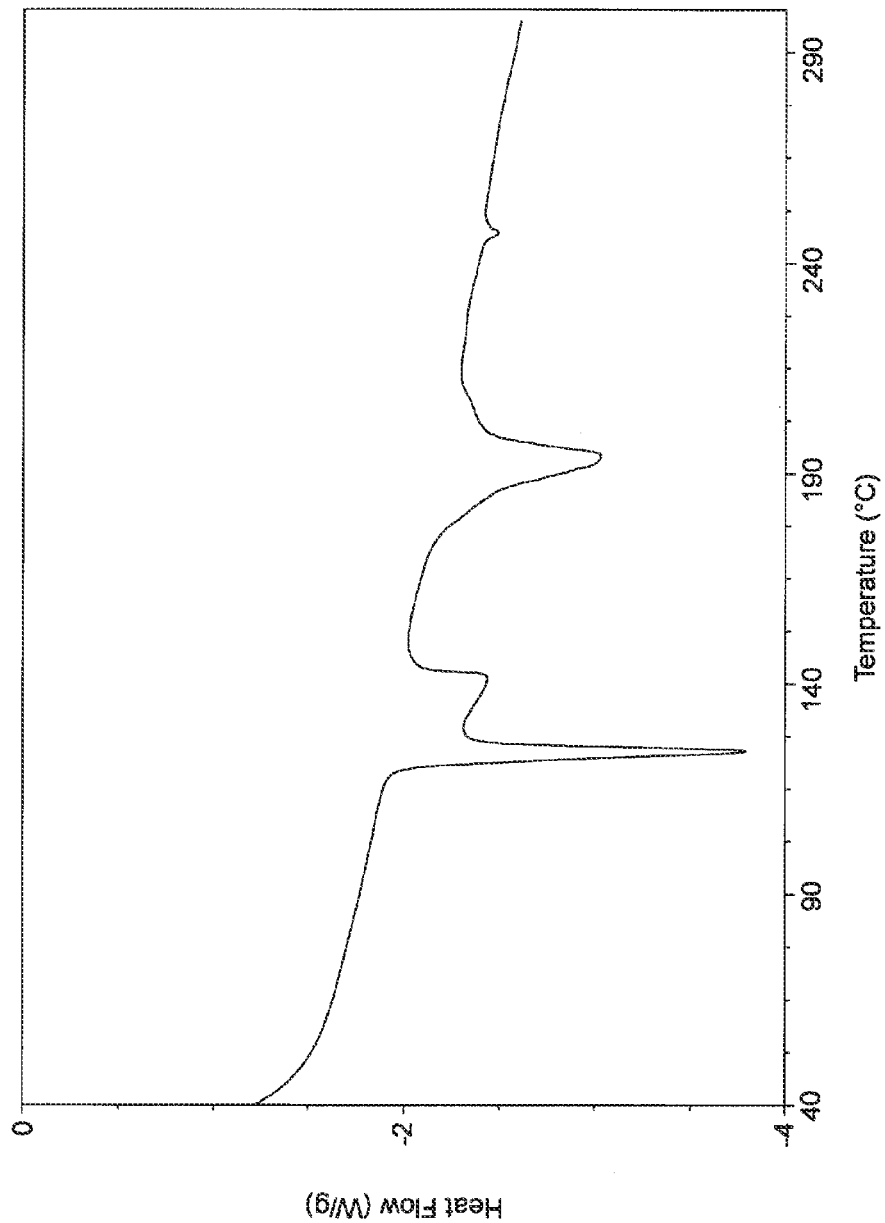
FIG. 20 is an examplary DSC thermogram of Compound 1:glyceryltiacetin.

The characterization of Compound 1:triacetin is detailed later in the Example section. FIG. 18 is an examplary XRPD pattern of Compound 1:triacetin. FIG. 19 is a 13C ssNMR spectrum of Compound 1:triacetin. FIG. 20 is a DSC thermogram of Compound 1:triacetin.

In one embodiment, Compound 1:triacetin is characterized as having an X-ray powder diffraction pattern with one or more characteristic peaks expressed in 2-theta±0.2 degrees at the following positions: 4.9, 9.5, 9.8, and 14.7.

In one embodiment, Compound 1:triacetin is characterized as having an X-ray powder diffraction pattern with one or more characteristic peaks expressed in 2-theta±0.2 degrees at the following positions: 4.9, 9.5, 9.8, 14.7, 16.5, 18.2, and 23.1.

In another embodiment, Compound 1:triacetin is characterized as having an XRPD powder diffraction pattern substantially the same as shown in FIG. 18. The X-ray powder diffraction patterns are obtained at room temperature using Cu K alpha radiation.

In one embodiment, Compound 1:triacetin is characterized as having a 13C ssNMR spectrum with characteristic peaks expressed in ppm±0.1 at the following positions: 178.2, 155.1, 154.8, 119.7, and 119.2.

In one embodiment, Compound 1:triacetin is characterized as having a 13C ssNMR spectrum with characteristic peaks expressed in ppm±0.1 at the following positions: 178.2, 155.1, 154.8, 134.1, 125.9, 125.6, 119.7, 119.2, and 35.3.

In one embodiment, Compound 1:triacetin is characterized as having a 13C ssNMR spectrum with characteristic peaks expressed in ppm±0.1 at the following positions: 178.2, 165.4, 164.3, 155.1, 154.8, 154.1, 149.4, 146.8, 145.6, 140.0, 134.1, 133.2, 132.3, 127.0, 125.9, 125.6, 124.3, 120.6, 119.7, 119.2, 118.3, 117.6, 111.9, 111.1, 110.4, 35.3, 35.0, 31.8, 29.8, 21.9, 20.4, and 18.9.

In one embodiment, Compound 1:triacetin is characterized as having an endothermic peak in differential scanning calorimetry (DSC) at 123.9° C. (peak) that corresponds to the melting of the Compound 1:glyceryltritriacetin co-crystal. This event is followed by another endotherm at 141.9° C. and yet another endotherm at 193.8° C.

Compound 1:Glyceryltributyrate

The co-crystal comprising Compound 1 and glyceryltributyrate is hereinafter referred to as "Compound 1:glyceryltributyrate".

Figure 21:
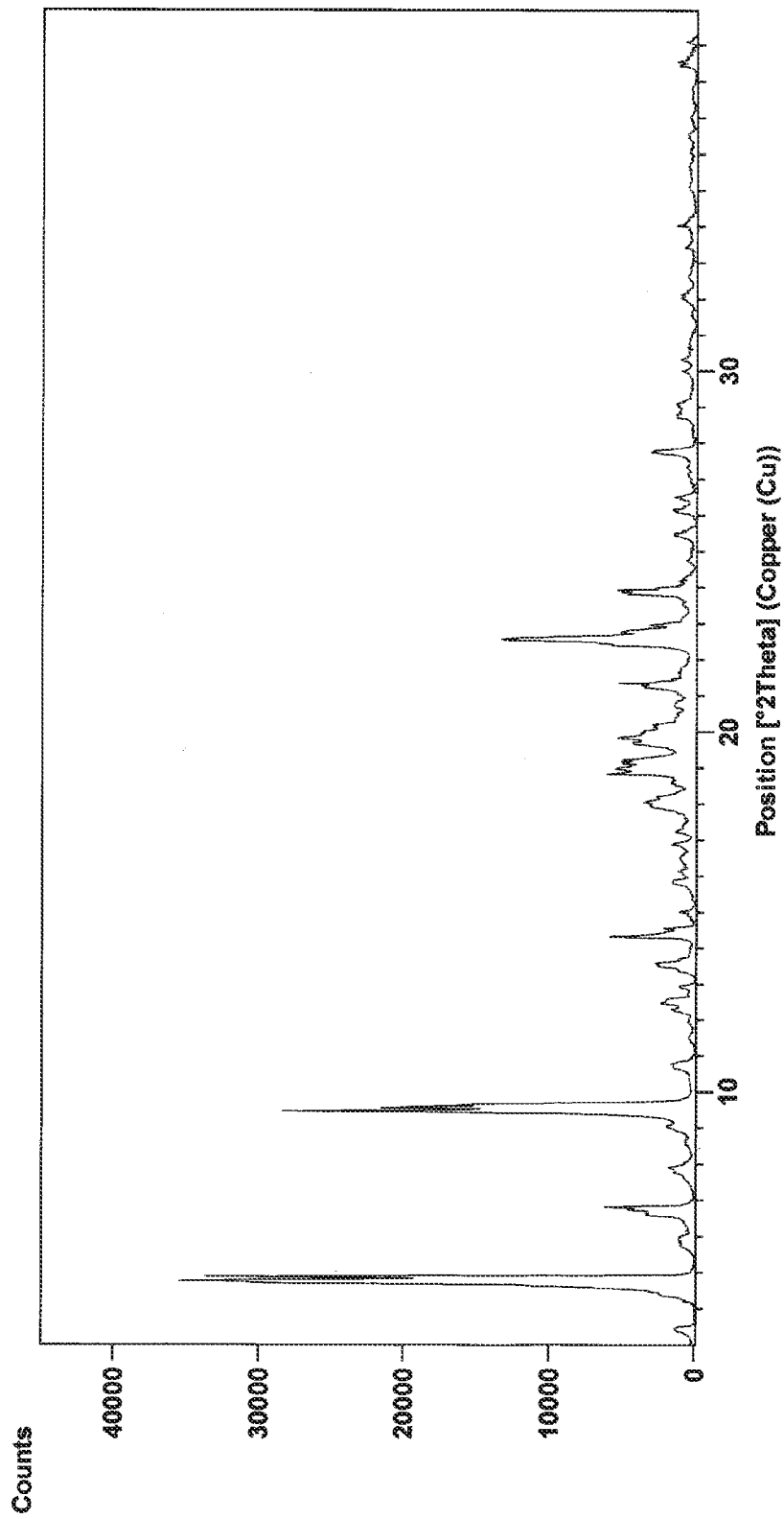
FIG. 21 is an examplary XPRD diffraction pattern of cocrystals of Compound 1 with glyceryltributyrate.

The characterization of Compound 1:glyceryltributyrate is detailed later in the Example section. FIG. 21 is an examplary XRPD pattern of Compound 1: glyceryltributyrate.

In one embodiment, Compound 1:glyceryltributyrate is characterized as having an X-ray powder diffraction pattern with one or more characteristic peaks expressed in 2-theta±0.2 degrees at the following positions: 6.8, 9.5, and 22.6.

In one embodiment, Compound 1:glyceryltributyrate is characterized as having an X-ray powder diffraction pattern with one or more characteristic peaks expressed in 2-theta±0.2 degrees at the following positions: 4.8, 4.9, 6.8, 9.5, 9.6, 14.3, 18.0, 19.0, 19.8, 21.4, 22.6, and 23.8.

In another embodiment, Compound 1:glyceryltributyrate is characterized as having an XRPD powder diffraction pattern substantially the same as shown in FIG. 21. The X-ray powder diffraction patterns are obtained at room temperature using Cu K alpha radiation.

Compound 1:Glyceryltristearate

The co-crystal comprising Compound 1 and glyceryltristearate is hereinafter referred to as "Compound 1:glyceryltristearate".

Figure 22:
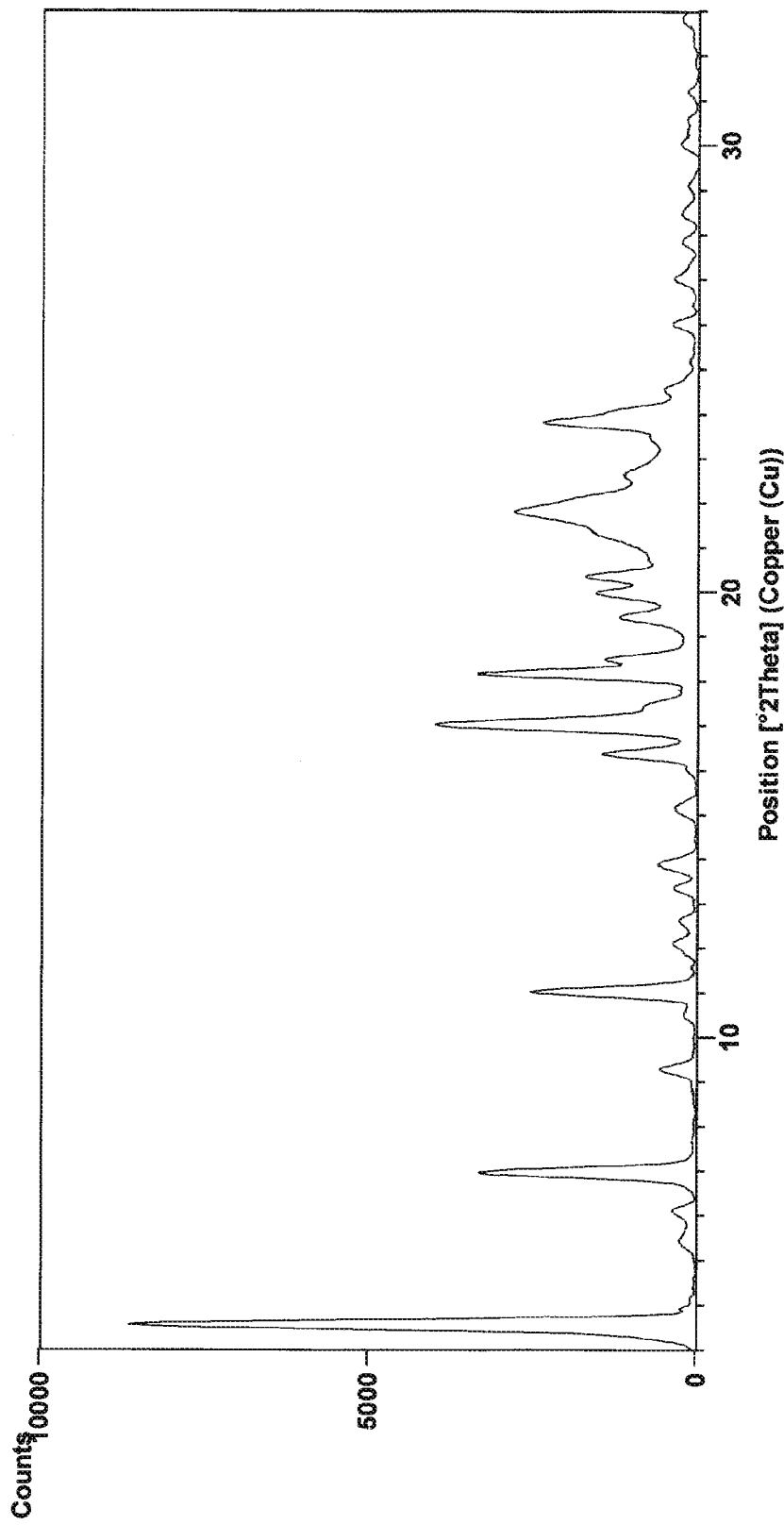
FIG. 22 is an examplary XRPD diffraction pattern of cocrystals of Compound 1 with glyceryltristearate.
Figure 23:
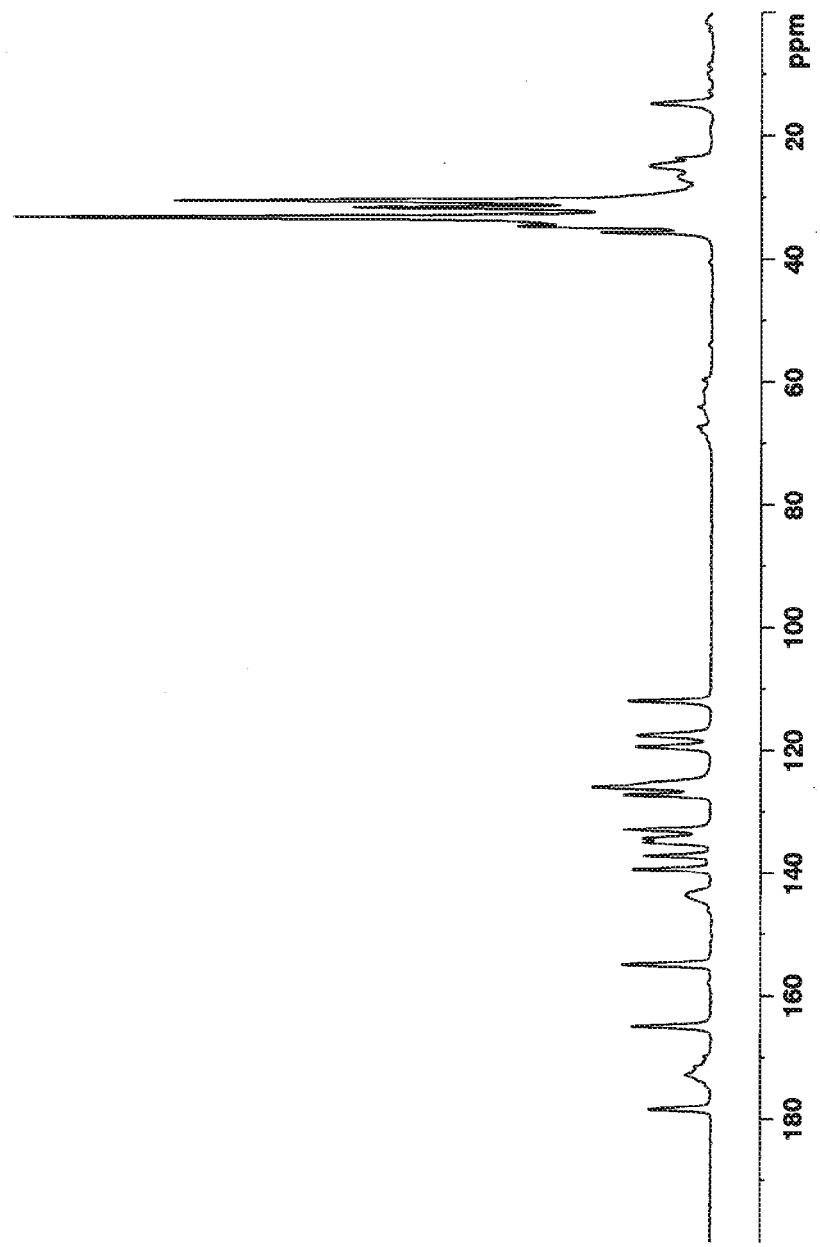
FIG. 23 is an examplary $^{13}C$ ssNMR spectrum of Compound 1:glyceryltristearate.
Figure 24:
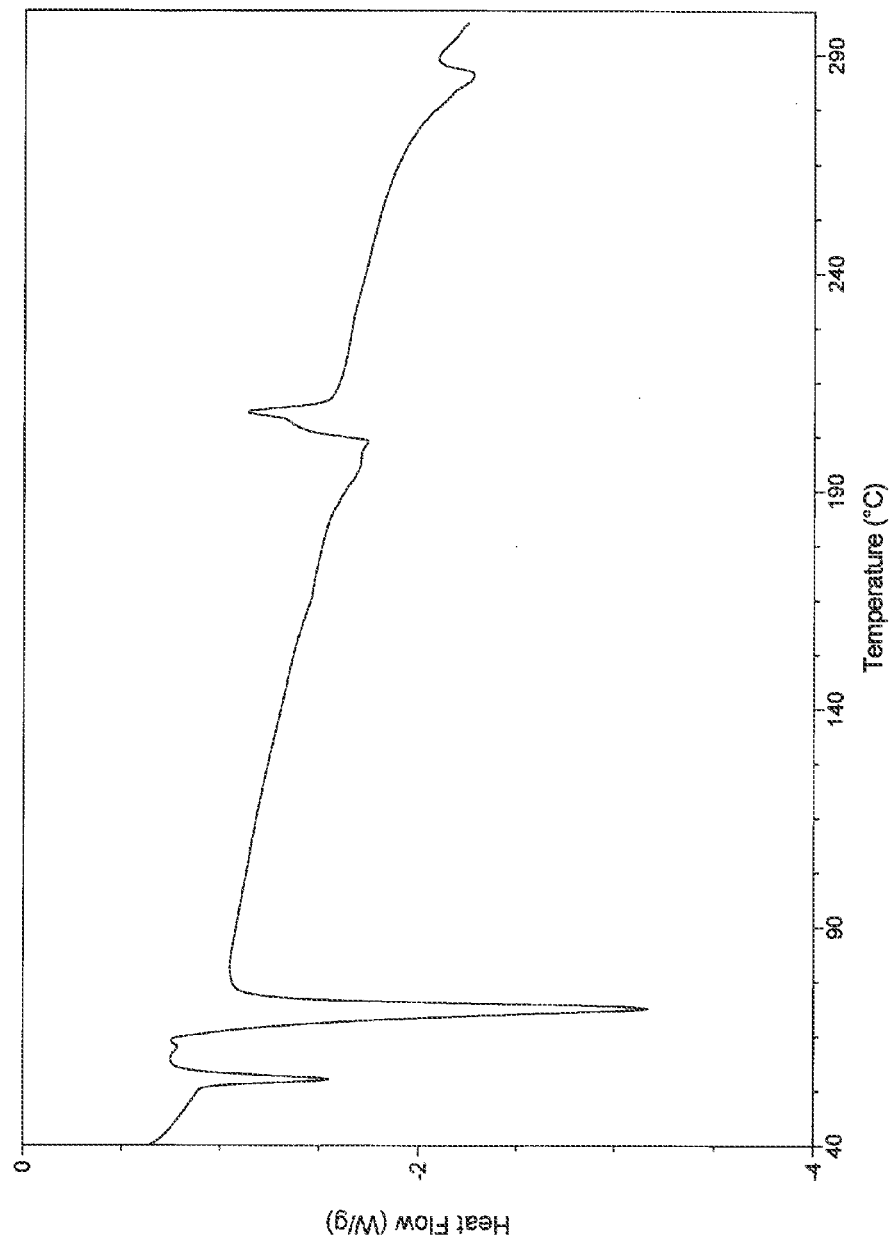
FIG. 24 is an examplary DSC thermogram of Compound 1:glyceryltristearate.

The characterization of Compound 1:glyceryltristearate is detailed later in the Example section. FIG. 22 is an examplary XRPD pattern of Compound 1: glyceryltristearate. FIG. 23 is a 13C ssNMR spectrum of Compound 1:glyceryltristearate. FIG. 24 is a DSC thermogram of Compound 1:glyceryltristearate.

In one embodiment, Compound 1:glyceryltristearate is characterized as having an X-ray powder diffraction pattern with one or more characteristic peaks expressed in 2-theta±0.2 degrees at the following positions: 3.6, 6.9, and 11.0.

In one embodiment, Compound 1:glyceryltristearate is characterized as having an X-ray powder diffraction pattern with one or more characteristic peaks expressed in 2-theta±0.2 degrees at the following positions: 3.6, 6.2, 6.9, 9.3, 11.0, 17.0, and 18.2.

In one embodiment, Compound 1:glyceryltristearate is characterized as having an X-ray powder diffraction pattern with one or more characteristic peaks expressed in 2-theta±0.2 degrees at the following positions: 3.6, 5.4, 6.2, 6.9, 9.3, 11.0, 12.1, 12.6, 13.4, 13.9, 15.4, 16.4, 17.0, 18.2, 18.5, 194, 20.0, 20.4, 21.8, 23.8, 26.0, 27.0, 28.4, 29.1, 29.9, 31.2, and 32.8.

In another embodiment, Compound 1:glyceryltristearate is characterized as having an XRPD powder diffraction pattern substantially the same as shown in FIG. 22. The X-ray powder diffraction patterns are obtained at room temperature using Cu K alpha radiation.

In one embodiment, Compound 1:glyceryltristearate is characterized as having a 13C ssNMR spectrum with characteristic peaks expressed in ppm±0.1 at the following positions: 178.5, 155.0, and 119.5.

In one embodiment, Compound 1:glyceryltristearate is characterized as having a 13C ssNMR spectrum with characteristic peaks expressed in ppm±0.1 at the following positions: 178.5, 155.0, 134.4, 126.1, 119.5, and 35.7.

In one embodiment, Compound 1:glyceryltristearate is characterized as having a 13C ssNMR spectrum with characteristic peaks expressed in ppm±0.1 at the following positions: 178.5, 172.9, 171.6, 169.9, 165.0, 155.0, 143.6, 139.4, 137.2, 135.1, 134.4, 133.0, 127.3, 126.1, 119.5, 117.6, 112.0, 67.3, 64.1, 59.6, 35.7, 34.7, 31.7, 30.6, 23.6, and 14.8.

In one embodiment, Compound 1:glyceryltristearate is characterized as having an endothermic peak in differential scanning calorimetry (DSC) at 55.1° C. that corresponds to the eutectic melt of Compound 1:glyceryltrilstearate co-crystal and glyceryltristearate. This event is followed by another endotherm at 71.3° C., corresponding to the melt of neat glyceryltristearate. Overlapping endotherm at 201.3° C. and exotherm at 208.1° C. correspond to the cocrystal melt and crystallization of neat Compound 1, respectively. Another endotherm at 284.7° C. corresponds to the melt of a neat form of Compound 1.

Compound 1:Glyceryltripalmitate

The co-crystal comprising Compound 1 and glyceryltripalmitate is hereinafter referred to as "Compound 1:glyceryltripalmitate".

Figure 25:
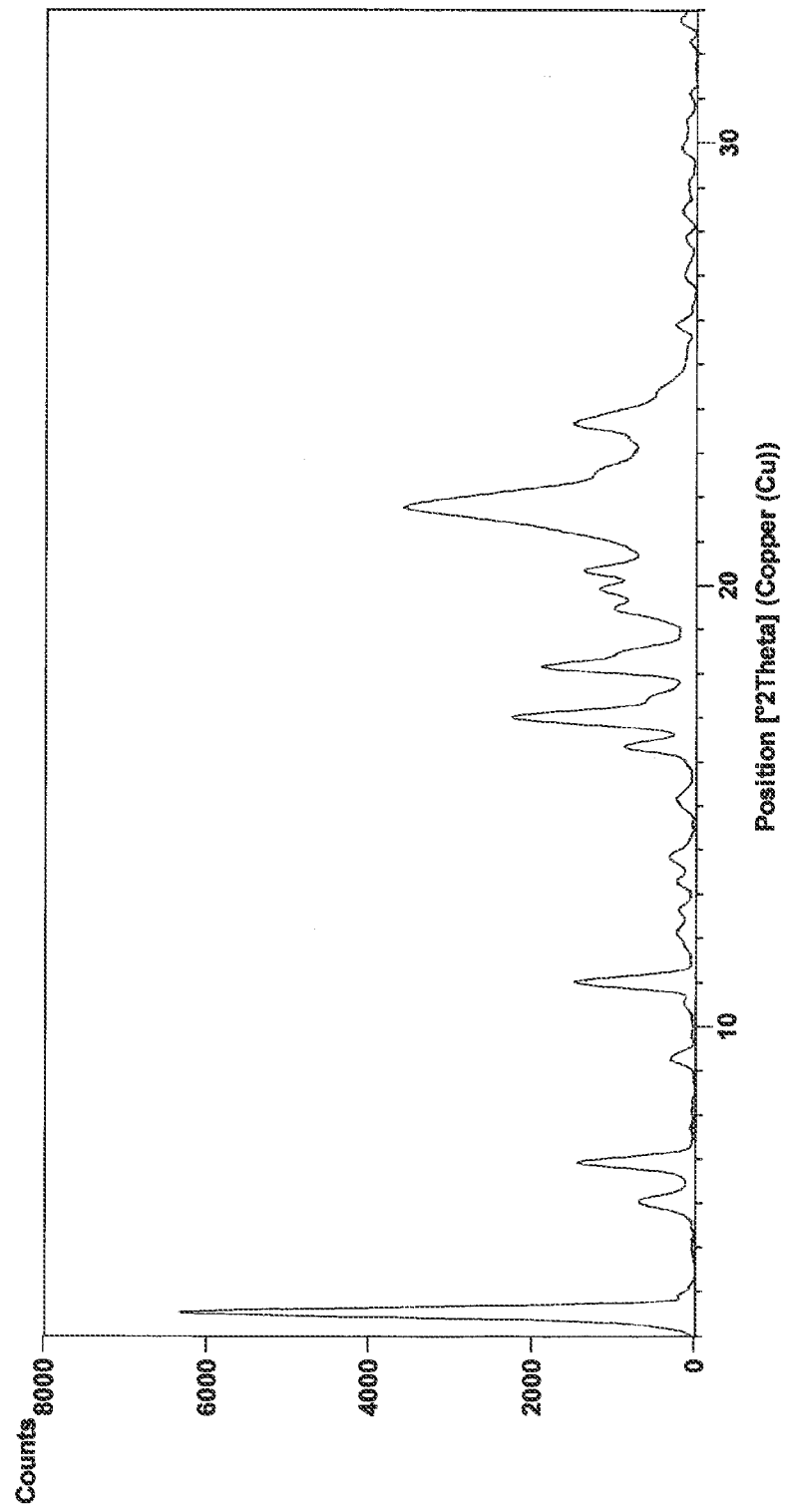
FIG. 25 is an examplary XRPD diffraction pattern of cocrystals of Compound 1 with glyceryltripalmitate.
Figure 26:
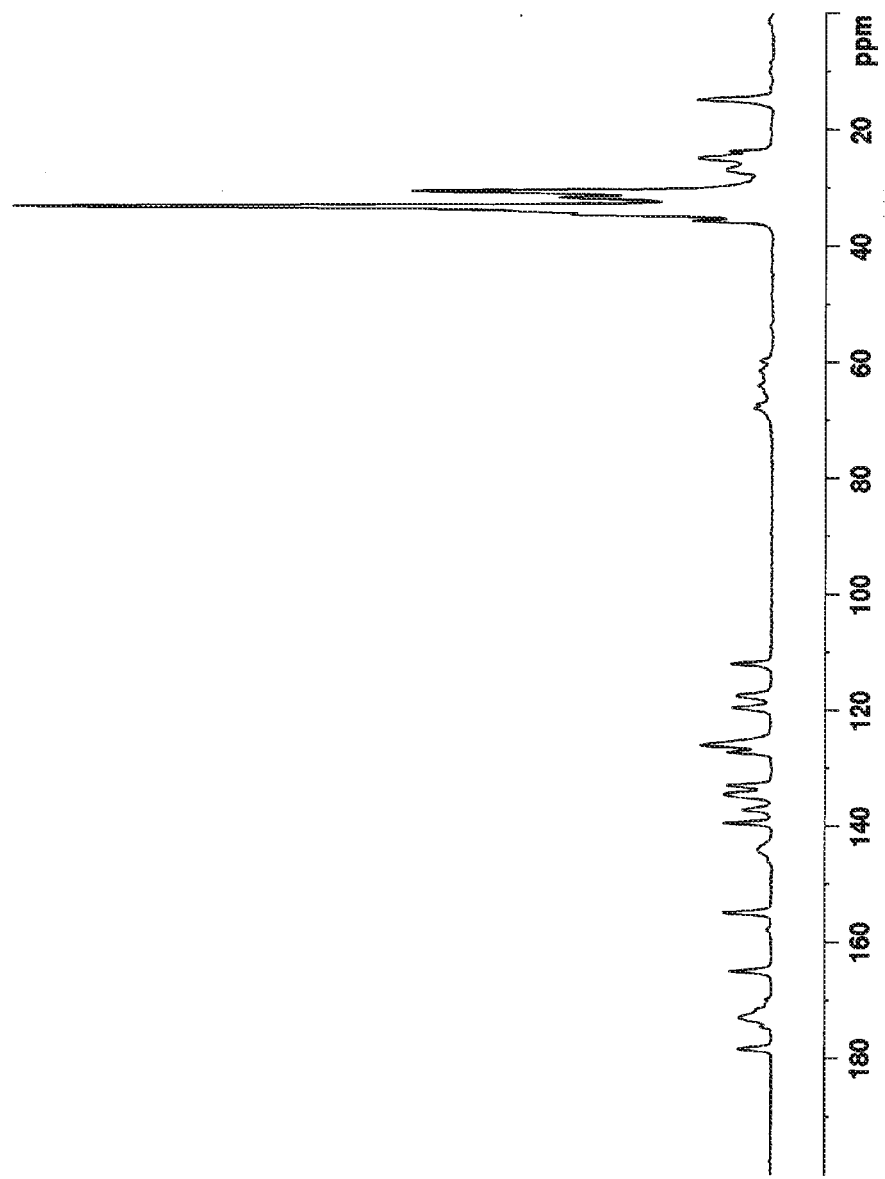
FIG. 26 is an examplary $^{13}C$ ssNMR spectrum of Compound 1:glyceryltripalmitate.
Figure 27:
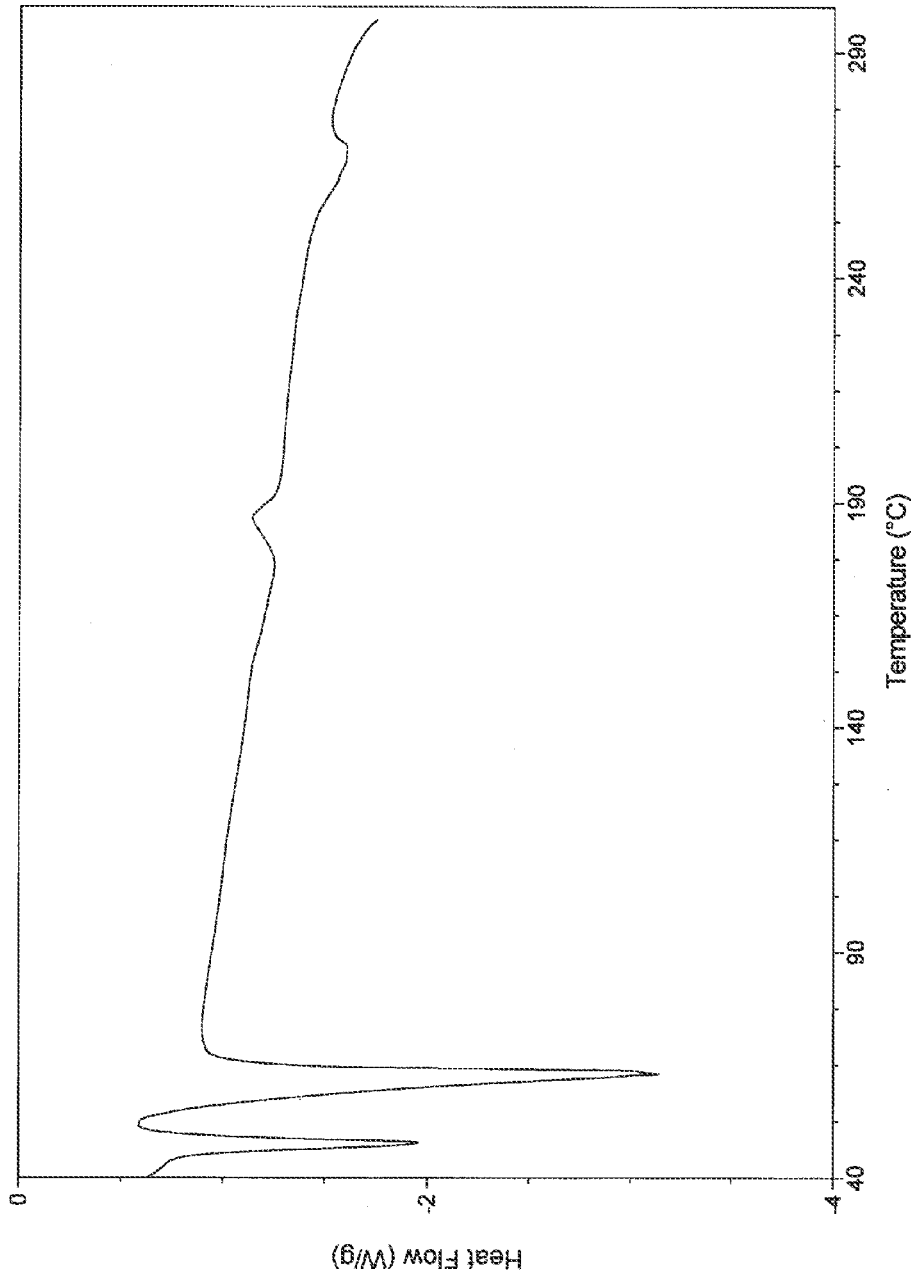
FIG. 27 is an examplary DSC thermogram of Compound 1:glyceryltripalmitate.

The characterization of Compound 1:glyceryltripalmitate is detailed later in the Example section. FIG. 25 is an examplary XRPD pattern of Compound 1: glyceryltripalmitate. FIG. 26 is a 13C ssNMR spectrum of Compound 1:glyceryltripalmitate. FIG. 27 is a DSC thermogram of Compound 1:glyceryltripalmitate.

In another embodiment, Compound 1:glyceryltripalmitate is characterized as having an X-ray powder diffraction pattern with one or more characteristic peaks expressed in 2-theta±0.2 degrees at the following positions: 3.5, 6.9, and 11.0.

In one embodiment, Compound 1:glyceryltripalmitate is characterized as having an X-ray powder diffraction pattern with one or more characteristic peaks expressed in 2-theta±0.2 degrees at the following positions: 3.5, 6.0, 6.9, 9.3, 17.0, 18.2, and 23.7.

In one embodiment, Compound 1:glyceryltripalmitate is characterized as having an X-ray powder diffraction pattern with one or more characteristic peaks expressed in 2-theta±0.2 degrees at the following positions: 3.5, 6.0, 6.9, 9.3, 11.0, 13.8, 15.1, 16.3, 17.0, 18.2, 19.4, 19.9, 20.3, 21.8, and 23.7.

In another embodiment, Compound 1:glyceryltripalmitate is characterized as having an XRPD powder diffraction pattern substantially the same as shown in FIG. 25. The X-ray powder diffraction patterns are obtained at room temperature using Cu K alpha radiation.

In one embodiment, Compound 1:glyceryltripalmitate is characterized as having a 13C ssNMR spectrum with characteristic peaks expressed in ppm±0.1 at the following positions: 178.4, 155.0, 144.0, and 119.6.

In one embodiment, Compound 1:glyceryltripalmitate is characterized as having a 13C ssNMR spectrum with characteristic peaks expressed in ppm±0.1 at the following positions: 178.4, 155.0, 134.5, 126.0, 119.6, and 35.7.

In one embodiment, Compound 1:glyceryltripalmitate is characterized as having a 13C ssNMR spectrum with characteristic peaks expressed in ppm±0.1 at the following positions: 178.4, 173.0, 169.9, 165.0, 155.0, 144.0, 139.5, 137.2, 134.5, 133.0, 127.2, 126.0, 119.6, 117.5, 112.0, 67.2, 64.0, 59.7, 35.7, 34.6, 31.7, 30.6, 23.7, and 14.8.

In one embodiment, Compound 1:glyceryltripalmitate is characterized as having an endothermic peak in differential scanning calorimetry (DSC) at 47.7° C. (peak) that corresponds to the eutectic melt of ivacaftor:glyceryltripalmitate co-crystal and glyceryltripalmitate. This event is followed by another endotherm at 63.0° C. (peak), corresponding to the melt of neat glyceryltripalmitate. Overlapping endotherm at 174.9° C. (peak) and exotherm at 186.7° C. (peak) correspond to the cocrystal melt and crystallization of neat ivacaftor, respectively. Another endotherm at 266.2° C. (peak) corresponds to the melt of a neat form of ivacaftor.

Compound 1:Glyceryltridodecanoate

The co-crystal comprising Compound 1 and glyceryltridodecanoate is hereinafter referred to as "Compound 1:glyceryltridodecanoate".

Figure 28:
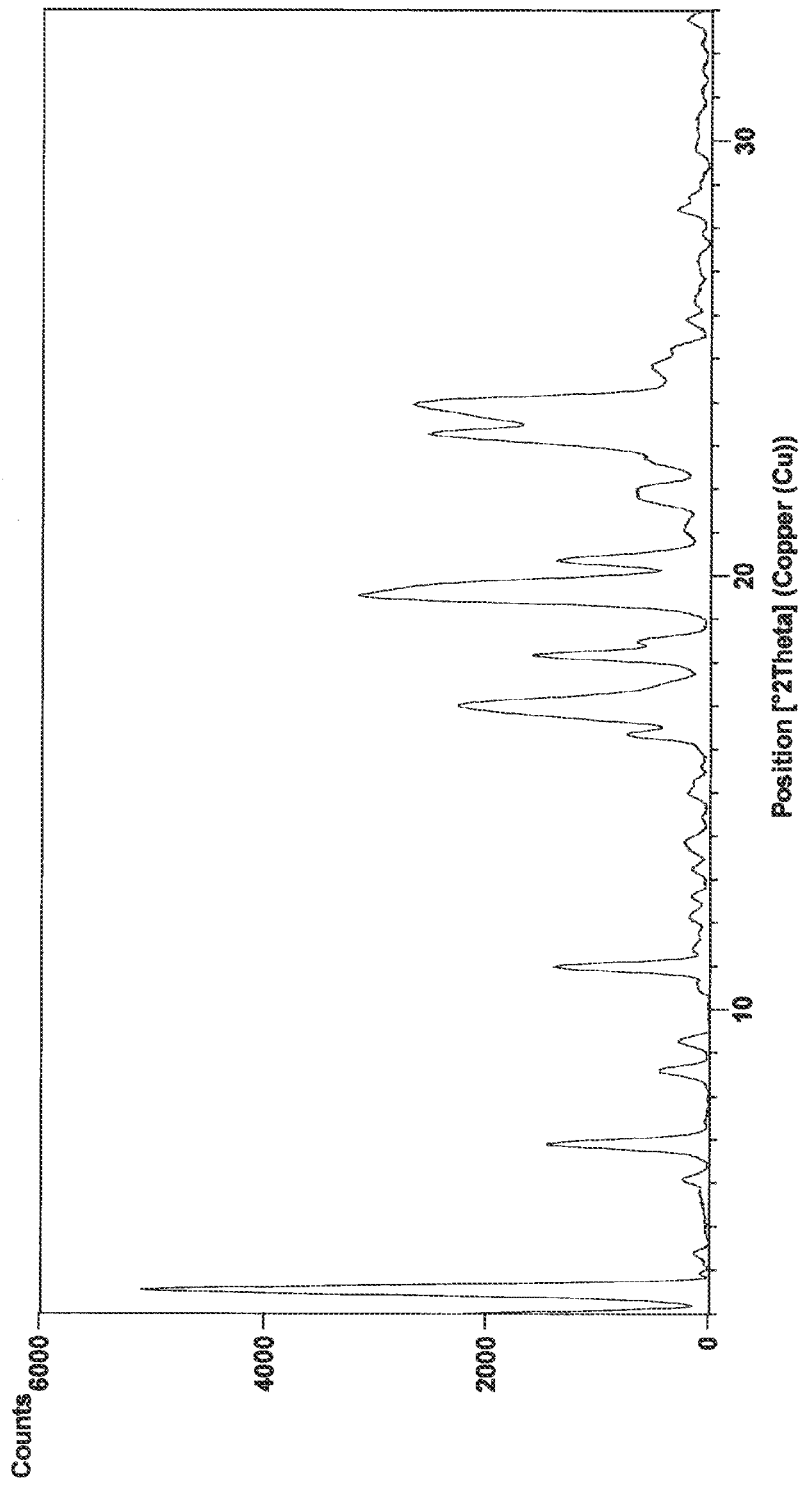
FIG. 28 is an examplary XRPD diffraction pattern of cocrystals of Compound 1 with glyceryltridodecanoate.
Figure 29:
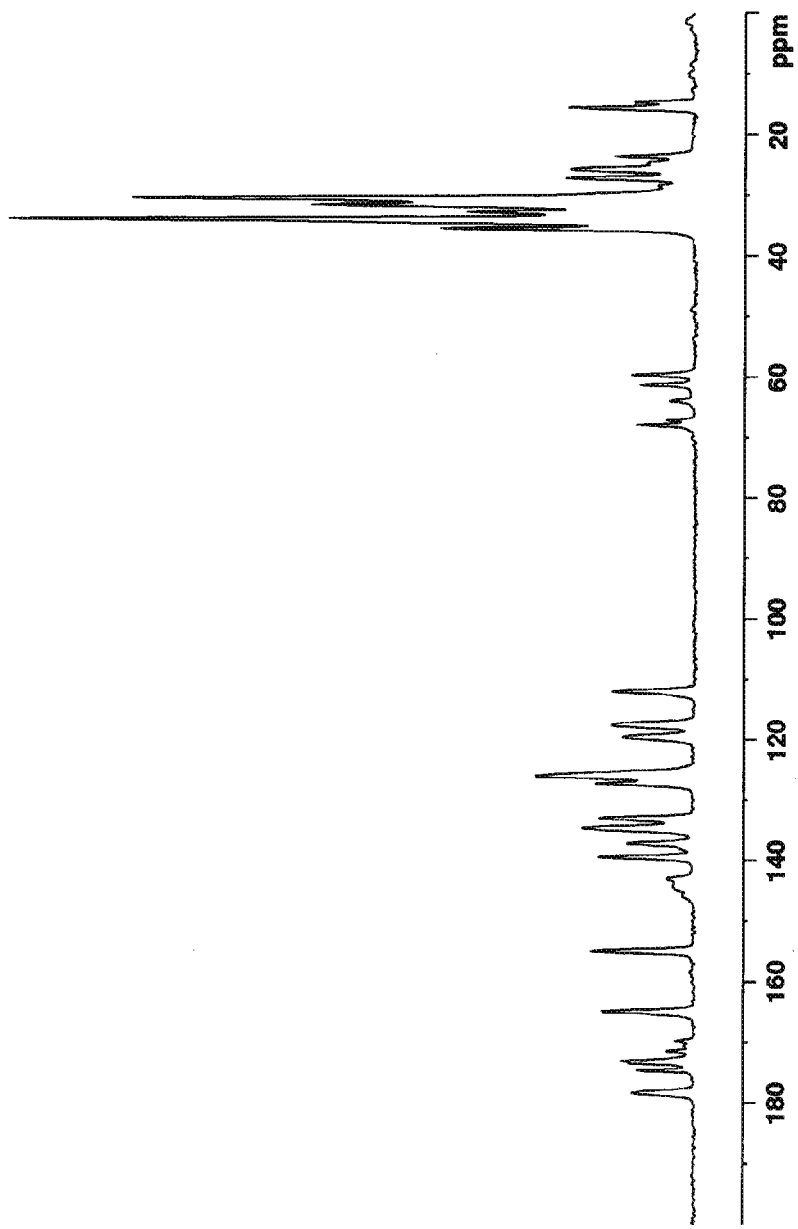
FIG. 29 is an examplary $^{13}C$ ssNMR spectrum of Compound 1:glyceryltridodecanoate.

The characterization of Compound 1:glyceryltridodecanoate is detailed later in the Example section. FIG. 28 is an examplary XRPD pattern of Compound 1:glyceryltridodecanoate. FIG. 29 is a 13C ssNMR spectrum of Compound 1:glyceryltridodecanoate.

In one embodiment, Compound 1:glyceryltridodecanoate is characterized as having an X-ray powder diffraction pattern with one or more characteristic peaks expressed in 2-theta±0.2 degrees at the following positions: 3.5, 4.4, 6.1, 6.9, 8.6, 9.3, 11.0, 12.1, 12.6, 13.2, 13.8, 15.0, 16.3, 17.0, 18.1, 19.5, 20.3, 21.9, 23.3, 23.9, 24.8, and 30.2.

In another embodiment, Compound 1:glyceryltridodecanoate is characterized as having an X-ray powder diffraction pattern with one or more characteristic peaks expressed in 2-theta±0.2 degrees at the following positions: 3.5, 6.9, and 11.0.

In another embodiment, Compound 1:glyceryltridodecanoate is characterized as having an X-ray powder diffraction pattern with one or more characteristic peaks expressed in 2-theta±0.2 degrees at the following positions: 3.5, 6.1, 6.9, 9.3, 11.0, 17.0, 18.1, and 23.3.

In another embodiment, Compound 1:glyceryltridodecanoate is characterized as having an XRPD powder diffraction pattern substantially the same as shown in FIG. 28. The X-ray powder diffraction patterns are obtained at room temperature using Cu K alpha radiation.

In one embodiment, Compound 1:glyceryltridodecanoate is characterized as having a 13C ssNMR spectrum with characteristic peaks expressed in ppm±0.1 at the following positions: 178.4, 155.0, and 119.6.

In one embodiment, Compound 1:glyceryltridodecanoate is characterized as having a 13C ssNMR spectrum with characteristic peaks expressed in ppm±0.1 at the following positions: 178.4, 155.0, 134.6, 126.1, 119.6, and 35.6.

In one embodiment, Compound 1:glyceryltridodecanoate is characterized as having a 13C ssNMR spectrum with characteristic peaks expressed in ppm±0.1 at the following positions: 178.4, 173.1, 171.5, 169.8, 165.0, 155.0, 143.0, 139.4, 137.2, 134.6, 133.0, 127.3, 126.1, 119.6, 117.6, 112.1, 67.1, 63.9, 59.7, 35.6, 31.7, 30.6, and 23.6.

Compound 1:Glyceryltrimyristate

The co-crystal comprising Compound 1 and glyceryltrimyristate is hereinafter referred to as "Compound 1:glyceryltrimyristate".

Figure 30:
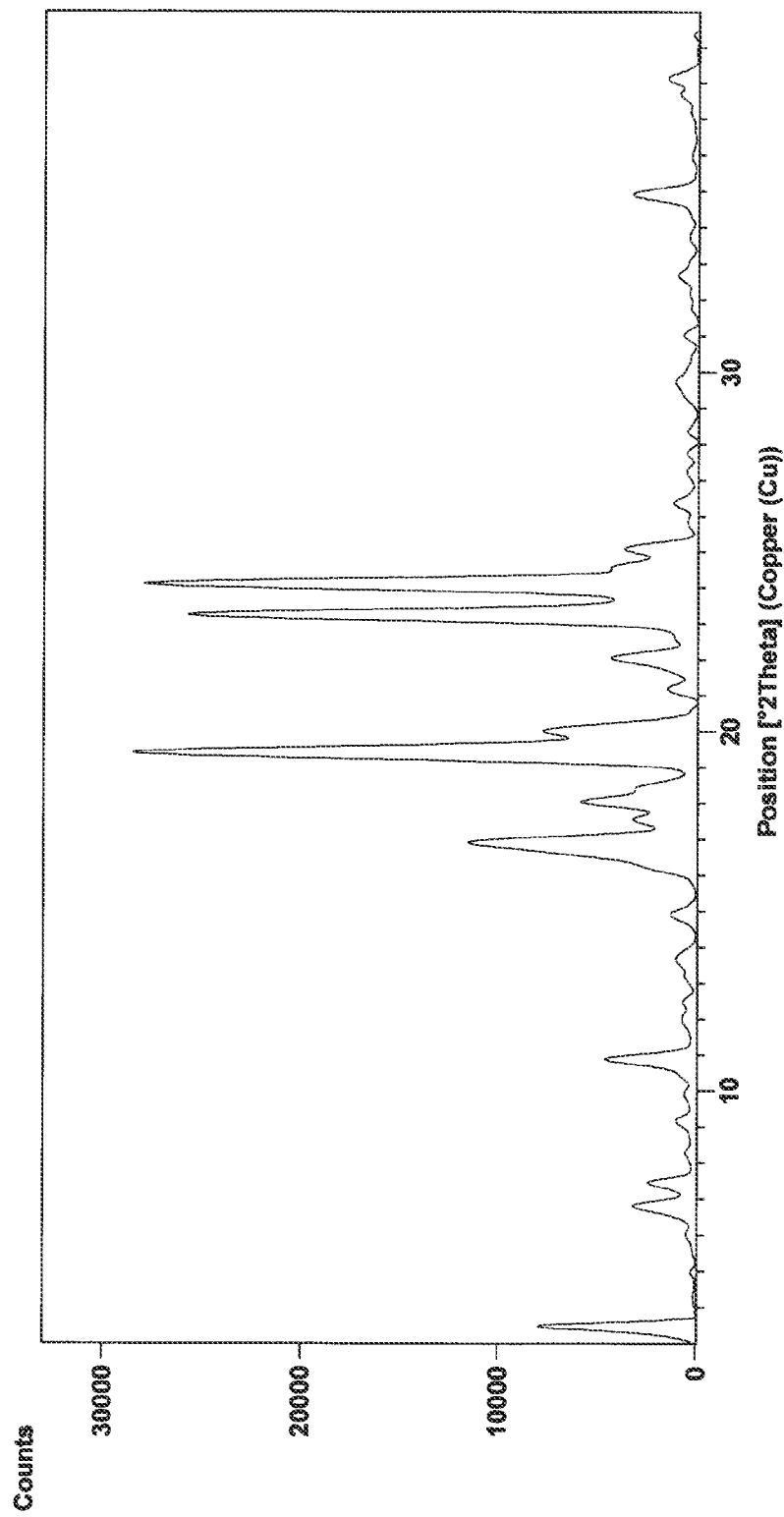
FIG. 30 is an examplary XRPD diffraction pattern of cocrystals of Compound 1 with glyceryltrimyristate.
Figure 31:
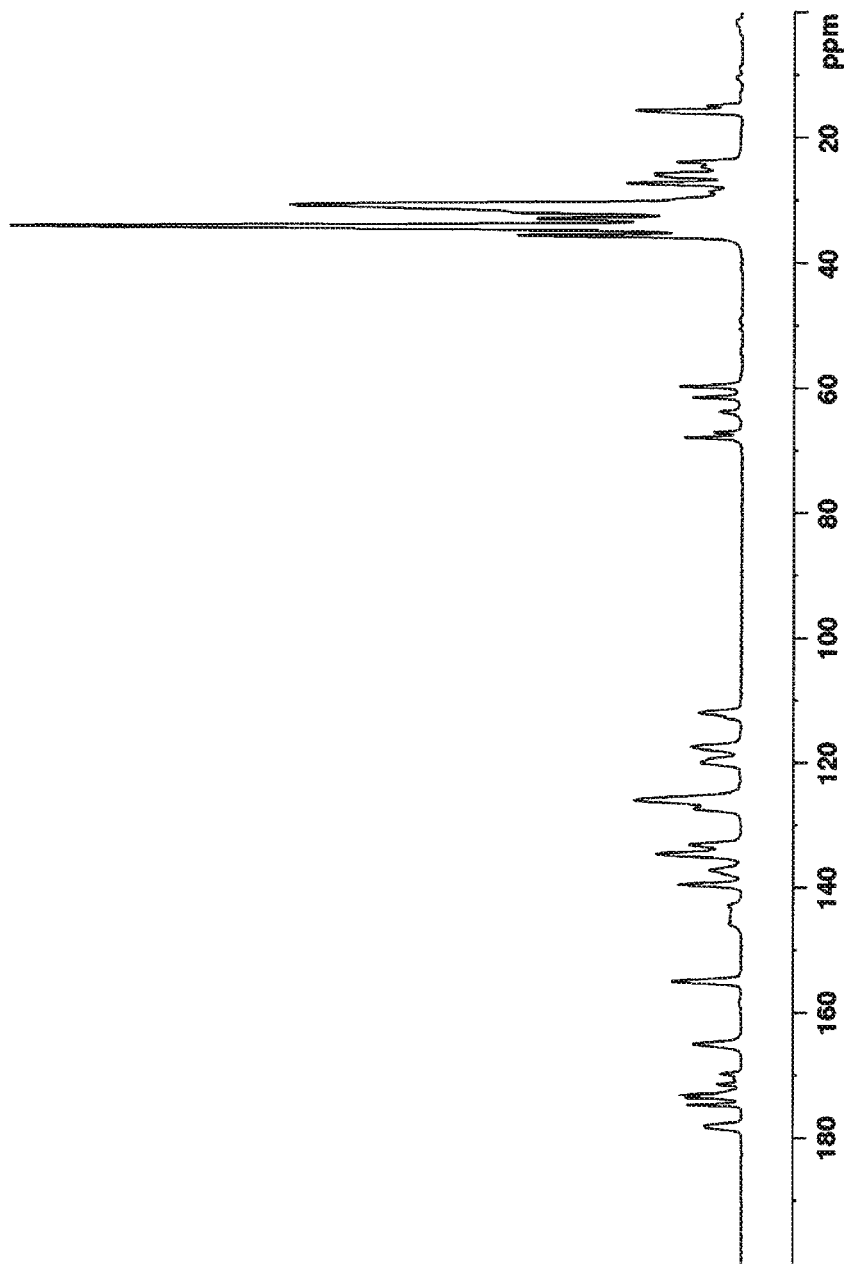
FIG. 31 is an examplary $^{13}C$ ssNMR spectrum of Compound 1:glyceryltrimyristate.
Figure 32:
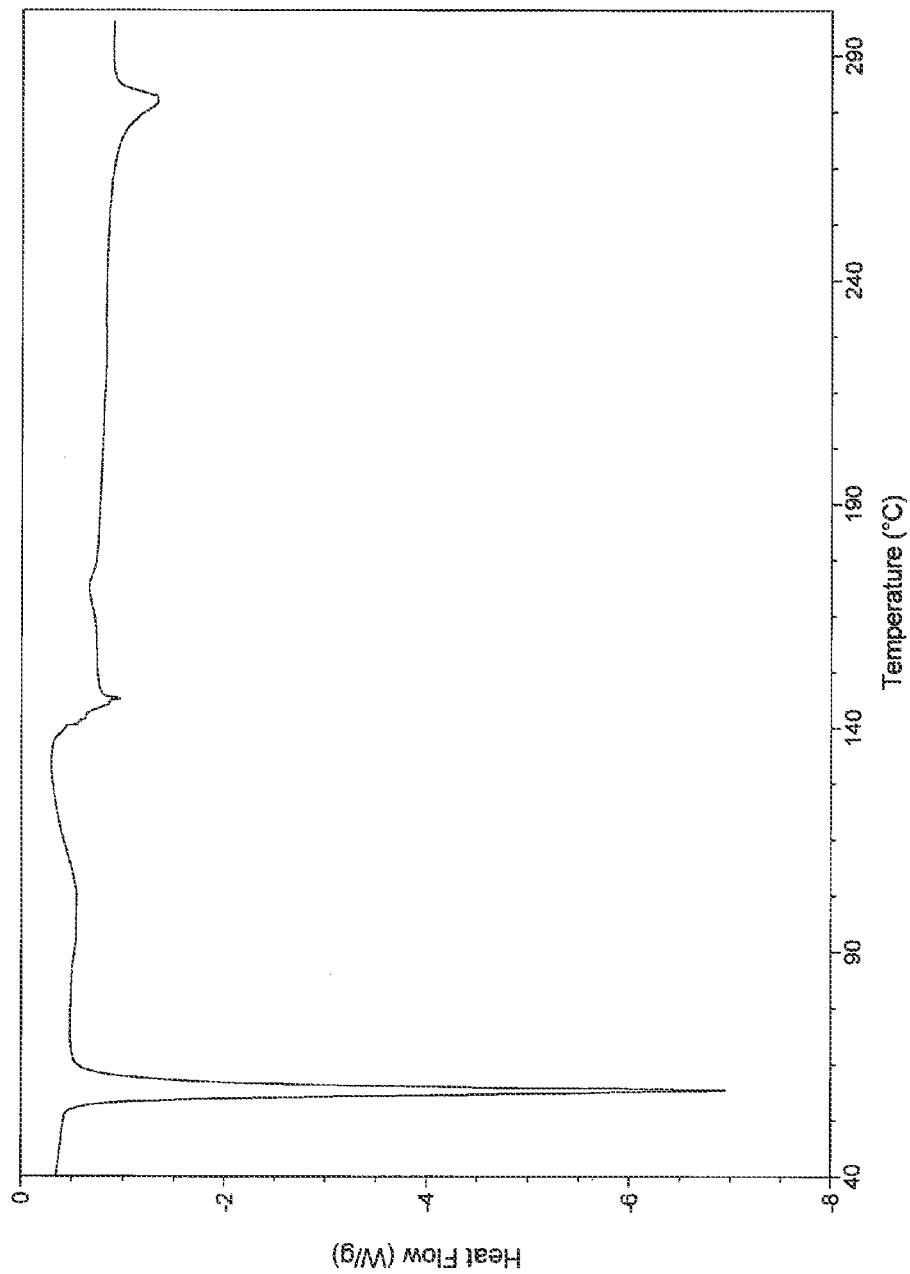
FIG. 32 is an examplary DSC thermogram of Compound 1:glyceryltrimyristate.

The characterization of Compound 1:glyceryltrimyristate is detailed later in the Example section. FIG. 30 is an examplary XRPD pattern of Compound 1:glyceryltrimyristate. FIG. 31 is a 13C ssNMR spectrum of Compound 1:glyceryltrimyristate. FIG. 32 is a DSC thermogram of Compound 1:glyceryltrimyristate.

In one embodiment, Compound 1:glyceryltrimyristate is characterized as having an X-ray powder diffraction pattern with one or more characteristic peaks expressed in 2-theta±0.2 degrees at the following positions: 3.5, 6.8, and 10.9.

In one embodiment, Compound 1:glyceryltrimyristate is characterized as having an X-ray powder diffraction pattern with one or more characteristic peaks expressed in 2-theta±0.2 degrees at the following positions: 3.5, 6,0, 6.8, 9.2, 10.9, 16.9, and 18.0.

In one embodiment, Compound 1:glyceryltrimyristate is characterized as having an X-ray powder diffraction pattern with one or more characteristic peaks expressed in 2-theta±0.2 degrees at the following positions: 3.5, 6.0, 6.8, 7.4, 8.3, 9.2, 9.9, 10.9, 12.0, 12.5, 13.2, 13.7, 14.9, 16.2, 16.9, 17.6, 18.0, 18.5, 19.4, 20.0, 21.2, 22.1, 23.2, 24.1, 25.1, 26.4, 27.2, 27.7, 28.3, 29.2, 29.7, 31.0, and 32.7.

In another embodiment, Compound 1:glyceryltrimyristate is characterized as having an XRPD powder diffraction pattern substantially the same as shown in FIG. 30. The X-ray powder diffraction patterns are obtained at room temperature using Cu K alpha radiation.

In one embodiment, Compound 1:glyceryltrimyristate is characterized as having a 13C ssNMR spectrum with characteristic peaks expressed in ppm±0.1 at the following positions: 178.1, 155.0, and 119.9, In one embodiment, Compound 1:glyceryltrimyristate is characterized as having a 13C ssNMR spectrum with characteristic peaks expressed in ppm±0.1 at the following positions: 178.1, 155.0, 134.6, 126.0, 119.9, and 35.6.

In one embodiment, Compound 1:glyceryltrimyristate is characterized as having a 13C ssNMR spectrum with characteristic peaks expressed in ppm±0.1 at the following positions: 178.1, 171.4, 169.8, 165.0, 155.0, 142.9, 139.5, 137.2, 134.6, 133.1, 127.3, 126.0, 119.9, 117.4, 112.0, 67.0, 63.7, 61.4, and 35.6.

In one embodiment, Compound 1:glyceryltrimyristate is characterized as having an endothermic peak in differential scanning calorimetry (DSC) at 59.2° C. that corresponds to the melt of glyceryltrimyristate. This event is followed by a broad exotherm at 134.4° C. that is overlapping with an endotherm. This event is followed by an exotherm at 171.3° C. corresponding to the crystallization of neat Compound 1. Another endotherm at 280.1° C. corresponds to the melt of a neat form of Compound 1.

Compound 1:Glyceryltrihexanoate

The co-crystal comprising Compound 1 and glyceryltrihexanoate is hereinafter referred to as "Compound 1:glyceryltrihexanoate".

Figure 33:
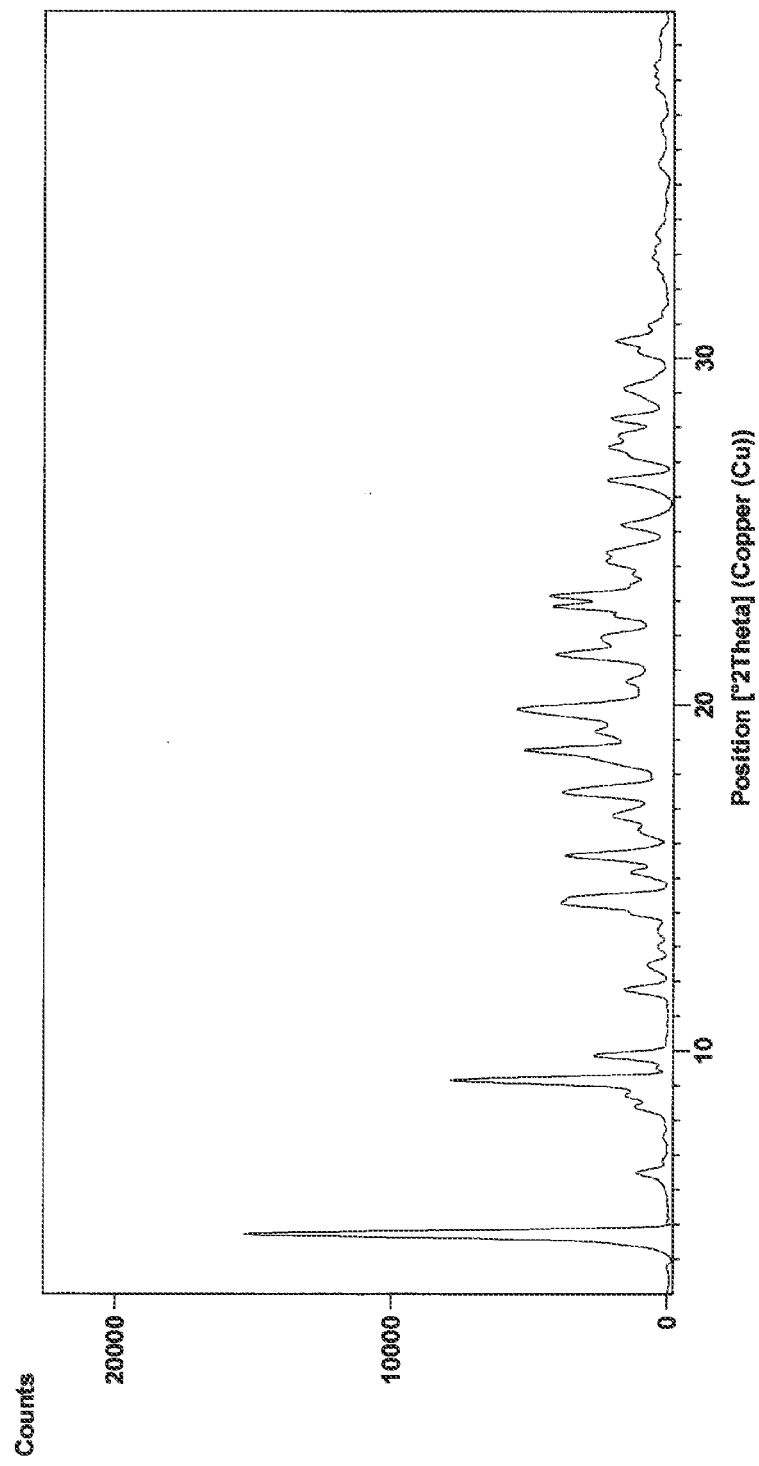
FIG. 33 is an examplary XRPD diffraction pattern of cocrystals of Compound 1 with glyceryltrihexanoate.

The characterization of Compound 1:glyceryltrihexanoate is detailed later in the Example section. FIG. 33 is an examplary XRPD pattern of Compound 1: glyceryltrihexanoate.

In one embodiment, Compound 1:glyceryltrihexanoate is characterized as having an X-ray powder diffraction pattern with one or more characteristic peaks expressed in 2-theta±0.2 degrees at the following positions: 6.5, 9.2, and 21.4.

In one embodiment, Compound 1:glyceryltrihexanoate is characterized as having an X-ray powder diffraction pattern with one or more characteristic peaks expressed in 2-theta±0.2 degrees at the following positions: 4.7, 6.5, 9.2, 14.5, 17.4, 18.7, 19.9, 21.4, and 24.4.

In one embodiment, Compound 1:glyceryltrihexanoate is characterized as having an X-ray powder diffraction pattern with one or more characteristic peaks expressed in 2-theta±0.2 degrees at the following positions: 4.7, 6.5, 9.2, 9.9, 11.8, 12.5, 14.5, 15.1, 15.6, 17.4, 18.7, 19.9, 21.4, 23.0, 24.4, 25.2, 26.5, 28.3, 29.1, 30.5, and 35.6.

In another embodiment, Compound 1:glyceryltrihexanoate is characterized as having an XRPD powder diffraction pattern substantially the same as shown in FIG. 33. The X-ray powder diffraction patterns are obtained at room temperature using Cu K alpha radiation.

Compound 1:glyceryltridecanoate

The co-crystal comprising Compound 1 and glyceryltridecanoate is hereinafter referred to as "Compound 1:glyceryltridecanoate".

Figure 34:
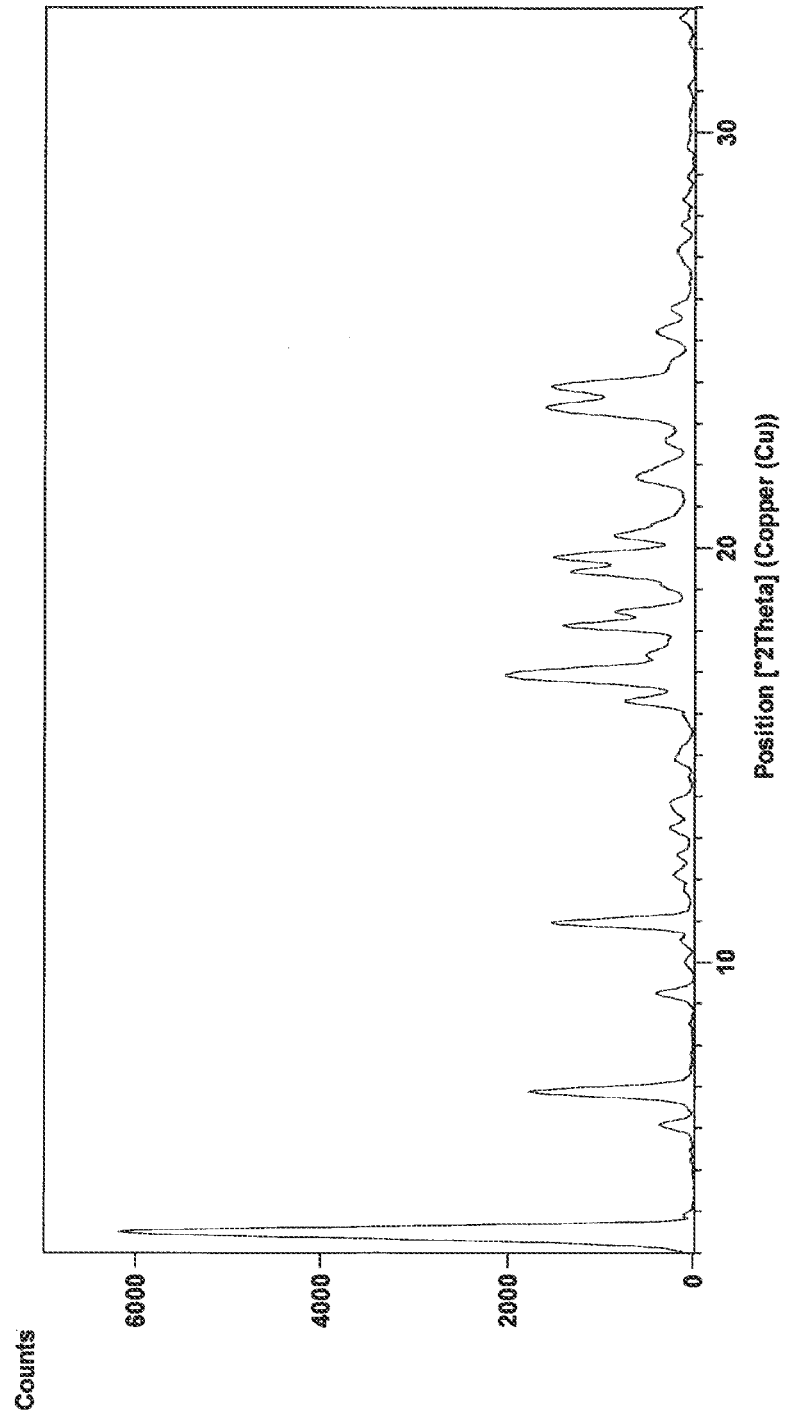
FIG. 34 is an examplary XRPD diffraction pattern of cocrystals of Compound 1 with glyceryltridecanoate.
Figure 35:
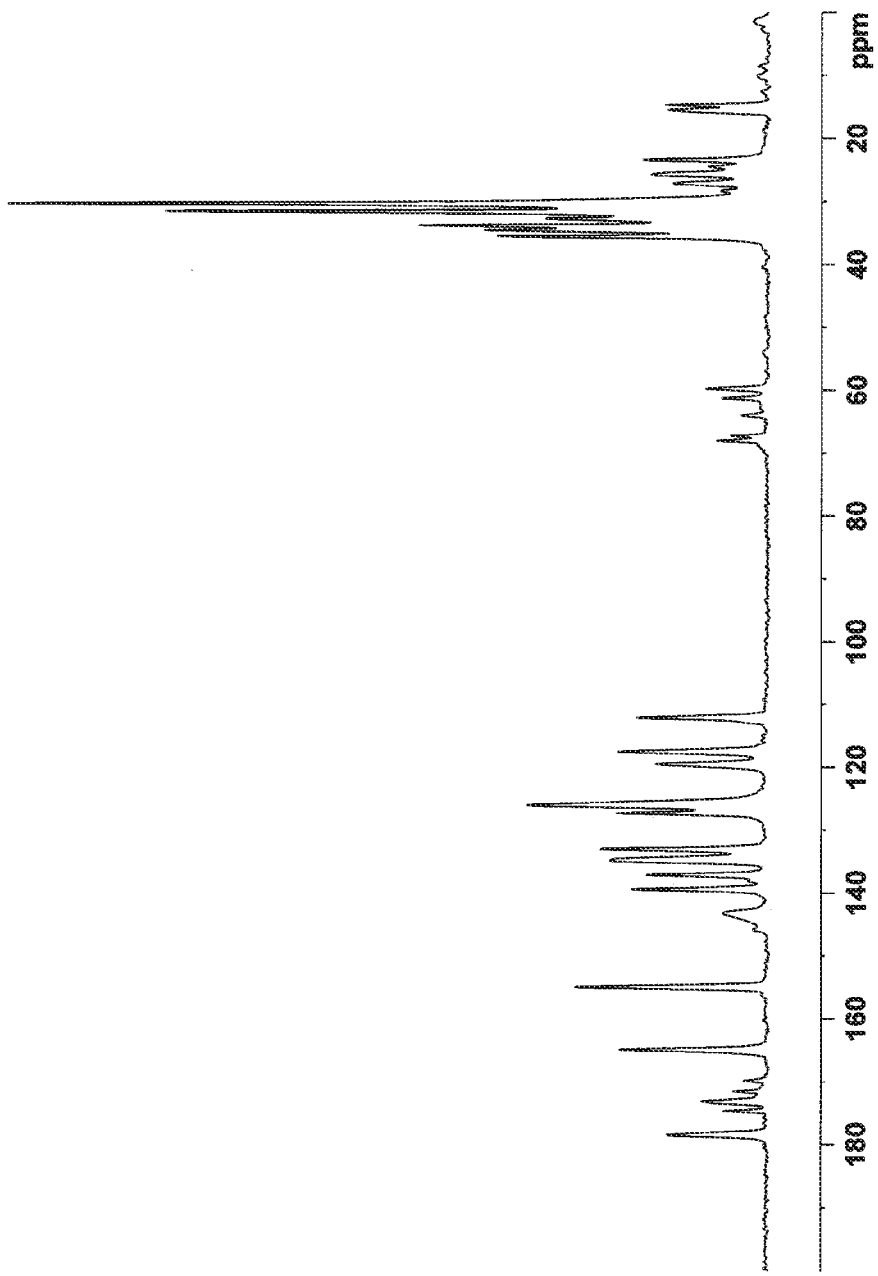
FIG. 35 is an examplary $^{13}C$ ssNMR spectrum of Compound 1:glyceryltridecanoate.

The characterization of Compound 1:glyceryltridecanoate is detailed later in the Example section. FIG. 34 is an examplary XRPD pattern of Compound 1:glyceryltridecanoate. FIG. 35 is a 13C ssNMR spectrum of Compound 1:glyceryltridecanoate.

In one embodiment, Compound 1:glyceryltridecanoate is characterized as having an X-ray powder diffraction pattern with one or more characteristic peaks expressed in 2-theta±0.2 degrees at the following positions: 3.5, 6.9, and 10.9.

In one embodiment, Compound 1:glyceryltridecanoate is characterized as having an X-ray powder diffraction pattern with one or more characteristic peaks expressed in 2-theta±0.2 degrees at the following positions: 3.5, 6.1, 6.9, 9.2, 10.9, 16.9, 18.1, and 23.9.

In one embodiment, Compound 1:glyceryltridecanoate is characterized as having an X-ray powder diffraction pattern with one or more characteristic peaks expressed in 2-theta±0.2 degrees at the following positions: 3.5, 6.1, 6.9, 9.2, 10.9, 11.8, 12.1, 12.6, 13.2, 13.8, 14.9, 16.3, 16.9, 18.1, 18.5, 19.4, 19.8, 20.3, 21.7, 23.4, 23.9, 25.2, 25.8, 27.2, and 28.4.

In another embodiment, Compound 1:glyceryltridecanoate is characterized as having an XRPD powder diffraction pattern substantially the same as shown in FIG. 34. The X-ray powder diffraction patterns are obtained at room temperature using Cu K alpha radiation.

In one embodiment, Compound 1:glyceryltridecanoate is characterized as having a 13C ssNMR spectrum with characteristic peaks expressed in ppm±0.1 at the following positions: 178.5, 155.0, and 119.5.

In one embodiment, Compound 1:glyceryltridecanoate is characterized as having a 13C ssNMR spectrum with characteristic peaks expressed in ppm±0.1 at the following positions: 178.5, 155.0, 134.9, 126.1, and 35.7.

In one embodiment, Compound 1:glyceryltridecanoate is characterized as having a 13C ssNMR spectrum with characteristic peaks expressed in ppm±0.1 at the following positions: 178.5, 171.6, 169.9, 165.0, 155.0, 143.3, 139.5, 137.2, 134.9, 133.0, 127.3, 126.1, 119.5, 117.6, 112.1, 67.2, 64.0, 59.8, 35.7, 34.7, 31.7, 30.5, and 25.8, 23.5.

Dissolution Comparison

Figure 36:
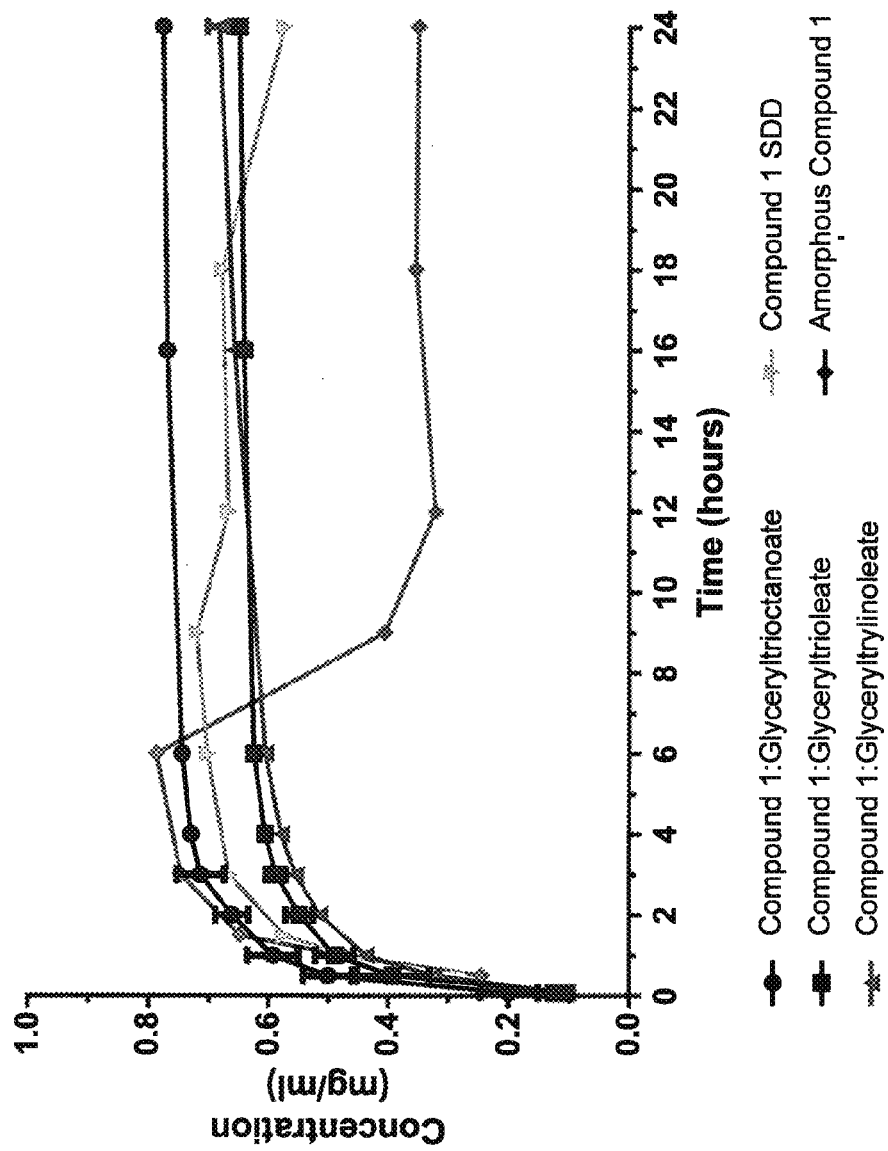
FIG. 36 is a comparison of examplary dissolution profiles in FeSSIF of Compound 1:glyceryltrioctanoate (filled circles) Compound 1:glyceryltrioleate (filled squares), and Compound 1:glyceryltrilinoleate (filled triangles) with amorphous Compound 1 (filled diamonds), Compound 1 spray dried dispersion (SDD) (filled upside-down triangles).

A comparison of the dissolution profiles in FeSSIF of the Compound 1:glyceryltrioctanoate, Compound 1:glyceryltrioleate, and Compound 1:glyceryltrilinoleate with amorphous Compound 1 and Compound 1 SDD (amorphous Compound 1 dispersed in HPMCAS (hydroxypropyl methylcellulose acetate succinate or hypromellose acetate succinate) (i.e., spray dried dispersion (SDD)) is shown in FIG. 36. Compound 1 has a solubility-limited oral bioavailability, and maintenance of high solution concentration in FeSSIF is required for any solid form of Compound 1 to be viable for oral dosage form development. The Compound 1:triglyceride co-crystals have similar performance in terms of dissolution rate and maintenance of the high solution concentrations in FeSSIF to each other. The Compound 1:triglyceride co-crystals also show a better maintenance of the supersaturation than both the neat amorphous and solid amorphous dispersed form of Compound 1 (Compound 1 SDD) over longer time periods. Furthermore, in-vivo the Compound 1:triglyceride co-crystals should be metabolized in the small intestine by lipid esterase (lipases), which would effectively remove the triglycerides and further boost the Compound 1 concentration according to Le-Chatelier's principle.

In addition, the crystalline Compound 1:triglyceride co-crystals may have the following advantages over the solid amorphous dispersed form (Compound 1 SDD) of Compound 1: (1) the co-crystals can be formulated, stored and used under conditions where they are thermodynamically stable; (2) a controlled crystallization can be developed that can reduces potential impurity levels (impurities include, but are not limited to, solvent); (3) a manufacturing process can be developed that is more efficient and cost effective (for example, less solvent can be used in manufacturing and a lower cost process than spray drying can be developed); and (4) a stabilizing polymer is not required for co-crystals.

In one embodiment, the co-crystal dissolves in simulated intestinal fluid in fed state (FeSSIF) to yield a concentration of Compound 1 of greater than 0.4 mg/mL. In another embodiment, the co-crystal dissolves in simulated intestinal fluid in fed state (FeSSIF) to yield a concentration of Compound 1 of greater than 0.4 mg/mL and the concentration is maintained for at least 10 hours. In another embodiment, the co-crystal dissolves in simulated intestinal fluid in fed state (FeSSIF) at a temperature of 37° C. to yield a concentration of Compound 1 of greater than 0.4 mg/mL and the concentration is maintained for at least 10 hours. In some embodiments, the co-crystal dissolves in simulated intestinal fluid in fed state (FeSSIF) to yield a concentration of Compound 1 of greater than 0.4 mg/mL within 2 hours. In another embodiment, the co-crystal dissolves in simulated intestinal fluid in fed state (FeSSIF) to yield a concentration of Compound 1 of greater than 0.4 mg/mL and the concentration is maintained for at least 10 hours without need for a stabilizing polymer. In some embodiments, the stabilizing polymer is HPMCAS.

Processes for Making Co-Crystal Forms

In one aspect, the present disclosure is directed to a method of preparing a co-crystal comprising Compound 1 and a co-former, wherein the co-crystal is chosen from the following structural formula:

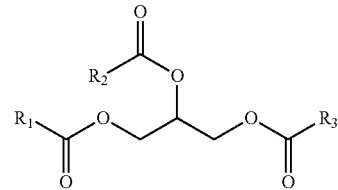

wherein $R_1$, $R_2$, and $R_3$ are independently $C_{1-29}$ aliphatic, wherein Compound 1 is represented by the following structural formula:

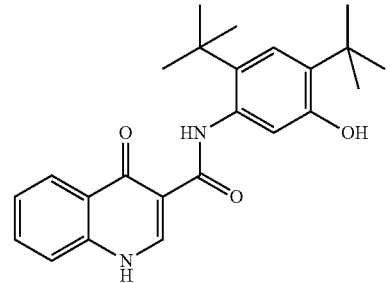 [SMILES: CC(C)(C)c1cc(C(C)(C)C)c(NC(=O)c2c[nH]c3ccccc3c2=O)cc1O]

comprising the step of:
stirring or mixing Compound 1 and the co-former to form the co-crystal.

In some embodiments, $R_1$, $R_2$, and $R_3$ are independently $C_{7-29}$ aliphatic In some embodiments, the co-former has an average molecular weight between 470 and 1400 Da.

In some embodiments, the co-former is chosen from glyceryl trioleate, glyceryl tristearate, glycerol tridecanoate, glycerol trihexanoate, glyceryl tritridecanoate, glycerol trioctanoate, glyceryl trimyristate, glyceryl tripalmitate, glyceryl tributyrate, glyceryl trilinoleate, glyceryl tridodecanoate, glyceryl decanoate, glyceryl tripalmitoleate, glycerol trierucate, glyceryl tripropionate, palmitodiolein, triarachidonin, glyceryl trilinolenate, trierucin, glycerol triarachidate, glyceryl tri(cis-13-docosenoate), glyceryl tripetroselinate, glyceryl tribehenate, glyceryl trielaidate, and triacetin.

In some embodiments, the co-former is chosen from

In one embodiment, Compound 1 is neat amorphous. In another embodiment, the co-former is neat. In one embodiment, Compound 1 and the co-former are stirred for at least 0.5 hours. In another embodiment, Compound 1 and co-former are stirred for 18 hours. In yet another embodiment, Compound 1 and the co-former are stirred for at least 18 hours. In one embodiment, Compound 1 and the co-former are stirred for more than 0.5 hours (including, but not limited

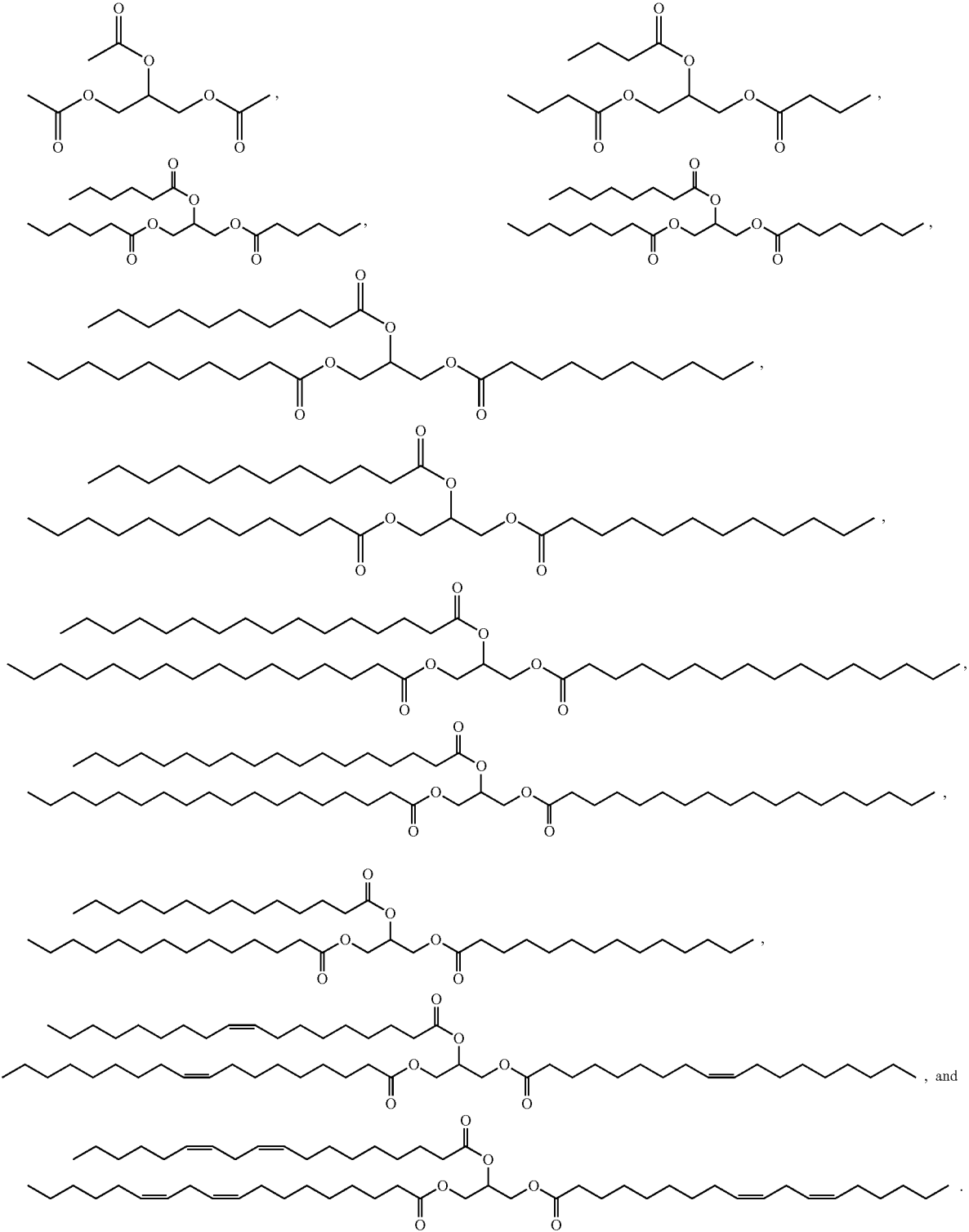

to, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours or 18 hours). In another embodiment, Compound 1 and the co-former are stirred at 40° C. In another embodiment, Compound 1 and the co-former are stirred at about 40° C. In yet other embodiments, Compound 1 and the co-former are stirred at 35-45° C. (for example, at 35° C., 36° C., 37° C., 38° C., 39° C., 40° C., 41° C., 42° C., 43° C., 44° C. or 45° C.). In one embodiment, Compound 1 and the co-former are stirred for at least 18 hours at 40° C. In one embodiment, Compound 1 and the co-former are stirred for at least 0.5 hours at 40° C. In one embodiment, Compound 1 and the co-former are stirred for at least 18 hours at 40° C.

As non-limiting examples, in one embodiment, Compound 1 and glyceryltrioctanoate are stirred for at least 0.5 hours; in yet one embodiment, Compound 1 and glyceryltrioctanoate are stirred for 0.5 hours; in yet another embodiment, Compound 1 and glyceryltrioctanoate are stirred for at least 0.5 hours at 40° C.; in also yet another embodiment, Compound 1 and glyceryltrioctanoate are stirred for 0.5 hours at 40° C.

In one embodiment, the present disclosure provides a method of preparing a co-crystal comprising Compound 1 and a co-former, wherein Compound 1 is represented by the following structural formula:

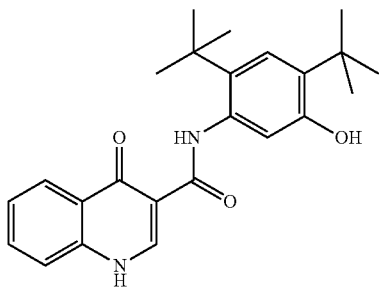 [SMILES: CC(C)(C)c1cc(C(C)(C)C)c(NC(=O)c2c[nH]c3ccccc3c2=O)cc1O]

wherein the co-former is chosen from the following structural formula:

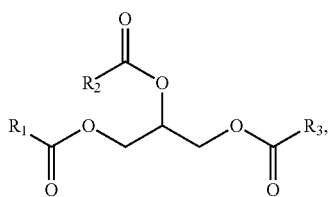

wherein $R_1$, $R_2$, and $R_3$ are independently $C_{1-29}$ aliphatic, comprising the steps of:
(a) preparing a mixture comprising Compound 1 and the triglyceride to form the co-crystal; and
(b) collecting the co-crystals by filtration.

In another embodiment, the method optionally, further comprises, the steps of:
(c) collecting mother liquor;
(d) stirring Compound 1 with the collected mother liquor for at least 18 hours; and
(e) collecting the co-crystals.

One aspect of the present disclosure provides for a method of preparing a co-crystal comprising Compound 1 and a co-former, wherein Compound 1 is represented by the following structural formula:

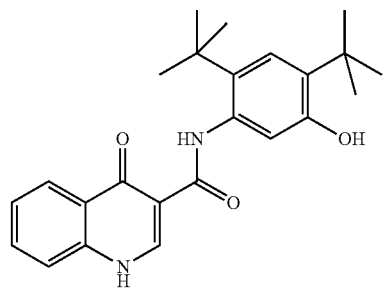 [SMILES: CC(C)(C)c1cc(C(C)(C)C)c(NC(=O)c2c[nH]c3ccccc3c2=O)cc1O]

and wherein the co-former is chosen from the following structural formula:

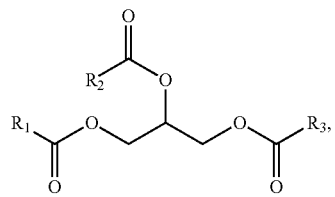

wherein R1, R2, and $R_3$ are independently $C_{1-29}$ aliphatic; comprising the steps of:
(a) preparing a mixture comprising Compound 1 and the co-former; and
(b) heating the mixture.

In one embodiment, Compound 1 and the co-former are heated to about 80° C. In one embodiment, Compound 1 and the co-former are heated to 80° C. In another embodiment, Compound 1 and the co-former are heated to about 80° C. for 12 hours. In yet another embodiment, Compound 1 and the co-former are heated to 80° C. for 12 hours. In another embodiment, Compound 1 and the co-former are heated to about 80° C. for 24 hours. In yet another embodiment, Compound 1 and the co-former are heated to 80° C. for 24 hours.

One aspect of the present disclosure provides for a method of preparing a co-crystal comprising Compound 1 and a co-former, wherein Compound 1 is represented by the following structural formula:

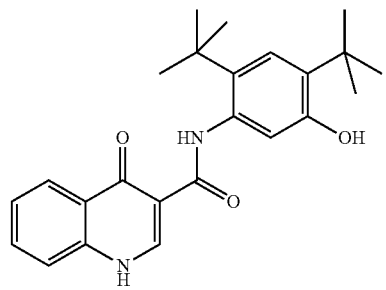 [SMILES: CC(C)(C)c1cc(C(C)(C)C)c(NC(=O)c2c[nH]c3ccccc3c2=O)cc1O]

the co-former is chosen from the following structural formula:

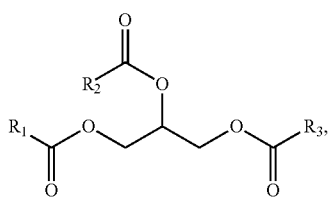

wherein $R_1$, $R_2$, and $R_3$ are independently $C_{1-29}$ aliphatic, comprising the steps of:

(c) preparing a mixture comprising Compound 1 and the co-former; and (d) heating the mixture to 80° C.

In yet another embodiment, Compound 1 and the co-former are heated to 80° C. for 12 hours. In yet another embodiment, Compound 1 and the co-former are heated to 80° C. for 24 hours.

Further another aspect of the present disclosure provides for a method of preparing co-crystals comprising Compound 1 and a co-former, wherein Compound 1 is represented by the following structural formula:

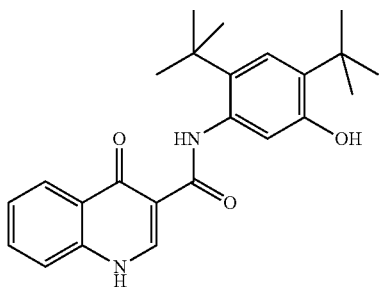 [SMILES: CC(C)(C)c1cc(C(C)(C)C)c(NC(=O)c2c[nH]c3ccccc3c2=O)cc1O]

the co-former is chosen from the following structural formula:

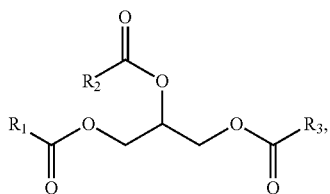

wherein $R_1$, $R_2$, and $R_3$ are independently $C_{1-29}$ aliphatic. comprising the steps of:

(a) preparing a mixture comprising Compound 1 and the co-former; and (b) heating the mixture to a temperature that is about 5 to 10° C. higher than the melting point of the co-former.

One aspect of the present disclosure provides for a method of preparing a co-crystal comprising Compound 1 and a co-former, wherein Compound 1 is represented by the following structural formula:

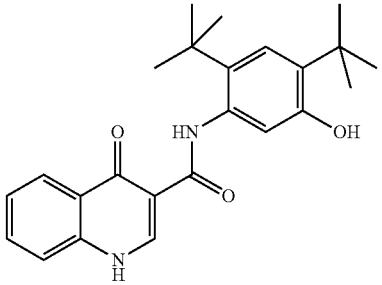 [SMILES: CC(C)(C)c1cc(C(C)(C)C)c(NC(=O)c2c[nH]c3ccccc3c2=O)cc1O]

wherein the co-former is chosen from the following structural formula:

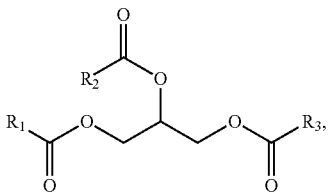

wherein $R_1$, $R_2$, and $R_3$ are independently $C_{1-29}$ aliphatic, comprising the steps of:

(a) preparing a mixture comprising Compound 1 and the co-former;

(b) heating the mixture;

(c) cooling the mixture down; and (d) repeating step (b) and (c).

In one embodiment, Compound 1 and the co-former are heated to about 80° C. In another embodiment, Compound 1 and the co-former are heated to about 80° C. and cooled down to about 40° C. In one embodiment, Compound 1 and the co-former are heated to 80° C. In another embodiment, Compound 1 and the co-former are heated to 80° C. and cooled down to 40° C. In another embodiment, Compound 1 and the co-former are heated to 80° C. for 12 hours. In another embodiment, Compound 1 and the co-former are heated to 80° C. for 24 hours. In yet another embodiment, Compound 1 and the co-former are heated to 80° C. for 12 hours and cooled down to about 40° C. In another embodiment, Compound 1 and the co-former are heated to 80° C. for 12 hours. In yet another embodiment, Compound 1 and the co-former are heated to 80° C. for 24 hours and cooled down to about 40° C. In any of the above embodiments, the steps of heating and cooling are repeated.

Another aspect of the present disclosure provides for a method of preparing a co-crystal comprising Compound 1 and a co-former, wherein Compound 1 is represented by the following structural formula:

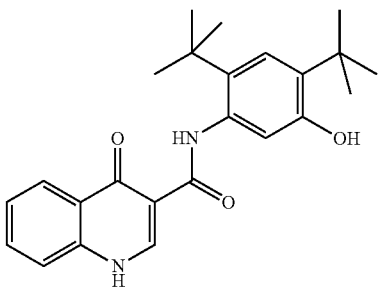 [SMILES: CC(C)(C)c1cc(C(C)(C)C)c(NC(=O)c2c[nH]c3ccccc3c2=O)cc1O]

wherein the co-former is chosen from the following structural formula:

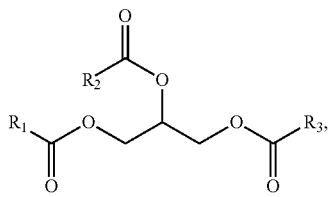

wherein $R_1$, $R_2$, and $R_3$ are independently $C_{1-29}$ aliphatic, comprising the steps of:
  (a) preparing a mixture comprising Compound 1 and the co-former;
  (b) heating the mixture to about 80° C.;
  (c) cooling the mixture down; and
  (d) repeating step (b) and (c).

In another embodiment, Compound 1 and the co-former are cooled down to 40° C.

Another aspect of the present disclosure provides for a method of preparing a co-crystal comprising Compound 1 and a co-former, wherein Compound 1 is represented by the following structural formula:

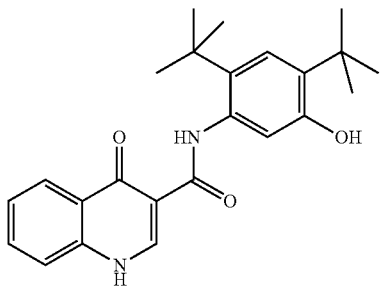 [SMILES: CC(C)(C)c1cc(C(C)(C)C)c(NC(=O)c2c[nH]c3ccccc3c2=O)cc1O]

wherein the co-former is chosen from the following structural formula:

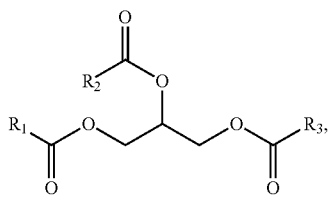

wherein $R_1$, $R_2$, and $R_3$ are independently $C_{1-29}$ aliphatic, comprising the steps of:
  (a) adding Compound 1 and the triglyceride;
  (b) heating to about 80° C.;
  (c) cooling down to about 40° C.; and
  (d) repeating step (b) and (c).

In some embodiments, co-crystals can be prepared by slurrying Compound 1 and a co-former in a suitable solvent at a slurry composition at which the co-crystal is stable in the ternary phase diagram, for example: by co-grinding Compound 1 and a co-former, by co-grinding Compound 1 and a co-former and adding a small amount of suitable solvent, by co-grinding Compound 1 and a co-former and subsequently annealing, by co-grinding Compound 1 and a co-former and subsequently annealing at elevated temperature, by co-grinding Compound 1 and a co-former and subsequently annealing at elevated humidity, by co-grinding Compound 1 and a co-former and subsequently annealing at elevated temperature and humidity, by mixing Compound 1 and a co-former at a temperature where at least the co-former is liquid, by mixing Compound 1 and a co-former at a temperature where at least the co-former is liquid and subsequent cooling after a crystallization period, by extruding Compound 1 and a co-former at a temperature and conformer composition at which the co-crystal is stable, or by dissolving Compound 1 and a co-former in suitable solvent, and evaporating the solvent. Co-crystals may be made with multiple co-formers in a similar manner.

In one embodiment, the co-crystals are collected by centrifugal filtration at a temperature above the melting temperature of the co-former.

In another embodiment, the co-crystals are washed after filtration to remove excess co-former.

Co-crystals produced by any of the methods above are isolated or purified. Co-crystals are pure as measured by HPLC. In one embodiment, the co-crystal is over 99% (w/w). In another embodiment, the Compound 1:triglyceride co-crystal is over 99.5% (w/w). In one embodiment, the Compound 1:triglyceride co-crystal is 99.5% (w/w). In another embodiment, the Compound 1:triglyceride co-crystal is 99.6% (w/w). In another embodiment, the Compound 1:triglyceride co-crystal is 99.7% (w/w). In another embodiment, the Compound 1:triglyceride co-crystal is 99.8% (w/w). In another embodiment, the Compound 1:triglyceride co-crystal is 99.9% (w/w)). In one embodiment, the Compound 1:glyceryltrioctanoate co-crystal is 99.9% (w/w). In another embodiment, the Compound 1:glyceryltrioleate co-crystal is 99.9% (w/w). In yet another embodiment, the Compound 1:glyceryltrilinoleate co-crystal is 99.5% (w/w). The detection limit for impurities by HPLC is 0.005%.

The present disclosure also provides a method of preparing a co-crystal comprising Compound 1 and a co-crystal former selected from the group consisting of glyceryltrioctanoate, glyceryltrioleate, and glyceryltrilinoleate, wherein Compound 1 is represented by the following structural formula:

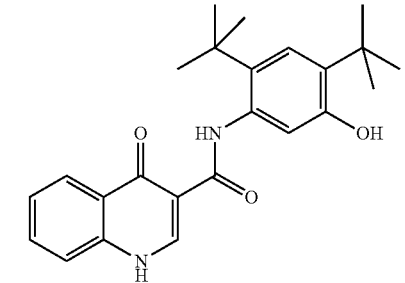 [SMILES: CC(C)(C)c1cc(C(C)(C)C)c(NC(=O)c2c[nH]c3ccccc3c2=O)cc1O]

comprising the step of:
  stirring Compound 1 and the co-crystal former to form the co-crystal.

In some embodiments, the co-crystal former is glyceryltrioctanoate.

In some embodiments, the co-crystal former is glyceryltrioleate.

In some embodiments, the co-crystal former is glyceryltrilinoleate.

The present disclosure also provides a method of preparing a co-crystal comprising Compound 1 and a co-crystal former selected from the group consisting of glyceryltrioctanoate, glyceryltrioleate, and glyceryltrilinoleate, wherein Compound 1 is represented by the following structural formula:

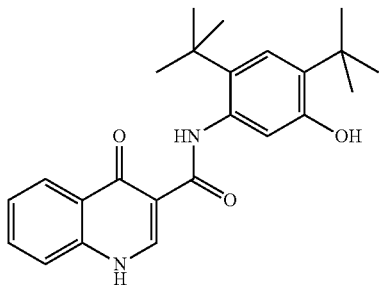 [SMILES: CC(C)(C)c1cc(C(C)(C)C)c(NC(=O)c2c[nH]c3ccccc3c2=O)cc1O]

comprising the steps of:
adding Compound 1 and the co-former together; and
heating.

Uses, Formulation and Administration

Pharmaceutically Acceptable Compositions

In one aspect of the present disclosure, pharmaceutically acceptable compositions are provided, wherein these compositions comprise co-crystal of any one of the embodiments above and a pharmaceutically acceptable carrier or excipient.

In some embodiments, at least 30% of Compound 1 present in the pharmaceutically acceptable compositions are in the form of Compound 1:triglyceride co-crystals described herein. As non-limiting example, at least 30%, 40%, 50%, 60%, 70%, 80%, 85%, 90%, 92.5%, 95%, 97.5%, 98%, or 99% of Compound 1 are present in the form of Compound 1:triglyceride co-crystals described herein.

In certain embodiments, these compositions optionally further comprise one or more additional therapeutic agents.

As described above, the pharmaceutically acceptable compositions of the present disclosure additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the disclosure, such as by producing any undesirable biological effect or otherwise interacting in a deleterious manner with any other component(s) of the pharmaceutically acceptable composition, its use is contemplated to be within the scope of this disclosure. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In addition to cystic fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome. COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymyositis/dermatomyositis. Defective protein trafficking is believed to cause the disease, for which treatment options are limited. Augmenters or inducers of CFTR activity may hydrate the various organs afflicted by the disease and help to elevate the associated symptoms.

In one aspect, the disclosure provides a method of treating or lessening the severity of a disease in a patient comprising administering to said patient co-crystals of any one of the embodiments described above, and said disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, Diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurohypophyseal DI, nephrogenic DI, Charcot-Marie Tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's, spinocerebellar ataxia type I, spinal and bulbar muscular atrophy, dentatorubral pallidoluysian atrophy, and myotonic dystrophy, as well as spongiform encephalopathies, such as hereditary Creutzfeldt-Jakob disease (due to prion protein processing defect), Fabry disease, Sträussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia. In some embodiments, the co-crystal is a Compound 1:triglyceride co-crystal as described herein.

In some embodiments, the method includes treating or lessening the severity of cystic fibrosis in a patient comprising administering to said patient a co-crystal of any one of the embodiments described above. In some embodiments, the co-crystal is a Compound 1:triglyceride co-crystal as described herein. In certain embodiments, the patient possesses mutant forms of human CFTR. In other embodiments, the patient possesses one or more of the following mutations ΔF508, R117H, and G551D of human CFTR. In one embodiment, the method includes treating or lessening the severity of cystic fibrosis in a patient possessing the ΔF508 mutation of human CFTR comprising administering to said patient Compound 1:triglyceride co-crystals described herein. In one embodiment, the method includes treating or lessening the severity of cystic fibrosis in a patient possessing the G551D mutation of human CFTR comprising administering to said patient Compound 1:triglyceride co-crystals described herein. In one embodiment, the method includes treating or lessening the severity of cystic fibrosis in a patient possessing the ΔF508 mutation of human CFTR on one allele comprising administering to said patient Compound 1:triglyceride co-crystals described herein. In one embodiment, the method includes treating or lessening the severity of cystic fibrosis in a patient possessing the ΔF508 mutation of human CFTR on both alleles comprising administering to said patient Compound 1:triglyceride co-crystals described herein. In one embodiment, the method includes treating or lessening the severity of cystic fibrosis in a patient possessing the G551D mutation of human CFTR on allele comprising administering to said patient Compound 1:triglyceride co-crystals described herein. In one embodiment, the method includes treating or lessening the severity of cystic fibrosis in a patient possessing the G551D mutation of human CFTR on both alleles comprising administering to said patient Compound 1:triglyceride co-crystals described herein.

In yet another aspect, the present disclosure provides a method of treating or lessening the severity of a condition, disease, or disorder implicated by CFTR mutation. In certain embodiments, the present disclosure provides a method of treating a condition, disease, or disorder implicated by a deficiency of the CFTR activity, the method comprising administering a composition comprising co-crystals of any one of the embodiments described above, to a subject, preferably a mammal, in need thereof. In some embodiments, the co-crystal is a Compound 1:triglyceride co-crystal as described herein.

In certain embodiments, the present disclosure provides a method of treating diseases associated with reduced CFTR function due to mutations in the gene encoding CFTR or environmental factors (e.g., smoke). These diseases include, cystic fibrosis, chronic bronchitis, recurrent bronchitis, acute bronchitis, male infertility caused by congenital bilateral absence of the vas deferens (CBAVD), female infertility caused by congenital absence of the uterus and vagina (CAUV), idiopathic chronic pancreatitis (ICP), idiopathic recurrent pancreatitis, idiopathic acute pancreatitis, chronic rhinosinusitis, primary sclerosing cholangitis, allergic bronchopulmonary aspergillosis, diabetes, dry eye, constipation, allergic bronchopulmonary aspergillosis (ABPA), bone diseases (e.g., osteoporosis), and asthma, comprising administering to said patient a co-crystal of any one of the embodiments described above. In some embodiments, the co-crystal is a Compound 1:triglyceride co-crystal as described herein.

In certain embodiments, the present disclosure provides a method for treating diseases associated with normal CFTR function. These diseases include, chronic obstructive pulmonary disease (COPD), chronic bronchitis, recurrent bronchitis, acute bronchitis, rhinosinusitis, constipation, pancreatitis including chronic pancreatitis, recurrent pancreatitis, and acute pancreatitis, pancreatic insufficiency, male infertility caused by congenital bilateral absence of the vas deferens (CBAVD), mild pulmonary disease, idiopathic pancreatitis, liver disease, hereditary emphysema, gallstones, gastroesophageal reflux disease, gastrointestinal malignancies, inflammatory bowel disease, constipation, diabetes, arthritis, osteoporosis, and osteopenia, comprising administering to said patient co-crystals of any one of the embodiments described above. In some embodiments, the co-crystals are Compound 1:triglyceride co-crystals as described herein.

In certain embodiments, the present disclosure provides a method for treating diseases associated with normal CFTR function including hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, Diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurohypophyseal DI, nephrogenic DI, Charcot-Marie Tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's, spinocerebellar ataxia type I, spinal and bulbar muscular atrophy, dentatorubral pallidoluysian atrophy, and myotonic dystrophy, as well as spongiform encephalopathies, such as hereditary Creutzfeldt-Jakob disease (due to prion protein processing defect), Fabry disease, Sträussler-Scheinker syndrome, Gorham's Syndrome, chloride channelopathies, myotonia congenita (Thomson and Becker forms), Bartter's syndrome type III, Dent's disease, epilepsy, hyperekplexia, lysosomal storage disease, Angelman syndrome, Primary Ciliary Dyskinesia (PCD), PCD with situs inversus (also known as Kartagener syndrome), PCD without situs inversus and ciliary aplasia, or Sjogren's disease, comprising the step of administering to said mammal an effective amount of co-crystals of any of the embodiments described above. In some embodiments, the co-crystals are Compound 1:triglyceride co-crystals as described herein.

According to an alternative embodiment, the present disclosure provides a method of treating cystic fibrosis comprising the step of administering to said mammal a composition comprising the step of administering to said mammal an effective amount of a composition comprising Compound 1:triglyceride co-crystals described herein.

According to the disclosure an "effective amount" of Compound 1:triglyceride co-crystals, or a pharmaceutically acceptable composition thereof is that amount effective for treating or lessening the severity of one or more of the diseases, disorders or conditions as recited above.

Compound 1:triglyceride co-crystals described herein, or a pharmaceutically acceptable composition thereof may be administered using any amount and any route of administration effective for treating or lessening the severity of one or more of the diseases, disorders or conditions as recited above.

In certain embodiments, Compound 1:triglyceride co-crystals described herein, or a pharmaceutically acceptable composition thereof is useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl— concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In another embodiment, Compound 1:triglyceride co-crystals described herein, described herein or a pharmaceutically acceptable composition thereof, is useful for treating or lessening the severity of cystic fibrosis in patients who have residual CFTR activity induced or augmented using pharmacological methods or gene therapy. Such methods increase the amount of CFTR present at the cell surface, thereby inducing a hitherto absent CFTR activity in a patient or augmenting the existing level of residual CFTR activity in a patient.

In one embodiment, Compound 1:triglyceride co-crystals described herein, or a pharmaceutically acceptable composition thereof, is useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, Type I, II, III, IV, and V cystic fibrosis Transmembrane Conductance Regulator Defects and Opportunities of Therapy; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, Compound 1:triglyceride co-crystals described herein, or a pharmaceutically acceptable composition thereof, is useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the disclosure are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this disclosure can be administered to humans and other animals orally, rectally, parenterally, intracistemally, intravaginally, intraperitoneally, topically (as by powders, ointments, drops or patch), bucally, as an oral or nasal spray, or the like, depending on the severity of the infection being treated. In certain embodiments, the compounds of the disclosure may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with a inert diluent such as sucrose, lactose or starch. Such dosage forms may also comprise additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this disclosure. Additionally, the present disclosure contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the co-crystals of any one of the embodiments described above (e.g., Compound 1:triglyceride co-crystals described herein) or a pharmaceutically acceptable composition thereof can be employed in combination therapies, that is, co-crystals of any of the embodiments described above (e.g., Compound 1:triglyceride co-crystals described herein) or a pharmaceutically acceptable composition thereof, can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated."

In one embodiment, the additional therapeutic agent is selected from a mucolytic agent, bronchodilator, an antibiotic, an anti-infective agent, an anti-inflammatory agent, a CFTR modulator other than a compound of the present disclosure, or a nutritional agent.

In one embodiment, the additional therapeutic agent is a compound that stabilizes the presence of CFTR at the cell surface such as activators of Rac1 signaling, of which hepatocyte growth factor (HGF) is an example.

In one embodiment, the additional therapeutic agent is an antibiotic. Examplary antibiotics useful herein include tobramycin, including tobramycin inhaled powder (TIP), azithromycin, cayston, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional therapeutic agent is a mucolyte. Examplary mucolytes useful herein includes Pulmozyme®.

In another embodiment, the additional therapeutic agent is a bronchodialator. Examplary bronchodialtors include albuterol, metaprotenerol sulfate, pirbuterol acetate, salmeterol, or tetrabuline sulfate.

In another embodiment, the additional therapeutic agent is effective in restoring lung airway surface liquid. Such agents improve the movement of salt in and out of cells, allowing mucus in the lung airway to be more hydrated and, therefore, cleared more easily. Examplary such agents include hypertonic saline, denufosol tetrasodium ([[(3S,5R)-5-(4-amino-2-oxopyrimidin-1-yl)-3-hydroxyoxolan-2-yl]methoxy-hydroxyphosphoryl][[(2R,3S,4R,5R)-5-(2,4-dioxopyrimidin-1-yl)-3, 4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional therapeutic agent is an anti-inflammatory agent, i.e., an agent that can reduce the inflammation in the lungs. Examplary such agents useful herein include ibuprofen, docosahexanoic acid (DHA), sildenafil, inhaled glutathione, pioglitazone, hydroxychloroquine, or simavastatin.

In another embodiment, the additional therapeutic agent is a compound that augments or induces CFTR activity other than a co-crystal of Compound 1. Examplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), and cobiprostone (7-{(2R,4aR,5R,7aR)-2-[(3S)-1,1-difluoro-3-methylpentyl]-2-hydroxy-6-oxooctahydrocyclopenta[b]pyran-5-yl}heptanoic acid).

In another embodiment, the additional therapeutic agent is a nutritional agent. Examplary nutritional agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In another embodiment, the additional therapeutic agent is a compound selected from gentamicin, curcumin, cyclophosphamide, 4-phenylbutyrate, miglustat, felodipine, nimodipine, Philoxin B, geniestein, Apigenin, cAMP/cGMP augmenters or inducers such as rolipram, sildenafil, milrinone, tadalafil, amrinone, isoproterenol, albuterol, and almeterol, deoxyspergualin, HSP 90 inhibitors, HSP 70 inhibitors, proteosome inhibitors such as epoxomicin, lactacystin, etc.

In another embodiment, the additional therapeutic agent reduces the activity of the epithelial sodium channel blocker (ENaC) either directly by blocking the channel or indirectly by modulation of proteases that lead to an increase in ENaC activity (e.g., seine proteases, channel-activating proteases). Examplary such agents include camostat (a trypsin-like protease inhibitor), QAU145, 552-02, GS-9411, INO-4995, Aerolytic, and amiloride. Additional therapeutic agents that reduce the activity of the epithelial sodium channel blocker (ENaC) can be found, for example in PCT Publication No. WO2009/074575, the entire contents of which are incorporated herein in their entirety.

Amongst other diseases described herein, combinations of CFTR modulators, such as Compound 1:triglyceride co-crystals described herein, and agents that reduce the activity of ENaC are used for treating Liddle's syndrome, cystic fibrosis, primary ciliary dyskinesia, chronic bronchitis, chronic obstructive pulmonary disease, asthma, respiratory tract infections, lung carcinoma, xerostomia and keratoconjunctivitis sire, respiratory tract infections (acute and chronic; viral and bacterial) and lung carcinoma.

Combinations of CFTR modulators, such as Compound 1:triglyceride co-crystals described herein, and agents that reduce the activity of ENaC are also useful for treating diseases mediated by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

Chronic obstructive pulmonary disease includes chronic bronchitis or dyspnea associated therewith, emphysema, as well as exacerbation of airways hyperreactivity consequent to other drug therapy, in particular, other inhaled drug therapy. In some embodiments, the combinations of CFTR modulators, such as Compound 1:triglyceride co-crystals described herein, and agents that reduce the activity of ENaC are useful for the treatment of bronchitis of whatever type or genesis including, e.g., acute, arachidic, catarrhal, croupus, chronic or phthinoid bronchitis.

In another embodiment, the additional therapeutic agent is a CFTR modulator other than Compound 1:triglyceride co-crystals described herein, i.e., an agent that has the effect of modulating CPR activity. Examplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), cobiprostone (7-{(2R,4aR,5R,7aR)-2-[(3S)-1,1-difluoro-3-methylpentyl]-2-hydroxy-6-oxooctahydrocyclopenta[b]pyran-5-yl}heptanoic acid), (3-(6-(1-(2,2-difluorobenzo[d][1,3]dioxol-5-yl)cyclopropanecarboxamido)-3-methylpyridin-2-yl)benzoic acid, or (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In one embodiment, the additional therapeutic agent is (3-(6-(1-(2,2-difluorobenzo[d][1,3]dioxol-5-yl)cyclopropanecarboxamido)-3-methylpyridin-2-yl)benzoic acid, or (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In another embodiment, the additional therapeutic agent is (3-(6-(1-(2,2-difluorobenzo[d][1,3]dioxol-5-yl)cyclopropanecarboxamido)-3-methylpyridin-2-yl)benzoic acid. In another embodiment, the additional therapeutic agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In one embodiment, the additional therapeutic agent is a CFTR modulator other than a compound of the present disclosure.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Co-crystals of any of the embodiments described above (e.g., Compound 1:triglyceride co-crystals described herein) or a pharmaceutically acceptable composition thereof, may also be incorporated into compositions for coating an implantable medical device, such as prostheses, artificial valves, vascular grafts, stents and catheters. Accordingly, the present disclosure, in another aspect, includes a composition for coating an implantable device comprising a compound of the present disclosure as described generally above, and in classes and subclasses herein, and a carrier suitable for coating said implantable device. In still another aspect, the present disclosure includes an implantable device coated with a composition comprising a compound of the present disclosure as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

In one embodiment, the disclosure features a kit comprising a tablet of the present disclosure, and a separate therapeutic agent or pharmaceutical composition thereof. In one embodiment, the additional therapeutic agent is a CFTR corrector. In another embodiment, the therapeutic agent is (3-(6-(1-(2,2-difluorobenzo[d][1,3]dioxol-5-yl)cyclopropanecarboxamido)-3-methylpyridin-2-yl)benzoic acid or (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In another embodiment, the therapeutic agent is (3-(6-(1-(2,2-difluorobenzo[d][1,3]dioxol-5-yl)cyclopropanecarboxamido)-3-methylpyridin-2-yl)benzoic acid. In another embodiment, the therapeutic agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In another embodiment, the tablet and the therapeutic agent are in separate containers. In another embodiment, the kits of the present disclosure are drawn to kits wherein the compounds or pharmaceutical compositions of the present disclosure and the one or more additional therapeutic agents) are in separate containers. In one embodiment, the separate containers are bottles. In another embodiment, the separate containers are vials. In another embodiment, the separate containers are blister packs. In another embodiment, the container is a bottle, vial, or blister pack or combination thereof.

Another aspect of the disclosure relates to modulating CFTR activity in a biological sample or a patient (e.g., in vitro or in vivo), which method comprises administering to the patient, or contacting said biological sample co-crystals of any of the embodiments described above (e.g., Compound 1:triglyceride co-crystals described herein) or a pharmaceutically acceptable composition thereof. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of CFTR in a biological sample is useful for a variety of purposes that are known to one of skill in the art. Examples of such purposes include, but are not limited to, the study of CFTR in biological and pathological phenomena; and the comparative evaluation of new modulators of CFTR.

In yet another embodiment, a method of modulating activity of an anion channel in vitro or in vivo, is provided comprising the step of contacting said channel with Compound 1:triglyceride co-crystals described herein or a pharmaceutically acceptable composition thereof. In some embodiments, the anion channel is a chloride channel or a bicarbonate channel. In other embodiments, the anion channel is a chloride channel.

According to an alternative embodiment, the present disclosure provides a method of increasing the number of functional CFTR in a membrane of a cell, comprising the step of contacting said cell with co-crystals of any one of the embodiments described above (e.g., Compound 1:triglyceride co-crystals described herein) or a pharmaceutically acceptable composition thereof.

According to another embodiment, the activity of the CFTR is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells." Biophys J 69(4): 1272-80, and Gonzalez, J. E. and R. Y. Tsien (1997); "Improved indicators of cell membrane potential that use fluorescence resonance energy transfer" Chem Biol 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" Drug Discov Today 4(9): 431-439).

These voltage sensitive assays are based on the change in fluorescence resonant energy transfer (FRET) between the membrane-soluble, voltage-sensitive dye, DiSBAC2(3), and a fluorescent phospholipid, CC2-DMPE, which is attached to the outer leaflet of the plasma membrane and acts as a FRET donor. Changes in membrane potential (Vm) cause the negatively charged DiSBAC2(3) to redistribute across the plasma membrane and the amount of energy transfer from CC2-DMPE changes accordingly. The changes in fluorescence emission can be monitored using VIPRTM II, which is an integrated liquid handler and fluorescent detector designed to conduct cell-based screens in 96- or 384-well microtiter plates.

In another aspect the present disclosure provides a kit for use in measuring the activity of CFTR or a fragment thereof in a biological sample in vitro or in vivo comprising (i) a composition comprising any of the co-crystals of the embodiments described above (e.g., Compound 1:triglyceride co-crystals described herein); and (ii) instructions for a) contacting the composition with the biological sample and b) measuring activity of said CFTR or a fragment thereof. In one embodiment, the kit further comprises instructions for a) contacting an additional composition with the biological sample; b) measuring the activity of said CFTR or a fragment thereof in the presence of said additional compound, and c) comparing the activity of the CFTR in the presence of the additional compound with the density of the CFTR in the presence of co-crystals of any of the embodiments described above (e.g., Compound 1:triglyceride co-crystals described herein). In some embodiments, the kit is used to measure the density of CFTR.

In another aspect, the disclosure provides a kit for use in measuring the activity of CFTR or a fragment thereof in a biological sample in vitro or in vivo, comprising:
  (i) a composition comprising co-crystals of any of the embodiments described above (e.g., Compound 1:triglyceride co-crystals);
  (ii) instructions for:
    (a) contacting the composition with the biological sample;
    (b) measuring activity of said CFTR or a fragment thereof.

In one embodiment, the kit further comprises instructions for:
  i. contacting an additional composition with the biological sample;
  ii. measuring the activity of said CFTR, or a fragment thereof, in the presence of said additional compound; and
  iii. comparing the activity of the CFTR, or fragment thereof, in the presence of the additional compound with the density of CFTR, or fragment thereof, in the presence of co-crystals of any of the embodiments described above (e.g., Compound 1:triglyceride co-crystals).

In another embodiment, the step of comparing the activity of said CFTR, or fragment thereof, provides a measure of the density of said CFTR, or fragment thereof In order that the disclosure described herein may be more fully understood, the following examples are set forth. It should be understood that these examples are for illustrative purposes only and are not to be construed as limiting this disclosure in any manner.

Examples

Initial Preparation of Compound 1

Compound 1 was prepared as described in WO 2010/018162, US 2010/0267768 and U.S. Pat. No. 8,476,442, which are incorporated by reference herein. The preparation is also described below.

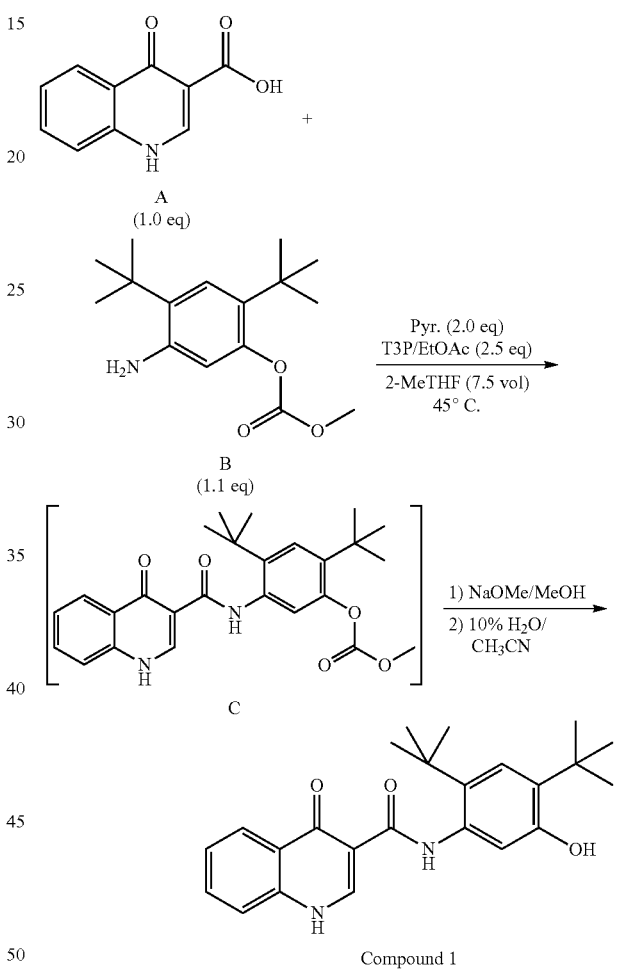

Compound A (1.0 eq.) and Compound B (1.1 eq.) were charged to a reactor. 2-MeTHF (4.0 vol., relative to Compound A) was added followed by T3P® 50% solution in EtOAc (2.5 eq.). The T3P charge vessel was washed with 2-MeTHF (3.5 vol.). Pyridine (2.0 eq.) was then charged. The resulting suspension was heated to 45.0 to 50.0° C. and held at this temperature for 15 hours. A sample was taken and checked for completion by HPLC. Once complete, the resulting mixture was cooled to 20.0° C.+/−5.0° C. 2-MeTHF was charged (12.5 vol.) to dilute the mixture. The reaction mixture was washed with water (10.0 vol.) 3 times. 2-MeTHF was charged to bring the total volume of reaction to 40.0 vol. (~16.5 vol. charged). Residual water was removed by continuous distillation at 35.0° C.+/−5° C. from 40 vol. to 30 vol. with 2-MeTHF until in-process control testing using the Karl Fisher method shows the water content to be no more than 1.0% w/w. The solution was cooled to 20.0° C.+/−5.0° C. To this solution was charged NaOMe/MeOH (1.7 equiv) to perform the hydrolysis of the carbonate. The reaction was stirred for no less than 1.0 hours, and checked for completion by HPLC. Once complete, the reaction was quenched with 1 N HCl/H$_2$O (10.0 vol.), and washed with 0.1 N HCl (10.0 vol.). The organic solution was polish filtered to remove any particulates and placed in a second flask. The filtered solution was concentrated at 25.0° C.+/−5.0° C. under reduced pressure to 20 vol. CH$_3$CN was added to 40 vol. and the solution concentrated at 25.0° C.+1-5.0° C. to 20 vol. The addition of CH$_3$CN and concentration was repeated 2 more times for a total of 3 additions of CH$_3$CN and 4 concentrations to 20 vol. After the final concentration to 20 vol., 16.0 vol. of CH$_3$CN was charged followed by 4.0 vol. of H$_2$O to make a final concentration of 40 vol. of 10% H$_2$O/CH$_3$CN relative to Compound A. This slurry was refluxed for 5 hours. The slurry was cooled to 20.0° C.+/−5° C. and filtered. The cake was washed with CH$_3$CN (5 vol.) 2 times. The resulting solid was dried in a vacuum oven at 50.0° C.+/−5.0° C. until a constant weight is attained.

Preparation of Neat Amorphous Compound 1

The following solution was prepared by stirring Compound 1, as prepared above, into 90% MEK/10% water according to Table A.

TABLE A

| (MEK/Water = 90/10) | Weight (g) |
|---|---|
| MEK | 360.00 |
| Water | 40.00 |
| Compound 1 (as prepared above) | 35.00 |
| Total Solution Weight | 400.00 |
| Solids Loading | 35.00 |

Spray drying was performed on a Buchi Mini Spray Dryer B-290 with dehumidifier B-296 and Inert Loop B-295 using the parameters used in Table B. The system was saturated with solvent that was to be sprayed, and inlet and outlet temperatures were allowed to equilibrate before spray drying. The powder from the collection vessel and the cyclone were combined in a shallow dish and dried in a vacuum oven with slight nitrogen purge for 7 days. The amorphous material was then dried in a vacuum oven at 75 to 80° C. and a pressure of approximately 0.1 mmHg until the MEK concentration was reduced to <1.0% w/w by 1H NMR (50 hours). The material was removed from the vacuum after cooling under N2 50° C.

TABLE B

| Spray Drying Parameters | |
|---|---|
| INLET Temperature | 110° C. |
| OUTLET Temperature | 50-60° C. |
| Nitrogen Pressure | 120 psi |
| Aspirator | 100% |
| Pump Rate | 45% |
| Nozzle | 1 mm |
| Atomizer | 35 mm |
| Filter Pressure | −50 to −70 mbar |
| Condenser Temperature | −5° C. |
| Run Time | 40 min. |

Preparation of Co-Crystals of Compound 1

Method 1:

All pure Compound 1 co-crystals were prepared by slurrying or stirring neat amorphous Compound 1 in neat triglyceride at a 5%-10% weight to volume solids load for at least 18 hours at 40° C. or 5° C.-10° C. above the triglyceride melting point in a HEL Polyblock synthesizer. The completion of the conversion was determined by birefringence of the suspended particles with polarized light microscopy. Crude co-crystals were isolated by centrifugal filtration using Millipore 2 ml centrifugation devices.

In some cases the mother liquor was collected for preparation of additional Compound 1 co-crystal to increase yield with respect to the triglyceride. This was achieved by slurrying or stirring neat amorphous Compound 1 at a 5%-10% weight to volume ratio in the mother liquor for at least 18 hours. The mother liquor was used not more than two times for additional conversions. The crude co-crystals of subsequent conversions were combined into 2 ml centrifugation devices and heptane was added at a 1.5 to 2 volume to weight ratio. After briefly vortexing of the mixture, the heptane was filtered by centrifugal filtration and the solids collected. Excess heptane was removed by drying in vacuum at 40 to 45° C. for at least 18 hours. The heptane content was checked periodically by 1H solution state NMR and drying was continued until the heptane was at acceptable levels, e.g., until there was no further decrease in the overlapping triglyceride and heptane CH3 resonance observed.

Method 2:

Approximately 50 mg neat amorphous Compound 1 was added to approximately 1 g triglyceride, heated to 80° C. and kept at this temperature for at least 1 hour. The solution was then cooled to a temperature above the melting point of the triglyceride to crystallize the Compound 1 co-crystal. In order to improve crystal quality and size the system was heated again to 80° C. and cooled down. The temperature cycling was repeated until crystals of suitable size for analysis were obtained. All Compound 1 co-crystals were isolated by centrifugal filtration at temperatures above the melting point of the triglyceride.

Characterization of Compound 1 Co-Crystals

Characterization Techniques Used:

X-Ray Powder Diffraction (XPRD) Analysis: The XRPD patterns were acquired at room temperature in reflection mode using a Pananalytical Empyrean II or a Bruker DS Advance diffractometer. The powder sample were placed in a Pananalytical stainless steel sample holder or a Bruker shallow cavity sample holder and spun at 15 rpm, respectively. Instrument parameters are listed in the table below.

| XRD System | Bruker D8 Advance | Panalytical Empyrean |
|---|---|---|
| Generator Voltage, kV | 40 | 45 |
| Generator Current, mA | 40 | 40 |
| Incident beam | Variable at | Programmable |
| Divergence slit | 12 mm | at 14 mm |
| Scan start (°2Θ) | 3 | 2.9989 |
| Scan end (°2Θ) | 40 | 40 |
| Step size (°2Θ) | 0.0144531 | 0.0131303 |
| Nominal number of detector channels | Default | 255 |
| Detector | VANTEC-1 | PIXcel 1D |
| Scan Type | Locked Coupled | Locked Coupled |
| Number of Steps | 2560 | 2818 |
| Time per step (sec) | 0.25 | 49.725 |
| Incident Anti Scatter Slit (°) | 0.5 | 2 |
| Rotation Speed (rpm) | 15 | 7.5 |
| Filter | Nickel | Nickel |
| Beam Knife | Yes | Yes |
| Incident Solar Slit (RAD) | N/A | 0.04 |
| Incident Mask (mm) | N/A | 10 |

| XRD System | Bruker D8 Advance | Panalytical Empyrean |
|---|---|---|
| Diffracted Anti Scatter Slit | Default | Automatic @ 14 mm |
| Diffracted Solar Slit (RAD) | N/A | 0.04 |
| Scan Speed (°/sec) | Default | 0.067335 |

$^{13}$C Solid State Nuclear Magnetic Resonance Spectroscopy ($^{13}$C ssNMR):

A Bruker-Biospin 400 MHz wide-bore AVance III spectrometer equipped with Bruker-Biospin 4 mm HFX probe was used for all $^{13}$C ssNMR experiments. Samples were packed into 4 mm $ZrO_2$ rotors and spun under magic angle spinning (MAS) condition with spinning speed of 12.5 kHz. The CP contact time of carbon CPMAS experiment was set to 2 ms. A CP proton pulse with linear ramp (from 50% to 100%) was employed. The Hartmann-Hahn match was optimized on external reference sample (glycine). TPPM15 decoupling sequence was used with the field strength of approximately 100 kHz. The relaxation delay was set to 5 s in all 13C CPMAS experiments. 1H T1 values were measured using a saturation recovery sequence. All spectra were reference externally to the upfield resonance of adamantine at 29.5 ppm. The temperature of the sample was controlled to 275 K.

Thermogravimetric Analysis (TGA):

Thermal gravimetric analysis (TGA) was conducted on a TA Instruments model Q5000 V3.8 thermogravimetric analyzer. Approximately 5-15 mg of solid sample was placed in a platinum sample pan and heated in a 60 mL/min sample and a 40 mL/min balance nitrogen stream at 10° C./min from ambient to 350° C. All thermograms were analyzed using TA Instruments Universal Analysis 2000 software V4.4A.

Differential Scanning Calorimetry (DSC):

The DSC traces were obtained using TA Instruments DSC Q2000 equipped with Universal Analysis 2000 software. An amount of 0.5-2 mg of Compound 1 co-crystal was weighed into an aluminum pan and sealed with a pinhole lid. The samples were heated from ambient to 350° C. or 300° C. at 10° C./min.

$^1$H Solution Nuclear Magnetic Resonance Spectroscopy ($^1$H NMR):

A Bruker narrow bore 400 MHz AvanceIII Nanobay spectrometer equipped with a Bruker-Biospin 5 mm broadband probe was used for all experiments. Approximately 0.5-2 mg of Compound 1 co-crystal samples were dissolved in 0.65 ml acetone-d6 (for Compound 1:glycereyltrioleate and Compound 1:glyceryltrilinoleate) or DMSO-d6 (for Compound 1:glyceryltrioctanoate) in a 5 mm NMR tube. A relaxation delay of 60 s was chosen to minimize differential relaxation of 1H between different proton positions on Compound 1 and triglyceride. All spectra are referenced using a tetramethylsilane internal standard at 0.0 ppm.

All $^1$H NMR solution state spectra are in accord with the presence of both Compound 1 and the respective triglyceride co-former and are consistent with chemically pure co-crystals. Significant shifts are absent in the spectra of the dissolved co-crystals for both Compound 1 and the triglycerides when compared to the spectra of the pure components individually. This provides evidence for dissociation of the co-crystals components in solution and confirms the weak association of Compound 1 and triglyceride association in the solid. The ratio of integrated intensity for protons in Compound 1:glyceryltrioctanoate in the $^1$H NMR spectra indicate a stoichiometry of 3:1 (Compound 1:triglyceride) in the co-crystal, whereas the integrated intensity of the Compound 1:glyceryltrioleate and Compound 1:glyceryltrilinoleate integrated intensities indicate a 6:1 (Compound 1:triglyceride) stoichiometry in the respective co-crystals. The stoichiometry determined by solution state $^1$H NMR is consistent with the stoichiometry determined by thermogravimetric analysis for the Compound 1:glyceryltrioctanoate co-crystal.

The $^1$H NMR results are consistent with high performance liquid chromatography analysis of the co-crystals. The assay values were determined to be 72.1% (w:w), 72.4% (w:w) and 68.6% (w:w) Compound 1 for the Compound 1:glyceryltrioctanoate, Compound 1:glyceryltrioleate and Compound 1:trilinoleate co-crystals. Impurities were found to be less than 0.5% total using UV detection.

Mass Spectrometry Analysis:

The mass spectrometry analysis was done as outlined for each complex below.

Single Crystal X-Ray Crystallography:

The single crystal was prepared by dissolving 56 mg of amorphous Compound 1 in 1000 mg triglyceride in an oven set to 80° C. Upon crystallization, a few crystals were removed for single crystal X-ray analysis. Diffraction data were acquired at ESFR synchrotron source with wavelength 0.70158 Å at 100K temperature (reference number Phil Pattison 130813). The structure was solved and refined using SHELX program (Sheldrick, G. M., Acta Cryst., (2008) A64, 112-122).

Characterization of Compound 1:Glyceryltrioctanoate

XRPD for Compound 1:Glyceryltrioctanoate:

An examplary X-Ray Powder Diffraction (XRPD) pattern of Compound 1:glyceryltrioctanoate in FIG. 3 was acquired using the Panalytical Empyrean II diffractometer. XRPD Representative peaks for Compound 1:glyceryltrioctanoate as observed in the XRPD pattern are provided in Table C below. All peaks listed below are greater than 5% of the maximum peak intensity.

TABLE C

| Peak # | Angle 2θ, in degrees (±0.2°) |
|---|---|
| 1 | 3.5 |
| 2 | 6.0 |
| 3 | 6.9 |
| 4 | 9.1 |
| 5 | 10.9 |
| 6 | 12.0 |
| 7 | 12.5 |
| 8 | 13.2 |
| 9 | 13.7 |
| 10 | 15.0 |
| 11 | 16.2 |
| 12 | 16.9 |
| 13 | 18.0 |
| 14 | 19.3 |
| 15 | 20.2 |
| 16 | 21.7 |
| 17 | 22.5 |
| 18 | 23.8 |
| 19 | 25.8 |
| 20 | 27.0 |
| 21 | 27.6 |
| 22 | 28.3 |
| 23 | 30.0 |
| 24 | 31.0 |
| 25 | 32.6 |

$^{13}$C ssNMR for Compound 1:Glyceryltrioctanoate

An examplary $^{13}$C solid state nuclear magnetic resonance spectroscopy ($^{13}$C ssNMR) spectrum of Compound 1:glyceryltrioctanoate is shown in FIG. 4. A listing of some of the $^{13}$C ssNMR peaks for Compound 1:glyceryltrioctanoate are provided in Table D below.

TABLE D

| Peak # | $^{13}C$ Chemical Shift (±0.1 ppm) |
|---|---|
| 1 | 178.6 |
| 2 | 172.9 |
| 3 | 171.6 |
| 4 | 169.9 |
| 5 | 165.1 |
| 6 | 155.0 |
| 7 | 143.2 |
| 8 | 139.4 |
| 9 | 137.3 |
| 10 | 134.6 |
| 11 | 133.0 |
| 12 | 126.0 |
| 13 | 119.4 |
| 14 | 117.7 |
| 15 | 112.1 |
| 16 | 67.3 |
| 17 | 64.0 |
| 18 | 62.0 |
| 19 | 59.6 |
| 20 | 54.2 |
| 21 | 35.8 |
| 22 | 34.8 |
| 23 | 31.7 |
| 24 | 30.5 |
| 25 | 23.5 |
| 26 | 14.6 |

TGA for Compound 1:Glyceryltrioctanoate:

An examplary thermal gravimetric analysis (TGA) trace of Compound 1:glyceryltrioctanoate is shown in FIG. 5. A weight loss of 28.3% corresponding to the evaporation of glyceryltriocanoate was observed from 150° C. to 300° C. for Compound 1:glyceryltrioctanoate. The calculated Compound 1 to glyceryltrioctanoate mole ratio based on the weight loss in the material is 1:3.1.

DSC for Compound 1:Glyceryltrioctanoate:

An examplary Differential Scanning calorimetry (DSC) thermogram of Compound 1:glyceryltrioctanoate is shown in FIG. 6. The thermogram had an endotherm at 186.7° C. that corresponds to the melting of the Compound 1:glyceryltrioctanoate. The error in the thermogram measurement is ±0.2° C. This endotherm was followed by an exotherm corresponding to a recrystallization to a neat form of Compound 1 which then melted in a later endothermic event.

$^1$H NMR for Compound 1:Glyceryltrioctanoate:

An examplary 1H Nuclear Magnetic Resonance (1H NMR) spectrum of Compound 1:glyceryltrioctanoate in DMSO-d6 is shown in FIG. 7.

Table E and Table F summarize the $^1$H NMR data and assign the Compound 1 and glyceryltrioctanoate hydrogens, respectively. The numbering system used for assignment of hydrogens in Compound 1 is as follows:

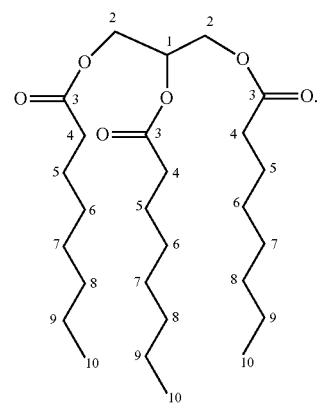

The numbering system used for assignment of hydrogens in glyceryltrioctanoate is as follows:

TABLE E

| Atom Number | $^1$H- Chemical Shift (ppm) | # of Protons | Multiplicity (J value) |
|---|---|---|---|
| 3 | 7.17 | 1 | s |
| 6 | 7.11 | 1 | s |
| 8 | 1.36 | 3 × 3 | s |
| 10 | 1.38 | 3 × 3 | s |
| 11 | 9.18 | 1 | s |
| 12 | 11.81 | 1 | s |
| 17 | 8.33 | 1 | d, J = 8.01 Hz |
| 18 | 7.52 | 1 | t, J = 7.46 Hz |
| 19 | 7.80 | 1 | t, J = 7.91 Hz |
| 20 | 7.75 | 1 | d, J = 8.21 Hz |
| 22 | 12.86 | 1 | s, broad |
| 23 | 8.87 | 1 | s |

TABLE F

| Atom Number | $^1$H- Chemical Shift (ppm) | # of Protons | Multiplicity (J value) | Theoretical signal intensity for 3:1 stoichiometry | Measured integrated signal intensity |
|---|---|---|---|---|---|
| 10 | 0.85 | 3 | t, J = 7 Hz | 3.00 | 3.06 |
| 6-9 | 1.24 | 8 | m, (overlapped) | 8.00 | 8.39 |
| 5 | 1.5 | 2 | m, (overlapped) | 2.00 | 2.19 |
| 4 | 2.27 | 0.67 | t, J = 7.3 Hz | 0.67 | 2.03 |

TABLE F-continued

| Atom Number | $^1$H-Chemical Shift (ppm) | # of Protons | Multiplicity (J value) | Theoretical signal intensity for 3:1 stoichiometry | Measured integrated signal intensity |
|---|---|---|---|---|---|
| 4 | 2.28 | 1.33 | t, J = 7.3 Hz | 1.33 | combined value reported above |
| 2a | 4.12 | 0.67 | dd (J = 6.6, J = 12.0) | 0.67 | 0.68 |
| 2b | 4.26 | 0.67 | dd (J = 12.0, J = 3.6 Hz) | 0.67 | 0.68 |
| 1 | 5.19 | 0.33 | tt (J = 3.6 Hz, J = 6.6 Hz) | 0.33 | 0.33 |

Integration was calibrated to yield 2.00 units for the combined integrated intensity for position 3 and 6 of Compound 1.

Mass Spectrometry Analysis:

The accurate mass of Compound 1:glyceryltrioctanoate was determined on the Agilent 6210 time of flight mass spectrometer. The sample was dissolved to approximately 0.1 mg/ml in MeOH and injected by direct flow injection using a syringe pump. A zero volume blank nut was used to do direct inject analysis.

The following masses were found and confirm the identity of the molecular components of the Compound 1:glyceryltriocanoate:

Compound 1:

HRMS (ESI-TOF) m/z: [M+H]$^+$ Calculated for C24H29N2O3$^+$ 393.2173. Found 393.2179.

Glyceryltrioctanoate:

HRMS (ESI-TOF) m/z: [M+NH3]+ Calculated for C27H54NO6+ 488.3947. Found 488.3951.

Molecular Ions and Exact Masses for Compound 1:Glyceryltrioctanoate:

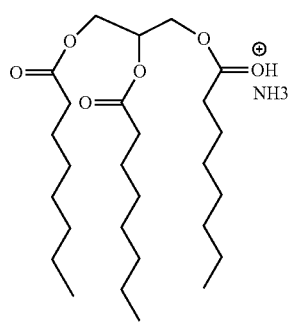

Chemical Formula: $C_{27}H_{54}NO_6^+$
Exact Mass: 488.39456

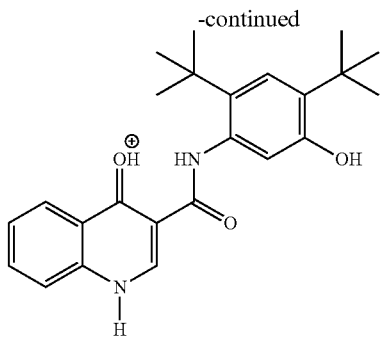

Chemical Formula: $C_{24}H_{29}N_2O_3^+$
Exact Mass: 393.21727

Characterization of Compound 1:Glyceryltrioleate

XRPD for Compound 1:Glyceryltrioleate:

An examplary XRPD pattern for Compound 1:glyceryltrioleate shown in FIG. 8 was acquired using the Panalytical Empyrean II diffractometer. Representative peaks for Compound 1:glyceryltrioleate as observed in the XRPD pattern are provided in Table G below. All peaks listed below are greater than 5% of the maximum peak intensity.

TABLE G

| Peak # | Angle 2θ, in degrees (±0.2°) |
|---|---|
| 1 | 3.5 |
| 2 | 6.9 |
| 3 | 9.2 |
| 4 | 9.8 |
| 5 | 10.4 |
| 6 | 10.9 |
| 7 | 12.0 |
| 8 | 12.7 |
| 9 | 13.3 |
| 10 | 13.8 |
| 11 | 15.1 |
| 12 | 16.3 |
| 13 | 16.9 |
| 14 | 18.1 |
| 15 | 18.5 |
| 16 | 19.4 |
| 17 | 19.9 |
| 18 | 20.2 |
| 19 | 21.2 |
| 20 | 21.8 |
| 21 | 22.6 |
| 22 | 23.8 |
| 23 | 26.0 |

TABLE G-continued

| Peak # | Angle 2θ, in degrees (±0.2°) |
|---|---|
| 24 | 27.0 |
| 25 | 27.8 |
| 26 | 28.5 |
| 27 | 30.0 |
| 28 | 30.6 |
| 29 | 32.7 |

$^{13}$C ssNMR for Compound 1:Glyceryltrioleate:

An examplary $^{13}$C ssNMR spectrum for Compound 1:glyceryltrioleate is shown in FIG. 9. A listing of some of the $^{13}$C ssNMR peaks for Compound 1:glyceryltrioleate are provided in Table H below.

TABLE H

| Peak # | $^{13}$C Chemical Shift (±0.1 ppm) |
|---|---|
| 1 | 178.6 |
| 2 | 172.9 |
| 3 | 171.6 |
| 4 | 169.9 |
| 5 | 165.0 |
| 6 | 155.0 |
| 7 | 142.9 |
| 8 | 139.3 |
| 9 | 137.4 |
| 10 | 134.5 |
| 11 | 133.0 |
| 12 | 130.5 |
| 13 | 127.3 |
| 14 | 126.0 |
| 15 | 119.3 |
| 16 | 117.7 |
| 17 | 112.1 |
| 18 | 67.2 |
| 19 | 63.9 |
| 20 | 59.6 |
| 21 | 35.8 |
| 22 | 34.8 |
| 23 | 31.7 |
| 24 | 30.5 |
| 25 | 28.2 |
| 26 | 24.6 |
| 27 | 23.6 |
| 28 | 14.7 |

TGA for Compound 1:Glyceryltrioleate:

An examplary TGA trace of Compound 1:glyceryltrioleate is shown in FIG. 10. A weight loss of 1.1% was observed from 150° C. to 300° C. for Compound 1:glyceryltrioleate. Evaporation of glyceryltrioleate was not observed due to its high boiling point.

DSC for Compound 1:Glyceryltrioleate:

An examplary DSC thermogram of Compound 1:glyceryltrioleate is shown in FIG. 11. The thermogram had an endotherm at 197.5° C. that corresponds to the melting of Compound 1:glyceryltrioleate. The error in the endotherm measurement is ±0.2° C. This endothermic event was followed by an exotherm, corresponding to the crystallization of a neat form of Compound 1. Another endotherm corresponding to the melting of this neat form of Compound 1 was observed. Another later exothermic recrystallization to a second neat form of Compound 1 was observed. A later endotherm corresponds to melting of this second form of Compound 1.

1H NMR for Compound 1:Glyceryltrioleate:

An examplary 1H NMR spectrum of Compound 1:glyceryltrioleate is shown in FIG. 12.

Table I and Table J summarize the 1H NMR data and assign the Compound 1 and glyceryltrioleate hydrogens, respectively. The numbering system used for assignment of hydrogens in Compound 1 was as previously shown above.

The numbering system used for assignment of hydrogens in glyceryltrioleate is as follows:

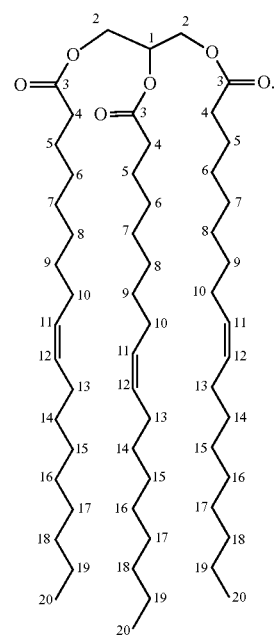 [SMILES: CCCCCCCC/C=C\CCCCCCCC(=O)OCC(COC(=O)CCCCCCC/C=C\CCCCCCCC)OC(=O)CCCCCCC/C=C\CCCCCCCC]

TABLE I

| Atom Number | $^1$H- Chemical Shift (ppm) | # of Protons | Multiplicity (J value) |
|---|---|---|---|
| 3 | 7.34 | 1 | d (1.1 Hz) |
| 6 | 7.29 | 1 | s |
| 8 | 1.41 | 3 × 3 | s |
| 10 | 1.47 | 3 × 3 | s |
| 23 | 8.95 | 1 | d, J = 6.8 Hz (overlapped)[1] |
| 22 | 11.7 | 1 | s, broad |
| 17 | 8.44 | 1 | d, J = 8.2 Hz |
| 18 | 7.53 | 1 | ddd, J = 1.6 Hz, J = 6.6 Hz, J = 8.2 Hz |
| 19 | 7.8 | 1 | t, J = 7.6 Hz |
| 20 | 7.75 | 1 | d, J = 8.21 Hz |
| 12 | 11.9 | 1 | s |
| 11 | 8.18 | 1 | s |

TABLE J

| Atom Number | $^1$H-Chemical Shift (ppm) | Multiplicity (J value) | # of Protons | Theoretical signal intensity for 6:1 stoichiometry | Measured integrated signal intensity |
|---|---|---|---|---|---|
| 20 | 0.89 | t, J = 7 Hz | 9 | 1.50 | 1.69 |
| 6-9, 14-19 | 1.34/1.30 | m, (overlapped) | 60 | 10.00 | 11.34 |
| 5 | 1.61 | m, (overlapped) | 6 | 1.00 | 1.18 |
| 10, 13 | overlapped w/solvent 2.06 | m, overlapped with acetone-d6 | 12 | 2.00 | n/a |
| 4 | 2.32 | t, J = 7.4 Hz | 6 | 1.00 | 1.06 |
| 2a | 4.18 | dd, J = 6.1, J = 12.0 | 2 | 0.33 | 0.36 |
| 2b | 4.34 | dd, J = 4.0, J = 12.0 | 2 | 0.33 | 0.36 |
| 1 | 5.28 | m | 1 | 0.17 | 0.19 |
| 11, 12 | 5.36 | m | 6 | 1.00 | 1.06 |

Integration was calibrated to yield 2.00 units for the combined integrated intensity for position 3 and 6 of Compound 1. Slow H-D exchange at position 22 of Compound 1 results in observation of both doublet (position 22 H) and singlet (position 22 D) for H23 for Compound 1.

Mass Spectrometry Analysis for Compound 1:Glyceryltrioleate:

The accurate mass of this complex was determined on a Thermo LTQ Orbi Trap XL mass spectrometer. The sample was dissolved to approximately 0.1 mg/ml in MeOH and infused by direct flow injection using a syringe pump at a rate of 50 μl/s. 50 scans were collected using the FTMS analyzer at a 30000 resolution setting.

The following masses were found and confirm the identity of the molecular components of the Compound 1:glyceryltrioleate:

Compound 1:

HRMS (ESI-TOF) m/z: [M+H]+Calculated for C24H29N2O3+ 393.2173. Found 393.2170.

Glyceryltrioleate:

HRMS (ESI-TOF) m/z: [M+Compound 1+H]+ Calculated for C81H133N2O9+ 1278.0006. Found 1277.9991.

Molecular Ions and Exact Masses Compound 1:Glyceryltrioleate:

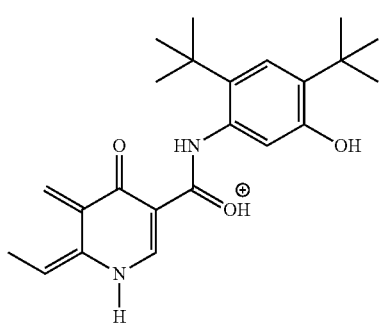

Chemical Formula: $C_{24}H_{29}N_2O_3^+$
Exact Mass: 393.21727

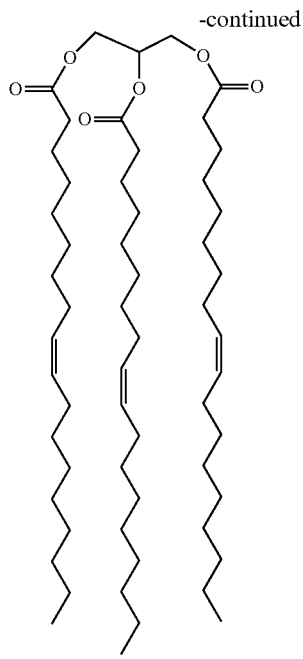

Glyceryl Trioleate
Chemical Formula: $C_{81}H_{133}N_2O_9^+$
Exact Mass: 1278.00056

Characterization of Compound 1:Glyceryltrilinoleate
XRPD for Compound 1:Glyceryltrilinoleate:

An examplary XRPD pattern for Compound 1:glyceryltrilinoleate shown in FIG. 13 was acquired using the Panalytical Empyrean II diffractometer. Representative peaks for Compound 1:glyceryltrilinoleate as observed in the XRPD pattern are provided in Table K below. All peaks listed below are greater than 5% of the maximum peak intensity.

TABLE K

| Peak # | Angle 2θ, in degrees (±0.2°) |
|---|---|
| 1 | 3.5 |
| 2 | 6.0 |

TABLE K-continued

| Peak # | Angle 2θ, in degrees (±0.2°) |
|---|---|
| 3 | 6.9 |
| 4 | 9.2 |
| 5 | 10.9 |
| 6 | 12.0 |
| 7 | 12.5 |
| 8 | 13.8 |
| 9 | 15.1 |
| 10 | 16.3 |
| 11 | 16.9 |
| 12 | 18.1 |
| 13 | 19.4 |
| 14 | 20.2 |
| 15 | 21.8 |
| 16 | 22.6 |
| 17 | 23.8 |
| 18 | 25.9 |
| 19 | 27.1 |
| 20 | 27.8 |
| 21 | 28.4 |
| 22 | 32.7 |

$^{13}$C ssNMR for Compound 1:Glyceryltrilinoleate:

An examplary $^{13}$C ssNMR spectrum for Compound 1:glyceryltrilinoleate is shown in FIG. 14. A listing of some of the $^{13}$C ssNMR peaks for Compound 1:glyceryltrilinoleate are provided in Table L below.

TABLE L

| Peak # | $^{13}$C Chemical Shift (±0.1 ppm) |
|---|---|
| 1 | 178.5 |
| 2 | 172.8 |
| 3 | 171.5 |
| 4 | 169.8 |
| 5 | 165.1 |
| 6 | 155.0 |
| 7 | 142.9 |
| 8 | 139.3 |
| 9 | 137.4 |
| 10 | 134.4 |
| 11 | 133.1 |
| 12 | 130.6 |
| 13 | 126.0 |
| 14 | 119.3 |
| 15 | 117.6 |
| 16 | 112.0 |
| 17 | 86.5 |
| 18 | 67.2 |
| 19 | 63.9 |
| 20 | 59.7 |
| 21 | 35.8 |
| 22 | 34.8 |
| 23 | 31.7 |
| 24 | 30.6 |
| 25 | 28.2 |
| 26 | 14.8 |

TGA for Compound 1:Glyceryltrilinoleate:

An examplary TGA trace of Compound 1:glyceryltrilinoleate is shown in FIG. 15. A weight loss of 1.7% was observed from 40° C. to 190° C. for Compound 1:glyceryltrlinioleate. Evaporation of glyceryltrilinoleate was not observed due to its high boiling point.

DSC for Compound 1:Glyceryltrilinoleate:

An examplary DSC thermogram for Compound 1:glyceryltrilinoleate is shown in FIG. 16. The thermogram of Compound 1:glyceryltrilinoleate in FIG. 16 had an endotherm at 182.3° C. that corresponds to the melting of Compound 1:glyceryltrilinoleate. The error in the endotherm measurement is ±0.2° C. This endothermic event was followed by an exotherm, corresponding to the crystallization of a neat form of Compound 1. Another endotherm corresponding to the melting of this neat form was observed. Another later exothermic recrystallization to a second neat form of Compound 1 was observed. A later endotherm corresponds to melting of this second form of Compound 1.

$^1$H NMR for Compound 1:Glyceryltrilinoleate:

An examplary 1H NMR spectrum of Compound 1:glyceryltrioleate is shown in FIG. 17.

Table M and Table N summarize the 1H NMR data and assign the Compound 1 and glyceryltrioleate hydrogens, respectively. The numbering system used for assignment of hydrogens in Compound 1 was previously shown above. Integration was calibrated to yield 2.00 units for the combined integrated intensity for position 3 and 6 of Compound 1.

The numbering system for the assignment of hydrogens in glyceryltrioleate is as follows:

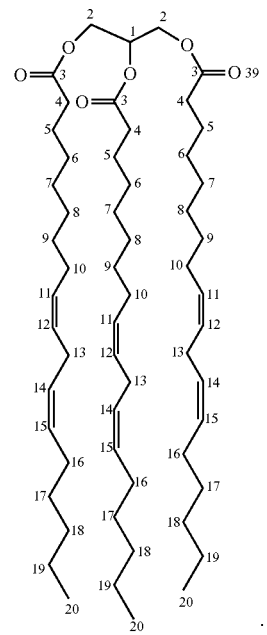 [SMILES: CCCCC/C=C\C/C=C\CCCCCCCC(=O)OCC(COC(=O)CCCCCCC/C=C\C/C=C\CCCCC)OC(=O)CCCCCCC/C=C\C/C=C\CCCCC]

TABLE M

| Atom Number | $^1$H- Chemical Shift (ppm) | # of Protons | Multiplicity (J value) |
|---|---|---|---|
| 3 | 7.33 | 1 | s |
| 6 | 7.29 | 1 | s |
| 8 | 1.4 | 3 × 3 | s |
| 10 | 1.47 | 3 × 3 | s |
| 23 | 8.95 | 1 | d, J = 6.8 Hz (overlapped)[1] |
| 22 | 11.7 | 1 | s, broad |
| 17 | 8.44 | 1 | d, J = 8.2 Hz |
| 18 | 7.53 | 1 | ddd, J = 1.6 Hz, J = 6.6 Hz, J = 8.2 Hz |
| 19 | 7.8 | 1 | t, J = 7.6 Hz |
| 20 | 7.76 | 1 | d, J = 7.8 Hz |
| 12 | 11.9 | 1 | s |
| 11 | 8.2 | 1 | s |

TABLE N

| Atom Number | $^1$H-Chemical Shift (ppm) | Multiplicity (J value) | # of Protons | Theoretical signal intensity for 6:1 stoichiometry | Measured integrated signal intensity[1] |
|---|---|---|---|---|---|
| 20 | 0.89 | t, J = 7 Hz | 9 | 1.50 | 1.42 |
| 6-9, 17-19 | 1.34 | m (overlapped) | 42 | 7.00 | 6.01 |
| 5 | 1.61 | m (overlapped) | 6 | 1.00 | 1.33 |
| 10, 16 | 2.08 | overlapped with acetone-d6 | 12 | 2.00 | n/a |
| 4 | 2.32 | t, J = 7.4 Hz | 6 | 1.00 | 0.91 |
| 13 | 2.80 | D, J = 12 Hz | 6 | 1.00 | n/a |
|  | overlapped w/HOD |  |  |  |  |
| 2a | 4.18 | dd, J = 6.1, J = 12.0 | 2 | 0.33 | 0.31 |
| 2b | 4.34 | dd, J = 4.0, J = 12.0 | 2 | 0.33 | 0.34 |
| 1 | 5.28 | m | 1 | 0.17 | 0.14 |
| 11, 12, 13, 14 | 5.36 | m | 12 | 2.00 | 1.08 |

Integration was calibrated to yield 2.00 units for the combined integrated intensity for position 3 and 6 of Compound 1. Slow H-D exchange at position 22 of Compound 1 results in observation of both doublet (position 22 H) and singlet (position 22 D) for H23 for Compound 1.

Mass Spectrometry Analysis for Compound 1:Glyceryltrilinoleate:

The accurate mass of this complex was determined on a LTQ Orbi Trap XL mass spectrometer. The sample was dissolved to approximately 0.1 mg/ml in MeOH and infused by direct flow injection using a syringe pump at a rate of 4 l/s. 50 scans were collected using the FTMS analyzer at a 30000 resolution setting.

The following masses were found and confirm the identity of the molecular components of Compound 1:glyceryltrilinoleate:

Compound 1:

HRMS (ESI-TOF) m/z: [M+H]+ Calculated for C24H29N2O3+ 393.2173. Found 393.2176.

Glyceryltrilinoleate:

HRMS (ESI-TOF) m/z: [M+Compound 1+H]+ Calculated for C81H127N2O9+ 1271.9536. Found 1271.9541.

Molecular Ions and Exact Masses Compound 1:Glyceryltrilinoleate:

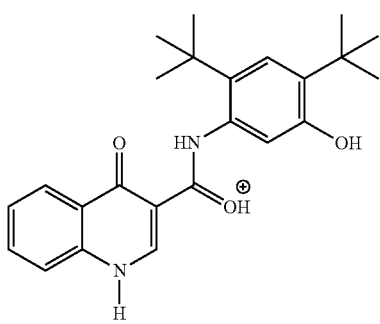

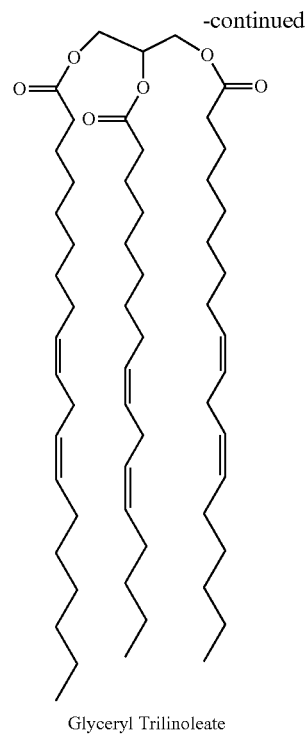

Glyceryl Trilinoleate

Chemical Formula: $C_{81}H_{127}N_2O_9^+$
Exact Mass: 1271.95361

Characterization of Compound 1:Triacetin

XRPD for Compound 1:Triacetin:

An examplary XRPD pattern for Compound 1:triacetin shown in FIG. 18 was acquired using the Panalytical Empyrean II diffractometer, Representative peaks for Compound 1:triacetin as observed in the XRPD pattern are provided in Table O below. All peaks listed below are greater than 5% of the maximum peak intensity.

TABLE O

| Peak # | Angle 2θ, in degrees (±0.2°) |
|---|---|
| 1 | 4.9 |
| 2 | 9.5 |
| 3 | 9.8 |
| 4 | 14.7 |
| 5 | 16.5 |
| 6 | 18.2 |
| 7 | 23.1 |

$^{13}$C ssNMR for Compound 1:Triacetin:

An examplary $^{13}$C ssNMR spectrum for Compound 1:triacetin is shown in FIG. 19. A listing of some of the $^{13}$C ssNMR peaks for Compound 1:glyceryltriacetate are provided in Table P below.

TABLE P

| Peak # | $^{13}$C Chemical Shift (±0.1 ppm) |
|---|---|
| 1 | 178.2 |
| 2 | 165.4 |
| 3 | 164.3 |
| 4 | 155.1 |
| 5 | 154.8 |
| 6 | 154.1 |
| 7 | 149.4 |
| 8 | 146.8 |
| 9 | 145.6 |
| 10 | 140.0 |
| 11 | 134.1 |
| 12 | 133.2 |
| 13 | 132.3 |
| 14 | 127.0 |
| 15 | 125.9 |
| 16 | 125.6 |
| 17 | 124.3 |
| 18 | 120.6 |
| 19 | 119.7 |
| 20 | 119.2 |
| 21 | 118.3 |
| 22 | 117.6 |
| 23 | 111.9 |
| 24 | 111.1 |
| 25 | 110.4 |
| 26 | 35.3 |
| 27 | 35.0 |
| 28 | 31.8 |
| 29 | 29.8 |
| 30 | 21.9 |
| 31 | 20.4 |
| 32 | 18.9 |

DSC for Compound 1:Triacetin:

An examplary DSC thermogram for Compound 1:triacetin is shown in FIG. 20. The thermogram of Compound 1:triacetin an endotherm at 123.9° C. that corresponds to the melting of the Compound 1:glyceryltritriacetin co-crystal. This event is followed by another endotherm at 141.9° C. and yet another endotherm at 193.8° C.

Characterization of Compound 1:Glyceryltributyrate

XRPD for Compound 1:Glyceryltributyrate:

An examplary XRPD pattern for Compound 1:glyceryltributyrate shown in FIG. 21 was acquired using the Panalytical Empyrean II diffractometer. Representative peaks for Compound 1:glyceryltributyrate as observed in the XRPD pattern are provided in Table Q below. All peaks listed below are greater than 5% of the maximum peak intensity.

TABLE Q

| Peak # | Angle 2θ, in degrees (±0.2°) |
|---|---|
| 1 | 4.8 |
| 2 | 4.9 |
| 3 | 6.8 |
| 4 | 9.5 |
| 5 | 9.6 |
| 6 | 14.3 |
| 7 | 18.0 |
| 8 | 19.0 |
| 9 | 19.8 |
| 10 | 21.4 |
| 11 | 22.6 |
| 12 | 23.8 |

Characterization of Compound 1:Glyceryltristearate

XRPD for Compound 1:Glyceryltristearate:

An examplary XRPD pattern for Compound 1:glyceryltristearate shown in FIG. 22 was acquired using the Broker D8 Advance diffractometer. Representative peaks for Compound 1:glyceryltristearate as observed in the XRPD pattern are provided in Table R below. All peaks listed below are equal to or greater than 1% of the maximum peak intensity.

TABLE R

| Peak # | Angle 2θ, in degrees (±0.2°) |
|---|---|
| 1 | 3.6 |
| 2 | 5.4 |
| 3 | 6.2 |
| 4 | 6.9 |
| 5 | 9.3 |
| 6 | 11.0 |
| 7 | 12.1 |
| 8 | 12.6 |
| 9 | 13.4 |
| 10 | 13.9 |
| 11 | 15.4 |
| 12 | 16.4 |
| 13 | 17.0 |
| 14 | 18.2 |
| 15 | 18.5 |
| 16 | 19.4 |
| 17 | 20.0 |
| 18 | 20.4 |
| 19 | 21.8 |
| 20 | 23.8 |
| 21 | 26.0 |
| 22 | 27.0 |
| 23 | 28.4 |
| 24 | 29.1 |
| 25 | 29.9 |
| 26 | 31.2 |
| 27 | 32.8 |

$^{13}$C ssNMR for Compound 1:Glyceryltristearate:

An examplary $^{13}$C ssNMR spectrum for Compound 1:glyceryltristearate is shown in FIG. 23. A listing of some of the $^{13}$C ssNMR peaks for Compound 1:glyceryltristearate are provided in Table S below.

TABLE S

| Peak # | $^{13}$C Chemical Shift (±0.1 ppm) |
|---|---|
| 1 | 178.5 |
| 2 | 172.9 |
| 3 | 171.6 |
| 4 | 169.9 |
| 5 | 165.0 |

TABLE S-continued

| Peak # | $^{13}$C Chemical Shift (±0.1 ppm) |
|---|---|
| 6 | 155.0 |
| 7 | 143.6 |
| 8 | 139.4 |
| 9 | 137.2 |
| 10 | 135.1 |
| 11 | 134.4 |
| 12 | 133.0 |
| 13 | 127.3 |
| 14 | 126.1 |
| 15 | 119.5 |
| 16 | 117.6 |
| 17 | 112.0 |
| 18 | 67.3 |
| 19 | 64.1 |
| 20 | 59.6 |
| 21 | 35.7 |
| 22 | 34.7 |
| 23 | 31.7 |
| 24 | 30.6 |
| 25 | 23.6 |
| 26 | 14.8 |

DSC for Compound 1:Glyceryltristearate:

An examplary DSC thermogram for Compound 1:glyceryltristearate is shown in FIG. 24. The thermogram of Compound 1:glyceryltristearate in FIG. 24 has an endotherm at 55.1° C. that corresponds to the eutectic melt of Compound 1:glyceryltrilstearate co-crystal and glyceryltristearate. This event is followed by another endotherm at 71.3° C., corresponding to the melt of neat glyceryltristearate. Overlapping endotherm at 201.3° C. and exotherm at 208.1° C. (peak) correspond to the cocrystal melt and crystallization of neat Compound 1, respectively. Another endotherm at 284.7° C. corresponds to the melt of a neat form of Compound 1.

Characterization of Compound 1:Glyceryltripalmitate

XRPD for Compound 1:Glyceryltripalmitate:

An examplary XRPD pattern for Compound 1:glyceryltripalmitate shown in FIG. 25 was acquired using the Bruker D8 Advance diffractometer. Representative peaks for Compound 1:glyceryltripalmitate as observed in the XRPD pattern are provided in Table T below. All peaks listed below are greater than 1% of the maximum peak intensity.

TABLE T

| Peak # | Angle 2θ, in degrees (±0.2°) |
|---|---|
| 1 | 3.5 |
| 2 | 6.0 |
| 3 | 6.9 |
| 4 | 9.3 |
| 5 | 11.0 |
| 6 | 13.8 |
| 7 | 15.1 |
| 8 | 16.3 |
| 9 | 17.0 |
| 10 | 18.2 |
| 11 | 19.4 |
| 12 | 19.9 |
| 13 | 20.3 |
| 14 | 21.8 |
| 15 | 23.7 |

$^{13}$C ssNMR for Compound 1:Glyceryltripalmitate:

An examplary $^{13}$C ssNMR spectrum for Compound 1:glyceryltripalmitate is shown in FIG. 26. A listing of some of the $^{13}$C ssNMR peaks for Compound 1:glyceryltripalmitate are provided in Table U below.

TABLE U

| Peak # | $^{13}$C Chemical Shift (± 0.1 ppm) |
|---|---|
| 1 | 178.4 |
| 2 | 173.0 |
| 3 | 169.9 |
| 4 | 165.0 |
| 5 | 155.0 |
| 6 | 144.0 |
| 7 | 139.5 |
| 8 | 137.2 |
| 9 | 134.5 |
| 10 | 133.0 |
| 11 | 127.2 |
| 12 | 126.0 |
| 13 | 119.6 |
| 14 | 117.5 |
| 15 | 112.0 |
| 16 | 67.2 |
| 17 | 64.0 |
| 18 | 59.7 |
| 19 | 35.7 |
| 20 | 34.6 |
| 21 | 31.7 |
| 22 | 30.6 |
| 23 | 23.7 |
| 24 | 14.8 |

DSC for Compound 1:Glyceryltripalmitate:

An examplary DSC thermogram for Compound 1:glyceryltripalmitate is shown in FIG. 27. The thermogram of Compound 1:glyceryltripalmitate in FIG. 27 has an endotherm at 47.7° C. that corresponds to the eutectic melt of Compound 1:glyceryltripalmitate co-crystal and glyceryltripalmitate. This event is followed by another endotherm at 63.0° C., corresponding to the melt of neat glyceryltripalmitate. Overlapping endotherm at 174.9° C. and exotherm at 186.7° C. correspond to the cocrystal melt and crystallization of neat Compound 1, respectively. Another endotherm at 266.2° C. corresponds to the melt of a neat form of Compound 1.

Characterization of Compound 1:Glyceryltridodecanoate

XRPD for Compound 1:Glyceryltridodecanoate:

An examplary XRPD pattern for Compound 1:glyceryldodecanoate is shown FIG. 28 was acquired using the Bruker D8 Advance diffractometer. Representative peaks for Compound 1:glyceryltridodecanoate as observed in the XRPD pattern are provided in Table V below. All peaks listed below are equal to or greater than 1% of the maximum peak intensity.

TABLE V

| Peak # | Angle 2θ, in degrees (±0.2°) |
|---|---|
| 1 | 3.5 |
| 2 | 6.1 |
| 3 | 6.9 |
| 4 | 9.2 |
| 6 | 10.9 |
| 7 | 11.8 |
| 8 | 12.1 |
| 9 | 12.6 |
| 10 | 13.2 |
| 11 | 13.8 |
| 12 | 14.9 |
| 13 | 16.3 |
| 14 | 16.9 |
| 15 | 18.1 |
| 16 | 18.5 |
| 17 | 19.4 |
| 18 | 19.8 |

TABLE V-continued

| Peak # | Angle 2θ, in degrees (±0.2°) |
|---|---|
| 19 | 20.3 |
| 20 | 21.7 |
| 21 | 23.4 |
| 22 | 23.9 |
| 23 | 25.2 |
| 24 | 25.8 |
| 25 | 27.2 |
| 26 | 28.4 |

$^{13}C$ ssNMR for Compound 1:Glyceryltridodecanoate:

An examplary $^{13}C$ ssNMR spectrum for Compound 1:glyceryltridodecanoate is shown in FIG. 29. A listing of some of the $^{13}C$ ssNMR peaks for Compound 1:glyceryltridodecanoate are provided in Table W below.

TABLE W

| Peak # | $^{13}C$ Chemical Shift (±0.1 ppm) |
|---|---|
| 1 | 178.4 |
| 2 | 173.1 |
| 3 | 171.5 |
| 4 | 169.8 |
| 5 | 165.0 |
| 6 | 155.0 |
| 7 | 143.0 |
| 8 | 139.4 |
| 9 | 137.2 |
| 10 | 134.6 |
| 11 | 133.0 |
| 12 | 127.3 |
| 13 | 126.1 |
| 14 | 119.6 |
| 15 | 117.6 |
| 16 | 112.1 |
| 17 | 67.1 |
| 18 | 63.9 |
| 19 | 59.7 |
| 20 | 35.6 |
| 21 | 31.7 |
| 22 | 30.6 |
| 23 | 23.6 |

Single Crystal X-Ray Crystallography for Compound 1:Glyceryltridodecanoate

Representative single crystal x-ray crystallography data for Compound 1:glyceryl tridodecanoate is provided in Tables X-i to X-vii.

TABLE X-i

Crystal data

| | |
|---|---|
| $C_{37}H_{52.67}N_2O_5$ | F(000) = 3944 |
| $M_r$ = 605.48 | $D_x$ = 1.099 g cm$^{-3}$ |
| Hexagonal, P$^-$31c | Synchrotron radiation, λ = 0.70158 Å |
| a = 29.1507 (10) Å | μ = 0.07 mm$^{-1}$ |
| c = 14.9118 (6) Å | T = 100 K |
| V = 10973.8 (7) Å$^3$ | Rod, colorless |
| Z = 12 | |

TABLE X-ii

Data collection

| | |
|---|---|
| Radiation source: synchrotron | $R_{int}$ = 0.076 |
| Graphite monochromator | $θ_{max}$ = 24.3°, $θ_{min}$ = 1.6° |

TABLE X-ii-continued

Data collection

| | |
|---|---|
| 66577 measured reflections | h = −34→32 |
| 5709 independent reflections | k = −33→34 |
| 4610 reflections with I > 2σ(I) | l = −17→14 |

TABLE X-iii

Refinement

| | |
|---|---|
| Refinement on F$^2$ | Primary atom site location: structure-invariant direct methods |
| Least-squares matrix: full | Secondary atom site location: difference Fourier map |
| R[F$^2$ > 2☒(F$^2$)] = 0.226 | Hydrogen site location: inferred from neighbouring sites |
| wR(F$^2$) = 0.545 | H atoms treated by a mixture of independent and constrained refinement |
| S = 2.03 | w = 1/[σ$^2$(F$_o^2$) + (0.2P)$^2$] where P = (F$_o^2$ + 2F$_c^2$)/3 |
| 5709 reflections | (Δ/σ)$_{max}$ = 3.947 |
| 361 parameters | Δ}$_{max}$ = 0.54 e Å$^{-3}$ |
| 19 restraints | Δ}$_{min}$ = −0.35 e Å$^{-3}$ |

TABLE X-iv

Special details

Geometry. All esds (except the esd in the dihedral angle between two l.s. planes) are estimated using the full covariance matrix. The cell esds are taken into account individually in the estimation of esds in distances, angles and torsion angles; correlations between esds in cell parameters are only used when they are defined by crystal symmetry. An approximate (isotropic) treatment of cell esds is used for estimating esds involving l.s. planes.
Refinement. Refinement of F$^2$ against ALL reflections. The weighted R-factor wR and goodness of fit S are based on F$^2$, conventional R-factors R are based on F, with F set to zero for negative F$^2$. The threshold expression of F$^2$ > 2sigma(F$^2$) is used only for calculating R-factors(gt) etc. and is not relevant to the choice of reflections for refinement. R-factors based on F$^2$ are statistically about twice as large as those based on F, and R- factors based on ALL data will be even larger.

TABLE X-v

Fractional atomic coordinates and isotropic or equivalent isotropic displacement parameters (Å$^2$)

| | x | y | z | $U_{iso}$*/$U_{eq}$ |
|---|---|---|---|---|
| C1 | 0.2708 (3) | 0.8168 (4) | 0.1302 (11) | 0.197 (5) |
| C2 | 0.3516 (3) | 0.8099 (3) | 0.1185 (11) | 0.197 (5) |
| C3 | 0.2429 (3) | 0.7620 (4) | 0.1281 (9) | 0.183 (4) |
| N1 | 0.4387 (3) | 0.8802 (2) | 0.0983 (10) | 0.226 (5) |
| H1 | 0.4223 | 0.8979 | 0.0865 | 0.271* |
| C4 | 0.4097 (3) | 0.8311 (3) | 0.1168 (11) | 0.209 (6) |
| C5 | 0.3276 (3) | 0.8423 (3) | 0.1157 (13) | 0.217 (6) |
| O2 | 0.4277 (2) | 0.7989 (2) | 0.1347 (11) | 0.274 (6) |
| C6 | 0.3197 (3) | 0.7569 (3) | 0.1298 (9) | 0.173 (4) |
| H6 | 0.3356 | 0.7356 | 0.1372 | 0.208* |
| O1 | 0.3551 (2) | 0.8934 (2) | 0.1076 (9) | 0.228 (5) |
| N2 | 0.2668 (2) | 0.7333 (2) | 0.1311 (6) | 0.164 (3) |
| H2 | 0.2477 | 0.6986 | 0.1340 | 0.197* |
| C7 | 0.1863 (4) | 0.7341 (5) | 0.1360 (15) | 0.244 (8) |
| H7 | 0.1667 | 0.6965 | 0.1396 | 0.292* |
| C8 | 0.5250 (4) | 0.9194 (3) | 0.1741 (16) | 0.228 (8) |
| H8 | 0.5060 | 0.9049 | 0.2282 | 0.274* |
| C9 | 0.2438 (4) | 0.8470 (4) | 0.1279 (14) | 0.233 (7) |
| H9 | 0.2629 | 0.8843 | 0.1202 | 0.280* |
| O3 | 0.6057 (3) | 0.9569) (3) | 0.2587 (12) | 0.253 (6) |
| H3 | 0.5836 | 0.9407 | 0.2996 | 0.380* |
| C10 | 0.1619 (5) | 0.7629 (6) | 0.1383 (17) | 0.270 (9) |

TABLE X-v-continued

Fractional atomic coordinates and isotropic or equivalent isotropic displacement parameters (Å$^2$)

|   | x | y | z | $U_{iso}$*/$U_{eq}$ |
|---|---|---|---|---|
| H10 | 0.1243 | 0.7450 | 0.1410 | 0.324* |
| C11 | 0.1907 (4) | 0.8204 (5) | 0.1369 (16) | 0.263 (9) |
| H11 | 0.1721 | 0.8393 | 0.1422 | 0.316* |
| C12 | 0.6673 (4) | 1.0096 (4) | 0.1039 (14) | 0.227 (7) |
| C13 | 0.6068 (4) | 0.9709 (4) | 0.1014 (15) | 0.220 (7) |
| C14 | 0.6792 (3) | 1.0569 (4) | 0.1638 (14) | 0.229 (7) |
| H14A | 0.6564 | 1.0445 | 0.2170 | 0.344* |
| H14B | 0.6723 | 1.0818 | 0.1304 | 0.344* |
| H14C | 0.7164 | 1.0747 | 0.1823 | 0.344* |
| C15 | 0.5781 (4) | 0.9486 (3) | 0.1736 (16) | 0.228 (8) |
| C37 | 0.5243 (15) | 0.9305 (18) | −0.1442 (11) | 0.57 (3) |
| H37A | 0.5473 | 0.9689 | −0.1506 | 0.857* |
| H37B | 0.4974 | 0.9174 | −0.1915 | 0.857* |
| H37C | 0.5457 | 0.9132 | −0.1493 | 0.857* |
| C17 | 0.5782 (4) | 0.9571 (5) | 0.0208 (16) | 0.279 (12) |
| H17 | 0.5998 | 0.9664 | −0.0312 | 0.334* |
| C18 | 0.5182 (5) | 0.9296 (5) | 0.0001 (12) | 0.289 (10) |
| C19 | 0.6974 (4) | 0.9824 (4) | 0.1357 (16) | 0.247 (8) |
| H19A | 0.7322 | 1.0090 | 0.1585 | 0.371* |
| H19B | 0.7020 | 0.9634 | 0.0855 | 0.371* |
| H19C | 0.6774 | 0.9572 | 0.1836 | 0.371* |
| C20 | 0.6882 (5) | 1.0244 (10) | 0.007 (2) | 0.336 (17) |
| H20A | 0.6658 | 0.9950 | −0.0336 | 0.504* |
| H20B | 0.7247 | 1.0313 | 0.0039 | 0.504* |
| H20C | 0.6873 | 1.0562 | −0.0118 | 0.504* |
| C21 | 0.4997 (5) | 0.9114 (4) | 0.0947 (14) | 0.209 (7) |
| C22 | 0.5057 (8) | 0.9220 (8) | −0.0808 (11) | 0.266 (9) |
| C23 | 0.4695 (12) | 0.864 (2) | −0.109 (5) | 0.68 (7) |
| H23A | 0.4703 | 0.8408 | −0.0635 | 1.018* |
| H23B | 0.4818 | 0.8581 | −0.1666 | 1.018* |
| H23C | 0.4332 | 0.8577 | −0.1161 | 1.018* |
| C24 | 0.4561 (6) | 0.9358 (7) | −0.0824 (14) | 0.252 (8) |
| H24A | 0.4709 | 0.9742 | −0.0812 | 0.378* |
| H24B | 0.4334 | 0.9199 | −0.0298 | 0.378* |
| H24C | 0.4351 | 0.9212 | −0.1370 | 0.378* |
| C31 | 0.3177 (9) | 0.7343 (12) | 0.873 (2) | 0.333 (15) |
| C32 | 0.2650 (16) | 0.731 (2) | 0.856 (6) | 0.64 (7) |
| C33 | 0.267 (2) | 0.7790 (16) | 0.891 (2) | 0.78 (9) |
| C35 | 0.190 (2) | 0.8034 (12) | 0.892 (4) | 1.05 (18) |
| C36 | 0.1312 (16) | 0.7838 (11) | 0.889 (3) | 0.325 (16) |
| C34 | 0.214 (2) | 0.770 (2) | 0.864 (2) | 0.53 (4) |
| C38 | 0.3078 (14) | 0.6793 (14) | 0.898 (3) | 0.40 (2) |
| C41 | 0.1040 (18) | 0.8161 (9) | 0.885 (2) | 1.05 (7) |
| C42 | 0.077 (3) | 0.846 (3) | 0.884 (5) | 0.73 (8) |
| O51 | 0.3333 | 0.6667 | 0.024 (2) | 0.325 (13) |
| O52 | 0.152 (5) | 0.937 (4) | 0.186 (6) | 0.97 (13) |

TABLE X-VI

Atomic displacement parameters (Å$^2$)

|   | $U^{11}$ | $U^{22}$ | $U^{33}$ | $U^{12}$ | $U^{13}$ | $U^{23}$ |
|---|---|---|---|---|---|---|
| C1 | 0.058 (4) | 0.076 (5) | 0.449 (17) | 0.027 (4) | 0.016 (7) | 0.001 (7) |
| C2 | 0.075 (4) | 0.062 (4) | 0.453 (16) | 0.033 (3) | −0.024 (7) | −0.083 (7) |
| C3 | 0.060 (4) | 0.077 (5) | 0.400 (14) | 0.026 (4) | 0.019 (6) | −0.012 (7) |
| N1 | 0.054 (3) | 0.062 (3) | 0.550 (16) | 0.020 (3) | 0.024 (6) | −0.045 (6) |
| C4 | 0.058 (4) | 0.059 (4) | 0.501 (17) | 0.022 (3) | 0.005 (7) | −0.063 (7) |
| C5 | 0.059 (4) | 0.057 (4) | 0.527 (19) | 0.023 (3) | −0.009 (7) | −0.036 (7) |
| O2 | 0.065 (3) | 0.067 (3) | 0.684 (19) | 0.030 (3) | −0.002 (6) | −0.084 (6) |
| C6 | 0.067 (4) | 0.060 (4) | 0.380 (13) | 0.023 (3) | 0.001 (6) | 0.006 (6) |
| O1 | 0.067 (3) | 0.059 (3) | 0.555 (14) | 0.029 (2) | 0.057 (7) | −0.008 (5) |
| N2 | 0.066 (3) | 0.054 (3) | 0.359 (9) | 0.022 (3) | 0.033 (4) | 0.016 (4) |
| C7 | 0.056 (4) | 0.104 (7) | 0.56 (2) | 0.030 (5) | 0.017 (9) | 0.026 (11) |
| C8 | 0.067 (5) | 0.052 (4) | 0.57 (3) | 0.036 (4) | 0.000 (10) | −0.038 (8) |
| C9 | 0.061 (4) | 0.092 (6) | 0.54 (2) | 0.032 (4) | 0.034 (9) | 0.023 (9) |
| O3 | 0.054 (4) | 0.077 (4) | 0.614 (19) | 0.022 (3) | 0.042 (7) | 0.033 (7) |
| C10 | 0.076 (6) | 0.127 (9) | 0.57 (3) | 0.020 (7) | 0.021 (11) | 0.021 (14) |
| C11 | 0.072 (5) | 0.108 (7) | 0.62 (3) | 0.050 (5) | 0.050 (11) | 0.021 (12) |
| C12 | 0.059 (5) | 0.100 (7) | 0.52 (2) | 0.036 (5) | 0.049 (9) | 0.004 (10) |
| C13 | 0.050 (5) | 0.074 (5) | 0.53 (2) | 0.022 (5) | 0.024 (10) | −0.057 (10) |
| C14 | 0.061 (4) | 0.077 (5) | 0.53 (2) | 0.016 (4) | 0.009 (8) | −0.061 (9) |
| C15 | 0.050 (5) | 0.041 (4) | 0.58 (3) | 0.014 (4) | 0.073 (11) | −0.022 (8) |
| C37 | 0.55 (5) | 1.09 (9) | 0.138 (9) | 0.46 (6) | 0.021 (16) | −0.21 (2) |
| C17 | 0.057 (6) | 0.150 (10) | 0.58 (3) | 0.017 (6) | 0.097 (12) | −0.125 (15) |
| C18 | 0.239 (14) | 0.157 (8) | 0.45 (2) | 0.085 (8) | 0.227 (15) | −0.110 (10) |
| C19 | 0.065 (4) | 0.096 (6) | 0.59 (3) | 0.046 (4) | −0.008 (9) | −0.014 (10) |
| C20 | 0.072 (7) | 0.26 (3) | 0.63 (3) | 0.053 (11) | 0.022 (15) | −0.10 (2) |
| C21 | 0.080 (6) | 0.090 (6) | 0.48 (2) | 0.057 (5) | 0.005 (10) | −0.056 (9) |
| C22 | 0.314 (17) | 0.332 (18) | 0.194 (10) | 0.193 (14) | 0.098 (11) | −0.123 (11) |
| C23 | 0.25 (4) | 1.05 (18) | 0.89 (11) | 0.45 (8) | −0.23 (6) | −0.40 (12) |
| C24 | 0.136 (10) | 0.189 (13) | 0.384 (18) | 0.046 (10) | 0.038 (11) | −0.106 (14) |
| C31 | 0.159 (17) | 0.27 (3) | 0.48 (3) | 0.035 (19) | 0.089 (18) | 0.06 (3) |
| C32 | 0.20 (3) | 0.28 (6) | 1.3 (3) | −0.01 (3) | −0.09 (6) | 0.16 (9) |
| C33 | 1.19 (18) | 0.21 (3) | 0.32 (3) | −0.11 (6) | −0.30 (6) | 0.11 (3) |
| C35 | 2.0 (4) | 0.083 (14) | 0.53 (7) | 0.12 (6) | −0.40 (17) | 0.00 (2) |
| C36 | 0.33 (4) | 0.136 (18) | 0.53 (4) | 0.13 (2) | −0.06 (3) | −0.07 (2) |
| C34 | 0.78 (11) | 0.36 (5) | 0.41 (6) | 0.26 (6) | −0.34 (6) | −0.05 (4) |
| C38 | 0.25 (3) | 0.29 (3) | 0.58 (5) | 0.07 (2) | 0.11 (3) | 0.26 (4) |
| C41 | 1.81 (15) | 0.26 (2) | 0.64 (5) | 0.19 (5) | −0.35 (7) | 0.34 (3) |
| C42 | 0.78 (13) | 0.47 (9) | 0.86 (13) | 0.25 (9) | 0.12 (10) | 0.45 (10) |
| O51 | 0.274 (18) | 0.274 (18) | 0.43 (3) | 0.137 (9) | 0.000 | 0.000 |
| O52 | 1.3 (4) | 1.1 (3) | 0.99 (16) | 1.0 (3) | −0.23 (16) | −0.40 (15) |

TABLE X-vii

Geometric parameters (Å, °) for (hexe)

| | | | |
|---|---|---|---|
| C1—C3 | 1.383 (13) | C12—C14 | 1.531 (19) |
| C1—C9 | 1.445 (14) | C12—C20 | 1.55 (3) |
| C1—C5 | 1.453 (12) | C13—C15 | 1.32 (2) |
| C2—C6 | 1.357 (12) | C13—C17 | 1.40 (2) |
| C2—C5 | 1.431 (12) | C37—C22 | 1.06 (2) |
| C2—C4 | 1.483 (11) | C17—C18 | 1.55 (2) |
| C3—N2 | 1.332 (10) | C18—C22 | 1.25 (2) |
| C3—C7 | 1.433 (13) | C18—C21 | 1.51 (2) |
| N1—C4 | 1.276 (12) | C22—C23 | 1.53 (4) |
| N1—C21 | 1.541 (15) | C22—C24 | 1.68 (2) |
| C4—O2 | 1.311 (13) | C31—C32 | 1.51 (4) |
| C5—O1 | 1.296 (10) | C31—C38 | 1.53 (4) |
| C6—N2 | 1.337 (11) | C32—C33 | 1.47 (5) |
| C7—C10 | 1.35 (2) | C33—C34 | 1.49 (5) |
| C8—C15 | 1.342 (15) | C35—C34 | 1.50 (4) |
| C8—C21 | 1.35 (2) | C35—C36 | 1.51 (5) |
| C9—C11 | 1.348 (15) | C36—C41 | 1.51 (4) |
| O3—C15 | 1.46 (2) | C38—C38$^i$ | 1.70 (6) |
| C10—C11 | 1.45 (2) | C38—C38$^{ii}$ | 1.70 (6) |
| C12—C19 | 1.524 (16) | C41—C42 | 1.45 (5) |
| C12—C13 | 1.546 (15) | | |
| C3—C1—C9 | 121.1 (7) | C15—C13—C17 | 114.7 (13) |
| C3—C1—C5 | 116.8 (7) | C15—C13—C12 | 123.4 (18) |
| C9—C1—C5 | 120.9 (8) | C17—C13—C12 | 121.9 (16) |
| C6—C2—C5 | 118.1 (7) | C13—C15—C8 | 124 (2) |
| C6—C2—C4 | 117.9 (7) | C13—C15—O3 | 117.9 (11) |
| C5—C2—C4 | 123.9 (7) | C8—C15—O3 | 117.8 (13) |
| N2—C3—C1 | 122.2 (7) | C13—C17—C18 | 132.6 (14) |
| N2—C3—C7 | 117.1 (8) | C22—C18—C21 | 145.1 (12) |
| C1—C3—C7 | 120.1 (8) | C22—C18—C17 | 116.1 (12) |
| C4—N1—C21 | 126.4 (8) | C21—C18—C17 | 96.2 (15) |
| N1—C4—O2 | 124.6 (7) | C8—C21—C18 | 133.6 (13) |
| N1—C4—C2 | 116.8 (8) | C8—C21—N1 | 116.1 (14) |
| O2—C4—C2 | 118.6 (8) | C18—C21—N1 | 110.1 (15) |
| O1—C5—C2 | 122.4 (7) | C37—C22—C18 | 139 (2) |
| O1—C5—C1 | 119.6 (7) | C37—C22—C23 | 90 (3) |
| C2—C5—C1 | 117.8 (8) | C18—C22—C23 | 116 (3) |
| N2—C6—C2 | 123.1 (7) | C37—C22—C24 | 110 (2) |
| C6—N2—C3 | 120.5 (6) | C18—C22—C24 | 100.4 (10) |
| C10—C7—C3 | 117.6 (9) | C23—C22—C24 | 93.1 (17) |
| C15—C8—C21 | 117.5 (19) | C32—C31—C38 | 109 (3) |
| C11—C9—C1 | 117.9 (9) | C33—C32—C31 | 109 (5) |
| C11—C10—C7 | 122.8 (10) | C32—C33—C34 | 102 (3) |
| C10—C11—C9 | 119.9 (9) | C34—C35—C36 | 123 (3) |
| C19—C12—C13 | 111.8 (9) | C35—C36—C41 | 128 (3) |
| C19—C12—C14 | 111.0 (14) | C35—C34—C33 | 126 (4) |
| C13—C11—C14 | 109.5 (10) | C31—C38—C38$^i$ | 155 (2) |
| C19—C12—C20 | 100.8 (14) | C31—C38—C38$^{ii}$ | 99 (3) |
| C13—C12—C20 | 109.1 (15) | C38$^i$—C38—C38$^{ii}$ | 60.000 (18) |
| C14—C12—C20 | 114.5 (14) | C42—C41—C36 | 178 (3) |

Symmetry codes:
$^i$ −y + 1, x − y + 1, z;
$^{ii}$ −x + y, −x + 1, z.

Characterization of Compound 1:Glyceryltrimyristate

XRPD for Compound 1:Glyceryltrimyristate:

An examplary XRPD pattern for Compound 1:glyceryltrimyristate shown in FIG. 30 was acquired using the Panalytical Empyrean II diffractometer. Representative peaks for Compound 1:glyceryltrimyristate as observed in the XRPD pattern are provided in Table X below. All peaks listed below are greater than 1% of the maximum peak intensity.

TABLE X

| Peak # | Angle 2θ, in degrees (±0.2°) |
|---|---|
| 1 | 3.5 |
| 2 | 6.0 |
| 3 | 6.8 |
| 4 | 7.4 |
| 5 | 8.3 |
| 6 | 9.2 |

TABLE X-continued

| Peak # | Angle 2θ, in degrees (±0.2°) |
|---|---|
| 7 | 9.9 |
| 8 | 10.9 |
| 9 | 12.0 |
| 10 | 12.5 |
| 11 | 13.2 |
| 12 | 13.7 |
| 13 | 14.9 |
| 14 | 16.2 |
| 15 | 16.9 |
| 16 | 17.6 |
| 17 | 18.0 |
| 18 | 18.5 |
| 19 | 19.4 |
| 20 | 20.0 |
| 21 | 21.2 |
| 22 | 22.1 |
| 23 | 23.2 |
| 24 | 24.1 |
| 25 | 25.1 |
| 26 | 26.4 |
| 27 | 27.2 |
| 28 | 27.7 |
| 29 | 28.3 |
| 30 | 29.2 |
| 31 | 29.7 |
| 32 | 31.0 |
| 36 | 32.7 |

$^{13}$C ssNMR for Compound 1:Glyceryltrimyristate:

An examplary $^{13}$C ssNMR spectrum for Compound 1:glyceryltrimyristate is shown in FIG. 31. A listing of some of the $^{13}$C ssNMR peaks for Compound 1:glyceryltrimyristate are provided in Table Y below.

TABLE Y

| Peak # | $^{13}$C Chemical Shift (±0.1 ppm) |
|---|---|
| 1 | 178.1 |
| 2 | 171.4 |
| 3 | 169.8 |
| 4 | 165.0 |
| 5 | 155.0 |
| 6 | 142.9 |
| 7 | 139.5 |
| 8 | 137.2 |
| 9 | 134.6 |
| 10 | 133.1 |
| 11 | 127.3 |
| 12 | 126.0 |
| 13 | 119.9 |
| 14 | 117.4 |
| 15 | 112.0 |
| 16 | 67.0 |
| 17 | 63.7 |
| 18 | 61.4 |
| 19 | 35.6 |

DSC for Compound 1:Glyceryltrimyristate:

An examplary DSC thermogram for Compound 1:glyceryltristearate is shown in FIG. 32. The thermogram of Compound 1:glyceryltrimyristate in FIG. 32 has an endotherm at 59.2° C. that corresponds to the melt of glyceryltrimyristate. This event is followed by a broad exotherm at 134.4° C. that is overlapping with an endotherm. This event is followed by an exotherm at 171.3° C. corresponding to the crystallization of neat Compound 1. Another endotherm at 280.1° C. corresponds to the melt of a neat form of Compound 1.

Characterization of Compound 1:Glyceryltrihexanoate

XRPD for Compound 1:Glyceryltrihexanoate:

An examplary XRPD pattern for Compound 1:glyceryltrihexanoate shown in FIG. 33 was acquired using the Panalytical Empyrean II diffractometer. Representative peaks for Compound 1:glyceryltrihexanoate as observed in the XRPD pattern are provided in Table Z below. All peaks listed below are greater than 1% of the maximum peak intensity.

TABLE Z

| Peak # | Angle 2θ, in degrees (±0.2°) |
|---|---|
| 1 | 4.7 |
| 2 | 6.5 |
| 3 | 9.2 |
| 4 | 9.9 |
| 5 | 11.8 |
| 6 | 12.5 |
| 7 | 14.5 |
| 8 | 15.1 |
| 9 | 15.6 |
| 10 | 17.4 |
| 11 | 18.7 |
| 12 | 19.9 |
| 13 | 21.4 |
| 14 | 23.0 |
| 15 | 24.4 |
| 16 | 25.2 |
| 17 | 26.5 |
| 18 | 28.3 |
| 19 | 29.1 |
| 20 | 30.5 |
| 21 | 35.6 |

Characterization of Compound 1:Glyceryltridecanoate

XRPD for Compound 1:Glyceryltridecanoate:

An examplary XRPD pattern for Compound 1:glyceryltridecanoate shown in FIG. 34 was acquired using the Broker D8 Advance diffractometer. Representative peaks for Compound 1: glyceryltridecanoate as observed in the XRPD pattern are provided in Table AA below. All peaks listed below are greater than 1% of the maximum peak intensity.

TABLE AA

| No. | Angle 2θ, in degrees (±0.2°) |
|---|---|
| 1 | 3.5 |
| 2 | 6.1 |
| 3 | 6.9 |
| 4 | 9.2 |
| 6 | 10.9 |
| 7 | 11.8 |
| 8 | 12.1 |
| 9 | 12.6 |
| 10 | 13.2 |
| 11 | 13.8 |
| 12 | 14.9 |
| 13 | 16.3 |
| 14 | 16.9 |
| 15 | 18.1 |
| 16 | 18.5 |
| 17 | 19.4 |
| 18 | 19.8 |
| 19 | 20.3 |
| 20 | 21.7 |
| 21 | 23.4 |
| 22 | 23.9 |
| 23 | 25.2 |
| 24 | 25.8 |
| 25 | 27.2 |
| 26 | 28.4 |

$^{13}$C ssNMR for Compound 1:Glyceryltridecanoate:

An examplary $^{13}$C ssNMR spectrum for Compound 1:glyceryltridecanoate is shown in FIG. 35, A listing of some of the $^{13}$C ssNMR peaks for Compound 1:glyceryltridodecanoate are provided in Table AB below.

TABLE AB

| Peak # | $^{13}$C Chemical Shift (±0.1 ppm) |
|---|---|
| 1 | 178.5 |
| 2 | 171.6 |
| 3 | 169.9 |
| 4 | 165.0 |
| 5 | 155.0 |
| 6 | 143.3 |
| 7 | 139.5 |
| 8 | 137.2 |
| 9 | 134.9 |
| 10 | 133.0 |
| 11 | 127.3 |
| 12 | 126.1 |
| 13 | 119.5 |
| 14 | 117.6 |
| 15 | 112.1 |
| 16 | 67.2 |
| 17 | 64.0 |
| 18 | 59.8 |
| 19 | 35.7 |
| 20 | 34.7 |
| 21 | 31.7 |
| 22 | 30.5 |
| 23 | 25.8 |
| 24 | 23.5 |

HPLC Analysis of Compound 1-Triglyceride Co-Crystals

Sample Preparation 30 mg Compound 1-triglyceride co-crystal samples were weighed and quantitatively transferred into a 100 mL amber volumetric flasks. 50 ml of diluent was added, and the sample preparation was sonicated for 15 minutes. Each sample preparation was then shaken on a mechanical shaker for 30 minutes at 200 motion/sec. Another 40 ml of diluent was added and the sample preparation was shaken on a mechanical shaker for 30 minutes at 200 motion/sec. The Compound 1-glyceryltrioctanoate sample preparation dissolved completely, was allowed to return to room temperature, then diluted to volume with diluent, and mixed well. The Compound 1-glyceryltrioleate and Compound 1-glyceryltrilinoleate sample preparations did not dissolve completely. These two sample preparations were each sonicated for 15 minutes and then shaken for 30 minutes at 200 motion/sec. The two sample preparations were still not dissolved. 8 ml of acetonitrile was added to each and the sample preparations were sonicated for 15 minutes and then shaken for 30 minutes at 200 motion/sec. The two sample preparations were still not dissolved. 1 ml of methanol was added to each and the two sample preparations were sonicated for 15 minutes and then shaken for 30 minutes at 200 motion/sec. The two sample preparations were still not dissolved. The sample preparations were allowed to return to room temperature, diluted to volume with methanol and mixed well. Both sample preparations were cloudy. An aliquot of the solutions were filtered through a 0.45 μm Whatman PVDF filter. The first 2 mL of the filtrate was discarded before collecting in amber HPLC vials for analysis.

Sample preparations were made for the HPLC method described below.

HPLC Method

Samples were analyzed using the method parameters described below. Mobile Phase A was 0.1% Phosphoric Acid in Water. Mobile Phase B was 0.1% Phosphoric Acid in Acetonitrile. Table AC below shows the gradient program used.

TABLE AC

Gradient program for the HPLC method.

| Time (min.) | % A | % B |
|---|---|---|
| 0.0 | 80 | 20 |
| 7.0 | 40 | 60 |
| 9.0 | 40 | 60 |
| 9.1 | 0 | 100 |
| 12.0 | 0 | 100 |
| 12.1 | 80 | 20 |
| 16.0 | 80 | 20 |

The HPLC was done using a Waters Symmetry Shield RP18, 4.6×50 mm, 3.5 μm column (P/N 186000177) column on an Agilent 1260 HPLC instrument. The diluent was 70:30 Acetonitrile:Water. The flow rate was 1.5 mL/minute. Column temperature was 35° C. The needle wash used was 90:10 (Acetonitrile: Water). injection volume was 10 μL. The detector wavelength was 235 nM. Data acquisition time was 10.0 minutes. The vial temperature was ambient or 25° C. Run time was 16 minutes. The syringe filter used was a 0.45 μm PVDF Syringe Filter. Sample and standard stability were both 2 days. Two standards of Compound 1 were prepared and used (75.12 mg of Compound 1 in 250 mL of diluent and 75.29 mg of Compound 1 in 250 mL of diluent).

The purity was determined for each co-crystal by totaling the relative integrated intensities of the impurity peaks and subtracting from 100%. The Compound 1:glyceryltrioctanoate co-crystal and the Compound 1:glyceryltrioleate co-crystal were each 99.9% (w/w). The Compound 1:glyceryltrilinoleate co-crystal was 99.5% (w/w). The detection limit for impurities by HPLC is 0.005%.

The stoichiometry for each co-crystal was also determined from this HPLC assay. As shown in Table AD below, the stoichiometry determined was consistent with the results from solution state $^1$H NMR and thermogravimetric analysis.

TABLE AD

| | Compound 1 % w:w | Stoichiometry Compound 11: Triglyeride | Note |
|---|---|---|---|
| Compound 1: glyceryltrioctanoate | | | |
| Solution 1H NMR | 71.9 | 3.1 | Compound 1 % w:w calculated based on observed stoichiomtry |
| TGA weight loss | 71.8 | 3.1 | Stoichiometry calculated based on observed glyceryltrioctanoate % weight loss |
| HPLC Assay | 72.1 | 3.1 | Stoichiometry calculated based on observed Ivacaftor % w:w |
| Compound 1: glyceryltrioleate | | | |
| Solution 1H NMR | 71.4 | 5.6 | Compound 1 % w:w calculated based on observed stoichiomtry |
| HPLC Assay | 72.4 | 5.9 | Stoichiometry calculated based on observed Ivacaftor % w:w |
| Compound 1: glyceryltrilinoleate | | | |
| Solution 1H NMR | 71.6 | 5.7 | Compound 1 % w:w calculated based on observed stoichiomtry |
| HPLC Assay | 68.6 | 4.9 | Stoichiometry calculated based on observed Ivacaftor % w:w |

Activity Assays

A. Protocol 1

Assays for Detecting and Measuring ΔF508-CFTR Potentiation Properties of Compounds Membrane Potential Optical Methods for Assaying ΔF508-CFTR Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional ΔF508-CFTR in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Potentiator Compounds

To identify potentiators of ΔF508-CFTR, a double-addition HIS assay format was developed. This HTS assay utilizes fluorescent voltage sensing dyes to measure changes in membrane potential on the FLIPR III as a measurement for increase in gating (conductance) of ΔF508 CFTR in temperature-corrected ΔF508 CFTR NIH 3T3 cells. The driving force for the response is a Cl$^-$ ion gradient in conjunction with channel activation with forskolin in a single liquid addition step using a fluorescent plate reader such as FLIPR III after the cells have previously been treated with potentiator compounds (or DMSO vehicle control) and subsequently loaded with a redistribution dye.

Solutions

Bath Solution #1:

(in mM) NaCl 160, KCl 4.5, CaCl$_2$ 2, MgCl$_2$ 1, HEPES 10, pH 7.4 with NaOH.

Chloride-Free Bath Solution:

Chloride salts in Bath Solution #1 (above) are substituted with gluconate salts.

Cell Culture

NIH3T3 mouse fibroblasts stably expressing ΔF508-CFTR are used for optical measurements of membrane potential.

The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at ~20,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours.

Electrophysiological Assays for assaying ΔF508-CFTR modulation properties of compounds.

Using Chamber Assay

Using chamber experiments were performed on polarized airway epithelial cells expressing ΔF508-CFTR to further characterize the ΔF508-CFTR modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) *In vitro Cell. Dev. Biol.* 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for ΔF508-CFTR.

HBE grown on Costar® Snapwell™ cell culture inserts were mounted in an Using chamber (Physiologic Instruments, Inc., San Diego, Calif.), and the transepithelial resistance and short-circuit current in the presence of a basolateral to apical Cl— gradient (ISC) were measured using a voltage-clamp system (Department of Bioengineering, University of Iowa, IA). Briefly, HBE were examined under voltage-clamp recording conditions (Vhold=0 mV) at 37° C. The basolateral solution contained (in mM) 145 NaCl, 0.83 K2HPO4, 3.3 KH2PO4, 1.2 MgCl2, 1.2 CaCl2, 10 Glucose, 10 HEPES (pH adjusted to 7.35 with NaOH) and the apical solution contained (in mM) 145 NaGluconate, 1.2 MgCl2, 1.2 CaCl2, 10 glucose, 10 HEPES (pH adjusted to 7.35 with NaOH).

Identification of Potentiator Compounds

Typical protocol utilized a basolateral to apical membrane Cl⁻ concentration gradient. To set up this gradient, normal ringers was used on the basolateral membrane, whereas apical NaCl was replaced by equimolar sodium gluconate (titrated to pH 7.4 with NaOH) to give a large Cl⁻ concentration gradient across the epithelium. Forskolin (10 μM) and all test compounds were added to the apical side of the cell culture inserts. The efficacy of the putative ΔF508-CFTR potentiators was compared to that of the known potentiator, genistein.

Patch-Clamp Recordings

Total Cl⁻ current in ΔF508-NIH3T3 cells was monitored using the perforated-patch recording configuration as previously described (Rae, J., Cooper, K., Gates, P., & Watsky, M. (1991) *J. Neurosci. Methods* 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 MgCl$_2$, 2 CaCl$_2$, 10 EGTA, 10 HEPES, and 240 μg/mL amphotericin-B (pH adjusted to 7.35 with HCl). The extracellular medium contained (in mM) 150 NMDG-Cl, 2 MgCl2, 2 CaCl$_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate ΔF508-CFTR, 10 μM forskolin and 20 μM genistein were added to the bath and the current-voltage relation was monitored every 30 sec.

Identification of Potentiator Compounds

The ability of ΔF508-CFTR potentiators to increase the macroscopic ΔF508-CFTR Cl⁻ current (1ΔF508) in NIH3T3 cells stably expressing ΔF508-CFTR was also investigated using perforated-patch-recording techniques. The potentiators identified from the optical assays evoked a dose-dependent increase in IΔ$_{F508}$ with similar potency and efficacy observed in the optical assays. In all cells examined, the reversal potential before and during potentiator application was around −30 mV, which is the calculated E$_{Cl}$ (−28 mV).

Cell Culture

NIH3T3 mouse fibroblasts stably expressing ΔF508-CFTR are used for whole-cell recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-Channel Recordings

Gating activity of wt-CFTR and temperature-corrected ΔF508-CFTR expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) *Nature* 354, 526-528) using an Axopatch 200B patch-clamp amplifier (Axon Instruments Inc.). The pipette contained (in mM): 150 NMDG, 150 aspartic acid, 5 CaCl$_2$, 2 MgCl2, and 10 HEPES (pH adjusted to 7.35 with Tris base). The bath contained (in mM): 150 NMDG-Cl, 2 MgCl$_2$, 5 EGTA, 10 TES, and 14 Tris base (pH adjusted to 7.35 with HCl). After excision, both wt- and ΔF508-CFTR were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability (P$_o$) were determined from 120 sec of channel activity. The P$_o$ was determined using the Bio-Patch software or from the relationship P$_o$=I/i(N), where I=mean current, i=single-channel current amplitude, and N=number of active channels in patch.

Cell Culture

NIH3T3 mouse fibroblasts stably expressing ΔF508-CFTR are used for excised-membrane patch-clamp recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For single channel recordings, 2,500-5,000 cells were seeded on poly-L-lysine-coated glass coverslips and cultured for 24-48 hrs at 27° C. before use.

Activity of the Compound 1

Compounds of the present disclosure are useful as modulators of ATP binding cassette transporters. Table AD below illustrates the EC50 and relative efficacy of certain embodiments in Table 1. In Table AE below, the following meanings apply. EC50: "+++" means <10 uM; "++" means between 10 uM to 25 uM; "+" means between 25 uM to 60 uM. % Efficacy: "+" means <25%; "++" means between 25% to 100%; "+++" means >100%.

TABLE AE

| Cmpd # | EC50 (uM) | % Activity |
|--------|-----------|------------|
| 1      | +++       | ++         |

B. Protocol 2

Assays for Detecting and Measuring ΔF508-CFTR Potentiation Properties of Compounds Membrane Potential Optical Methods for Assaying ΔF508-CFTR Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional ΔF508-CFTR in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Potentiator Compounds

To identify potentiators of ΔF508-CFTR, a double-addition HTS assay format was developed. This HTS assay utilizes fluorescent voltage sensing dyes to measure changes in membrane potential on the FLIPR III as a measurement for increase in gating (conductance) of ΔF508 CFTR in temperature-corrected ΔF508 CFTR NIH 3T3 cells. The driving force for the response is a $Cl^-$ ion gradient in conjunction with channel activation with forskolin in a single liquid addition step using a fluorescent plate reader such as FLIPR III after the cells have previously been treated with potentiator compounds (or DMSO vehicle control) and subsequently loaded with a redistribution dye.

Solutions

Bath Solution #1:

(in mM) NaCl 160, KCl 4.5, $CaCl_2$ 2, $MgCl_2$ 1, HEPES 10, pH 7.4 with NaOH.

Chloride-Free Bath Solution:

Chloride salts in Bath Solution #1 (above) are substituted with gluconate salts.

Cell Culture

NIH3T3 mouse fibroblasts stably expressing ΔF508-CFTR are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For all optical assays, the cells were seeded at ~20,000/well in 384-well matrigel-coated plates and cultured for 2 hrs at 37° C. before culturing at 27° C. for 24 hrs, for the potentiator assay. For the correction assays, the cells are cultured at 27° C. or 37° C. with and without compounds for 16-24 hours.

Electrophysiological Assays for assaying ΔF508-CFTR modulation properties of compounds.

Using Chamber Assay

Using chamber experiments were performed on polarized airway epithelial cells expressing ΔF508-CFTR to further characterize the ΔF508-CFTR modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) In vitro Cell. Dev. Biol. 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for ΔF508-CFTR.

HBE grown on Costar® Snapwell™ cell culture inserts were mounted in an Using chamber (Physiologic Instruments, Inc., San Diego, Calif.), and the transepithelial resistance and short-circuit current in the presence of a basolateral to apical $Cl^-$ gradient ($I_{SC}$) were measured using a voltage-clamp system (Department of Bioengineering, University of Iowa, IA). Briefly, HBE were examined under voltage-clamp recording conditions ($V_{hold}$=0 mV) at 37° C. The basolateral solution contained (in mM) 145 NaCl, 0.83 $K_2HPO_4$, 3.3 $KH2PO_4$, 1.2 $MgCl_2$, 1.2 $CaCl_2$, 10 Glucose, 10 HEPES (pH adjusted to 7.35 with NaOH) and the apical solution contained (in mM) 145 NaGluconate, 1.2 $MgCl_2$, 1.2 $CaCl_2$, 10 glucose, 10 HEPES (pH adjusted to 7.35 with NaOH).

Identification of Potentiator Compounds

Typical protocol utilized a basolateral to apical membrane $Cl^-$ concentration gradient. To set up this gradient, normal ringers was used on the basolateral membrane, whereas apical NaCl was replaced by equimolar sodium gluconate (titrated to pH 7.4 with NaOH) to give a large $Cl^-$ concentration gradient across the epithelium. Forskolin (10 μM) and all test compounds were added to the apical side of the cell culture inserts. The efficacy of the putative ΔF508-CFTR potentiators was compared to that of the known potentiator, genistein.

Patch-Clamp Recordings

Total $Cl^-$ current in ΔF508-NIH3T3 cells was monitored using the perforated-patch recording configuration as previously described (Rae, J., Cooper, K., Gates, P., & Watsky, M. (1991) J. Neurosci. Methods 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 $MgCl_2$, 2 CaCl2, 10 EGTA, 10 HEPES, and 240 μg/mL amphotericin-B (pH adjusted to 7.35 with HCl). The extracellular medium contained (in mM) 150 NMDG-Cl, 2 $MgCl_2$, 2 $CaCl_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate ΔF508-CFTR, 10 μM forskolin and 20 μM genistein were added to the bath and the current-voltage relation was monitored every 30 sec.

Identification of Potentiator Compounds

The ability of ΔF508-CFTR potentiators to increase the macroscopic ΔF508-CFTR $Cl^-$ current ($I_{ΔF508}$) in NIH3T3 cells stably expressing ΔF508-CFTR was also investigated using perforated-patch-recording techniques. The potentiators identified from the optical assays evoked a dose-dependent increase in $IΔ_{F508}$ with similar potency and efficacy observed in the optical assays. In all cells examined, the reversal potential before and during potentiator application was around −30 mV, which is the calculated $E_{Cl}$ (−28 mV).

Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-Channel Recordings

Gating activity of wt-CFTR and temperature-corrected ΔF508-CFTR expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) Nature 354, 526-528) using an Axopatch 200B patch-clamp amplifier (Axon Instruments Inc.). The pipette contained (in mM): 150 NMDG, 150 aspartic acid, 5 $CaCl_2$, 2 $MgCl_2$, and 10 HEPES (pH adjusted to 7.35 with Tris base). The bath contained (in mM): 150 NMDG-Cl, 2 $MgCl_2$, 5 EGTA, 10 TES, and 14 Tris base (pH adjusted to 7.35 with HCl). After excision, both wt- and ΔF508-CFTR were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

Dissolution

Dissolution in Fed Intestinal Fluid (FeSSIF)

Dissolution tests of Compound 1 co-crystals were run in 50 ml amber bottles placed in jacketed vessels. The temperature of the jacketed vessel was controlled by an Iso Temp 360 water bath/chiller and set to 37° C. Twenty milliliters of simulated fed intestinal fluids were placed in the bottles and allowed to equilibrate to 37° C. for one hour while stirring at 125 rpm. Pre-weighed amounts (See Table AD, target concentration of Compound 1~1 mg/ml) of Compound 1:triglyceride co-crystal were then added to each bottle and allowed to stir at 37° C. for the duration of the dissolution study. One microliter samples were collected at selected time points (5 and 30 minutes, and 1, 2, 3, 4, 6, 16, and 24 hours). The samples were filtered using Millex®-LH 0.45 μm PTFE syringe filters and analyzed by HPLC for concentration levels.

Dissolution tests of Compound 1 SDD and Compound 1 amorphous were run in a Varian VK700 dissolution system. The temperature of the dissolution bath was controlled and set to 37° C. Five hundred milliliters of simulated fed intestinal fluids were placed in the dissolution vessels and allowed to equilibrate to 37° C. while stirring. Pre-weighed amounts (target concentration of Compound 1~1 mg/mL) of Compound 1 were then added to each vessel and allowed to stir at 37° C. for the duration of the dissolution study. Three milliliter samples were collected at selected time points (0.5, 1, 1.5, 3, 6, 9, 12, 18, 24, 48 hours). The samples were filtered using Whatman 25 mm with 0.45 μm PTFE syringe filters and analyzed by HPLC for concentration levels.

TABLE AF

Weights of Compound added to each vessel for dissolution

| experiment # | Weight of Compound 1: triglyceride co-crystal [mg] |
| --- | --- |
| 1 | 31.9 |
| 2 | 31.6 |
| 3 | 32.6 |
| 4 | 33.1 |
| 5 | 32.5 |
| 6 | 31.2 |
| 7 | 30.2 |
| 8 | 32.0 |
| 9 | 34.1 |

FIG. 36 shows the comparison of dissolution profiles up to 24 hours of Compound 1:glyceryltrioctanoate, Compound 1:glyceryltrioleate and Compound 1:glyceryltrilinoleate with amorphous Compound 1 and Compound 1 SDD in FeSSIF.

Solid Materials Isolated from the Mixture of Infant Formula and Amorphous Compound 1

Abbot Iron fortified infant formula was mixed with amorphous Compound 1 at approximate 7% w/v solids ratio (i.e., 7 g of amorphous Compound 1 in 100 ml of reconstituted formula). The suspension was slurried at ambient conditions and solids were isolated by vacuum filtration. The recovered solids were air dried for at least 1 hour prior to analysis.

FIG. 37 shows examplary low angle XRPD patterns of co-crystals of Compound 1 with different pure triglycerides and solid materials isolated from the mixture of infant formula and Compound 1. Based on the data shown in FIG. 37, the solid materials isolated from the mixture of infant formula and Compound 1 may consist either of a mixture of different cocrystals of Compound 1:triglycerides or a cocrystal of Compound 1 with a range of triglycerides in the crystal structure.

In addition, based on aromatic Compound 1 signal intensity in 13C CPMAS spectra, an average amount of 22% of Compound 1 was present in the form of the solid materials isolated from the mixture of infant formula during contacts ranging from 1 hour to 24 hours.

The invention claimed is:

1. A pharmaceutical composition comprising a co-crystal of Compound 1 and only one triglyceride, wherein the triglyceride is chosen from the following structural formula:

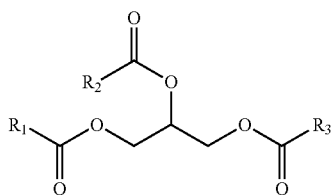

wherein $R_1$, $R_2$, and $R_3$ are independently $C_{1-29}$ aliphatic, and wherein Compound 1 is represented by the following structural formula:

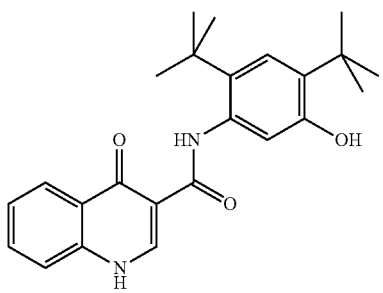 [SMILES: CC(C)(C)c1cc(C(C)(C)C)c(NC(=O)c2c[nH]c3ccccc3c2=O)cc1O]

and wherein the pharmaceutical composition is a solid formulated for oral administration.

2. The pharmaceutical composition of claim 1, wherein the co-crystal is characterized as having an X-ray powder diffraction pattern with characteristic peaks expressed in 2-theta±0.2 degrees at the following positions: 3.5, 6.9, and 10.9.

3. The pharmaceutical composition of claim 1, wherein the co-crystal is characterized as having an X-ray powder diffraction pattern with characteristic peaks expressed in 2-theta±0.2 degrees at the following positions: 3.5, 6.9, 9.2, 10.9, 16.9, 18.0, and 23.8.

4. The pharmaceutical composition of claim 1, wherein the co-crystal is characterized as having a $^{13}C$ ssNMR spectrum with characteristic peaks expressed in ppm±0.1 at the following positions: 178.6, 155.0, and 119.4.

5. The pharmaceutical composition of claim 1, wherein the co-crystal is characterized as having a $^{13}C$ ssNMR spectrum with characteristic peaks expressed in ppm±0.1 at the following positions: 178.6, 155.0, 130.5, and 119.4.

6. The pharmaceutical composition of claim 1, wherein the stoichiometry of Compound 1 to the triglyceride in the co-crystal is 3 to 1.

7. The pharmaceutical composition of claim 1, wherein the stoichiometry of Compound 1 to the triglyceride in the co-crystal is 6 to 1.

8. The pharmaceutical composition of claim 1, wherein Compound 1 forms a hexamer in the co-crystal and further wherein $R_1$, $R_2$, and $R_3$ are independently $C_{7-29}$ aliphatic.

9. The pharmaceutical composition of claim 1, wherein the co-crystal dissolves in simulated intestinal fluid in fed state (FeSSIF) to yield a concentration of Compound 1 of greater than 0.4 mg/mL and the concentration is maintained for at least 10 hours.

10. The pharmaceutical composition of claim 1, wherein the triglyceride is chosen from: glyceryl trioleate, glyceryl tristearate, glycerol tridecanoate, glycerol trihexanoate, glyceryl tritridecanoate, glycerol trioctanoate, glyceryl trimyristate, glyceryl tripalmitate, glyceryl tributyrate, glyceryl trilinoleate, glyceryl tridodecanoate, glyceryl decanoate, glyceryl tripalmitoleate, glycerol trierucate, glyceryl tripropionate, palmitodiolein, triarachidonin, glyceryl trilinolenate, trierucin, glycerol triarachidate, glyceryl tri(cis-13-docosenoate), glyceryl tripetroselinate, glyceryl tribehenate, glyceryl trielaidate, and triacetin.

11. A pharmaceutical composition comprising a therapeutically effective amount of Compound 1 and a pharmaceutically acceptable carrier or excipient, wherein Compound 1 is represented by the following structural formula:

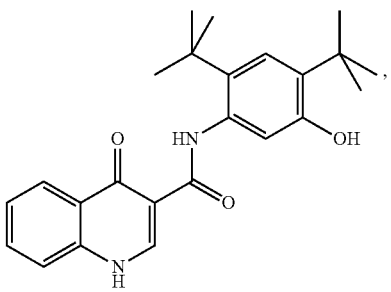 [SMILES: CC(C)(C)c1cc(C(C)(C)C)c(NC(=O)c2c[nH]c3ccccc3c2=O)cc1O]

and further wherein at least 30% of Compound 1 is present as a co-crystal comprising Compound 1 and a triglyceride, wherein the triglyceride is chosen from the following structural formula:

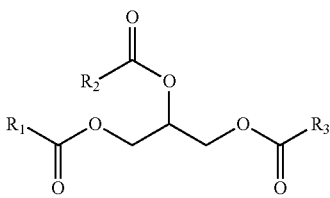

wherein $R_1$, $R_2$, and $R_3$ are independently $C_{1-29}$ aliphatic, and wherein the pharmaceutical composition is a solid formulated for oral administration.

12. The pharmaceutical composition according to claim 11, further comprising an additional therapeutic agent selected from a mucolytic agent, a bronchodilator, an antibiotic, an anti-infective agent, an anti-inflammatory agent, a CFTR modulator other than Compound 1, or a nutritional agent, or combinations thereof.

13. The pharmaceutical composition according to claim 12, wherein the additional therapeutic agent is a CFTR modulator other than Compound 1.

14. The pharmaceutical composition according to claim 13, wherein the CFTR modulator is (3-(6-(1-(2,2-difluorobenzo[d][1,3]dioxol-5-yl)cyclopropanecarboxamido)-3-methylpyridin-2-yl)benzoic acid or (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide.

15. A method of treating or lessening the severity of a disease in a patient, wherein said disease is selected from cystic fibrosis, hereditary emphysema, COPD, or dry-eye disease, the method comprising the step of administering to the patient a therapeutic effective amount of the co-crystal of claim 1.

16. The method according to claim 15, wherein the disease is cystic fibrosis.

17. The method according to claim 15, further comprising co-administering one or more additional therapeutic agents to the subject.

18. The method according to claim 17, wherein the additional therapeutic agent is (3-(6-(1-(2,2-difluorobenzo[d][1,3]dioxol-5-yl)cyclopropanecarboxamido)-3-methylpyridin-2-yl)benzoic acid or (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

19. The method according to claim 18, wherein the additional therapeutic agent is administered concurrently with, prior to, or subsequent to the co-crystal.

20. A method of preparing a co-crystal comprising Compound 1 and a triglyceride,
   wherein Compound 1 is represented by the following structural formula:

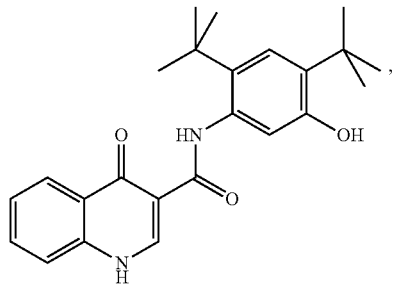 [SMILES: CC(C)(C)c1cc(C(C)(C)C)c(NC(=O)c2c[nH]c3ccccc3c2=O)cc1O]

and wherein the triglyceride is chosen from the following structural formula:

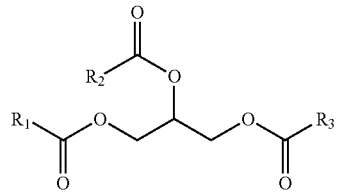

wherein $R_1$, $R_2$, and $R_3$ are independently $C_{1-29}$ aliphatic;
comprising the steps of:
(a) preparing a mixture comprising Compound 1 and the triglyceride; and
(b) heating the mixture.

21. The pharmaceutical composition according to claim 1 or 11,
   wherein the solid formulated for oral administration is a capsule, a tablet, a pill, a powder, or a granule.

* * * * *